United States Patent
Ishihara

(10) Patent No.: US 9,650,619 B2
(45) Date of Patent: *May 16, 2017

(54) MODIFIED ALPHA-GLUCOSIDASE AND APPLICATIONS OF SAME

(71) Applicant: Amano Enzyme Inc., Nagoya-shi (JP)

(72) Inventor: Satoru Ishihara, Kakamigahara (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/278,556

(22) Filed: Sep. 28, 2016

(65) Prior Publication Data

US 2017/0009218 A1    Jan. 12, 2017

Related U.S. Application Data

(62) Division of application No. 14/005,076, filed as application No. PCT/JP2012/055558 on Mar. 5, 2012, now Pat. No. 9,493,753.

(30) Foreign Application Priority Data

Mar. 16, 2011 (JP) ................. 2011-057386

(51) Int. Cl.
| | | |
|---|---|---|
| C12N 9/26 | (2006.01) | |
| C12P 19/20 | (2006.01) | |
| C12P 19/16 | (2006.01) | |
| C12P 19/04 | (2006.01) | |

(52) U.S. Cl.
CPC ............ *C12N 9/2408* (2013.01); *C12P 19/04* (2013.01); *C12P 19/16* (2013.01); *C12P 19/20* (2013.01); *C12Y 302/0102* (2013.01)

(58) Field of Classification Search
CPC .. C12N 9/1051; C12N 9/2408; C12N 9/2428; C12P 19/16; C12P 19/18; C12Y 302/0102; Y02P 20/52
See application file for complete search history.

(56) References Cited

FOREIGN PATENT DOCUMENTS

| | | | |
|---|---|---|---|
| JP | 2001-046096 | A | 2/2001 |
| JP | 2001-302440 | A | 10/2001 |
| JP | 2002-531581 | A | 9/2002 |
| JP | 2003-088365 | A | 3/2003 |
| JP | 2004-501446 | A | 1/2004 |
| JP | 2005-253302 | A | 9/2005 |
| JP | 2009-022204 | A | 2/2009 |
| JP | 2009-022267 | A | 2/2009 |
| WO | WO-00/34451 | A1 | 6/2000 |
| WO | WO-01/92990 | A2 | 12/2001 |
| WO | WO-2010/010463 | A2 | 1/2010 |

OTHER PUBLICATIONS

Mariko Nishimura et al., "Schwanniomyces occidentalis Yurai GH31 a-glucosidase eno Hen'i Donyu ni yoru Glucoside Ketsugo Sentakusei no Henkan", Annual Meeting of JSBBA(Japan Society for Bioscience, Biotechnology, and Agrochemistry) 2008, pp. 33, 2A09a13.
Masayuki Okuyama "Glycosidase that lost hydrolytic activity catalyzes oligosaccharide synthesis. Efficient synthesis of oligosaccharides by glycosynthase", Kagaku to Seibutsu (JSBBA) 2003, 41(7), pp. 422-425.
Hironori Hondo et al., "Dextran glucosidase no Kasui Bunkai Oyobi to Ten'i Hanno ni Okeru Kishitsu Tokuisei no Henkan", J.Appl. Glycosci., 2008, 55(Suppl), p. 62, S-6.
Fumiaki Sato et al., "Glucoamylase originating from Schwanniomyces occidentalis is a typical alpha-glucosidase." Biosci. Biotechnol. Biochem., Oct. 2005, 69(10), pp. 1905-1913.
International Search Report dated Jun. 5, 2012, issued for PCT/JP2012/055558.
"Alpha-glucosidase [Aspergillus niger CBS 513.88]", Genebank XP_001402053.
Masayuki Okuyama et al., "α-Glucosidase Mutant Catalyzes "α-Glycosynthase"-type Reaction", Biosci. Biotechnol. Biochem., 66 (4), 2002, pp. 928-933.
Office Action dated Aug. 27, 2014, issued for the Chinese patent application No. 201280013352.X.
Kato Naoki et al., "Novel alpha-glucosidase from *Aspergillus nidulans* with strong transglycosylation activity", Applied and Environmental Microbiology, vol. 68, No. 3, Mar. 1, 2002, pp. 1250-1256.
Sárka Malá et al., "Towards regioselective synthesis of oligosaccharides by use of alpha-glucosidases with different substrate specificity", Carbohydrate Research, vol. 322, No. 3-4, Dec. 12, 1999, pp. 209-218.
Database Geneseq [Online], Oct. 16, 2008, "Cochliobolus heterostrophus alpha-glucosidase, SEQ ID 6," (2 pages).
Database Geneseq [Online], Mar. 9, 2006, "Aspergillus fumigatus alpha-glucosidase (Ag13) protein," (1 page).
Hendrik Hellmuth et al., "Engineering the glucansucrase GTFR enzyme reaction and glycosidic bond specificity: Toward tailor-made polymer and oligosaccharide products", Biochemistry, vol. 47, No. 25, Jun. 2008, pp. 6678-6684.
Supplementary European Search Report dated Nov. 7, 2014, issued for the corresponding European patent application No. 12758032.2.
Nakamura et al., J. Biotechnol. 53:75-84, 1997.
Guo et al., PNAS 101(25):9205-9210, 2004.
Branden et al., Introduction to Protein Structure, Garland Publishing Inc., New York, p. 247, 1991.
Seffernick et al., J. Bacteriol. 183(8):2405-2410, 2001.
Witkowski et al., Biochemistry 38:11643-11650, 1999.
Sadowski et al., Current Opinion in Structural Biology 19:357-362, 2009.
Minetoki et al., Biosci. Biotech. Biochem. 59(8):1516-1521, 1995.
Matsubara, T., GenBank accession No. Q76KT3, Jul. 5, 2004.
Hunziker et al., Cell 46:227-234, 1986.
Japanese Office Action dated Dec. 28, 2015—English translation not available.

*Primary Examiner* — Delia Ramirez

(74) *Attorney, Agent, or Firm* — Locke Lord, LLP; James E. Armstrong, IV; Nicholas R. Herrel

(57) ABSTRACT

The object is to provide an α-glucosidase in which a transglycosylation activity predominates, and use thereof, and the like. A modified α-glucosidase consisting of an amino acid sequence in which one or two or more of the amino acid(s) is selected from a group of specific amino acids.

4 Claims, 27 Drawing Sheets

Aspergillus niger

Aspergillus nidulans (a) WT (c) WT:S495P = 1:2

(b) S495P (d) Area of tri- or more saccharides

MODIFIED ALPHA-GLUCOSIDASE AND APPLICATIONS OF SAME

This application is a divisional application of U.S. application Ser. No. 14/005,076, filed Sep. 13, 2013 which claims the right of priority under 35 U.S.C. §119 based on Japanese Patent Application No. 2011-057386 filed Mar. 16, 2011.

TECHNICAL FIELD

The present invention relates to a modified α-glucosidase. Specifically, the present invention relates to a modified α-glucosidase, a method of designing and a method of preparing the modified α-glucosidase, and use of the modified α-glucosidase. The present application claims priority based on Japanese Patent Application No. 2011-057386 filed on Mar. 16, 2011, and the whole content of the patent application is incorporated herein by reference.

BACKGROUND ART

Glycoside hydrolases are enzymes that cleave ester bonds, and many glycoside hydrolases that concurrently have a transglycosylation activity have also been reported. α-Glucosidase, which can be said to be a typical glycoside hydrolase, generally has a hydrolysis activity (hydrolysis reaction) and a transglycosylation activity (condensation reaction) in combination. α-Glucosidase is widely present in nature, from microorganisms to higher animals and higher plants. α-Glucosidase is the most useful enzyme in industries, and is utilized for the decomposition, synthesis and the like of saccharides.

Due to advances in technology, it has become possible to vary (improve) the characteristics of enzymes. Various attempts for modification have also been made for α-glucosidase (for example, see Patent Documents 1 to 3).

PRIOR ART DOCUMENT

Patent Literature

Patent Document 1: Japanese Unexamined Patent Publication No. 2003-88365
Patent Document 2: Japanese Unexamined Patent Publication No. 2005-253302
Patent Document 3: Japanese Unexamined Patent Publication No. 2009-22204
Patent Document 4: Japanese Unexamined Patent Publication No. 2001-046096

SUMMARY OF THE INVENTION

Problems to be Solved by the Invention

Since either the hydrolysis activity or transglycosylation activity is generally used in the case where α-glucosidase is used in industrial use, it is preferable that the other activity that is not used is low. In the case where α-glucosidase is used for the production of an oligosaccharide, transglycosylation activity of the enzyme could be decreased by increasing the hydrolysis activity. Therefore, the object of the present invention is to provide an α-glucosidase in which the transglycosylation activity predominates, which is suitable for the production of oligosaccharides. Furthermore, another object of the present invention is to provide the use thereof, and the like.

Means for Solving the Problem

The present inventors attempted to modify the structure of existing α-glucosidase at the molecular level for the purpose of designing a novel enzyme having an improved oligosaccharide production ability. Specifically, they conducted computer simulation and alignment comparison with four kinds of homologues by utilizing a result of an X-ray crystal structure analysis of α-glucosidase derived from human small intestine (Human Maltase-glucoamylase). As a result, three amino acids that constitute the substrate pockets of the enzyme were identified. Subsequently, amino acids that correspond to the amino acids were specified on the amino acid sequence of *Aspergillus niger* α-glucosidase, and modification was introduced into the those amino acids. As a result of an investigation on the characteristics of the obtained modified forms, it was confirmed that the characteristics of the enzyme (specifically the balance between the hydrolysis activity and transglycosylation activity) had significantly changed. Among the modified forms, those not showing a hydrolysis activity against α-1,4 glucosidic linkages and α-1,6 glucosidic linkages, those having a remarkably decreased hydrolysis activity against α-1,6 glucosidic linkages, those having a significantly decreased hydrolysis activity against α-1,3 glucosidic linkages and α-1,6 glucosidic linkages, and the like were observed. It is noteworthy that the wild-type enzymes catalyze formation of α-1,6 glucosidic linkages, mainly, whereas the modified forms (type W343M and type W343M/S496T) catalyze formation of α-1,4 glucosidic linkages, mainly. These facts mean that the above-mentioned amino acid positions that were successfully identified are effective as positions to which mutation is to be added, in the case where structural modification is performed for the purpose of obtaining an α-glucosidase that is suitable for the production of an oligosaccharide, and the like (i.e., an α-glucosidase in which the transglycosylation activity predominates). Furthermore, it can be said that the amino acid positions are especially effective as positions for mutation for acquiring an α-glucosidase having a unique characteristic that it shows a transglycosylation activity to form α-1,4 glucosidic linkages. On the other hand, modified α-glucosidases that are successfully obtained themselves are of great value in industry.

The present inventors further advanced their investigation and decided to consider annotated amino acids by a novel procedure. Specifically, first, steric structure models were constructed for *Aspergillus niger* α-glucosidase and *Aspergillus nidulans* α-glucosidase by using another computer simulation software. Subsequently, a docking simulation analysis was performed to thereby predict substrate pockets. Furthermore, based on the results, the amino acids to be an active center were searched, and the positions in each steric structure model were specified. Next, the amino acid sequences were compared between *Aspergillus niger* α-glucosidase and *Aspergillus nidulans* α-glucosidase, and the amino acids that were mismatched among the amino acids of the substrate pockets were specified as amino acids that are suitable for introducing modification. Subsequently, in order to confirm whether or not these amino acids are suitable for introducing mutation (in other words, whether or not these amino acids are beneficial for structural modification), mutation was actually introduced into two amino acids to give modified forms. As a result of the investigation on the characteristics of the obtained modified forms, a modified form showing a transglycosylation activity to form α-1,6 glucosidic linkages and a modified form showing a transglycosylation activity to form α-1,4 glucosidic linkages were observed. This fact supports that the amino acid positions that were successfully identified are effective for structural modification. On the other hand, the modified α-glucosidases that were successfully obtained themselves are of great value in industry.

On the other hand, as a result of further research, it was confirmed that the modified forms that were successfully obtained are useful for the generation or production of oligosaccharides. It is noteworthy that the modified form showing a transglycosylation activity to form α-1,6 glucosidic linkages was able to form oligosaccharides also from substrates having α1,4 glucosidic linkages by using the modified form in combination with a wild type α-glucosidase.

Meanwhile, it is often experienced that it is highly possible that an additive or synergistic effect is generated by combining effective two amino acid substitutions. Therefore, it can be said that the three mutation positions that were successfully identified are effective for changing the characteristics (especially for improving a transglycosylation activity), not only alone but also for the combinations thereof. Actually, the transglycosylation activity was also improved in the case where amino acid substitutions at two positions were combined (Examples mentioned below).

Furthermore, considering the technical common knowledge that enzymes of the same kind are highly similar in structures (primary structure and steric structure) and that it is highly possible that similar mutation generates a similar effect, it can be said that the mutation technique found by the present inventors can be applied to not only the α-glucosidase derived from *Aspergillus niger* as shown in the following Examples, but also α-glucosidases derived from other organisms.

The present invention shown below is based on the above-mentioned accomplishment and observation.

[1] A modified α-glucosidase consisting of an amino acid sequence in which one or two or more of the amino acid(s) selected from the group consisting of the following (1) to (14) has/have been substituted by other amino acid in the amino acid sequence of α-glucosidase:

(1) an amino acid corresponding to the amino acid at the position 385 of the amino acid sequence of SEQ ID NO. 1;
(2) an amino acid corresponding to the amino acid at the position 491 of the amino acid sequence of SEQ ID NO. 1;
(3) an amino acid corresponding to the amino acid at the position 535 of the amino acid sequence of SEQ ID NO. 1;
(4) an amino acid corresponding to the amino acid at the position 450 of the amino acid sequence of SEQ ID NO. 1;
(5) an amino acid corresponding to the amino acid at the position 534 of the amino acid sequence of SEQ ID NO. 1;
(6) an amino acid corresponding to the amino acid at the position 537 of the amino acid sequence of SEQ ID NO. 1;
(7) an amino acid corresponding to the amino acid at the position 538 of the amino acid sequence of SEQ ID NO. 1;
(8) an amino acid corresponding to the amino acid at the position 554 of the amino acid sequence of SEQ ID NO. 1;
(9) an amino acid corresponding to the amino acid at the position 556 of the amino acid sequence of SEQ ID NO. 1;
(10) an amino acid corresponding to the amino acid at the position 579 of the amino acid sequence of SEQ ID NO. 2;
(11) an amino acid corresponding to the amino acid at the position 585 of the amino acid sequence of SEQ ID NO. 2;
(12) an amino acid corresponding to the amino acid at the position 630 of the amino acid sequence of SEQ ID NO. 1;
(13) an amino acid corresponding to the amino acid at the position 683 of the amino acid sequence of SEQ ID NO. 1; and
(14) an amino acid corresponding to the amino acid at the position 689 of the amino acid sequence of SEQ ID NO. 1.

[2] The modified α-glucosidase according to [1], wherein the α-glucosidase is Human Maltase-glucoamylase, *Aspergillus niger* alpha-glucosidase, Human Neutral alpha-glucosidase C, Mouse Lysosomal alpha-glucosidase, Yeast GLU2A, *Aspergillus nidulans* Alpha-glucosidase AgdA, *Aspergillus nidulans* Alpha-glucosidase AgdB, *Mucor javanicus* alpha-glucosidase, *Aspergillus oryzae* alpha-glucosidase, *Mortierella alliacea* alpha-glucosidase, *Schizosaccharomyces pombe* alpha-glucosidase, *Debaryomyces occidentalis* alpha-glucosidase, *Hordeum vulgare* subsp. *vulgare* alpha-glucosidase, *Arabidopsis thaliana* alpha-glucosidase, *Spinacia oleracea* alpha-glucosidase, Beta vulgaris alpha-glucosidase or *Solanum tuberosum* alpha-glucosidase.

[3] The modified α-glucosidase according to [1], wherein the amino acid sequence of the α-glucosidase is the amino acid sequence of SEQ ID NO. 2, and the amino acid of (1) is the amino acid at the position 343 of the amino acid sequence, the amino acid of (2) is the amino acid at the position 452 of the amino acid sequence, the amino acid of (3) is the amino acid at the position 496 of the amino acid sequence, the amino acid of (4) is the amino acid at the position 410 of the amino acid sequence, the amino acid of (5) is the amino acid at the position 495 of the amino acid sequence, the amino acid of (6) is the amino acid at the position 498 of the amino acid sequence, the amino acid of (7) is the amino acid at the position 499 of the amino acid sequence, the amino acid of (8) is the amino acid at the position 531 of the amino acid sequence, the amino acid of (9) is the amino acid at the position 533 of the amino acid sequence, the amino acid of (12) is the amino acid at the position 662 of the amino acid sequence, the amino acid of (13) is the amino acid at the position 715 of the amino acid sequence, and the amino acid of (14) is the amino acid at the position 721 of the amino acid sequence.

[4] The modified α-glucosidase according to [3], wherein the amino acid to be substituted is the amino acid of (1), and the amino acid after the substitution is cysteine, aspartic acid, methionine, histidine, alanine, phenylalanine, glycine, threonine, glutamic acid, valine, glutamine, asparagine or isoleucine.

[5] The modified α-glucosidase according to [3], wherein the amino acid to be substituted is the amino acid of (2), and the amino acid after the substitution is glycine, aspartic acid or glutamic acid.

[6] The modified α-glucosidase according to [3], wherein the amino acid to be substituted is the amino acid of (3), and the amino acid after the substitution is asparagine, glutamine or valine.

[7] The modified α-glucosidase according to [3], wherein the amino acids to be substituted are the amino acid of (1) and the amino acid of (2), and the amino acids after the substitution are aspartic acid for the amino acid of (1) and alanine or glycine for the amino acid of (2).

[8] The modified α-glucosidase according to [3], wherein the amino acids to be substituted are the amino acid of (1) and the amino acid of (3), and the amino acids after the substitution are aspartic acid or methionine for the amino acid of (1) and isoleucine, arginine, cysteine or threonine for the amino acid of (3).

[9] The modified α-glucosidase according to [3], wherein the amino acid to be substituted is the amino acid of (5), and the amino acid after the substitution is glycine, proline or valine.

[10] The modified α-glucosidase according to [3], wherein the amino acid to be substituted is the amino acid of (6), and the amino acid after the substitution is leucine or serine.

[11] The modified α-glucosidase according to [1], which is consisting of any of the amino acid sequences of SEQ ID Nos. 18 to 42 and 77 to 78.

[12] The modified α-glucosidase according to [1], which is consisting of any of the amino acid sequences of SEQ ID Nos. 74 to 76.

[13] A gene coding for the modified α-glucosidase according to any one of [1] to [12].

[14] The gene according to [13], which comprises any of base sequences of SEQ ID Nos. 43 to 67 and 79 to 83.

[15] A recombinant DNA comprising the gene according to [13] or [14].

[16] A microorganism having the recombinant DNA according to [15].

[17] An enzyme agent comprising the modified α-glucosidase according to any one of [1] to [12].

[18] A method for producing an oligosaccharide, comprising reacting the modified α-glucosidase according to any one of [1] to [8], [10] and [11] with an oligosaccharide or polysaccharide of di- or more saccharides having α-1,4 glucosidic linkage.

[19] A method for producing an oligosaccharide, comprising reacting the modified α-glucosidase according to [9] or [12] with an oligosaccharide or polysaccharide of di- or more saccharides having α-1,6 glucosidic linkage.

[20] The method for producing an oligosaccharide according to [18] or [19], comprising using a wild type enzyme in combination.

[21] A method for producing an oligosaccharide, comprising reacting the modified α-glucosidase according to [9] or [12] and a wild type enzyme with an oligosaccharide or polysaccharide of di- or more saccharides having α-1,4 glucosidic linkage(s).

[22] A pharmaceutical composition, a quasi-drug composition, a cosmetic composition, a food composition or a feed composition, comprising the modified α-glucosidase according to any one of [1] to [12] or the enzyme agent according to [17].

[23] A method for designing a modified α-glucosidase, comprising the following steps (i) and (ii):

(i) a step of identifying one or two or more amino acid(s) selected from the group consisting of the following (1) to (14) in the amino acid sequence of α-glucosidase as an enzyme to be mutated:

(1) an amino acid corresponding to the amino acid at the position 385 of the amino acid sequence of SEQ ID NO. 1;

(2) an amino acid corresponding to the amino acid at the position 491 of the amino acid sequence of SEQ ID NO. 1;

(3) an amino acid corresponding to the amino acid at the position 535 of the amino acid sequence of SEQ ID NO. 1;

(4) an amino acid corresponding to the amino acid at the position 450 of the amino acid sequence of SEQ ID NO. 1;

(5) an amino acid corresponding to the amino acid at the position 534 of the amino acid sequence of SEQ ID NO. 1;

(6) an amino acid corresponding to the amino acid at the position 537 of the amino acid sequence of SEQ ID NO. 1;

(7) an amino acid corresponding to the amino acid at the position 538 of the amino acid sequence of SEQ ID NO. 1;

(8) an amino acid corresponding to the amino acid at the position 554 of the amino acid sequence of SEQ ID NO. 1;

(9) an amino acid corresponding to the amino acid at the position 556 of the amino acid sequence of SEQ ID NO. 1;

(10) an amino acid corresponding to the amino acid at the position 579 of the amino acid sequence of SEQ ID NO. 2;

(11) an amino acid corresponding to the amino acid at the position 585 of the amino acid sequence of SEQ ID NO. 2;

(12) an amino acid corresponding to the amino acid at the position 630 of the amino acid sequence of SEQ ID NO. 1;

(13) an amino acid corresponding to the amino acid at the position 683 of the amino acid sequence of SEQ ID NO. 1; and

(14) an amino acid corresponding to the amino acid at the position 689 of the amino acid sequence of SEQ ID NO. 1.

(ii) a step of constructing an amino acid sequence in which the amino acid sequence(s) identified in the step (i) has/have been substituted by other amino acid, based on the amino acid sequence of the enzyme to be mutated.

[24] The designing method according to [23], wherein the α-glucosidase is Human Maltase-glucoamylase, *Aspergillus niger* alpha-glucosidase, Human Neutral alpha-glucosidase C, Mouse Lysosomal alpha-glucosidase, Yeast GLU2A, *Aspergillus nidulans* Alpha-glucosidase AgdA, *Aspergillus nidulans* Alpha-glucosidase AgdB, *Mucor javanicus* alpha-glucosidase, *Aspergillus oryzae* alpha-glucosidase, *Mortierella alliacea* alpha-glucosidase, *Schizosaccharomyces pombe* alpha-glucosidase, *Debaryomyces occidentalis* alpha-glucosidase, *Hordeum vulgare* subsp. *vulgare* alpha-glucosidase, *Arabidopsis thaliana* alpha-glucosidase, *Spinacia oleracea* alpha-glucosidase, Beta vulgaris alpha-glucosidase or *Solanum tuberosum* alpha-glucosidase.

[25] The designing method according to [23], wherein the α-glucosidase comprises any of the amino acid sequences of SEQ ID Nos. 1 to 17.

[26] The designing method according to [23], wherein the α-glucosidase is consisting of the amino acid sequence of SEQ ID NO. 2, and the amino acid(s) that is/are substituted in the step (i) is/are one amino acid selected from (1) to (14), two amino acids selected from (1) to (14) or three amino acids selected from (1) to (14).

[27] A method for preparing a modified α-glucosidase, comprising the following steps (I) to (III):

(I) a step of preparing a nucleic acid that codes for any of the amino acid sequences of SEQ ID Nos. 18 to 42 and 74 to 78 or an amino acid sequence constituted by the designing method according to any one of [23] to [26];

(II) a step of expressing the nucleic acid, and (III) a step of collecting an expression product.

[28] An α-glucosidase having a transglycosylation activity to form α-1,4 or α-1,6 glucosidic linkages.

DESCRIPTION OF EMBODIMENTS

Figure 1:
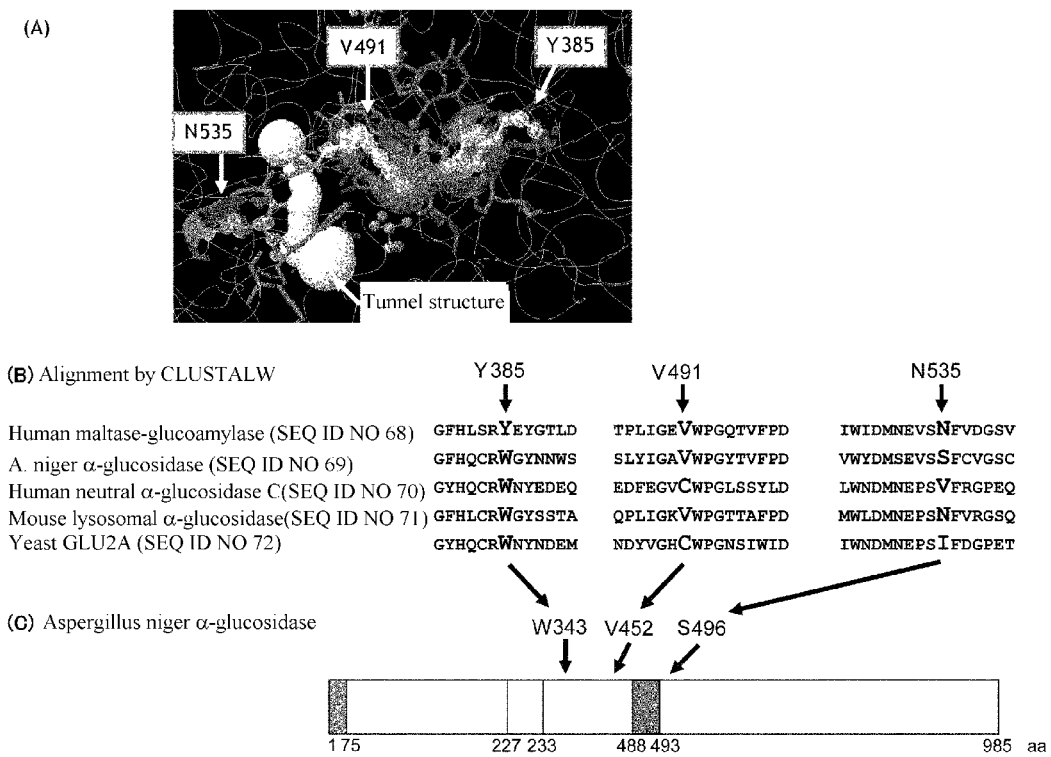
FIG. 1 shows positions of annotated amino acids in human α-glucosidase (A), comparison of alignments (B), and the positions of the amino acids corresponding to the annotated amino acids in an amino acid sequence of *Aspergillus niger* (C).

For convenience in explanation, a part of the terms used with respect to the present invention will be defined below.

TERMS

α-Glucosidase is also referred to as transglucosidase. In the present specification, the term "α-glucosidase" and the term "transglucosidase" are interchangeably used. The term "modified α-glucosidase" is an enzyme that is obtained by modifying or mutating "a base α-glucosidase" by the means disclosed by the present specification. In the present specification, the term "modified α-glucosidase", the term "modified α-glucosidase", the term "modified enzyme" and the term "modified enzyme" are interchangeably used. The base α-glucosidase is typically a wild type α-glucosidase. However, this does not interfere with the application of α-glucosidase that has already undergone an artificial operation to the present invention as the "base α-glucosidase". The "base α-glucosidase" is also referred to as "α-glucosidase to be mutated" or "enzyme to be mutated" in the present specification. In the present specification, an amino acid on a mutation introduction point is expressed by a combination of a single letter that represents the kind of the amino acid and a number that represents the position of the amino acid. For example, when the tryptophan at the position 343 is a mutation introduction point, the amino acid is expressed as "W343".

(Modified α-Glucosidase)

The first aspect of the present invention relates to a modified α-glucosidase (modified enzyme). The modified enzyme of the present invention has an amino acid sequence in which one or two or more of the amino acid(s) selected from the group consisting of the following (1) to (14) has/have been substituted by other amino acid(s) in the amino acid sequence of an enzyme to be mutated.

(1) an amino acid corresponding to the amino acid at the position 385 of the amino acid sequence of SEQ ID NO. 1

(2) an amino acid corresponding to the amino acid at the position 491 of the amino acid sequence of SEQ ID NO. 1

(3) an amino acid corresponding to the amino acid at the position 535 of the amino acid sequence of SEQ ID NO. 1

(4) an amino acid corresponding to the amino acid at the position 450 of the amino acid sequence of SEQ ID NO. 1

(5) an amino acid corresponding to the amino acid at the position 534 of the amino acid sequence of SEQ ID NO. 1

(6) an amino acid corresponding to the amino acid at the position 537 of the amino acid sequence of SEQ ID NO. 1

(7) an amino acid corresponding to the amino acid at the position 538 of the amino acid sequence of SEQ ID NO. 1

(8) an amino acid corresponding to the amino acid at the position 554 of the amino acid sequence of SEQ ID NO. 1

(9) an amino acid corresponding to the amino acid at the position 556 of the amino acid sequence of SEQ ID NO. 1

(10) an amino acid corresponding to the amino acid at the position 579 of the amino acid sequence of SEQ ID NO. 2

(11) an amino acid corresponding to the amino acid at the position 585 of the amino acid sequence of SEQ ID NO. 2

(12) an amino acid corresponding to the amino acid at the position 630 of the amino acid sequence of SEQ ID NO. 1

(13) an amino acid corresponding to the amino acid at the position 683 of the amino acid sequence of SEQ ID NO. 1

(14) an amino acid corresponding to the amino acid at the position 689 of the amino acid sequence of SEQ ID NO. 1

As shown in Examples mentioned below, the amino acid at the position 385, the amino acid at the position 491 and the amino acid at the position 535 mentioned above are amino acids that were expected to be important for the functions of enzymes as a result of making full use of the steric structure analysis and prediction of functions of Human Maltase-glucoamylase (SEQ ID NO. 1), as well as techniques such as alignment comparison with homologues, and the like. In one embodiment of the present invention, the structure of the enzyme is modified by mutating amino acids that correspond to these amino acids to thereby change the characteristics of α-glucosidase. The "characteristics" herein are a transglycosylation activity and a hydrolysis activity. In the modified enzyme of the present invention, the balance between the transglycosylation activity and hydrolysis activity has shifted to the direction in which the transglycosylation activity predominates, on the basis of the balance before the modification. Typically, as a result of the modification, improvement of the transglycosylation activity or lowering of the hydrolysis activity, or both generate(s), and thus the enzyme enables effective transglycosylation.

On the other hand, the amino acids shown in the above-mentioned (4) to (14) are amino acids that were expected to be effective for structure modification as a result of making use of the comparison of the steric structures and the comparison of the amino acid sequences in *Aspergillus niger* alpha-glucosidase and *Aspergillus nidulans* alpha-glucosidase. In another embodiment of the present invention, the structure of the enzyme is modified by mutating amino acids that correspond to these amino acids to thereby change the characteristics of α-glucosidase.

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1 or SEQ ID NO: 2) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank.

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, it is preferable that a protein to which a substrate or its analogous compound as a ligand is bound is used for crystallization.

(2) The prepared crystal is irradiated with X-ray to collect diffraction data. There are many cases that a protein crystal is damaged due to X-ray irradiation and the diffraction ability is deteriorated. In such cases, a low-temperature measurement technique of rapidly cooling the crystal to about −173° C. and collecting diffraction data in the state has recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X-ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structure refinement is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver.11.

Examples of the enzyme to be mutated in the present invention are Human Maltase-glucoamylase, *Aspergillus niger* alpha-glucosidase, Human Neutral alpha-glucosidase C, Mouse Lysosomal alpha-glucosidase, Yeast GLU2A, *Aspergillus nidulans* Alpha-glucosidase AgdA, *Aspergillus nidulans* Alpha-glucosidase AgdB, *Mucor javanicus* alpha-glucosidase, *Aspergillus oryzae* alpha-glucosidase, *Mortierella alliacea* alpha-glucosidase, *Schizosaccharomyces pombe* alpha-glucosidase, *Debaryomyces occidentalis* alpha-glucosidase, *Hordeum vulgare* subsp. *vulgare* alpha-glucosidase, *Arabidopsis thaliana* alpha-glucosidase, *Spinacia oleracea* alpha-glucosidase, Beta vulgaris alpha-glucosidase and *Solanum tuberosum* alpha-glucosidase. The amino acid sequences of these α-glucosidases, which are registered with public database, are shown below.

Human Maltase-glucoamylase: SEQ ID NO. 1
*Aspergillus niger* alpha-glucosidase: SEQ ID NO. 2
Human Neutral alpha-glucosidase C: SEQ ID NO. 3
Mouse Lysosomal alpha-glucosidase: SEQ ID NO. 4
Yeast GLU2A: SEQ ID NO. 5
*Aspergillus nidulans* Alpha-glucosidase AgdA: SEQ ID NO. 6
*Aspergillus nidulans* Alpha-glucosidase AgdB: SEQ ID NO. 7
*Mucor javanicus* alpha-glucosidase: SEQ ID NO. 8
*Aspergillus oryzae* alpha-glucosidase: SEQ ID NO. 9
*Mortierella alliacea* alpha-glucosidase: SEQ ID NO. 10
*Schizosaccharomyces pombe* alpha-glucosidase: SEQ ID NO. 11
*Debaryomyces occidentalis* alpha-glucosidase: SEQ ID NO. 12
*Hordeum vulgare* subsp. *vulgare* alpha-glucosidase: SEQ ID NO. 13
*Arabidopsis thaliana* alpha-glucosidase: SEQ ID NO. 14
*Spinacia oleracea* alpha-glucosidase: SEQ ID NO. 15
Beta vulgaris alpha-glucosidase: SEQ ID NO. 16
*Solanum tuberosum* alpha-glucosidase: SEQ ID NO. 17

Here, when the α-glucosidase derived from *Aspergillus niger* having the amino acid sequence of SEQ ID NO. 2 is an enzyme to be mutated, the amino acid of the above-mentioned (1) is the amino acid at the position 343 of SEQ ID NO. 2, the amino acid of the above-mentioned (2) is the amino acid at the position 452 of SEQ ID NO. 2, the amino acid of the above-mentioned (3) is the amino acid at the position 496 of SEQ ID NO. 2, the amino acid of the above-mentioned (4) is the amino acid at the position 410 of SEQ ID NO. 2, the amino acid of the above-mentioned (5) is the amino acid at the position 495 of SEQ ID NO. 2, the amino acid of the above-mentioned (6) is the amino acid at the position 498 of SEQ ID NO. 2, the amino acid of the above-mentioned (7) is the amino acid at the position 499 of SEQ ID NO. 2, the amino acid of the above-mentioned (8) is the amino acid at the position 531 of SEQ ID NO. 2, the amino acid of the above-mentioned (9) is the amino acid at the position 533 of SEQ ID NO. 2, the amino acid of the above-mentioned (10) is the amino acid at the position 579 of SEQ ID NO. 2, the amino acid of the above-mentioned (11) is the amino acid at the position 585 of SEQ ID NO. 2, the amino acid of the above-mentioned (12) is the amino acid at the position 662 of SEQ ID NO. 2, the amino acid of the above-mentioned (13) is the amino acid at the position 715 of SEQ ID NO. 2, and the amino acid of the above-mentioned (14) is the amino acid at the position 721 of SEQ ID NO. 2.

A kind of an amino acid after substitution is not particularly limited. Thus, it may be "conservative amino acid substitution" or "non-conservative amino acid substitution". The "conservative amino acid substitution" herein refers to substituting a certain amino acid residue with an amino acid residue having a side chain with the same characteristics. Amino acid residues are classified into some families according to their side chains, such as basic side chains (e.g., lysine, arginine, and histidine), acidic side chains (e.g., asparaginic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is typically substitution between amino acid residues in the same family.

When the α-glucosidase derived from *Aspergillus niger* having the amino acid sequence of SEQ ID NO. 2 is an enzyme to be mutated, examples of the amino acids after the substitution are cysteine, aspartic acid, methionine, histidine, alanine, phenylalanine, glycine, threonine, glutamic acid, valine, glutamine, asparagine or isoleucine for the amino acid of (1); glycine, aspartic acid, glutamic acid or alanine for the amino acid of (2); valine, asparagine, glutamine, isoleucine, arginine, cysteine or threonine for the amino acid of (3); glycine, proline or valine for the amino acid of (5); and leucine or serine for the amino acid of (6).

Two or more amino acids among the above-mentioned amino acids (1) to (14) may be substituted. As combinations of the amino acids to be substituted, a combination of (1) and (2) and a combination of (1) and (3) can be exemplified. These combinations correspond to the modified enzymes that were obtained in the Examples mentioned below.

Here, examples of the amino acid sequences of the modified enzymes are shown in SEQ ID Nos. 18 to 42 and 74 to 78. These sequences are the amino acid sequences of the modified enzymes obtained by conducting substitution of one amino acid (on any of the amino acids of (1) to (3), (5) and (6)), substitution of two amino acids (on the amino acids of (1) and (2), the amino acids of (1) and (3), or the amino acids of (2) and (3)) or substitution of three amino acids (on the amino acids of (1), (2) and (3)) on *Aspergillus niger* α-glucosidase. The corresponding relations of the sequence identification numbers and the amino acid substitutions are as follows. In the amino acid sequence of *Aspergillus niger* α-glucosidase (SEQ ID NO. 2), the tryptophan at the position 343 (W343) corresponds to the amino acid of (1), the valine at the position 452 (V452) corresponds to the amino acid of (2), the serine at the position 496 (S496) corresponds to the amino acid of (3), the isoleucine at the position 410 (I410) corresponds to the amino acid of (4), the valine at the position 499 (V499) corresponds to the amino acid of (7), the glutamic acid at the position 531 (E531) corresponds to the amino acid of (8), the phenylalanine at the position 533 (F533) corresponds to the amino acid of (9), the histidine at the position 579 (H579) corresponds to the amino acid of (10), the asparagine at the position 585 (N585) corresponds to the amino acid of (11), the tyrosine at the position 662 (Y662) corresponds to the amino acid of (12), the tyrosine at the position 715 (Y715) corresponds to the amino acid of (13), and the leucine at the position 721 (L721) corresponds to the amino acid of (14). Furthermore, in the amino acid sequence of *Aspergillus nidulans* α-glucosidase AgdB (SEQ ID NO. 7), the tyrosine at the position 296 (Y296) corresponds to the amino acid of (1), the asparagine at the position 456 (N456) corresponds to the amino acid of (3), the methionine at the position 363 (M363) corresponds to the amino acid of (4), the alanine at the position 455 (A455) corresponds to the amino acid of (5), the tyrosine at the position 458 (Y458) corresponds to the amino acid of (6), the asparagine at the position 459 (N459) corresponds to the amino acid of (7), the aspartic acid at the position 488 (D488) corresponds to the amino acid of (8), the leucine at the position 490 (L490) corresponds to the amino acid of (9), the arginine at the position 565 (R565) corresponds to the amino acid of (10), the glutamine at the position 571 (Q571) corresponds to the amino acid of (11), the isoleucine at the position 646 (I646) corresponds to the amino acid of (12), the phenylalanine at the position 700 (F700) corresponds to the amino acid of (13), and the isoleucine at the position 706 (I706) corresponds to the amino acid of (14).

Amino acid sequence: substitution of amino acid
A. SEQ ID NO. 18: W343C
B. SEQ ID NO. 19: W343D
C. SEQ ID NO. 20: W343M
D. SEQ ID NO. 21: W343H
E. SEQ ID NO. 22: W343A
F. SEQ ID NO. 23: W343F
G. SEQ ID NO. 24: W343G
H. SEQ ID NO. 25: W343T
I. SEQ ID NO. 26: W343E
J. SEQ ID NO. 27: W343V
K. SEQ ID NO. 28: W343Q
L. SEQ ID NO. 29: W343N
M. SEQ ID NO. 30: W343I
N. SEQ ID NO. 31: V452G
O. SEQ ID NO. 32: V452D
P. SEQ ID NO. 33: V452E
Q. SEQ ID NO. 34: S496V
R. SEQ ID NO. 35: S496N
S. SEQ ID NO. 36: S496Q
T. SEQ ID NO. 37: W343D and V452A
U. SEQ ID NO. 38: W343D and V452G
V. SEQ ID NO. 39: W343D and S496I
W. SEQ ID NO. 40: W343D and S496R
X. SEQ ID NO. 41: W343M and S496C
Y. SEQ ID NO. 42: W343M and S496T
a. SEQ ID NO. 74: S495G
b. SEQ ID NO. 75: S495P
c. SEQ ID NO. 76: S495V
d. SEQ ID NO. 77: C498L
e. SEQ ID NO. 78: C498S In light of the experimental results shown in the following Examples (confirmation of the effect of amino acid substitution), the modified α-glucosidases of A to C, O and Q to S are highly useful in that they are specifically excellent in transglycosylation activity. Furthermore, V and W are highly useful in that they have a quite low hydrolysis activity. On the other hand, U, X and Y are highly useful in that they have a quite low decomposition activity against α-1,6 glucosidic linkages. Y is highly useful also in that it is excellent in transglycosylation activity. Furthermore, a to c are characterized in that they show a transglycosylation activity to form α-1,6 glucosidic linkages. d and e are excellent in transglycosylation activity to form α-1,4 glucosidic linkages.

Generally, when a part of an amino acid sequence of a certain protein is modified, the modified protein may have the equal function to that of the protein before the modification. That is to say, the modification of the amino acid sequence may not have a substantial effect on the function of the protein, so that the function of the protein may be maintained before and after the modification. When this technical common sense is considered, an enzyme that has a recognizable slight difference in the amino acid sequence (provided that the difference occurs in sites other than the sites in which the above substitutions have been made) and has Nos.ubstantially recognizable difference in the function can be regarded as an enzyme that is substantially the same as the above modified enzyme in comparison with the modified enzyme comprising the amino acid sequence in which one or more amino acids selected from the group consisting of the above (1) to (14) have been substituted with another amino acid. The term "slight difference in the amino acid sequence" as used herein typically means that the amino acid sequence is mutated (changed) by the deletion or substitution of one to several amino acids (the upper limit: e.g. 3, 5, 7, or 10 amino acids) constituting the amino acid sequence, or by the addition, insertion, or combination thereof, of one to several amino acids (the upper limit: e.g. 3, 5, 7, or 10 amino acids). The identity (%) of between the amino acid sequence in the "substantially the same enzyme" and the amino acid sequence of the above modified enzyme as a standard is preferably 90% or more, more preferably 95% or more, yet more preferably 98% or more, and most preferably 99% or more. In addition, the difference in the amino acid sequence may occur in a plurality of positions. The "slight difference in the amino acid sequences" is preferably generated by a conservative amino acid substitution.

(Nucleic Acid Coding for Modified α Glucosidase, Etc.)

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further mutant of an enzyme.

The "gene coding for a modified enzyme" herein refers to a nucleic acid capable of obtaining the modified enzyme when it is expressed, and includes, as a matter of course of a nucleic acid having a nucleotide sequence corresponding to the amino acid sequence of the modified enzyme, also a nucleic acid obtained by adding a sequence that does not code for an amino acid sequence to such a nucleic acid. Degeneracy of a codon is also considered.

Examples of sequences (nucleotide sequences) of genes coding for the modified enzyme are shown in SEQ ID Nos.: 43 to 67 and 79 to 83. These sequences are genes coding for the modified enzyme obtained by specific amino acids substitution to *Aspergillus niger* a glucosidase. The relationship between a SEQ ID NO and an amino acid substitution is as follows.

nucleotide sequence: amino acid substitution
A. SEQ ID NO 43: W343C
B. SEQ ID NO 44: W343D
C. SEQ ID NO 45: W343M
D. SEQ ID NO 46: W343H
E. SEQ ID NO 47: W343A
F. SEQ ID NO 48: W343F
G. SEQ ID NO 49: W343G
H. SEQ ID NO 50: W343T
I. SEQ ID NO 51: W343E
J. SEQ ID NO 52: W343V
K. SEQ ID NO 53: W343Q L. SEQ ID NO 54: W343N
M. SEQ ID NO 55: W343I
N. SEQ ID NO 56: V452G
O. SEQ ID NO 57: V452D
P. SEQ ID NO 58: V452E
Q. SEQ ID NO 59: S496V
R. SEQ ID NO 60: S496N
S. SEQ ID NO 61: S496Q
T. SEQ ID NO 62: W343D and V452A
U. SEQ ID NO 63: W343D and V452G
V. SEQ ID NO 64: W343D and S496I
W. SEQ ID NO 65: W343D and S496R
X. SEQ ID NO 66: W343M and S496C
Y. SEQ ID NO 67: W343M and S496T
a. SEQ ID NO 79: S495G
b. SEQ ID NO 80: S495P
c. SEQ ID NO 81: S495V
d. SEQ ID NO 82: C498L
e. SEQ ID NO 83: C498S The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a nucleotide sequence in a part (hereinafter also referred to as a "homologous nucleic acid", and a nucleotide sequence defining a homologous nucleic acid is also referred to as a "homologous nucleotide sequence") as compared to the nucleotide sequence of the gene coding for the modified enzyme of the invention, although functions of a protein coded by the nucleic acid are equal. An example of the homologous nucleic acid includes a DNA composed of a nucleotide sequence containing substitution, deletion, insertion, addition or inversion of 1 to several nucleotides on the basis of the nucleotide sequence of the nucleic acid coding for the modified enzyme of the present invention and coding for a protein having enzyme activity characteristic to the modified enzyme (i.e. glycosyltransferase activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having the complementary nucleotide sequence to the nucleotide sequence of the gene coding for the modified enzyme of the invention. Another embodiment of the present invention provides a nucleic acid having a nucleotide sequence with an identity of at least about 60%, 70%, 80%, 90%, 95%, 99%, or 99.9% to the nucleotide sequence of the gene coding for the modified enzyme of the invention or the complementary nucleotide sequence Another embodiment of the present invention relates to a nucleic acid having a nucleotide sequence hybridizing to the complementary nucleotide sequence to the nucleotide sequence of the gene coding for the modified enzyme of the invention or its homologous nucleotide sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 µg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of modified salmon sperm DNA, and a 50 mM phosphate buffer (pH 7.5) as a hybridization liquid.

Another embodiment of the present invention provides a nucleic acid (nucleic acid fragment) having a part of the nucleotide sequence of the gene coding for the modified enzyme of the invention or the complementary nucleotide sequence. Such a nucleic acid fragment can be used in detection, identification, and/or amplification of a nucleic acid having the nucleotide sequence of the gene coding for the modified enzyme of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the nucleotide sequence of the gene coding for the modified enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a modified enzyme can be used. Examples of *Escherichia coli* include *Escherichia coli* BL21 (DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Feigner, P. L. et al., Proc. Natl. Acad. Sci. U.S.A. 84, 7413-7417 (1984)). Note that the microorganism of the present invention can be used in producing the modified enzyme of the present invention (see the section of the preparation method of modified α glucosidase described later).

(Enzyme Agent Containing Modified α-Glucosidase)

The modified enzyme of the present invention is provided, for example, in the form of an enzyme agent. The enzyme agent may contain an excipient, a buffer agent, a suspending agent, a stabilizer, a preservative, an antiseptic, saline and the like besides the active ingredient (the modified enzyme of the present invention). As the excipient, starch, dextrin, maltose, trehalose, lactose, D-glucose, sorbitol, D-mannitol, white soft sugar, glycerol and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, ethanol, benzalkonium chloride, paraoxybenzoic acid, chlorobutanol and the like can be used.

(Use of Modified α-Glucosidase)

A further aspect of the present invention relates to use of the modified enzyme. As one of the use, a method for producing an oligosaccharide is provided. In the first embodiment of the method for producing an oligosaccharide of the present invention, in order to utilize the feature of the modified enzyme of the present invention of high specificity against α-1,4 glucosidic linkages, an oligosaccharide or polysaccharide of di- or more saccharides having α-1,4 glucosidic linkage(s) is used as a substrate, and the modified enzyme of the present invention is reacted with the substrate.

In this embodiment, enzymes having high specificity against α-1,4 glucosidic linkages such as modified enzymes W343M, W343M/S496T, C498L and C498S shown in the following Examples, and the like are used. Examples of the substrate are maltose, maltotriose, panose, pullulan, maltotetraose, maltopentaose, maltohexaose, maltoheptaose, maltooctaose, dextrin, starches (potato starch, sweet potato starch, corn starch, wheat starch, tapioca starch and the like), and the like. A mixture of two or more oligosaccharides or polysaccharides may be the substrate. According to the production method of the present invention, an oligosaccharide having low-branched chains can be produced in a specific and efficient manner. The reaction conditions may follow those generally adopted in the generation of an oligosaccharide using α-glucosidase.

In the second embodiment of the method for producing an oligosaccharide of the present invention, modified enzymes that show a transglycosylation activity to form α-1,6 glucosidic linkages (for example, S495G, S495P and S495V shown in the following Examples) are used. Examples of the substrate in this case are isomaltose, isomaltotriose, panose, isopanose, starches (potato starch, sweet potato starch, corn starch, wheat starch, tapioca starch and the like). According to this embodiment, typically, an oligosaccharide having much branched chains can be produced in a specific and efficient manner.

In order to increase the generation amount of the intended oligosaccharide (an oligosaccharide having low-branched chains in the case of the first embodiment, or typically an oligosaccharide having much branched chains in the case of the second embodiment), a wild type enzyme may be used in addition to the modified enzyme. The wild type enzyme is not specifically limited as long as it is suitable for the generation of the intended oligosaccharide. For example, a wild type enzyme that corresponds to the modified enzyme to be used (i.e., an enzyme that has undergone modification for obtaining the modified enzyme) can be adopted. In contrast to this example, a modified enzyme and wild type enzyme whose origins are different can be used in combination. As an example, an enzyme obtained by modifying *Aspergillus niger* α-glucosidase (modified enzyme) and *Aspergillus nidulans* wild type α-glucosidase AgdB are used in combination.

Here, as shown in the following Examples, it has become clear that an oligosaccharide can be formed from a substrate having α-1,4 glucosidic linkages when a modified enzyme that shows a transglycosylation activity to form α-1,6 glucosidic linkages and a wild type enzyme in combination. Therefore, in a further embodiment of the present invention, a modified enzyme that shows a transglycosylation activity to form α-1,6 glucosidic linkages (for example, S495G, S495P and S495V shown in the following Examples) is reacted in combination with a wild type enzyme to give an oligosaccharide.

Due to the transglycosylation activity of the modified enzyme of the present invention, an effect of preventing aging of starches, an effect of improving flavors of foods, an effect of regulating the intestines and the like can be expected. Therefore, examples of the use of the modified enzyme of the present invention may include prevention of the aging of starches in foods, improvement of the flavors of foods and regulation of the function of the intestines. Assuming application to these uses, the present invention provides compositions containing the modified enzyme (a pharmaceutical composition, a quasi-drug composition, a cosmetic composition, a food composition or a feed composition) as a further aspect.

The pharmaceutical composition or quasi-drug composition of the present invention can be formulated according to a conventional method. In the case of the formulation, other components that are acceptable in formulation (for example, a carrier, an excipient, a disintegrating agent, a buffer agent, an emulsifying agent, a suspending agent, a soothing agent, a stabilizer, a preservative, an antiseptic, saline and the like) can be incorporated. As the excipient, lactose, starch, sorbitol, D-mannitol, white soft sugar and the like can be used. As the disintegrating agent, starch, carboxymethyl cellulose, calcium carbonate and the like can be used. As the buffer agent, phosphates, citrates, acetates and the like can be used. As the emulsifier, gum arabic, sodium alginate, tragacanth and the like can be used. As the suspending agent, glycerin monostearate, aluminum monostearate, methyl cellulose, carboxymethyl cellulose, hydroxymethyl cellulose, sodium lauryl sulfate and the like can be used. As the soothing agent, benzyl alcohol, chlorobutanol, sorbitol and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

The dosage form in the case of the formulation is also not specifically limited, and the pharmaceutical composition or quasi-drug composition of the present invention can be provided, for example, as a tablet, a powder, a fine granule, a granular agent, a capsule agent, a syrup agent, an injection agent, an external preparation and a suppository, and the like.

The pharmaceutical composition of the present invention contains an active ingredient (modified enzyme) in an amount necessary to obtain the expected therapeutic effect or prophylactic effect (i.e., a therapeutically effective amount). Similarly, the quasi-drug composition of the present invention contains an active ingredient in an amount necessary to obtain the expected improvement effect, prophylactic effect and the like. Although the amount of the active ingredient contained in the pharmaceutical composition or quasi-drug composition of the present invention generally differs depending on the dosage form or form, the amount of the active ingredient is set within the range of, for example, about 0.1% by weight to about 95% by weight so that a desired dose can be achieved.

The pharmaceutical composition or quasi-drug composition of the present invention is applied to a subject in an oral or parenteral manner (intravenous, intraarterial, subdermal, intramuscular, or interperitoneal injection, transdermal, pernasal, transmucosal, application, or the like) depending on the dosage form and form thereof. The "subject" as used herein is not specifically limited, and includes humans and mammals other than humans. (Pet animals, farm animals, and experimental animals are included. Specific examples are mice, rats, guinea pigs, hamsters, monkeys, cows, pigs, goats, sheep, dogs, cats, chickens, quails and the like.) In a preferable embodiment, the subject to be applied is a human.

The doses and use amounts of the pharmaceutical composition and quasi-drug composition of the present invention are preset so that expected effects would be obtained. In the setting of an effective dose, the symptom, age, sex, body weight and the like of a subject to be applied are considered. Any person skilled in the art can set a suitable dose with consideration for these matters. As an administration schedule, for example, once to several times a day, once every second day, or once every third day can be adopted. In the preparation of the administration schedule, the symptom of the subject, the duration of the effect of the active ingredient, and the like can be considered.

The cosmetic composition of the present invention can be obtained by incorporating the modified enzyme, and components and substrates that are generally used in cosmetics (for example, various fats and oils, mineral oils, vaseline, squalane, lanolin, beeswax, modified alcohols, dextrin palmitate, glycerin, fatty acid esters of glycerin, ethylene glycol, paraben, camphor, menthol, various vitamins, zinc oxide, titanium oxide, benzoic acid, edetic acid, chamomile oil, carrageenan, chitin powder, chitosan, perfume materials, coloring materials and the like). As the forms of the cosmetic composition, an emulsion liquid for face or body, a skin lotion, a cream, a lotion, an essence, an oil, a pack, a sheet, a cleanser and the like can be exemplified. The addition amount of the modified enzyme in the cosmetic composition is not specifically limited. For example, the modified enzyme can be added so as to be 0.01% by weight to 10% by weight.

On the other hand, examples of the "food composition" in the present invention may include general foods (cooked rice, bread, cereal, vegetables, edible meat, various processed foods, sweets, milk, soft drink, alcohol beverages and the like), nutritional supplements (supplements, nutrition-supplement drinks and the like) and food additives. In the cases of the nutritional supplement or food additive, it can be provided in the form of a powder, a granule, a tablet, a paste, a liquid or the like.

Examples of the "feed composition" of the present invention are pet foods (feeds for dogs, cats, birds, fishes, reptiles, amphibians, rodents and the like) and feedstuffs (feeds for farm animals, poultries, cultured fishes and the like).

(Method for Designing Modified α-Glucosidase)

A further aspect of the present invention relates to a method of designing the modified enzyme. In the designing method of the present invention, the following steps (i) and (ii) are carried out.

Step (i): one or two or more amino acid(s) selected from the group consisting of the following (1) to (14) is/are identified in the amino acid sequence of α-glucosidase as an enzyme to be mutated:

(1) an amino acid corresponding to the amino acid at the position 385 of the amino acid sequence of SEQ ID NO. 1

(2) an amino acid corresponding to the amino acid at the position 491 of the amino acid sequence of SEQ ID NO. 1

(3) an amino acid corresponding to the amino acid at the position 535 of the amino acid sequence of SEQ ID NO. 1

(4) an amino acid corresponding to the amino acid at the position 450 of the amino acid sequence of SEQ ID NO. 1

(5) an amino acid corresponding to the amino acid at the position 534 of the amino acid sequence of SEQ ID NO. 1

(6) an amino acid corresponding to the amino acid at the position 537 of the amino acid sequence of SEQ ID NO. 1

(7) an amino acid corresponding to the amino acid at the position 538 of the amino acid sequence of SEQ ID NO. 1

(8) an amino acid corresponding to the amino acid at the position 554 of the amino acid sequence of SEQ ID NO. 1

(9) an amino acid corresponding to the amino acid at the position 556 of the amino acid sequence of SEQ ID NO. 1

(10) an amino acid corresponding to the amino acid at the position 579 of the amino acid sequence of SEQ ID NO. 2

(11) an amino acid corresponding to the amino acid at the position 585 of the amino acid sequence of SEQ ID NO. 2

(12) an amino acid corresponding to the amino acid at the position 630 of the amino acid sequence of SEQ ID NO. 1

(13) an amino acid corresponding to the amino acid at the position 683 of the amino acid sequence of SEQ ID NO. 1

(14) an amino acid corresponding to the amino acid at the position 689 of the amino acid sequence of SEQ ID NO. 1

The amino acids to be substituted (1) to (14) are amino acids that have been identified as amino acids that are important for the characteristics of enzymes. Therefore, it can be highly expected that change in the characteristics of α-glucosidase is generated if these amino acids are substituted. The characteristics for which change is especially expected are a transglycosylation activity and a hydrolysis activity. The designing method of the present invention is especially useful as a means for designing an enzyme in which the balance of these two activities has been changed. For example, the designing method of the present invention can be utilized for the purpose of decreasing or eliminating a hydrolysis activity and increasing a transglycosylation activity.

The enzyme to be mutated in the designing method of the invention is α-glucosidase. The enzyme to be mutated is typically a wild type enzyme (an enzyme found in nature). However, this does not interfere use of an enzyme that has already undergone any mutation or modification as an enzyme to be mutated. Examples of the enzyme to be mutated are Human Maltase-glucoamylase, *Aspergillus niger* alpha-glucosidase, Human Neutral alpha-glucosidase C, Mouse Lysosomal alpha-glucosidase, Yeast GLU2A, *Aspergillus nidulans* Alpha-glucosidase AgdA, *Aspergillus nidulans* Alpha-glucosidase AgdB, *Mucor javanicus* alpha-glucosidase, *Aspergillus oryzae* alpha-glucosidase, *Mortierella alliacea* alpha-glucosidase, *Schizosaccharomyces pombe* alpha-glucosidase, *Debaryomyces occidentalis* alpha-glucosidase, *Hordeum vulgare* subsp. *vulgare* alpha-glucosidase, *Arabidopsis thaliana* alpha-glucosidase, *Spinacia oleracea* alpha-glucosidase, Beta vulgaris alpha-glucosidase and *Solanum tuberosum* alpha-glucosidase. As mentioned above, the amino acid sequences of these α-glucosidases are registered with public database (SEQ ID Nos. 1 to 17). In a preferable embodiment, an enzyme consisting of any of these amino acid sequences is an enzyme to be mutated.

In the present invention, the following step (ii) is conducted after the step (i).

Step (ii): an amino acid sequence in which the amino acid sequence(s) identified in the step (i) has/have been substituted by other amino acid is constructed based on the amino acid sequence of the enzyme to be mutated.

The kind(s) of the amino acid(s) after the substitution is/are not specifically limited. Therefore, either conservative amino acid substitution or non-conservative amino acid substitution is acceptable.

EXAMPLES

Preparation Method of Modified α Glucosidase

A further aspect of the present invention relates to a preparation method of a modified enzyme. In one embodiment of the preparation method of a modified enzyme of the present invention, the modified enzyme that the present inventors succeeded in obtaining is prepared in a genetic engineering technique. In the case of this embodiment, a nucleic acid coding for any one of the amino acid sequences of SEQ ID Nos.: 18 to 42 and 74 to 78, is prepared (step (I)). Herein, "a nucleic acid coding for a specific amino acid sequence" is a nucleic acid capable of obtaining a polypeptide having the amino acid sequence in the case of being expressed, and as a matter of course of a nucleic acid having a nucleotide sequence corresponding to the amino acid sequence, may be a nucleic acid added with an extra sequence (may be a sequence coding for an amino acid sequence or a sequence not coding for an amino acid sequence). Degeneracy of a codon is also considered. "A nucleic acid coding for any one of the amino acid sequences of SEQ ID Nos.: 18 to 42 and 74 to 78" can be prepared into a state of being isolated by using a standard genetic engineering technique, molecular biological technique, biochemical technique, and the like in reference to sequence information disclosed in the present specification or the appended sequence listing. Herein, all of the amino acid sequences of SEQ ID Nos.: 18 to 42 and 74 to 78 are obtained by mutation to the amino acid sequence of the *Aspergillus niger*-derived a glucosidase. Therefore, a nucleic acid (gene) coding for any one of the amino acid sequences of SEQ ID Nos.: 7 to 10 can be obtained also by adding necessary mutation to the gene coding for the *Aspergillus niger*-derived a glucosidase (SEQ ID NO: 73). A large number of methods for site-directed mutagenesis have been known in the present technical field (for example, see Molecular Cloning, Third Edition, Cold Spring Harbor Laboratory Press, New York), and among those methods, a suitable method can be selected to be used. A method of saturation mutagenesis can be adopted as the method of site-directed mutagenesis. The method of saturation mutagenesis is a "semi-rational, semi-random" technique of assuming a position which relates to a desired function based on a conformation of a protein and introducing amino acid saturation (J. Mol. Biol. 331, 585-592 (2003)). For example, use of a kit such as KOD-Plus-Mutagenesis Kit (TOYOBO CO., LTD.), Quick change (Stratagene Corporation) and Overlap extension PCR (Nucleic Acid Res. 16, 7351-7367 (1988)) makes it possible to introduce position specific amino acid saturation. A Taq polymerase and the like can be used for a DNA polymerase used in PCR. Provided that a DNA polymerase having high precision such as KOD-PLUS-(TOYOBO CO., LTD.) or Pfu turbo (Stratagene Corporation) is preferably used.

In another embodiment of the present invention, a modified enzyme is prepared based on an amino acid sequence that is designed by the designing method of the present invention. In the case of this embodiment, a nucleic acid coding for an amino acid sequence constructed by the designing method of the present invention is prepared in the step (I). For example, based on the amino acid sequence constructed by the designing method of the present invention, necessary mutation (that is, substitution of an amino acid in a specific position in a protein that is an expressed product) is added to a gene coding for a modified enzyme and a nucleic acid (gene) coding for the modified enzyme is obtained.

Following the step (I), the prepared nucleic acid is expressed (step (II)). For example, firstly, an expression vector inserted with the above described nucleic acid is prepared and a host cell is transformed using this constructed vector. The "expression vector" refers to a vector that can introduce a nucleic acid inserted therein into a desired cell (host cell) and is capable of being expressed in the cell. The expression vector generally contains a promoter sequence that is necessary for expression of an inserted nucleic acid, an enhancer sequence that promotes expression, and the like. An expression vector containing a selection marker can also be used. When such an expression vector is used, presence or absence (and its degree) of the expression vector can be confirmed by using a selection marker.

Then, a transformant is cultured under the condition of producing a modified enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 37° C.). A culture time can be set by considering growing characteristics of a transformant to be cultured and production characteristics of a mutant-type enzyme. A pH of a medium is set within the range wherein a transformant grows and an enzyme is produced. The pH of a medium is preferably set at about 6.0 to 9.0 (preferably at around pH 7.0).

Subsequently, the expressed product (modified enzyme) is recovered (step (III)). A culture liquid containing fungas bodies after culture may be used as an enzyme solution directly or after undergoing condensation, removal of impurities, or the like, but the expressed product is generally once recovered from the culture liquid or fungas bodies. When the expressed product is a secretion type protein, it can be recovered from the culture liquid, and in other cases, the expressed product can be recovered from cells. In the case of recovering from the culture liquid, for example, an undissolved substance is removed by filtration and centrifugation on a culture supernatant, and then, a purified product of a modified enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of recovering the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a modified enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and recovery of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

A. Acquirement of Modified α-Glucosidase 1

Using α-glucosidase (also referred to as transglucosidase. Hereinafter referred to as "TG".) as a model, a technique for directing a hydrolysis reaction and a dehydration condensation reaction in one direction (One direction technology) was studied by using protein engineering. TG is an enzyme used for the production of oligosaccharides and has an activity to hydrolyze glucosidic linkages and also has a transglycosylation activity, and thus forms oligosaccharides from maltose. The study proceeded in an effort to develop a TG that conducts transglycosylation more efficiently.

(1) Study of Annotated Amino Acids Using Computer Program

Computer study was carried out aiming at designing a novel enzyme having improved oligosaccharide-producing ability by the structure modification of TG at the molecular level. Using α-glucosidase derived from human small intestine (SEQ ID NO. 1), for which an X-ray crystal structure analysis was reported, annotated amino acids were determined by computer simulation based on the steric structure of TG and functional expectation based on evolutionary findings. Specifically, amino acids that are expected to be annotated amino acids in human α-glucosidase were calculated by using HotSpot Wizard program (Non-patent Document: Pavelka et al., Nucleic Acids Res. 37 W376-83. (2009)), and the three amino acids (the amino acid at the position 385: Y385, the amino acid at the position 491: V491, the amino acid at the position 535: N535) were selected. Since all of the amino acids are present on the regions that contact with a substrate, it can be expected that the amino acids are involved in the activity of the enzymes (FIG. 1, A). Subsequently, five kinds of α-glucosidase homologues were selected, and the sequences in the vicinity of the above-mentioned annotated amino acids were subjected to alignment comparison by using CLUSTALW. Since the homology of the sequences in the vicinity was high and highly conserved in all of Y385, V491 and N535, it was able to be expected that the regions are regions that are important for the functions of the enzyme. The amino acids corresponding to these annotated amino acids were identified by a *Aspergillus niger* TG (Asp. *Niger*) (FIG. 1, C). The amino acid corresponding to Y385 is W343, the amino acid corresponding to V491 is V452, and the amino acid corresponding to N535 is 5496. A primer for introducing mutation into these amino acids was designed, and mutation was introduced by an inverse PCR method using a random primer. Transformation into *Escherichia coli* was conducted, and a sequence analysis was conducted after miniprep to confirm introduction of mutation.

(2) Development of Screening System

The plasmid prepared was transformed into yeast INVsc1 strain and cultured. The culture supernatant was collected by centrifugation, and the secreted enzyme was used as modified TG. The broth was concentrated and desalted by ultrafiltration using a spin column. Consequently, an enzyme sample concentrated to approximately 10 to 50-fold was obtained.

Using maltose, which is an enzyme substrate, the hydrolysis activity was measured. The substrate was adjusted so as to have a final concentration of 1%, and the glucose formed by hydrolysis was reacted with an aminoantipyrine-phenol color developing liquid containing glucose oxidase (GO) and peroxidase (PO) to give a color and quantified by measuring OD500. A calibration curve (standard) was prepared by a glucose standard preparation, and the amount of the generated glucose was calculated from the absorbance.

In order to examine the oligosaccharide synthesis activities, the generated oligosaccharide was analyzed by HPLC. Using a 50% maltose aqueous solution as a substrate, the generated oligosaccharide was determined. The conditions for HPLC were as follows.

Figure 2:
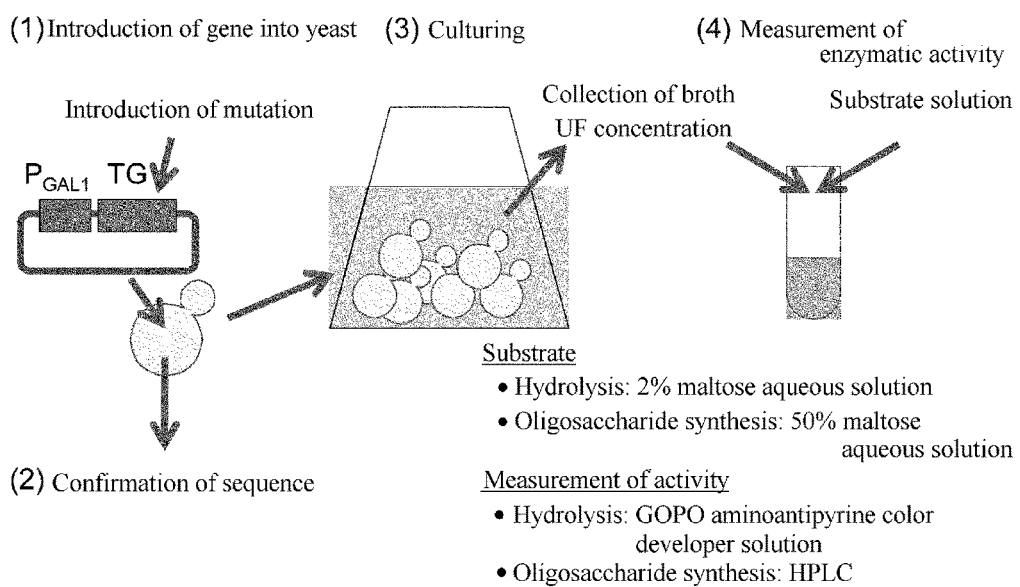
FIG. 2 shows a scheme of a modified TG (transglucosidase) screening system using yeast.

Column: TSKGEL Amido-80 (Tosoh Corporation)
Solvent: MeCN/H$_2$O=2/1
Detection: RI The area surface areas of HPLC were represented as a graph to thereby estimate the respective saccharide numbers of the generated oligosaccharides. The scheme of the above-mentioned screening method is shown in FIG. 2.

(3) Evaluation of Modified TG by Substitution of One Amino Acid

Random mutation was introduced by a PCR method into the position corresponding to the above-mentioned mutation introduction point (Y385, V491, N535), i.e., W343, V452 or 5496, in *Aspergillus niger* α-glucosidase (SEQ ID NO. 2) (substitution of one amino acid). After the introduction of mutation, sequencing was conducted to thereby identify the introduced point mutation. The obtained three modified TGs (W343M, V452G and S496V) were analyzed. In addition, a preliminary experiment was conducted to confirm that a protein derived from the plasmid was expressed in the culture supernatant, and that the enzyme had a hydrolysis activity.

Figure 3:
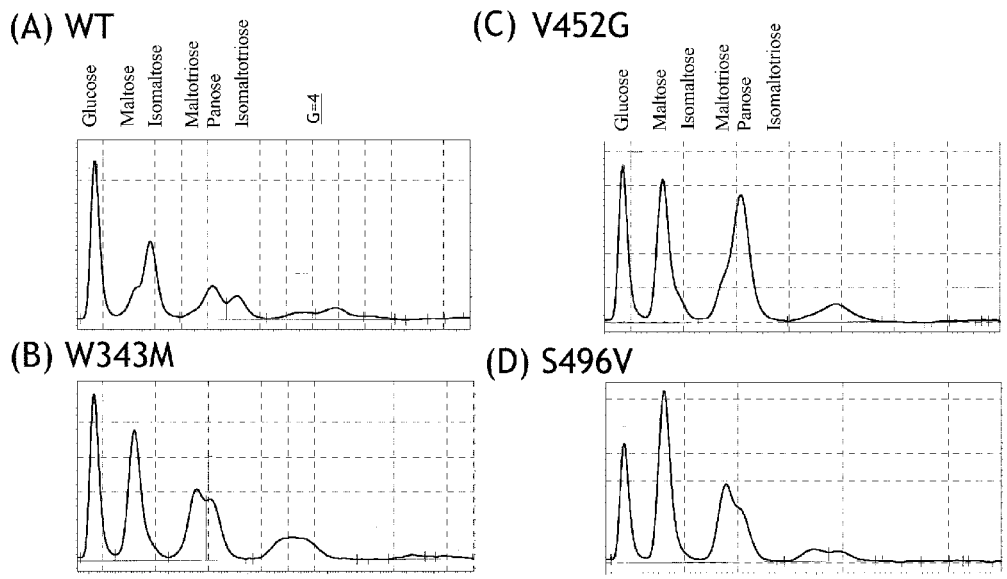
FIG. 3 compares oligosaccharide synthesis activities by HPLC. The oligosaccharide synthesis activities of a WT (wild type) (A) and modified TGs (W343M (B), V452G (C) and S496V (D)) were compared.

First, the oligosaccharide synthesis activities were measured by using a high-concentration maltose solution as a substrate. A typical HPLC pattern as the result thereof is shown in FIG. 3. In a sample in which a wild type (WT) TG was expressed, the peak of the substrate maltose decreased, and the peaks of glucose, isomaltose, panose and isomaltotriose were seen (FIG. 3, A). Furthermore, a bipartite peak was seen in the area of the tetrasaccharide (FIG. 3, A).

On the other hand, as compared to the WT, in the modified TGs, the peak of the substrate maltose decreased, and peaks of glucose, maltotriose and panose were seen (FIG. 3, B to D). Furthermore, gathered peaks were seen in the area of the tetrasaccharide (FIG. 3, B to D). In the oligosaccharides formed by the modified TGs, unlike the WT, the generation amount of the isomalto-based oligosaccharide significantly decreased.

Figure 4:
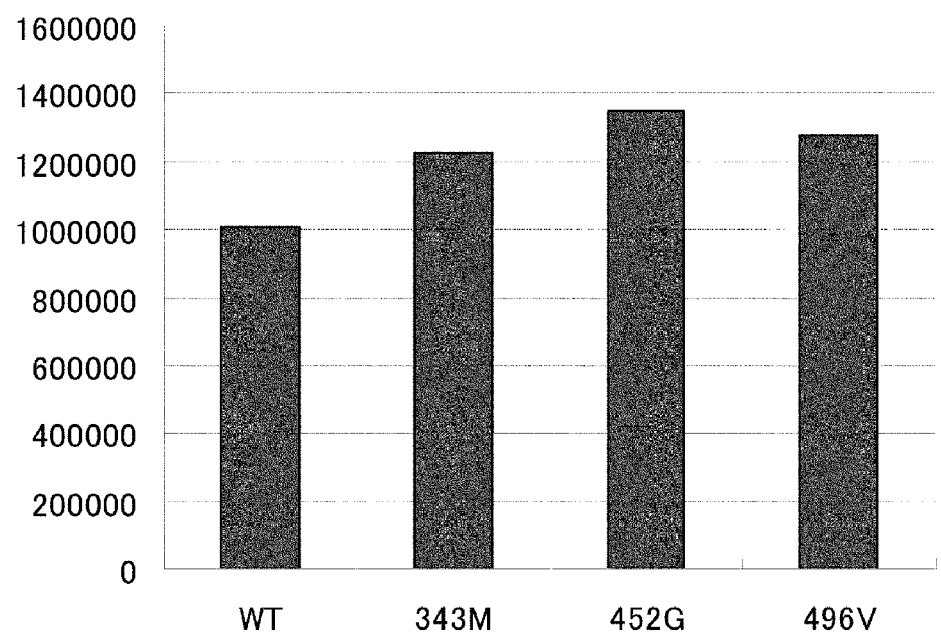
FIG. 4 compares synthesis amounts of the oligosaccharides of tri- or more saccharides.

Subsequently, the oligosaccharide synthesis activities of the modified TGs were compared to that of the WT by quantifying the area surface areas of HPLC. The graph in FIG. 4 shows the total of the area surface areas of tri- or more saccharides. Oligosaccharides of tri- or more saccharides were formed also in the WT, but the area surface areas of the formed oligosaccharides were larger than those of the WT in all of the modified TGs (increased by approximately 20%).

Figure 5:
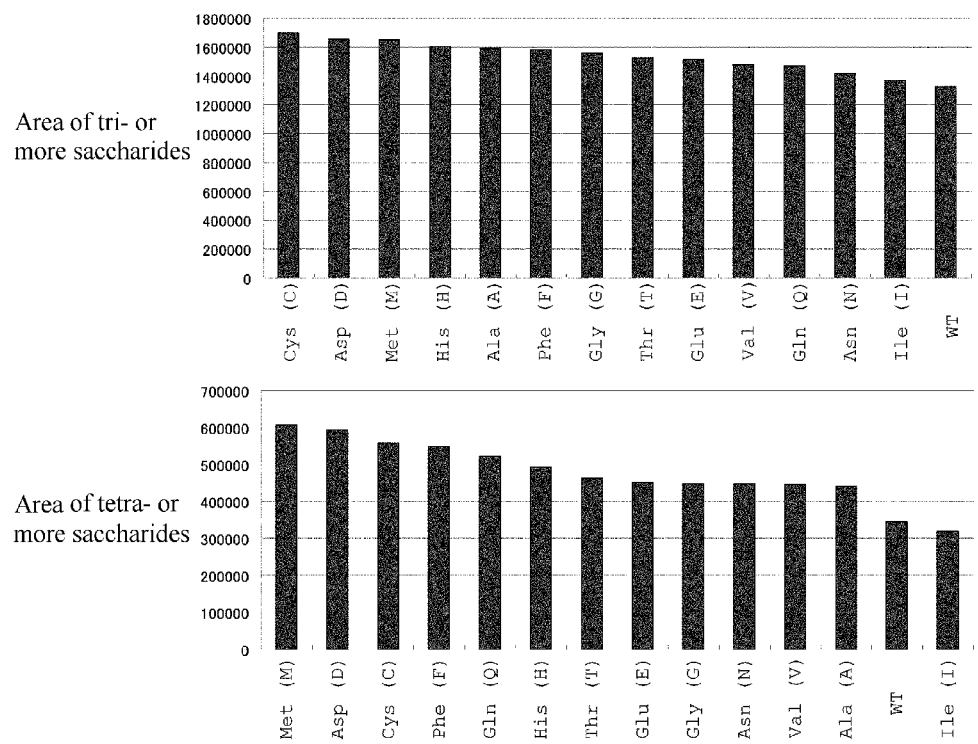
FIG. 5 compares the synthesis amounts of the oligosaccharides of tri- or more saccharides (upper) and compares the synthesis amounts of the oligosaccharides of tetra- or more saccharides (lower). The amounts of the generated oligosaccharides were compared among the modified TGs having different amino acids after substitution (indicated below the graph).

For the purpose of investigating the relationship between the kinds of the amino acids after substitution and the transglycosylation activity, various modified TGs were prepared with respect to the amino acid W343 corresponding to the mutation introduction point (385Y), and the oligosaccharide synthesizing abilities were compared. As a result, in the cases where the amino acid after the substitution was cysteine (W343C), aspartic acid (W343D), methionine (W343M), histidine (W343H), alanine (W343A), phenylalanine (W343F), glycine (W343G), threonine (W343T), glutamic acid (W343E), valine (W343V), glutamine (W343Q), asparagine (W343N) or isoleucine (W343I), the amount of the oligosaccharides of tri- or more saccharides formed by the modified TG increased more than that in the WT (FIG. 5, upper). Similar comparison was made for the oligosaccharides of tetra- or more saccharides, and consequently found that the modified TG had more excellent synthesis ability than that of the WT in the cases where the amino acid after the substitution was methionine (W343M), aspartic acid (W343D), cysteine (W343C), phenylalanine (W343F), glutamine (W343Q), histidine (W343H), threonine (W343T), glutamic acid (W343E), glycine (W343G), asparagine (W343N), valine (W343V) or alanine (W343A) (FIG. 5, lower). It can be evaluated that the modified TGs that were in the upper level for either of the synthesized amount of the oligosaccharides of tri- or more saccharides and the synthesized amount of the oligosaccharides of tetra- or more saccharides, i.e., W343C, W343D and W343M, are especially excellent in oligosaccharide synthesis ability. Furthermore, it is suggested that W343M, W343D, W343C, W343F, W343Q and W343H, in which the synthesized amount of the oligosaccharides of tetra- or more saccharides is significantly higher than that in the WT, are advantageous for the synthesis of oligosaccharides having longer chains.

Figure 6:
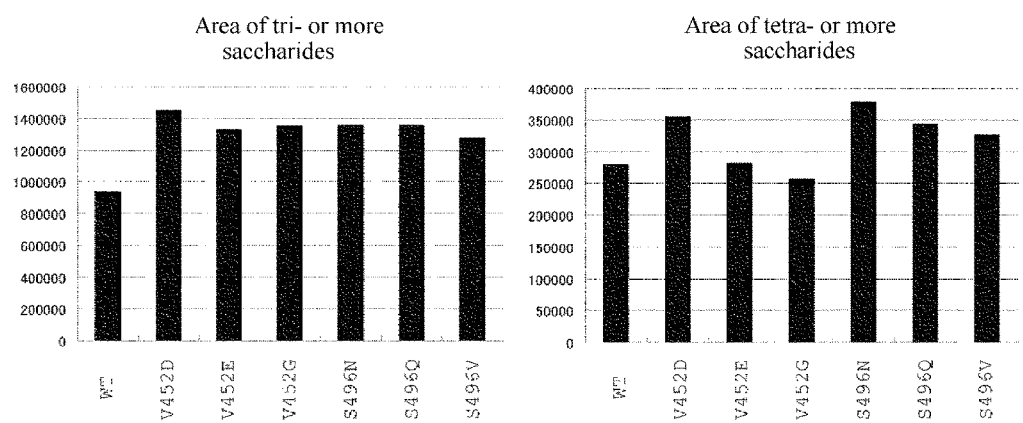
FIG. 6 compares the synthesis amounts of the oligosaccharides of tri- or more saccharides (left) and compares the synthesis amounts of the oligosaccharides of tetra- or more saccharides (right). The amounts of the generated oligosaccharides were compared among the modified TGs having different amino acids after substitution (indicated below the graph).

The transglycosylation activities of the modified TGs were compared to that of the WT by quantifying the area surface areas of HPLC. Various modified TGs were prepared with respect to the amino acid V452, and the oligosaccharide synthesis abilities were compared. As a result, in the cases where the amino acid after the substitution was glycine, aspartic acid or glutamic acid, the amount of the oligosaccharides of tri- or more saccharides increased more than that in the WT (FIG. 6). Furthermore, the oligosaccharides of tetra- or more saccharides were similarly compared, and consequently found that the modified TG in which the amino acid after the substitution was aspartic acid (V452D) was superior to the WT in synthesis ability (FIG. 6). Similarly, various modified TGs were prepared with respect to the amino acid S496, and the oligosaccharide synthesis abilities were compared. As a result, in the cases where the amino acid after the substitution was valine, asparagine or glutamine, the modified TGs were superior to the WT in synthesis ability in both cases of the oligosaccharides of tri- or more saccharides and the oligosaccharides of tetra- or more saccharides (FIG. 6).

Figure 7:
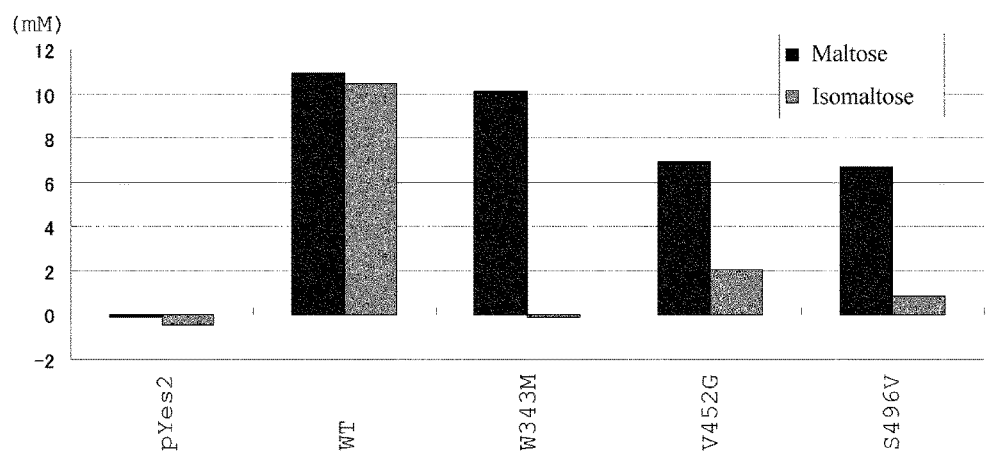
FIG. 7 compares substrate specificities relating to hydrolysis activities.

As mentioned above, it was found that the generation amount of the isomalto-based oligosaccharide was greatly decreased in the modified TGs. Therefore, it was thought that the reactivity against glucosidic linkages should change, and thus the hydrolysis activities against various glucosidic linkages were investigated. As enzyme substrates, aqueous solutions of maltose ($\alpha$-1,4) and isomaltose ($\alpha$-1,6), which are disaccharides, were prepared. The WT showed substrate affinity for both $\alpha$-1,4 glucosidic linkages and $\alpha$-1,6 glucosidic linkages (FIG. 7). In contrast, in the modified TGs, the hydrolysis activity against $\alpha$-1,4 glucosidic linkages was approximately the same as that of the wild type, whereas the hydrolysis activity against $\alpha$-1,6 glucosidic linkages decreased to one-fifth or less (FIG. 7).

(4) Evaluation of Modified TG by Substitution of Two Amino Acids

Figure 8:
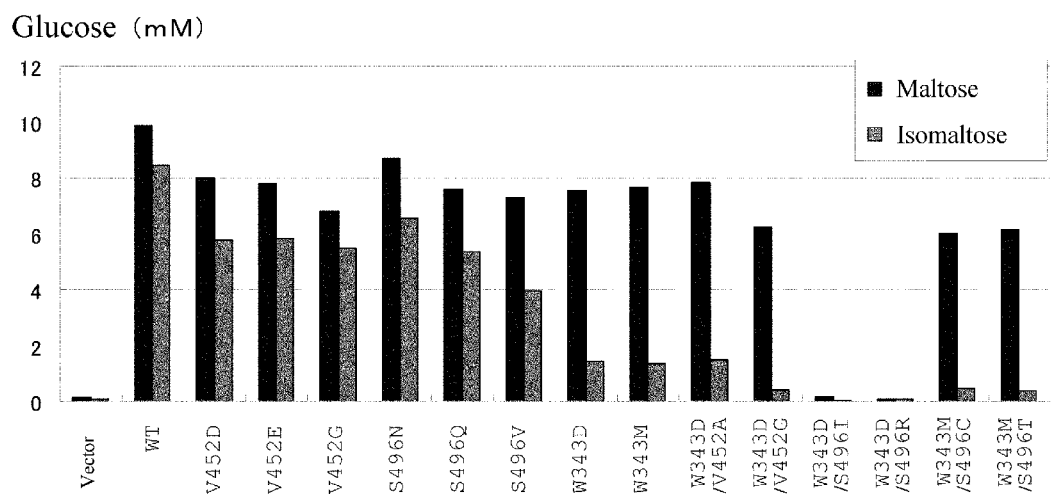
FIG. 8 shows the hydrolysis activities of the modified TGs by substitution of two amino acids.

Modified TGs in which mutation had been introduced into two amino acids were prepared by introducing further mutation (either of the two amino acids present on the surface of the tunnel structure (V452 and S496)) in the modified TG in which the tryptophan at the position 343 had been substituted. The hydrolysis activities of the obtained modified TGs were measured. As shown in FIG. 8, the activity was not able to be detected at all for W343D/S496I (the W at the position 343 was substituted by D and the S at the position 496 was substituted by I) and W343D/S496R (the W at the position 343 was substituted by D and the S at the position 496 was substituted by R). On the other hand, the hydrolysis activity of isomaltose greatly decreased (approximately 1/20) in the three kinds of modified TGs: W343D/V452G (the W at the position 343 was substituted by D and the V at the position 452 was substituted by G), W343M/S496C (the W at the position 343 was substituted by M and the S at the position 496 was substituted by C) and W343M/S496T (the W at the position 343 was substituted by M and the S at the position 496 was substituted by T).

Figure 9:
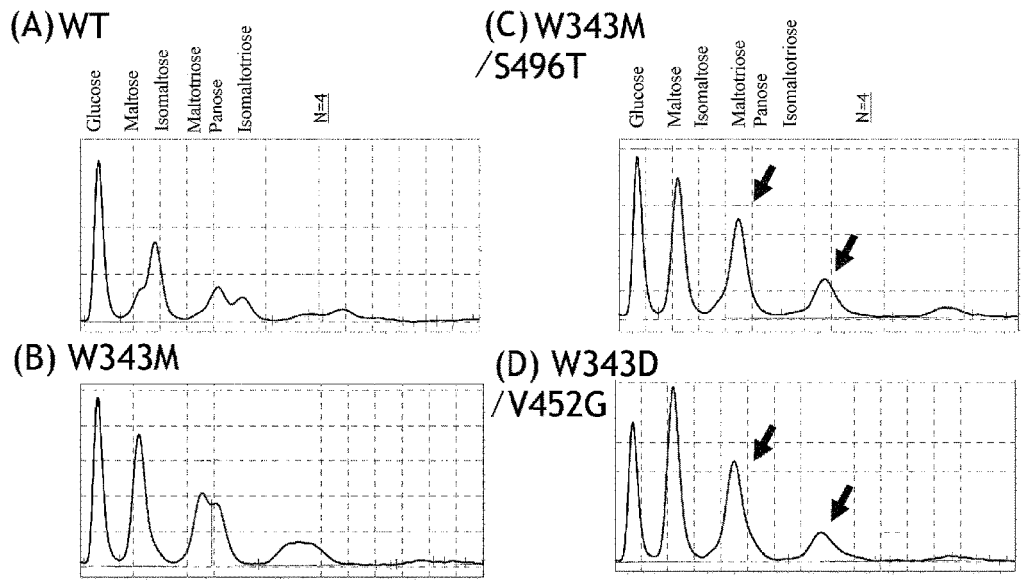
FIG. 9 shows the oligosaccharide synthesis activities of the modified TGs by substitution of two amino acids. The oligosaccharide synthesis activities of the WT (wild type) (A) and modified TGs (W343M (B), W343M/S496T (C) and W343D/V452G (D)) were compared.

Subsequently, the oligosaccharide synthesis activities were measured. In the samples in which the wild type TG was expressed, the peaks of panose and isomaltotriose were seen with respect to trisaccharides (FIG. 9, A). On the other hand, in W343M, the peaks of maltotriose and panose were seen with respect to the trisaccharides as in the previous results (FIG. 9, B). In W343M/S496T and W343D/V452G, which are TGs in which two amino acids have been substituted, only one peak was seen with respect to a trisaccharide, and the peak was anticipated to be of maltotriose (FIG. 9, the arrows in C and D). Furthermore, the peak seen in HPLC was only one also in the region of four saccharides, and this resulted in an analysis pattern greatly different from the analysis pattern of the wild type (FIGS. 9, C and D). This peak for the tetrasaccharide is a peak that is seen in only TGs in which two amino acids have been substituted, and shows that the generated oligosaccharide is different from the wild type.

Figure 10:
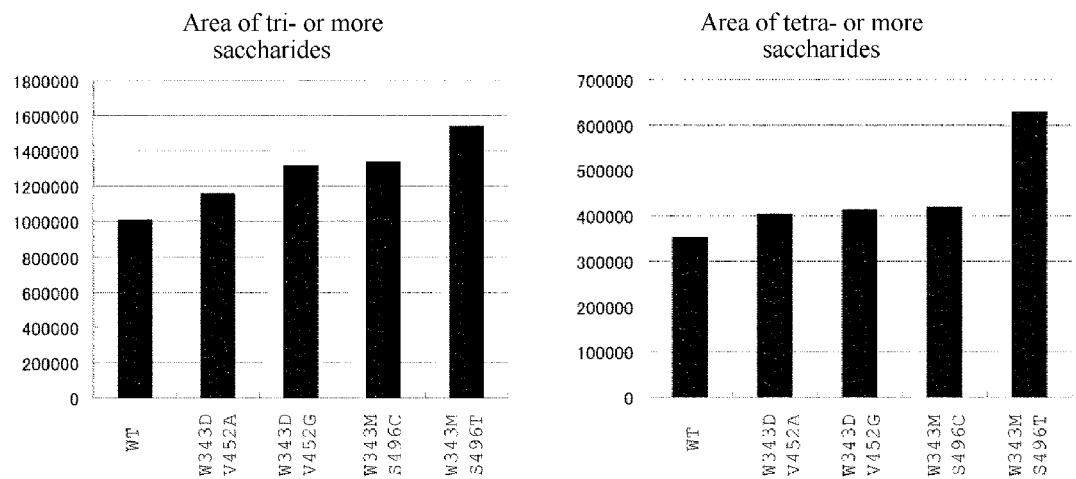
FIG. 10 compares the synthesis amounts of the oligosaccharides of tri- or more saccharides (left) and the comparison of the synthesis amounts of the oligosaccharides of tetra- or more saccharides (right). The amounts of the generated oligosaccharides were compared among the modified TGs having different amino acids after substitution (indicated below the graph).

The transglycosylation activities of the modified TGs were compared to that of the WT by quantifying the area surface areas of HPLC. In all of the TGs in which two amino acids had been substituted, the area surface areas of the generated oligosaccharides were larger than that in the WT, and the synthesis amount of the oligosaccharide of tri- or more saccharides increased by 20 to 50% (FIG. 10). Furthermore, in W343M/S496T, the synthesis amount of the oligosaccharides of tetra- or more saccharides was significantly larger than that of the WT, and increased by about 70% (FIG. 10).

Figure 11:
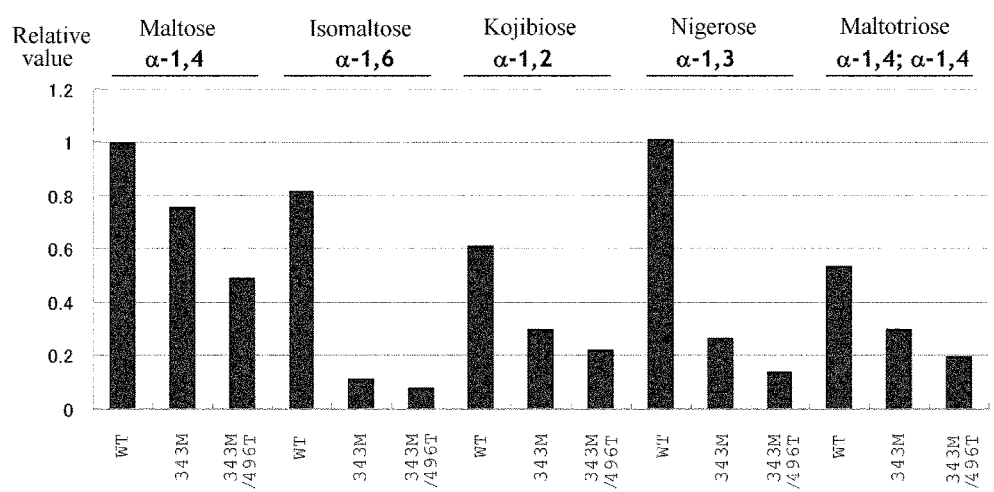
FIG. 11 shows the substrate specificities of the modified TGs by substitution of two amino acids.

On the other hand, the hydrolysis activities against glucosidic linkages of the modified TGs were studied. In W343M/S496T, the hydrolysis activities against maltose and maltotriose were each 50%, and the hydrolysis activity against isomaltose was 10% or less (FIG. 11). The hydrolysis activity against kojibiose was approximately 40%, and the hydrolysis activity against nigerose decreased to approximately 10% (FIG. 11). It is suggested that the hydrolysis activity decreased in the modified TGs in which two amino acids had been substituted, and that the hydrolysis activities against specifically $\alpha$-1,6 glucosidic linkages and $\alpha$-1,3 glucosidic linkages greatly decreased.

(5) Analysis of Oligosaccharides Formed by Modified TGs

Figure 12:
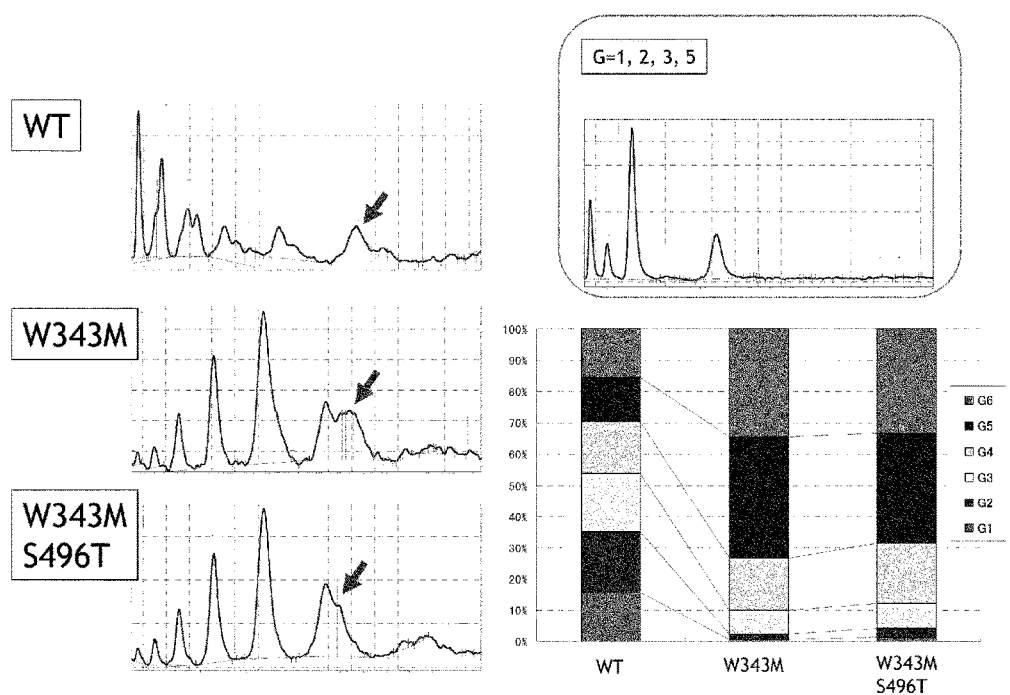
FIG. 12 compares the oligosaccharides that are formed when maltopentaose is used as a start substrate.

According to the previous reports, when the number of saccharides in an initial substrate used for the synthesis of an oligosaccharide is increased, the ratio of the $\alpha$-1,6 glucosidic linkages in the oligosaccharide formed by a TG increases. Therefore, oligosaccharide synthesis reactions were conducted by using maltopentaose, which is a pentasaccharide, as a substrate, and the formed oligosaccharides were compared between the wild type and modified TGs. First, as a standard, glucose (G=1), maltose (G=2), maltotriose (G=3) and maltopentaose (G=5) were measured, and the positions of the peaks were confirmed (FIG. 12). In the wild type TG, decomposition and production widely occurred from glucose to the areas of hepta- or more saccharides (FIG. 12). However, the ratio of penta- or less saccharides was large, and thus it was suggested that hydrolysis proceeded more than oligosaccharide synthesis did. On the other hand, in the modified TGs (W343M and W343M/S496T), saccharides that had been hydrolyzed to monosaccharide and disaccharide were decreased, and hexa- or more saccharides had been formed more (FIG. 12). In the areas indicated by the arrows in FIG. 12, the difference is specifically great between the WT and modified TGs.

Figure 13:
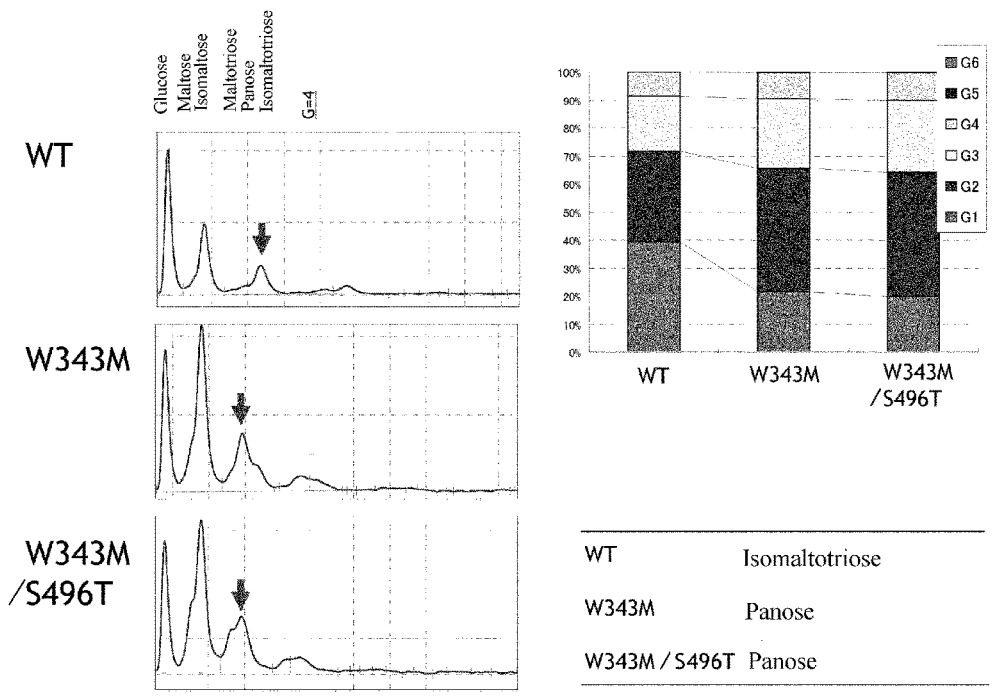
FIG. 13 compares the oligosaccharides that are formed when a mixture of maltose and isomaltose is used as the start substrate.

Next, oligosaccharide synthesis was conducted in a mixed solution of maltose and isomaltose as a start substrate. Although the ratio of the generated oligosaccharides was not greatly changed, a difference appeared in the kinds of the generated trisaccharides. In the wild type, isomaltotriose, which has two $\alpha$-1,6 glucosidic linkages, was formed much (FIG. 13). On the other hand, in the modified TGs (W343M and W343M/S496T), panose, which has an $\alpha$-1,4 glucosidic linkage and an $\alpha$-1,6 glucosidic linkage was formed most (FIG. 13, arrow). Furthermore, the isomaltose as a start substrate was decomposed little in the cases of modified TGs.

It was suggested by the above-mentioned results that the modified TGs specifically have a transglycosylation activity to form α-1,4 glucosidic linkages, in contrast to that the wild type TG mainly have a transglycosylation activity to form α-1,6 glucosidic linkages.

The amino acid sequences of the various modified TGs prepared in the investigation at this time are shown below.
SEQ ID NO. 18: W343C
SEQ ID NO. 19: W343D
SEQ ID NO. 20: W343M
SEQ ID NO. 21: W343H
SEQ ID NO. 22: W343A
SEQ ID NO. 23: W343F
SEQ ID NO. 24: W343G
SEQ ID NO. 25: W343T
SEQ ID NO. 26: W343E
SEQ ID NO. 27: W343V
SEQ ID NO. 28: W343Q
SEQ ID NO. 29: W343N
SEQ ID NO. 30: W343I
SEQ ID NO. 31: V452G
SEQ ID NO. 32: V452D
SEQ ID NO. 33: V452E
SEQ ID NO. 34: S496V
SEQ ID NO. 35: S496N
SEQ ID NO. 36: S496Q
SEQ ID NO. 37: W343D/V452A
SEQ ID NO. 38: W343D/V452G
SEQ ID NO. 39: W343D/S496I
SEQ ID NO. 40: W343D/S496R
SEQ ID NO. 41: W343M/S496C
SEQ ID NO. 42: W343M/S496T B. Acquirement of Modified α-Glucosidase 2
(1) Study of Annotated Amino Acids Using Computer Software MOE For the purpose of identifying annotated amino acids by a novel means, the annotated amino acids of TGs were studied by using computer software MOE (Chemical Computing Group). At this time, the annotated amino acids were selected by comparing the sequences of *Aspergillus niger* and *Aspergillus nidulans*.

The amino acid sequences of the *Aspergillus niger* TG and *Aspergillus nidulans* TG (α-glucosidase B) were obtained from known data bank and read into MOE, and protein modeling was builted on a computer. Based on the respective amino acid sequences, sequences having high homology were searched on the database of MOE. As a result, the same sequence was hit in both cases, and human TG was selected. Subsequently, using the steric structures as templates, the respective proteins are modeled. The force field was "AMBER99", five intermediate models were prepared and one model structure was finally prepared.

Subsequently, a docking simulation analysis was performed to thereby expect the substrate pockets. The force field was set to "MMFF99x", and the pockets were searched by Site Finder of MOE. As a result, a plurality of candidate regions having possibility of becoming pockets in view of the steric structures were predicted. Therefore, amino acids that become the active center of TG reported in previous articles and the like were searched, and the position of each amino acid on a model was determined. Furthermore, the region containing a plurality of amino acids, which is an active center, was determined as a substrate pocket calculated by the simulation.

Figure 14:
FIG. 14 are computer-simulated steric structure models of α-glucosidase. Left: *Aspergillus niger* TG, right: *Aspergillus nidulans* TG
Figure 14:
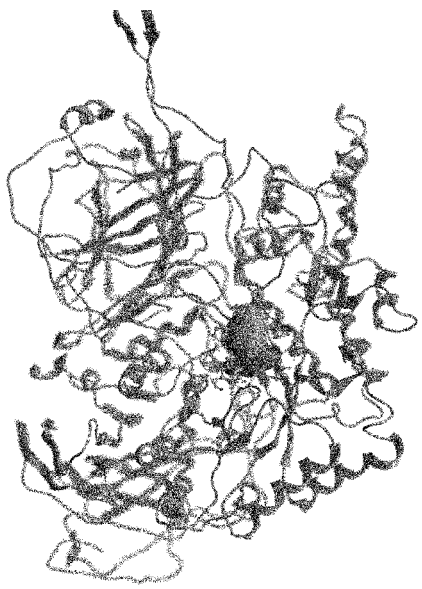

The steric structures that were successfully modeled are shown in FIG. 14. When the structures of *Aspergillus niger* TG and *Aspergillus nidulans* TG were compared, a significant difference was observed between the respective steric structures even though they were modeled based on the same steric structure of human TG When the simulated substrate pockets were compared, the substrate pocket of *Aspergillus nidulans* was smaller than that of *Aspergillus niger*. The substrate pocket was composed of 30 amino acids in *Aspergillus niger*, whereas the substrate pocket was composed of 22 amino acids in *Aspergillus nidulans* (FIG. 14).

Figure 15:
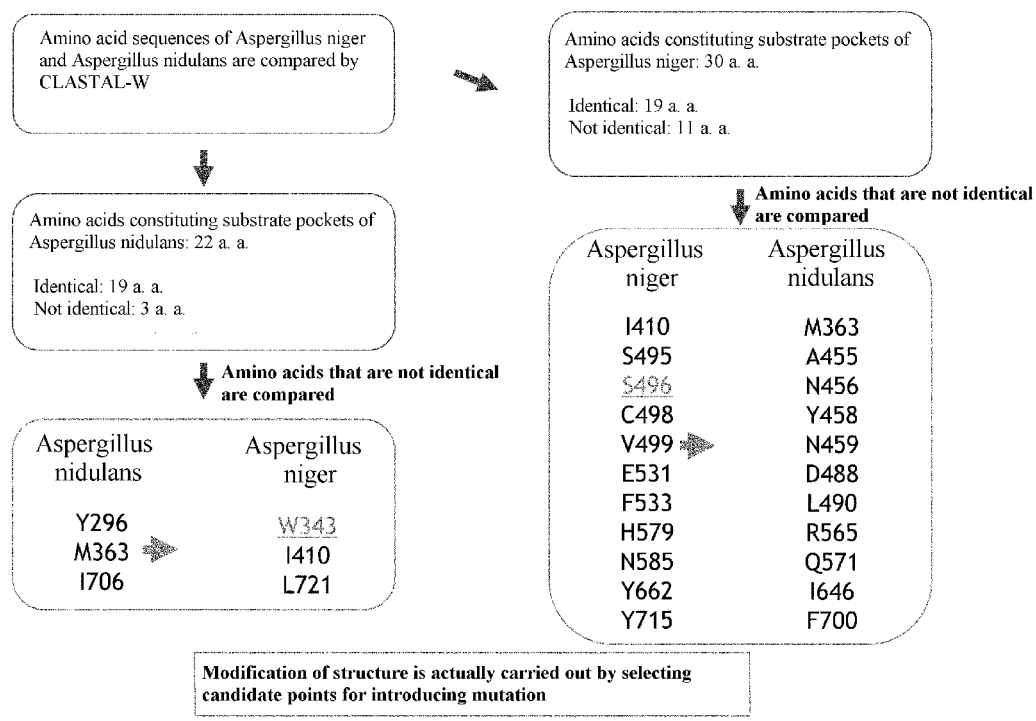
FIG. 15 shows the scheme for considering annotated amino acids based on computer simulation.

Subsequently, the amino acid sequence of *Aspergillus niger* TG and the amino acid sequence of *Aspergillus nidulans* TG were aligned by CLASTAL-W. When the whole amino acid sequences were compared, the homology of these proteins was low, and the ratio at which the amino acids were identical was calculated as 35%. However, in the case where only the sequences of the substrate pockets were compared, the sequences had high homology, and 19 of 30 amino acids were identical in the substrate pocket of *Aspergillus niger* and 19 of 22 amino acids were identical in *Aspergillus nidulans* (FIG. 15). This result suggests that the amino acids relating to the activity are highly conserved as compared to the entire sequence. On the other hand, we predicted the amino acids that were not identical have low evolutionary conservation property, and thus it was expected that mutation can be introduced. Therefore, these amino acids were used as candidate annotated amino acids for introducing mutation (FIG. 15). Furthermore, since W343 and S496 in which mutation had been already introduced were selected, it was thought that there is a correlation with simulation by Hot spots wizard using human TG that has been used in the past.

Primers were designed so as to actually introduce mutation into *Aspergillus niger* TG, and mutation was introduced by an inverse PCR method using a random primer. Transformation into *Escherichia coli* was conducted, and a sequence analysis was conducted after miniprep to confirm introduction of mutation. Furthermore, transformation into yeast was conducted, and a recombinant modified TG was expressed and analyzed. The analysis results for two amino acids: S495 and C498 among the actual preparation are shown.

(2) Evaluation of S495-Modified TG

In *Aspergillus niger* TG, random mutation was introduced into the 495th serine (S495) by a PCR method (substitution of one amino acid). Sequence was conducted to identify the introduced point mutation, and the modified TG was analyzed.

These modified TGs were compared by measuring the oligosaccharide synthesis activities by using HPLC. A 50% maltose aqueous solution, an isomaltose aqueous solution, and an aqueous solution of maltopentaose, which is an oligosaccharide of a pentasaccharide, were used as substrates. The aqueous solutions were incubated at a reaction temperature of 50° C. for a predetermined time (48 hours for maltose and maltopentaose, and 96 hours for isomaltose).

Figure 16:
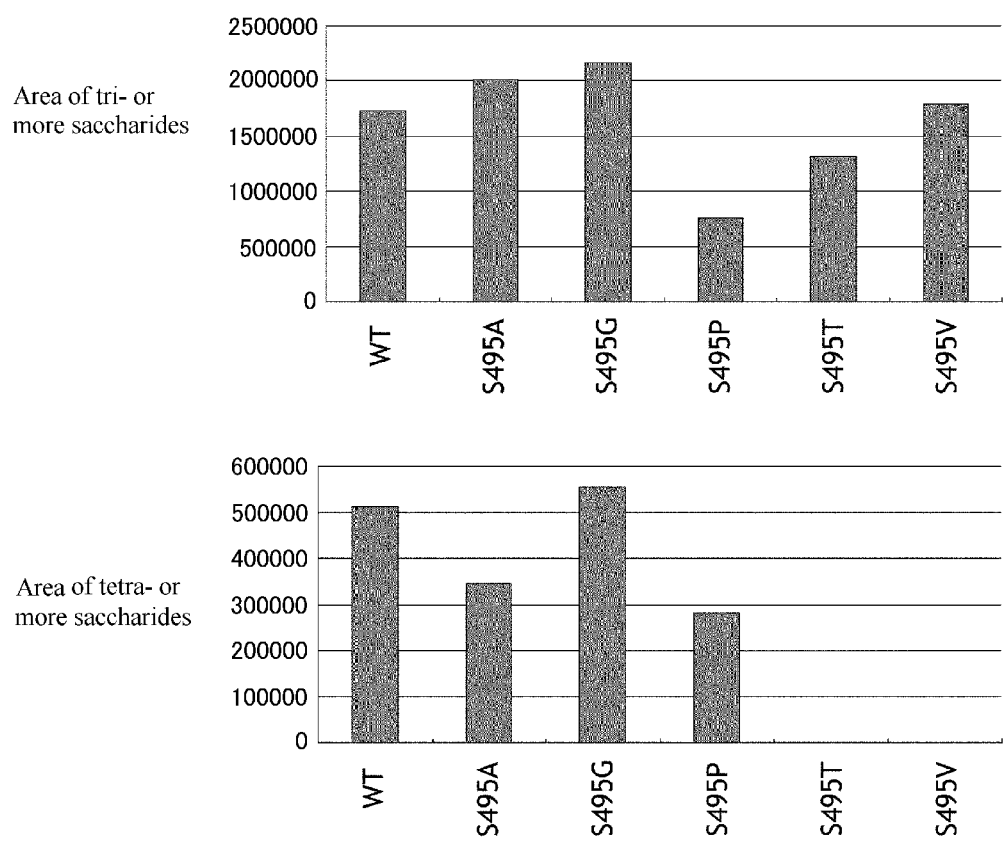
FIG. 16 compares the oligosaccharide synthesis activities of the modified TGs (S495X). Maltose was used as the substrate. The synthesis amount of the oligosaccharides of tri- or more saccharides (upper) and the synthesis amount of the oligosaccharides of tetra- or more saccharides (lower) were compared.

The oligosaccharide synthesis activities of the modified TGs were compared by quantifying the area surface areas of HPLC. In the case where the substrate was maltose, the total of the area surface areas of the tri- or more saccharides and tetra- or more saccharides was larger than that of the WT in S495G but was conversely decreased in S495P and S495T (FIG. 16).

Figure 17:
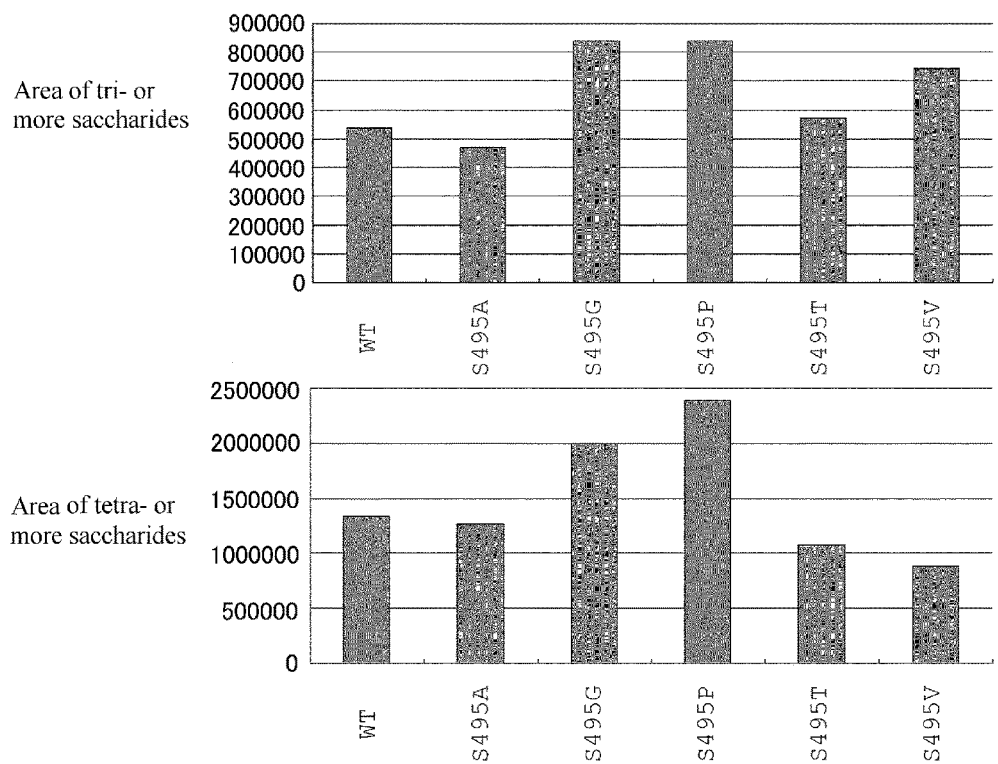
FIG. 17 compares the oligosaccharide synthesis activities of the modified TGs (S495X). Isomaltose was used as the substrate. The synthesis amount of the oligosaccharides of tri- or more saccharides (upper) and the synthesis amount of the oligosaccharides of tetra- or more saccharides (lower) were compared.

In the case where the substrate was isomaltose, the total of the area surface areas of the tri- or more saccharides was larger than that of the WT in S495G, S495P and S495V (FIG. 17). Furthermore, the total of the area surface areas of the tetra- or more saccharides was larger than that of the WT in S495G and S495P, and thus it was suggested that the oligosaccharide synthesis ability was improved (FIG. 17). When the peaks in the HPLC are observed, isomaltotriose increased in the trisaccharides, and thus it can be presumed that the modified TGs have a transglycosylation activity to form α-1,6 glucosidic linkages as in the WT. It was found from the above-mentioned results that the three kinds: S495G, S495P and S495V increase oligosaccharides with α-1,6 glucosidic linkages by 50% or more.

Figure 18:
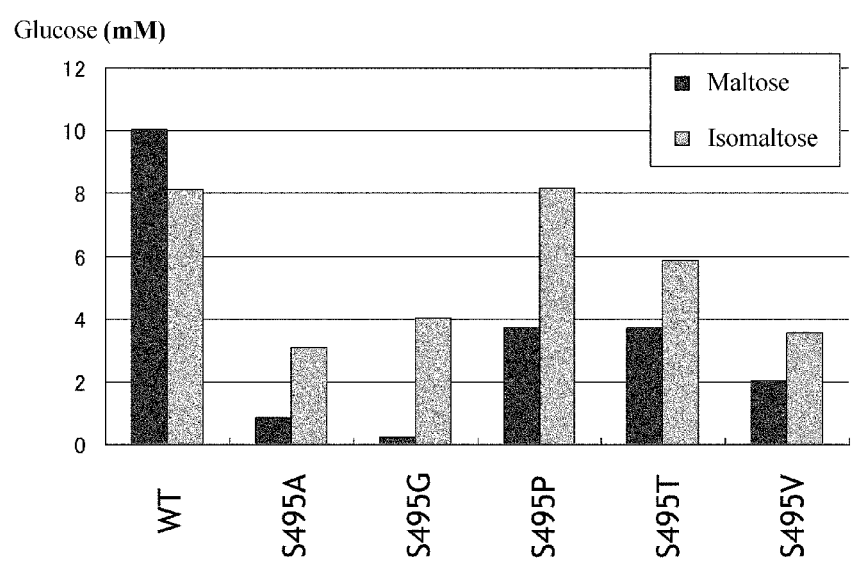
FIG. 18 shows the hydrolysis activities of the modified TGs (S495X).

Therefore, it was thought that the reactivity against glucosidic linkages should differ in the modified TGs, and thus the hydrolysis activities against various glucosidic linkages were studied (FIG. 18). Using a maltose aqueous solution and an isomaltose aqueous solution as substrates, the amounts of the generated glucose were quantified to thereby evaluate the hydrolysis activities. It is shown that the WT has substrate affinity for both α-1,4 glucosidic linkages and α-1,6 glucosidic linkages against glucosidic linkages. On the other hand, the hydrolysis activity of maltose decreased more than in the WT whereas the hydrolysis activity of isomaltose relatively increased in S495A, S495G, S495P, S495T and S495V. As mentioned above, the modified TG in which S495 had been substituted had increased transglycosylation activity to form α-1,6 glucosidic linkages.

Figure 19:
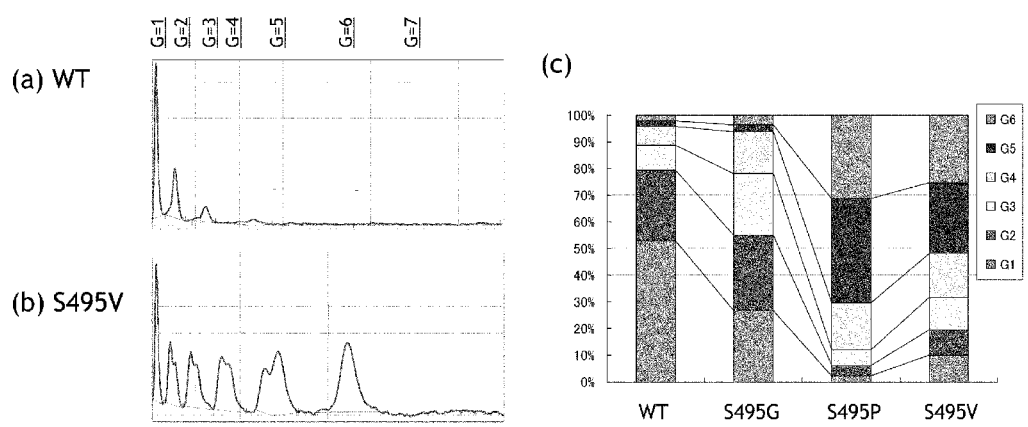
FIG. 19 compares the oligosaccharide synthesis activities of the modified TGs. Maltopentaose was used as the substrate. (a) A HPLC chart of the WT (wild type). (b) The HPLC chart of the modified TG (S495V). (c) A ratio of the generated oligosaccharides.

Finally, oligosaccharide synthesis reactions were conducted by using maltopentaose, which is a pentasaccharide, as an initial substrate, and the generated oligosaccharides were compared between the wild type TG and modified TGs (FIG. 19). In the wild type TG, decomposition and generation occurred widely in the areas from glucose to hexa- or more saccharides. When a graph was drawn, the amount of monosaccharide was the largest, and hydrolysis proceeded during the reaction. Increase in the oligosaccharides was observed in all of the modified TGs. Specifically, in the modified TGs of S495P-type and S495V-type, the hydrolyzed saccharides were small, whereas hexa- or more saccharides were formed much (FIG. 19*c*).

As mentioned above, three kind of modified TGs having transglycosylation activity to form α-1,6 glucosidic linkages were successfully obtained. Furthermore, it was found that the oligosaccharides formed by the modified TGs are polymerized by a bonding manner including α1,6 glucosidic linkages to thereby increase the formation amounts of the oligosaccharides.

(3) Evaluation of C498-Modified TG

In *Aspergillus niger* TG, random mutation was introduced into the 498th cysteine (C498) by a PCR method (substitution of one amino acid). Sequence was conducted to identify the introduced point mutation, and the modified TG was analyzed.

These modified TGs were compared by measuring the oligosaccharide synthesis activities by using HPLC. Using a 60% maltose aqueous solution as a substrate, incubation was conducted at a reaction temperature of 50° C. for 48 hours.

Figure 20:
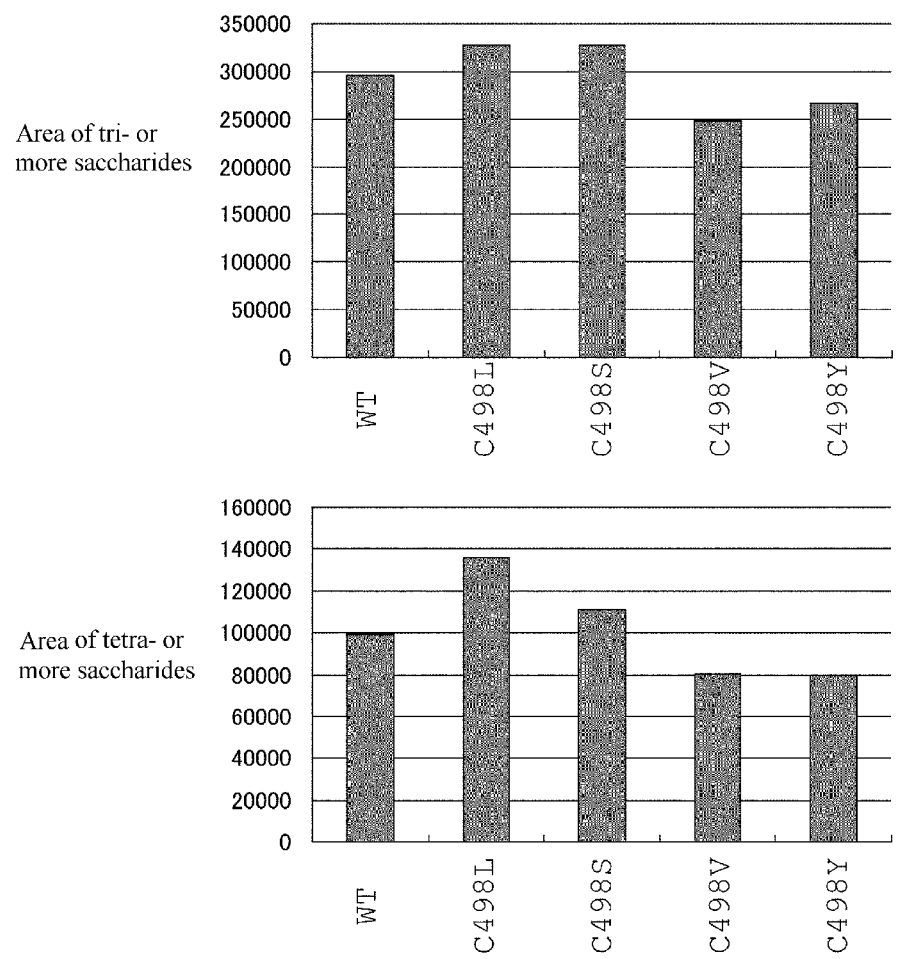
FIG. 20 compares the oligosaccharide synthesis activities of the modified TGs (C498X). Maltose was used as substrate.

The oligosaccharide synthesis activities of the modified TGs were compared by quantifying the area surface areas of HPLC (FIG. 20). When the totals of the area surface areas of tri- or more saccharides were compared, the area surface areas were larger in C498L and C498S than that of the WT. Furthermore, increase in the total of the area surface areas of tetra- or more saccharides was similarly observed in C498L and C498S as compared to the WT.

Figure 21:
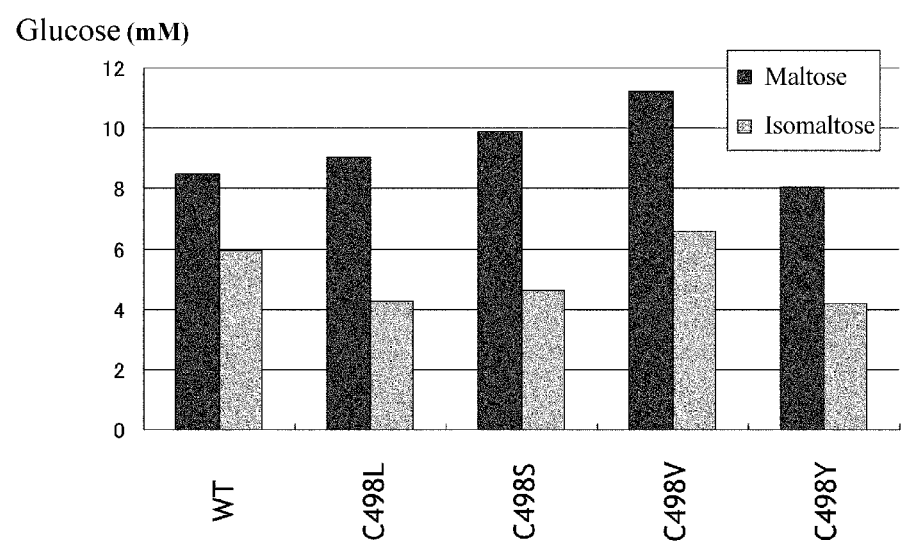
FIG. 21 shows the hydrolysis activities of the modified TGs (C498X).

It was thought based on the results that the reactivity against glucosidic linkages could be changed in the modified TGs, and thus the hydrolysis activities were measured. Using a maltose aqueous solution and an isomaltose aqueous solution as substrates, the amounts of the generated glucose were quantified. As shown in FIG. 21, it was found that the hydrolysis activity of maltose was higher in C498L and C498S as compared to the WT. Furthermore, it is also understood that a significant change was observed in the ratio of the maltose hydrolysis activity and isomaltose hydrolysis activity and thus the specificity against α-1,4 glucosidic linkages was improved in these modified TGs.

As mentioned above, it was shown that the synthesis of oligosaccharides is increased in C498 by introducing mutation. Furthermore, two kinds of modified TGs (these show transglycosylation activity to form α-1,4 glucosidic linkages) in which the ability of synthesizing oligosaccharides had been enhanced were successfully obtained.

The amino acid sequences of the various modified TGs prepared in the investigation at this time are shown below.
SEQ ID NO. 74: S495G
SEQ ID NO. 75: S495P
SEQ ID NO. 76: S495V
SEQ ID NO. 77: C498L
SEQ ID NO. 78: C498S C. Application of Modified TGs to Field of Foods In order to evaluate the possibility of application of modified TGs to the field of health foods, an experiment using an artificial digestion model system was conducted. In this model system, how TGs act on oligosaccharides that are formed by decomposing porridge by amylase derived from saliva is evaluated. Amylase and TG were reacted with commercially available porridge at an acidic region being close to the pH of gastric juice (30 minutes to 2 hours, warmed at 37° C.), sampling was then conducted, and the enzymatic reaction was stopped. Furthermore, the generated oligosaccharides were analyzed by HPLC. The amount of the added amylase was 1.45 U/ml, which corresponds to the amount of the amylase in saliva. Furthermore, in light of the result of the preliminary research, the amount of TG was set to 20 μg/mL. The specific of the experimental protocol is shown below.

(Protocol)
(i) Porridge (Ajinomoto Co., Inc.) is crushed in a blender, and 1M NaOAc buffer (pH 5.0) is added in an amount of ⅟20.
(ii) 340 μl of an enzyme solution is prepared (protein concentration: 20 μg/mL).
(iii) 0.65 g of the porridge of (i), 1.45 U of amylase and 340 μl of the enzyme solution are put into a glass test tube.
(iv) Incubation is conducted in a hot water bath at 37° C., and 200 μl is sampled into a micro test tube every 30 minutes.
(v) Boiling is conducted for 5 minutes to thereby stop the enzymatic reaction.
(vi) Centrifugation is conducted at 12,000 rpm, and the supernatant is transferred to a new tube.
(vii) 120 μl is sorted out and diluted to three-fold with MilliQ (registered trademark) water.
(viii) An HPLC analysis is conducted under the following conditions.

Figure 22:
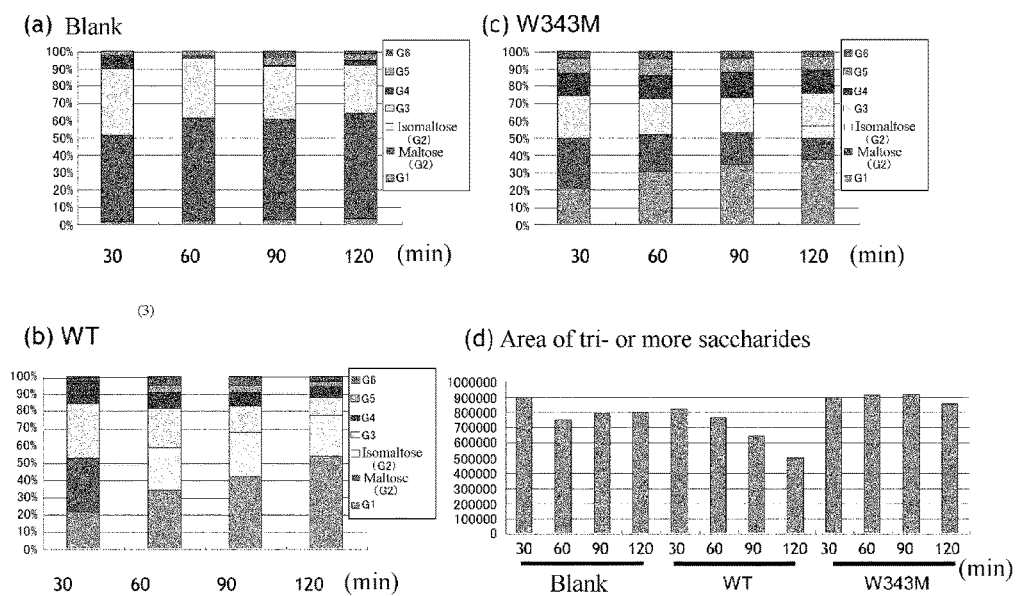
FIG. 22 compares the oligosaccharide-synthesis ability. (a) The case where TG is not added, (b) the case where TG of the WT (wild type) is added, (c) the case where the modified TG (W343M) was added, and (d) comparison of an area surface areas of the tri- or more saccharides.
Figure 23:
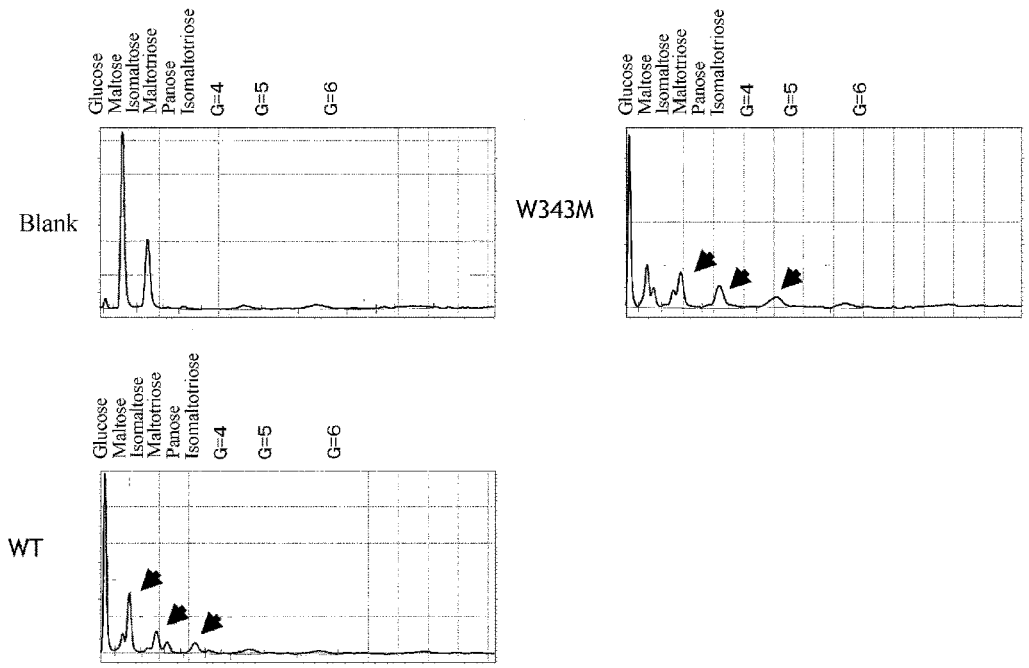
FIG. 23 is the HPLC chart of the oligosaccharides formed from porridge (at 90 minutes after the initiation of the reaction).

(Column Conditions)
Column; TSKGEL Amido-80
Solvent; MeCN/H2O=2/1
Detector; RI
Flow rate; 1 ml/min The result of the analysis of the obtained oligosaccharides by HPLC is shown in FIG. 22. By adding amylase, 40 to 50% of the whole saccharides becomes maltose (FIG. 22 (*a*)). Furthermore, maltotriose, which is a trisaccharide, and maltotetraose, which is a tetrasaccharide, are formed. Glucose generates little, and decomposition does not proceed from disaccharides. In the case where a wild type (WT) TG was added, the generation amount of glucose increased over time, generation of isomaltose was observed from 60 minutes after the initiation of the reaction, and the oligosaccharides of tri- or more saccharides decreased over the passage of time (FIGS. 22 (*b*) and (*d*)). In the case where W343M, which is a modified TG having a transglycosylation activity to form α-1,4 glucosidic linkages is added, maltose is decomposed as in the case of the wild type TG and a transglycosylation reaction proceeds. At 30 minutes after the initiation of the reaction, the generated oligosaccharides are not significantly different from those in the wild type TG, and the peaks of maltotriose, maltose and glucose are observed (FIG. 22 (*c*)). On the other hand, W343M transfers maltose to oligosaccharides of tri- or more saccharides while suppressing the generation of glucose (FIG. 22 (*c*)). In contrast to the wild type TG, in the case where W343M is added, the decrease in the tri- or more oligosaccharides is small, and the amount of the finally generated oligosaccharides is dramatically large (FIG. 22 (*d*)). When the actual HPLC pattern (at 90 minutes after the initiation of the reaction) was seen, in the case where W343M was added, the peak of isomaltose was not observed, and the peaks of the oligosaccharides having larger sizes were seen (FIG. 23).

As mentioned above, when W343M, which is a modified TG, was used, the generation amount of isomaltose decreased as compared to the case where the wild type TG was used, whereas the generation amounts of the oligosaccharides with α-1,4 glucosidic linkages having long chain lengths such as maltotriose increased. When compared at 90 minutes after the initiation of the reaction, the generation amount of glucose in the modified TG decreased by 19.2%, and the generation amount of the oligosaccharides of tri- or more saccharides increased by 42.7%, as compared to that in the wild type TG Therefore, the usefulness of the modified TG, i.e., the modified TG is suitable for the generation of oligosaccharides even in an artificial digestion model system, was demonstrated.

D. Combination Use of Wild Type (WT) TG and Modified TG (1) Synthesis of Oligosaccharides Using Maltose as Substrate When a reaction for synthesizing oligosaccharides was attempted by using a modified TG having a transglycosylation activity to form α-1,6 glucosidic linkages and using maltose, which is a disaccharide with an α1,4 glucosidic linkage, as a substrate, the synthesis of oligosaccharides did not proceed. The reason therefor was considered that the modified TG having a transglycosylation activity to form α-1,6 glucosidic linkages has low reactivity against α-1,4 glucosidic linkages, and thus the reaction for synthesizing oligosaccharides does not sufficiently proceed even when maltose is used as a substrate. Therefore, it was thought that a reaction for synthesizing oligosaccharides could proceed even when maltose is used as a substrate, if an enzyme that supplies isomaltose is used in combination, and thus the synthesis of oligosaccharides was conducted by using a wild type TG having an enzyme activity to convert maltose to isomaltose and a modified TG (S495P) in combination. The generated oligosaccharides were analyzed by HPLC. In addition, a 50% maltose aqueous solution was used as a substrate, and the reaction was conducted at 50° C. for 48 hours.

Figure 24:
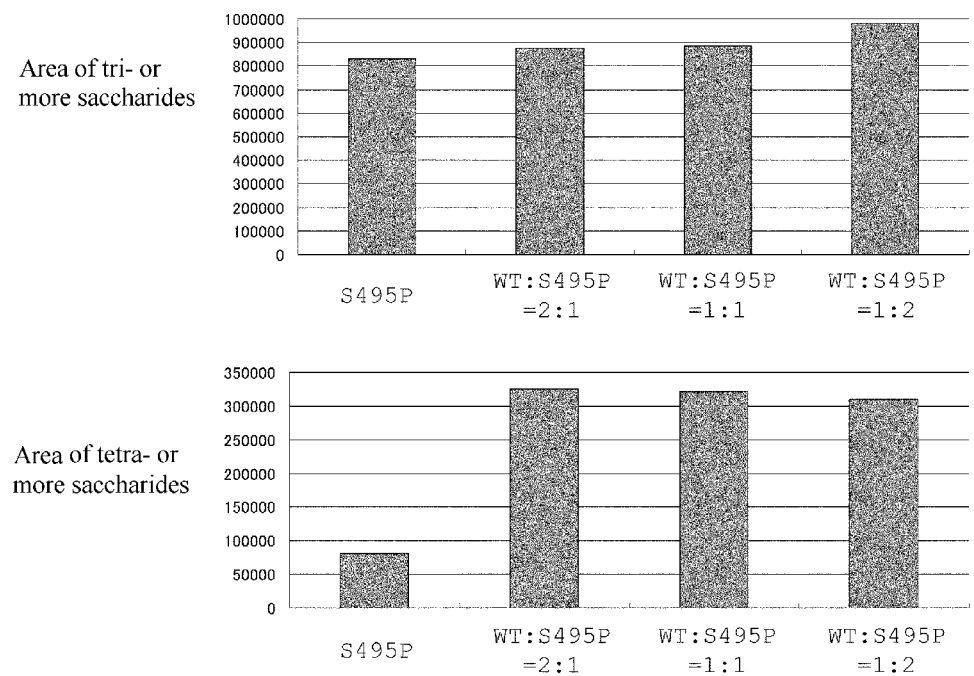
FIG. 24 compares the oligosaccharide synthesis activities. The synthesis amount of the oligosaccharides of tri- or more saccharides (upper) and the synthesis amount of the oligosaccharides of tetra- or more saccharides (lower) were compared in the case where the modified TG (S495P) was used alone and the cases where the wild type was used in combination. Maltose was used as the substrate.
Figure 25:
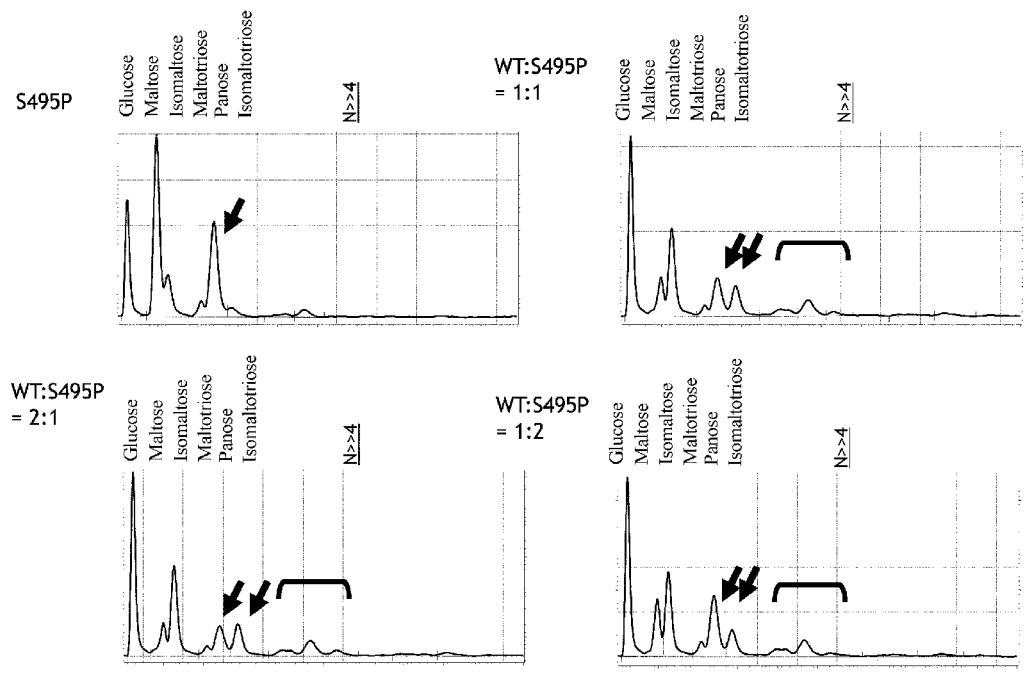
FIG. 25 is the HPLC chart of the oligosaccharides formed from maltose (substrate) (at 48 hours after the initiation of the reaction).

The synthesis of oligosaccharides was conducted for the case of S495P alone and the cases where wild type and S495P were mixed (mixing ratio 2:1, 1:1 or 1:2), and the generated oligosaccharides were analyzed by HPLC. In the case of S495P alone, panose, which is a trisaccharide, is formed, whereas the generation of oligosaccharides of tetra- or more saccharides is very low. Namely, the reactions of the tetra- or more saccharides do not proceed (S495P in FIG. 24, and S495P in FIG. 25). On the other hand, in the case where the wild type and S495P were used in combination, both of the amount of the tri- or more oligosaccharides and the amount of the tetra- or more oligosaccharides increased in either mixing ratio (WT/S495P=2/1, WT/S495P=1/1 and WT/S495P=1/2 in FIG. 24). Of particular note is that most of the generated oligosaccharides was panose in the case of S495P alone, whereas in the case where the wild type and S495P were used in combination, generation of panose and isomaltotriose was observed (FIG. 25, the peaks indicated by the arrows), and the generation of oligosaccharides of tetra- or more saccharides was further observed. As mentioned above, combination use of the wild type and the modified TG having a transglycosylation activity to form α-1,6 glucosidic linkages was effective, and it was possible to generate oligosaccharides also from a saccharide with an α-1,4 glucosidic linkage on which a reaction does not proceed by single use of the modified TG having an α-1,6 transglycosylation activity.

(2) Application of Modified TG to Field of Foods

For a modified TG having a transglycosylation activity to form α-1,6 glucosidic linkages, an experiment using an artificial digestion model system was conducted. The protocol is the same as in the case of the above-mentioned C.

In the case where only amylase is added to porridge, 40 to 50% of the generated saccharides is maltose. Furthermore, maltotriose, which is a trisaccharide, and maltotetraose, which is a tetrasaccharide, are formed. Since all of these are saccharides with α-1,4 glucosidic linkages, it was thought that the reaction does not proceed by single use of a modified α-glucosidase having a transglycosylation activity to form α-1,4 glucosidic linkages. Therefore, similarly to (1) of D, synthesis of oligosaccharides was attempted by using a wild type TG and a modified TG (S495P) in combination.

Figure 26:
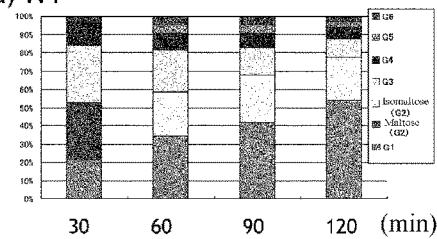
FIG. 26 compares the oligosaccharide-synthesis ability. (a) The case where the WT (wild type) TG is added, (b) the case where the modified TG (S495P) is added, (c) the case where the WT (wild type) and the modified TG (S495P) are used in combination, and (d) comparison of the area surface areas of the tri- or more saccharides.
Figure 26:
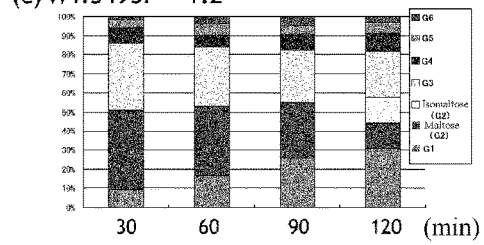
Figure 26:
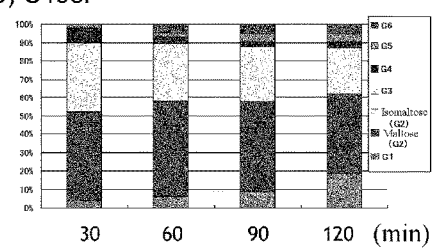
Figure 26:
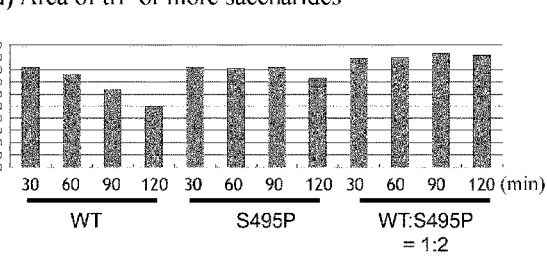
Figure 27:
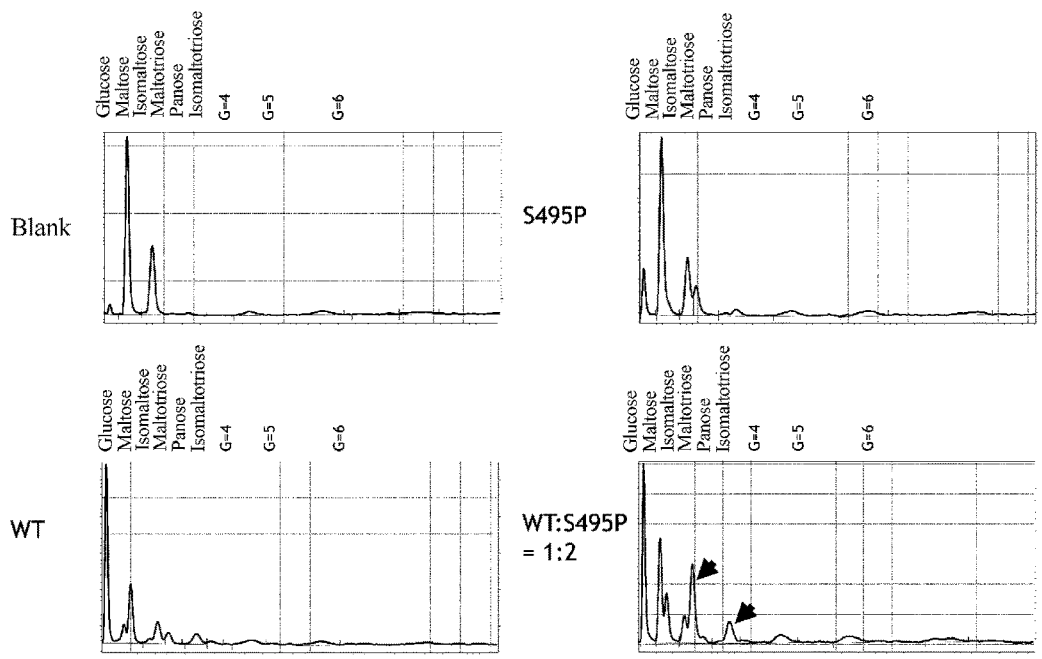
FIG. 27 is the HPLC chart of the oligosaccharides formed from porridge (at 90 minutes after the initiation of the reaction).

First, in the case where amylase and the wild type were added to porridge, the reaction proceeded from after 30 minutes, and the generation amount of glucose gradually increased (FIG. 26 (*a*)). Furthermore, isomaltose was formed from 60 minutes after the initiation of the reaction, and the tri- or more oligosaccharides gradually decreased. On the other hand, in the case where amylase and S495P were added to porridge, only generation of saccharides by amylase occurred, and even at 120 minutes after the initiation of the reaction, most of the saccharides remained as maltose, maltotriose and maltotetraose (FIG. 26 (*b*)). In contrast, in the case where three kinds of enzymes: amylase, a wild type and S495P were used in combination (the mixing ratio of the wild type and S495P was 1:2), the decomposition of maltose occurred and a transglycosylation reaction proceeded. After 60 minutes after the initiation of the reaction, oligosaccharides of tri- or more saccharides increased as compared to that in the wild type alone (FIG. 26 (*d*)). In the case where three kinds of enzymes were used in combination, decrease in the maltose and increase in the ratio of the oligosaccharides of tri- or more saccharides were observed (FIG. 26 (*c*)), and thus it is thought that the synthesis of the oligosaccharides proceeded. When the actual HPLC pattern is seen, in the case where the three kinds of enzymes were used in combination, the peaks of the maltose and maltotriose generated by amylase decreased, whereas the peaks of panose and oligosaccharides of tetra- or more saccharides were observed (the arrows at the lower right of FIG. 27). Furthermore, it was found that the oligosaccharides of tri- or more saccharides decreased little as compared to the case where only the wild type was used in combination with amylase (FIG. 27, lower left), and thus it can be said that combination use of three kinds of enzymes (amylase, wild type and S495P) is effective for the generation of oligosaccharides.

Accordingly, it was shown that combination use of a wild type and a modified TG having a transglycosylation activity to form α-1,4 glucosidic linkages is extremely effective for generating oligosaccharides.

INDUSTRIAL APPLICABILITY

The modified α-glucosidase of the present invention has a high transglycosylation activity. By utilizing this property, utilization in the production (synthesis) of oligosaccharides is expected. Furthermore, the designing method of the present invention is useful as a means for enhancing the transglycosylation activities of wild type enzymes and the like, and thus can be used for the modification of various α-glucosidases.

This invention is not limited at all by the above-mentioned embodiments for carrying out the invention and the explanations in the Examples. Various modified embodiments are also encompassed in this invention within a scope that does not deviate from the recitation of the claims and can be easily conceived by a person skilled in the art. All of the contents of the articles, patent publications and patent gazettes that are clearly indicated in the present specification are incorporated herein by reference.

The invention claimed is:

1. A modified α-glucosidase which (a) consists of an amino acid sequence which is identical to SEQ ID NO: 2 except for a substitution at a position corresponding to position 495 of SEQ ID NO: 2, or (b) comprises an amino acid sequence which has 95% or more identity with SEQ ID NO: 2 and comprises a substitution at a position corresponding to position 495 of SEQ ID NO: 2,
wherein the amino acid at position 495 is substituted by a alanine, glycine, proline, threonine or valine, and
wherein the modified α-glucosidase has increased transglycosylation activity to form α-1,6 glucosidic linkages compared to the α-glucosidase of SEQ ID NO: 2.

2. A method for producing an oligosaccharide, comprising reacting the modified α-glucosidase of claim 1 with an oligosaccharide or polysaccharide having an α-1,4 glucosidic linkage.

3. A method for producing an oligosaccharide, comprising reacting the modified α-glucosidase of claim 1 with an oligosaccharide or polysaccharide having α-1,6 glucosidic linkage.

4. The modified α-glucosidase of claim 1, wherein said modified α-glucosidase comprises an amino acid sequence which has 95% or more identity with SEQ ID NO: 2 and comprises a substitution at a position corresponding to position 495 of SEQ ID NO: 2, wherein the amino acid at position 495 is substituted by a alanine, glycine, proline, threonine or valine, wherein the modified α-glucosidase has increased transglycosylation activity to form α-1,6 glucosidic linkages compared to the α-glucosidase of SEQ ID NO: 2, and wherein said modified α-glucosidase further comprises one or more amino acid substitutions at an amino acid selected from the group consisting of:

(i) an amino acid corresponding to the amino acid at position 343 of SEQ ID NO: 2;
(ii) an amino acid corresponding to the amino acid at position 452 of SEQ ID NO: 2;
(iii) an amino acid corresponding to the amino acid at position 496 of SEQ ID NO: 2;
(iv) an amino acid corresponding to the amino acid at position 410 of SEQ ID NO: 2;
(v) an amino acid corresponding to the amino acid at position 498 of SEQ ID NO: 2;
(vi) an amino acid corresponding to the amino acid at position 499 of SEQ ID NO: 2;
(vii) an amino acid corresponding to the amino acid at position 531 of SEQ ID NO: 2;
(viii) an amino acid corresponding to the amino acid at position 533 of SEQ ID NO: 2;
(ix) an amino acid corresponding to the amino acid at position 579 of SEQ ID NO: 2;
(x) an amino acid corresponding to the amino acid at position 585 of SEQ ID NO: 2;
(xi) an amino acid corresponding to the amino acid at position 662 of SEQ ID NO: 2;
(xii) an amino acid corresponding to the amino acid at position 715 of SEQ ID NO: 2; and
(xiii) an amino acid corresponding to the amino acid at position 721 of SEQ ID NO: 2.

* * * * *

```
SEQUENCE LISTING

<160> NUMBER OF SEQ ID NOS: 83

<210> SEQ ID NO 1
<211> LENGTH: 1857
<212> TYPE: PRT
<213> ORGANISM: Homo sapiens

<400> SEQUENCE: 1

Met Ala Arg Lys Lys Leu Lys Lys Phe Thr Thr Leu Glu Ile Val Leu
1               5                   10                  15

Ser Val Leu Leu Leu Val Leu Phe Ile Ile Ser Ile Val Leu Ile Val
                20                  25                  30

Leu Leu Ala Lys Glu Ser Leu Lys Ser Thr Ala Pro Asp Pro Gly Thr
            35                  40                  45

Thr Gly Thr Pro Asp Pro Gly Thr Thr Gly Thr Pro Asp Pro Gly Thr
        50                  55                  60

Thr Gly Thr Thr His Ala Arg Thr Thr Gly Pro Pro Asp Pro Gly Thr
65                  70                  75                  80

Thr Gly Thr Thr Pro Val Ser Ala Glu Cys Pro Val Val Asn Glu Leu
                85                  90                  95

Glu Arg Ile Asn Cys Ile Pro Asp Gln Pro Pro Thr Lys Ala Thr Cys
                100                 105                 110

Asp Gln Arg Gly Cys Cys Trp Asn Pro Gln Gly Ala Val Ser Val Pro
            115                 120                 125

Trp Cys Tyr Tyr Ser Lys Asn His Ser Tyr His Val Glu Gly Asn Leu
        130                 135                 140

Val Asn Thr Asn Ala Gly Phe Thr Ala Arg Leu Lys Asn Leu Pro Ser
145                 150                 155                 160

Ser Pro Val Phe Gly Ser Asn Val Asp Asn Val Leu Leu Thr Ala Glu
                165                 170                 175

Tyr Gln Thr Ser Asn Arg Phe His Phe Lys Leu Thr Asp Gln Thr Asn
            180                 185                 190

Asn Arg Phe Glu Val Pro His Glu His Val Gln Ser Phe Ser Gly Asn
        195                 200                 205

Ala Ala Ala Ser Leu Thr Tyr Gln Val Glu Ile Ser Arg Gln Pro Phe
    210                 215                 220

Ser Ile Lys Val Thr Arg Arg Ser Asn Asn Arg Val Leu Phe Asp Ser
225                 230                 235                 240

Ser Ile Gly Pro Leu Leu Phe Ala Asp Gln Phe Leu Gln Leu Ser Thr
                245                 250                 255

Arg Leu Pro Ser Thr Asn Val Tyr Gly Leu Gly Glu His Val His Gln
```

```
             260                 265                 270
Gln Tyr Arg His Asp Met Asn Trp Lys Thr Trp Pro Ile Phe Asn Arg
            275                 280                 285

Asp Thr Thr Pro Asn Gly Asn Gly Thr Asn Leu Tyr Gly Ala Gln Thr
        290                 295                 300

Phe Phe Leu Cys Leu Glu Asp Ala Ser Gly Leu Ser Phe Gly Val Phe
305                 310                 315                 320

Leu Met Asn Ser Asn Ala Met Glu Val Val Leu Gln Pro Ala Pro Ala
                325                 330                 335

Ile Thr Tyr Arg Thr Ile Gly Gly Ile Leu Asp Phe Tyr Val Phe Leu
            340                 345                 350

Gly Asn Thr Pro Glu Gln Val Val Gln Glu Tyr Leu Glu Leu Ile Gly
        355                 360                 365

Arg Pro Ala Leu Pro Ser Tyr Trp Ala Leu Gly Phe His Leu Ser Arg
370                 375                 380

Tyr Glu Tyr Gly Thr Leu Asp Asn Met Arg Glu Val Val Glu Arg Asn
385                 390                 395                 400

Arg Ala Ala Gln Leu Pro Tyr Asp Val Gln His Ala Asp Ile Asp Tyr
                405                 410                 415

Met Asp Glu Arg Arg Asp Phe Thr Tyr Asp Ser Val Asp Phe Lys Gly
            420                 425                 430

Phe Pro Glu Phe Val Asn Glu Leu His Asn Asn Gly Gln Lys Leu Val
        435                 440                 445

Ile Ile Val Asp Pro Ala Ile Ser Asn Asn Ser Ser Ser Lys Pro
450                 455                 460

Tyr Gly Pro Tyr Asp Arg Gly Ser Asp Met Lys Ile Trp Val Asn Ser
465                 470                 475                 480

Ser Asp Gly Val Thr Pro Leu Ile Gly Glu Val Trp Pro Gly Gln Thr
                485                 490                 495

Val Phe Pro Asp Tyr Thr Asn Pro Asn Cys Ala Val Trp Trp Thr Lys
            500                 505                 510

Glu Phe Glu Leu Phe His Asn Gln Val Glu Phe Asp Gly Ile Trp Ile
        515                 520                 525

Asp Met Asn Glu Val Ser Asn Phe Val Asp Gly Ser Val Ser Gly Cys
530                 535                 540

Ser Thr Asn Asn Leu Asn Asn Pro Pro Phe Thr Pro Arg Ile Leu Asp
545                 550                 555                 560

Gly Tyr Leu Phe Cys Lys Thr Leu Cys Met Asp Ala Val Gln His Trp
                565                 570                 575

Gly Lys Gln Tyr Asp Ile His Asn Leu Tyr Gly Tyr Ser Met Ala Val
            580                 585                 590

Ala Thr Ala Glu Ala Lys Thr Val Phe Pro Asn Lys Arg Ser Phe
        595                 600                 605

Ile Leu Thr Arg Ser Thr Phe Ala Gly Ser Gly Lys Phe Ala Ala His
610                 615                 620

Trp Leu Gly Asp Asn Thr Ala Thr Trp Asp Asp Leu Arg Trp Ser Ile
625                 630                 635                 640

Pro Gly Val Leu Glu Phe Asn Leu Phe Gly Ile Pro Met Val Gly Pro
                645                 650                 655

Asp Ile Cys Gly Phe Ala Leu Asp Thr Pro Glu Glu Leu Cys Arg Arg
            660                 665                 670

Trp Met Gln Leu Gly Ala Phe Tyr Pro Phe Ser Arg Asn His Asn Gly
        675                 680                 685
```

```
Gln Gly Tyr Lys Asp Gln Asp Pro Ala Ser Phe Gly Ala Asp Ser Leu
        690             695                 700

Leu Leu Asn Ser Ser Arg His Tyr Leu Asn Ile Arg Tyr Thr Leu Leu
705             710                 715                     720

Pro Tyr Leu Tyr Thr Leu Phe Phe Arg Ala His Ser Arg Gly Asp Thr
                725                 730                 735

Val Ala Arg Pro Leu Leu His Glu Phe Tyr Glu Asp Asn Ser Thr Trp
            740                 745                 750

Asp Val His Gln Gln Phe Leu Trp Gly Pro Gly Leu Leu Ile Thr Pro
        755                 760                 765

Val Leu Asp Glu Gly Ala Glu Lys Val Met Ala Tyr Val Pro Asp Ala
    770                 775                 780

Val Trp Tyr Asp Tyr Glu Thr Gly Ser Gln Val Arg Trp Arg Lys Gln
785             790                 795                     800

Lys Val Glu Met Glu Leu Pro Gly Asp Lys Ile Gly Leu His Leu Arg
                805                 810                 815

Gly Gly Tyr Ile Phe Pro Thr Gln Gln Pro Asn Thr Thr Leu Ala
            820                 825                 830

Ser Arg Lys Asn Pro Leu Gly Leu Ile Ile Ala Leu Asp Glu Asn Lys
        835                 840                 845

Glu Ala Lys Gly Glu Leu Phe Trp Asp Asn Gly Glu Thr Lys Asp Thr
    850                 855                 860

Val Ala Asn Lys Val Tyr Leu Leu Cys Glu Phe Ser Val Thr Gln Asn
865             870                 875                     880

Arg Leu Glu Val Asn Ile Ser Gln Ser Thr Tyr Lys Asp Pro Asn Asn
                885                 890                 895

Leu Ala Phe Asn Glu Ile Lys Ile Leu Gly Thr Glu Glu Pro Ser Asn
            900                 905                 910

Val Thr Val Lys His Asn Gly Val Pro Ser Gln Thr Ser Pro Thr Val
        915                 920                 925

Thr Tyr Asp Ser Asn Leu Lys Val Ala Ile Ile Thr Asp Ile Asp Leu
    930                 935                 940

Leu Leu Gly Glu Ala Tyr Thr Val Glu Trp Ser Ile Lys Ile Arg Asp
945             950                 955                     960

Glu Glu Lys Ile Asp Cys Tyr Pro Asp Glu Asn Gly Ala Ser Ala Glu
                965                 970                 975

Asn Cys Thr Ala Arg Gly Cys Ile Trp Glu Ala Ser Asn Ser Ser Gly
            980                 985                 990

Val Pro Phe Cys Tyr Phe Val Asn Asp Leu Tyr Ser Val Ser Asp Val
        995                 1000                1005

Gln Tyr Asn Ser His Gly Ala Thr Ala Asp Ile Ser Leu Lys Ser
    1010                1015                1020

Ser Val Tyr Ala Asn Ala Phe Pro Ser Thr Pro Val Asn Pro Leu
    1025                1030                1035

Arg Leu Asp Val Thr Tyr His Lys Asn Glu Met Leu Gln Phe Lys
    1040                1045                1050

Ile Tyr Asp Pro Asn Lys Asn Arg Tyr Glu Val Pro Val Pro Leu
    1055                1060                1065

Asn Ile Pro Ser Met Pro Ser Ser Thr Pro Glu Gly Gln Leu Tyr
    1070                1075                1080

Asp Val Leu Ile Lys Lys Asn Pro Phe Gly Ile Glu Ile Arg Arg
    1085                1090                1095
```

-continued

Lys Ser Thr Gly Thr Ile Ile Trp Asp Ser Gln Leu Leu Gly Phe
1100             1105             1110

Thr Phe Ser Asp Met Phe Ile Arg Ile Ser Thr Arg Leu Pro Ser
1115             1120             1125

Lys Tyr Leu Tyr Gly Phe Gly Glu Thr Glu His Arg Ser Tyr Arg
1130             1135             1140

Arg Asp Leu Glu Trp His Thr Trp Gly Met Phe Ser Arg Asp Gln
1145             1150             1155

Pro Pro Gly Tyr Lys Lys Asn Ser Tyr Gly Val His Pro Tyr Tyr
1160             1165             1170

Met Gly Leu Glu Glu Asp Gly Ser Ala His Gly Val Leu Leu Leu
1175             1180             1185

Asn Ser Asn Ala Met Asp Val Thr Phe Gln Pro Leu Pro Ala Leu
1190             1195             1200

Thr Tyr Arg Thr Thr Gly Gly Val Leu Asp Phe Tyr Val Phe Leu
1205             1210             1215

Gly Pro Thr Pro Glu Leu Val Thr Gln Gln Tyr Thr Glu Leu Ile
1220             1225             1230

Gly Arg Pro Val Met Val Pro Tyr Trp Ser Leu Gly Phe Gln Leu
1235             1240             1245

Cys Arg Tyr Gly Tyr Gln Asn Asp Ser Glu Ile Ala Ser Leu Tyr
1250             1255             1260

Asp Glu Met Val Ala Ala Gln Ile Pro Tyr Asp Val Gln Tyr Ser
1265             1270             1275

Asp Ile Asp Tyr Met Glu Arg Gln Leu Asp Phe Thr Leu Ser Pro
1280             1285             1290

Lys Phe Ala Gly Phe Pro Ala Leu Ile Asn Arg Met Lys Ala Asp
1295             1300             1305

Gly Met Arg Val Ile Leu Ile Leu Asp Pro Ala Ile Ser Gly Asn
1310             1315             1320

Glu Thr Gln Pro Tyr Pro Ala Phe Thr Arg Gly Val Glu Asp Asp
1325             1330             1335

Val Phe Ile Lys Tyr Pro Asn Asp Gly Asp Ile Val Trp Gly Lys
1340             1345             1350

Val Trp Pro Asp Phe Pro Asp Val Val Val Asn Gly Ser Leu Asp
1355             1360             1365

Trp Asp Ser Gln Val Glu Leu Tyr Arg Ala Tyr Val Ala Phe Pro
1370             1375             1380

Asp Phe Phe Arg Asn Ser Thr Ala Lys Trp Trp Lys Arg Glu Ile
1385             1390             1395

Glu Glu Leu Tyr Asn Asn Pro Gln Asn Pro Glu Arg Ser Leu Lys
1400             1405             1410

Phe Asp Gly Met Trp Ile Asp Met Asn Glu Pro Ser Ser Phe Val
1415             1420             1425

Asn Gly Ala Val Ser Pro Gly Cys Arg Asp Ala Ser Leu Asn His
1430             1435             1440

Pro Pro Tyr Met Pro His Leu Glu Ser Arg Asp Arg Gly Leu Ser
1445             1450             1455

Ser Lys Thr Leu Cys Met Glu Ser Gln Gln Ile Leu Pro Asp Gly
1460             1465             1470

Ser Leu Val Gln His Tyr Asn Val His Asn Leu Tyr Gly Trp Ser
1475             1480             1485

Gln Thr Arg Pro Thr Tyr Glu Ala Val Gln Glu Val Thr Gly Gln

```
                    1490                1495                1500
Arg Gly Val Val Ile Thr Arg Ser Thr Phe Pro Ser Ser Gly Arg
    1505                1510                1515

Trp Ala Gly His Trp Leu Gly Asp Asn Thr Ala Ala Trp Asp Gln
    1520                1525                1530

Leu Lys Lys Ser Ile Ile Gly Met Met Glu Phe Ser Leu Phe Gly
    1535                1540                1545

Ile Ser Tyr Thr Gly Ala Asp Ile Cys Gly Phe Phe Gln Asp Ala
    1550                1555                1560

Glu Tyr Glu Met Cys Val Arg Trp Met Gln Leu Gly Ala Phe Tyr
    1565                1570                1575

Pro Phe Ser Arg Asn His Asn Thr Ile Gly Thr Arg Arg Gln Asp
    1580                1585                1590

Pro Val Ser Trp Asp Val Ala Phe Val Asn Ile Ser Arg Thr Val
    1595                1600                1605

Leu Gln Thr Arg Tyr Thr Leu Leu Pro Tyr Leu Tyr Thr Leu Met
    1610                1615                1620

His Lys Ala His Thr Glu Gly Val Thr Val Arg Pro Leu Leu
    1625                1630                1635

His Glu Phe Val Ser Asp Gln Val Thr Trp Asp Ile Asp Ser Gln
    1640                1645                1650

Phe Leu Leu Gly Pro Ala Phe Leu Val Ser Pro Val Leu Glu Arg
    1655                1660                1665

Asn Ala Arg Asn Val Thr Ala Tyr Phe Pro Arg Ala Arg Trp Tyr
    1670                1675                1680

Asp Tyr Tyr Thr Gly Val Asp Ile Asn Ala Arg Gly Glu Trp Lys
    1685                1690                1695

Thr Leu Pro Ala Pro Leu Asp His Ile Asn Leu His Val Arg Gly
    1700                1705                1710

Gly Tyr Ile Leu Pro Trp Gln Glu Pro Ala Leu Asn Thr His Leu
    1715                1720                1725

Ser Arg Gln Lys Phe Met Gly Phe Lys Ile Ala Leu Asp Asp Glu
    1730                1735                1740

Gly Thr Ala Gly Gly Trp Leu Phe Trp Asp Asp Gly Gln Ser Ile
    1745                1750                1755

Asp Thr Tyr Gly Lys Gly Leu Tyr Tyr Leu Ala Ser Phe Ser Ala
    1760                1765                1770

Ser Gln Asn Thr Met Gln Ser His Ile Ile Phe Asn Asn Tyr Ile
    1775                1780                1785

Thr Gly Thr Asn Pro Leu Lys Leu Gly Tyr Ile Glu Ile Trp Gly
    1790                1795                1800

Val Gly Ser Val Pro Val Thr Ser Val Ser Ile Ser Val Ser Gly
    1805                1810                1815

Met Val Ile Thr Pro Ser Phe Asn Asn Asp Pro Thr Thr Gln Val
    1820                1825                1830

Leu Ser Ile Asp Val Thr Asp Arg Asn Ile Ser Leu His Asn Phe
    1835                1840                1845

Thr Ser Leu Thr Trp Ile Ser Thr Leu
    1850                1855

<210> SEQ ID NO 2
<211> LENGTH: 985
<212> TYPE: PRT
<213> ORGANISM: Aspergillus niger
```

<400> SEQUENCE: 2

```
Met Val Lys Leu Thr His Leu Leu Ala Arg Ala Trp Leu Val Pro Leu
  1               5                  10                  15

Ala Tyr Gly Ala Ser Gln Ser Leu Leu Ser Thr Thr Ala Pro Ser Gln
             20                  25                  30

Pro Gln Phe Thr Ile Pro Ala Ser Ala Asp Val Gly Ala Gln Leu Ile
         35                  40                  45

Ala Asn Ile Asp Asp Pro Gln Ala Asp Ala Gln Ser Val Cys Pro
     50                  55                  60

Gly Tyr Lys Ala Ser Lys Val Gln His Asn Ser Arg Gly Phe Thr Ala
 65                  70                  75                  80

Ser Leu Gln Leu Ala Gly Arg Pro Cys Asn Val Tyr Gly Thr Asp Val
                 85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
        130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
```

```
                405                 410                 415
Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
                500                 505                 510

His Pro Ser Phe Leu Leu Pro Gly Glu Pro Gly Asp Ile Ile Tyr Asp
            515                 520                 525

Tyr Pro Glu Ala Phe Asn Ile Thr Asn Ala Thr Glu Ala Ala Ser Ala
            530                 535                 540

Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
                595                 600                 605

Glu Glu Tyr Asp Val His Gly Leu Tyr Gly His Gln Gly Leu Asn Ala
            610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
            690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
            770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830
```

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Leu Gln Asn Leu Thr Lys Gly Gly Ala
                965                 970                 975

Trp Ala Glu Asn Trp Val Leu Glu Trp
            980                 985

<210> SEQ ID NO 3
<211> LENGTH: 914
<212> TYPE: PRT
<213> ORGANISM: Homo sapiens

<400> SEQUENCE: 3

Met Glu Ala Ala Val Lys Glu Glu Ile Ser Leu Glu Asp Glu Ala Val
1               5                   10                  15

Asp Lys Asn Ile Phe Arg Asp Cys Asn Lys Ile Ala Phe Tyr Arg Arg
            20                  25                  30

Gln Lys Gln Trp Leu Ser Lys Lys Ser Thr Tyr Gln Ala Leu Leu Asp
            35                  40                  45

Ser Val Thr Thr Asp Glu Asp Ser Thr Arg Phe Gln Ile Ile Asn Glu
50                  55                  60

Ala Ser Lys Val Pro Leu Leu Ala Glu Ile Tyr Gly Ile Glu Gly Asn
65                  70                  75                  80

Ile Phe Arg Leu Lys Ile Asn Glu Glu Thr Pro Leu Lys Pro Arg Phe
            85                  90                  95

Glu Val Pro Asp Val Leu Thr Ser Lys Pro Ser Thr Val Arg Leu Ile
            100                 105                 110

Ser Cys Ser Gly Asp Thr Gly Ser Leu Ile Leu Ala Asp Gly Lys Gly
            115                 120                 125

Asp Leu Lys Cys His Ile Thr Ala Asn Pro Phe Lys Val Asp Leu Val
            130                 135                 140

Ser Glu Glu Glu Val Val Ile Ser Ile Asn Ser Leu Gly Gln Leu Tyr
145                 150                 155                 160

Phe Glu His Leu Gln Ile Leu His Lys Gln Arg Ala Ala Lys Glu Asn
            165                 170                 175

Glu Glu Glu Thr Ser Val Asp Thr Ser Gln Glu Asn Gln Glu Asp Leu
            180                 185                 190

Gly Leu Trp Glu Glu Lys Phe Gly Lys Phe Val Asp Ile Lys Ala Asn
            195                 200                 205

Gly Pro Ser Ser Ile Gly Leu Asp Phe Ser Leu His Gly Phe Glu His

```
            210                 215                 220
Leu Tyr Gly Ile Pro Gln His Ala Glu Ser His Gln Leu Lys Asn Thr
225                 230                 235                 240

Gly Asp Gly Asp Ala Tyr Arg Leu Tyr Asn Leu Asp Val Tyr Gly Tyr
                245                 250                 255

Gln Ile Tyr Asp Lys Met Gly Ile Tyr Gly Ser Val Pro Tyr Leu Leu
                260                 265                 270

Ala His Lys Leu Gly Arg Thr Ile Gly Ile Phe Trp Leu Asn Ala Ser
                275                 280                 285

Glu Thr Leu Val Glu Ile Asn Thr Glu Pro Ala Val Glu Tyr Thr Leu
                290                 295                 300

Thr Gln Met Gly Pro Val Ala Ala Lys Gln Lys Val Arg Ser Arg Thr
305                 310                 315                 320

His Val His Trp Met Ser Glu Ser Gly Ile Ile Asp Val Phe Leu Leu
                325                 330                 335

Thr Gly Pro Thr Pro Ser Asp Val Phe Lys Gln Tyr Ser His Leu Thr
                340                 345                 350

Gly Thr Gln Ala Met Pro Pro Leu Phe Ser Leu Gly Tyr His Gln Cys
                355                 360                 365

Arg Trp Asn Tyr Glu Asp Glu Gln Asp Val Lys Ala Val Asp Ala Gly
                370                 375                 380

Phe Asp Glu His Asp Ile Pro Tyr Asp Ala Met Trp Leu Asp Ile Glu
385                 390                 395                 400

His Thr Glu Gly Lys Arg Tyr Phe Thr Trp Asp Lys Asn Arg Phe Pro
                405                 410                 415

Asn Pro Lys Arg Met Gln Glu Leu Leu Arg Ser Lys Lys Arg Lys Leu
                420                 425                 430

Val Val Ile Ser Asp Pro His Ile Lys Ile Asp Pro Asp Tyr Ser Val
                435                 440                 445

Tyr Val Lys Ala Lys Asp Gln Gly Phe Phe Val Lys Asn Gln Glu Gly
                450                 455                 460

Glu Asp Phe Glu Gly Val Cys Trp Pro Gly Leu Ser Ser Tyr Leu Asp
465                 470                 475                 480

Phe Thr Asn Pro Lys Val Arg Glu Trp Tyr Ser Ser Leu Phe Ala Phe
                485                 490                 495

Pro Val Tyr Gln Gly Ser Thr Asp Ile Leu Phe Leu Trp Asn Asp Met
                500                 505                 510

Asn Glu Pro Ser Val Phe Arg Gly Pro Glu Gln Thr Met Gln Lys Asn
                515                 520                 525

Ala Ile His His Gly Asn Trp Glu His Arg Glu Leu His Asn Ile Tyr
                530                 535                 540

Gly Phe Tyr His Gln Met Ala Thr Ala Glu Gly Leu Ile Lys Arg Ser
545                 550                 555                 560

Lys Gly Lys Glu Arg Pro Phe Val Leu Thr Arg Ser Phe Phe Ala Gly
                565                 570                 575

Ser Gln Lys Tyr Gly Ala Val Trp Thr Gly Asp Asn Thr Ala Glu Trp
                580                 585                 590

Ser Asn Leu Lys Ile Ser Ile Pro Met Leu Leu Thr Leu Ser Ile Thr
                595                 600                 605

Gly Ile Ser Phe Cys Gly Ala Asp Ile Gly Gly Phe Ile Gly Asn Pro
                610                 615                 620

Glu Thr Glu Leu Leu Val Arg Trp Tyr Gln Ala Gly Ala Tyr Gln Pro
625                 630                 635                 640
```

```
Phe Phe Arg Gly His Ala Thr Met Asn Thr Lys Arg Glu Pro Trp
                645                 650                 655

Leu Phe Gly Glu Glu His Thr Arg Leu Ile Arg Glu Ala Ile Arg Glu
            660                 665                 670

Arg Tyr Gly Leu Leu Pro Tyr Trp Tyr Ser Leu Phe Tyr His Ala His
        675                 680                 685

Val Ala Ser Gln Pro Val Met Arg Pro Leu Trp Val Glu Phe Pro Asp
    690                 695                 700

Glu Leu Lys Thr Phe Asp Met Glu Asp Glu Tyr Met Leu Gly Ser Ala
705                 710                 715                 720

Leu Leu Val His Pro Val Thr Glu Pro Lys Ala Thr Thr Val Asp Val
            725                 730                 735

Phe Leu Pro Gly Ser Asn Glu Val Trp Tyr Asp Tyr Lys Thr Phe Ala
        740                 745                 750

His Trp Glu Gly Gly Cys Thr Val Lys Ile Pro Val Ala Leu Asp Thr
    755                 760                 765

Ile Pro Val Phe Gln Arg Gly Ser Val Ile Pro Ile Lys Thr Thr
770                 775                 780

Val Gly Lys Ser Thr Gly Trp Met Thr Glu Ser Ser Tyr Gly Leu Arg
785                 790                 795                 800

Val Ala Leu Ser Thr Lys Gly Ser Ser Val Gly Glu Leu Tyr Leu Asp
            805                 810                 815

Asp Gly His Ser Phe Gln Tyr Leu His Gln Lys Gln Phe Leu His Arg
        820                 825                 830

Lys Phe Ser Phe Cys Ser Ser Val Leu Ile Asn Ser Phe Ala Asp Gln
    835                 840                 845

Arg Gly His Tyr Pro Ser Lys Cys Val Val Glu Lys Ile Leu Val Leu
    850                 855                 860

Gly Phe Arg Lys Glu Pro Ser Ser Val Thr Thr His Ser Ser Asp Gly
865                 870                 875                 880

Lys Asp Gln Pro Val Ala Phe Thr Tyr Cys Ala Lys Thr Ser Ile Leu
            885                 890                 895

Ser Leu Glu Lys Leu Ser Leu Asn Ile Ala Thr Asp Trp Glu Val Arg
        900                 905                 910

Ile Ile

<210> SEQ ID NO 4
<211> LENGTH: 953
<212> TYPE: PRT
<213> ORGANISM: Mus musculus

<400> SEQUENCE: 4

Met Asn Ile Arg Lys Pro Leu Cys Ser Asn Ser Val Val Gly Ala Cys
1               5                   10                  15

Thr Leu Val Ser Leu Thr Thr Ala Val Ile Leu Gly His Leu Met Leu
            20                  25                  30

Arg Glu Leu Met Leu Leu Pro Gln Asp Leu His Glu Ser Ser Ser Gly
        35                  40                  45

Leu Trp Lys Thr Tyr Arg Pro His His Gln Glu Ser Tyr Glu Pro Ala
    50                  55                  60

Pro Leu His Ile Gln Glu His Ala Glu Gln Leu Arg Ala Val Pro Thr
65                  70                  75                  80

Gln Cys Asp Val Thr Pro Asn Ser Arg Phe Asp Cys Ala Pro Asp Lys
            85                  90                  95
```

-continued

```
Gly Ile Thr Gln Glu Gln Cys Glu Ala Arg Gly Cys Cys Trp Val Pro
                100                 105                 110
Ala Gly Gln Val Leu Asn Gly Pro Val Met Gly Gln Pro Trp Cys Phe
            115                 120                 125
Phe Pro Pro Ser Tyr Pro Ser Tyr Arg Leu Glu Asn Leu Ser Ser Thr
130                 135                 140
Glu Ser Gly Tyr Thr Ala Thr Leu Thr Arg Thr Ser Pro Thr Phe Phe
145                 150                 155                 160
Pro Lys Asp Val Leu Thr Leu Gln Leu Glu Val Leu Met Glu Thr Asp
                165                 170                 175
Ser Arg Leu His Phe Met Ile Lys Asp Pro Thr Ser Lys Arg Tyr Glu
                180                 185                 190
Val Pro Leu Glu Thr Pro Arg Val Leu Ser Gln Ala Pro Ser Pro Leu
            195                 200                 205
Tyr Ser Val Glu Phe Ser Glu Glu Pro Phe Gly Val Ile Val Arg Arg
210                 215                 220
Lys Leu Gly Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln His
                245                 250                 255
Ile Ala Gly Leu Gly Glu His Leu Ser Pro Leu Met Leu Ser Thr Glu
                260                 265                 270
Trp Thr Arg Ile Thr Leu Trp Asn Arg Asp Val Ala Pro Ser Gln Gly
            275                 280                 285
Val Asn Leu Tyr Gly Ser His Pro Phe Tyr Leu Ala Leu Glu Asp Gly
            290                 295                 300
Gly Leu Ala His Gly Val Phe Leu Leu Asn Ser Asn Ala Met Asp Val
305                 310                 315                 320
Val Leu Gln Pro Ser Pro Ala Leu Thr Trp Arg Ser Thr Gly Gly Ile
                325                 330                 335
Leu Asp Val Tyr Val Phe Leu Gly Pro Glu Pro Lys Ser Val Val Gln
                340                 345                 350
Gln Tyr Leu Asp Val Val Gly Tyr Pro Phe Met Pro Pro Tyr Trp Gly
            355                 360                 365
Leu Gly Phe His Leu Cys Arg Trp Gly Tyr Ser Ser Thr Ala Ile Val
370                 375                 380
Arg Gln Val Val Glu Asn Met Thr Arg Thr His Phe Pro Leu Asp Val
385                 390                 395                 400
Gln Trp Asn Asp Leu Asp Tyr Met Asp Ala Arg Arg Asp Phe Thr Phe
                405                 410                 415
Asn Gln Asp Gly Phe Ala Asp Phe Pro Asp Met Val His Glu Leu His
                420                 425                 430
Gln Gly Gly Arg Arg Tyr Met Met Ile Val Asp Pro Ala Ile Ser Ser
            435                 440                 445
Ser Gly Pro Ala Gly Ser Tyr Arg Pro Tyr Asp Glu Gly Leu Arg Arg
            450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Glu Thr Leu
                485                 490                 495
Asp Trp Trp Gln Asp Met Val Ser Glu Phe His Ala Gln Val Pro Phe
                500                 505                 510
```

-continued

```
Asp Gly Met Trp Ile Asp Met Asn Glu Pro Ser Asn Phe Ile Arg Gly
            515                 520                 525
Ser Gln Gln Gly Cys Pro Asp Asn Glu Leu Glu Asn Pro Pro Tyr Val
        530                 535                 540
Pro Gly Val Val Gly Gly Ala Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser Ser Arg Ala Leu Val Lys Thr Arg Gly
            580                 585                 590
Thr Arg Pro Phe Val Ile Ser Arg Ser Thr Phe Ala Gly His Gly Arg
        595                 600                 605
Tyr Ala Gly His Trp Thr Gly Asp Val Trp Ser Ser Trp Glu His Leu
610                 615                 620
Ala Tyr Ser Val Pro Glu Ile Leu Gln Phe Asn Leu Leu Gly Val Pro
625                 630                 635                 640
Leu Val Gly Ala Asp Ile Cys Gly Phe Gln Gly Asn Thr Thr Glu Glu
                645                 650                 655
Leu Cys Val Arg Trp Thr Gln Leu Gly Ala Phe Tyr Pro Phe Met Arg
            660                 665                 670
Asn His Asn Asp Leu Asn Ser Leu Pro Gln Glu Pro Tyr Arg Phe Ser
        675                 680                 685
Glu Thr Ala Gln Gln Ala Met Arg Lys Ala Phe Thr Leu Arg Tyr Ala
690                 695                 700
Leu Leu Pro Tyr Leu Tyr Thr Leu Phe His Gly Ala His Val Lys Gly
705                 710                 715                 720
Asp Thr Val Ala Arg Pro Leu Phe Leu Glu Phe Pro Glu Asp Pro Ser
                725                 730                 735
Thr Trp Ser Val Asp Arg Gln Leu Leu Trp Gly Pro Ala Leu Leu Ile
            740                 745                 750
Thr Pro Val Leu Glu Pro Gly Lys Thr Asp Val Thr Gly Tyr Phe Pro
        755                 760                 765
Lys Gly Met Trp Tyr Asn Leu Gln Met Val Pro Val Glu Thr Leu Gly
770                 775                 780
Ser Leu Pro Ser Ser Pro Ala Ser Ser Phe Arg Ser Ile Val His
785                 790                 795                 800
Ser Lys Gly Gln Trp Leu Thr Leu Glu Ala Pro Leu Asp Thr Ile Asn
                805                 810                 815
Val His Leu Arg Ala Gly Tyr Ile Ile Pro Leu Gln Gly Pro Ser Leu
            820                 825                 830
Thr Thr Thr Glu Ser Arg Lys Gln Pro Met Ala Leu Ala Val Ala Leu
        835                 840                 845
Thr Glu Ser Gly Glu Ala Ser Gly Glu Leu Phe Trp Asp Asp Gly Glu
850                 855                 860
Ser Leu Gly Val Leu Glu Arg Gly Ala Tyr Thr Leu Val Thr Phe Ser
865                 870                 875                 880
Ala Lys Asn Asn Thr Ile Val Asn Lys Leu Val His Val Thr Lys Glu
                885                 890                 895
Gly Gly Glu Leu Gln Leu Arg Glu Val Thr Ile Leu Gly Val Thr Thr
            900                 905                 910
Ala Pro Thr Gln Val Leu Ser Asn Gly Ile Ser Val Ser Asn Phe Thr
        915                 920                 925
Tyr Ser Pro Asp Asp Lys Ser Leu Ser Ile Pro Val Ser Leu Leu Met
```

```
                      930                 935                 940
Gly Glu Arg Phe Gln Ile Asp Trp Ser
945                 950

<210> SEQ ID NO 5
<211> LENGTH: 954
<212> TYPE: PRT
<213> ORGANISM: Saccharomyces cerevisiae

<400> SEQUENCE: 5

Met Val Leu Leu Lys Trp Leu Val Cys Gln Leu Val Phe Phe Thr Ala
1               5                   10                  15

Phe Ser His Ala Phe Thr Asp Tyr Leu Leu Lys Lys Cys Ala Gln Ser
                20                  25                  30

Gly Phe Cys His Arg Asn Arg Val Tyr Ala Glu Asn Ile Ala Lys Ser
            35                  40                  45

His His Cys Tyr Tyr Lys Val Asp Ala Glu Ser Ile Ala His Asp Pro
        50                  55                  60

Leu Glu Asn Val Leu His Ala Thr Ile Ile Lys Thr Ile Pro Arg Leu
65                  70                  75                  80

Glu Gly Asp Asp Ile Ala Val Gln Phe Pro Phe Ser Leu Ser Phe Leu
                85                  90                  95

Gln Asp His Ser Val Arg Phe Thr Ile Asn Glu Lys Glu Arg Met Pro
            100                 105                 110

Thr Asn Ser Ser Gly Leu Leu Ile Ser Ser Gln Arg Phe Asn Glu Thr
        115                 120                 125

Trp Lys Tyr Ala Phe Asp Lys Lys Phe Gln Glu Ala Asn Arg Thr
    130                 135                 140

Ser Ile Pro Gln Phe His Phe Leu Lys Gln Lys Gln Thr Val Asn Ser
145                 150                 155                 160

Phe Trp Ser Lys Ile Ser Ser Phe Leu Ser Leu Ser Asn Ser Thr Ala
                165                 170                 175

Asp Thr Phe His Leu Arg Asn Gly Asp Val Ser Val Glu Ile Phe Ala
            180                 185                 190

Glu Pro Phe Gln Leu Lys Val Tyr Trp Gln Asn Ala Leu Lys Leu Ile
        195                 200                 205

Val Asn Glu Gln Asn Phe Leu Asn Ile Glu His His Arg Thr Lys Gln
    210                 215                 220

Glu Asn Phe Ala His Val Leu Pro Glu Glu Thr Thr Phe Asn Met Phe
225                 230                 235                 240

Lys Asp Asn Phe Leu Tyr Ser Lys His Asp Ser Met Pro Leu Gly Pro
                245                 250                 255

Glu Ser Val Ala Leu Asp Phe Ser Phe Met Gly Ser Thr Asn Val Tyr
            260                 265                 270

Gly Ile Pro Glu His Ala Thr Ser Leu Arg Leu Met Asp Thr Ser Gly
        275                 280                 285

Gly Lys Glu Pro Tyr Arg Leu Phe Asn Val Asp Val Phe Glu Tyr Asn
    290                 295                 300

Ile Gly Thr Ser Gln Pro Met Tyr Gly Ser Ile Pro Phe Met Phe Ser
305                 310                 315                 320

Ser Ser Ser Thr Ser Ile Phe Trp Val Asn Ala Ala Asp Thr Trp Val
                325                 330                 335

Asp Ile Lys Tyr Asp Thr Ser Lys Asn Lys Thr Met Thr His Trp Ile
            340                 345                 350
```

```
Ser Glu Asn Gly Val Ile Asp Val Met Ser Leu Gly Pro Asp Ile
        355                 360                 365

Pro Thr Ile Ile Asp Lys Phe Thr Asp Leu Thr Gly Arg Pro Phe Leu
        370                 375                 380

Pro Pro Ile Ser Ser Ile Gly Tyr His Gln Cys Arg Trp Asn Tyr Asn
385                 390                 395                 400

Asp Glu Met Asp Val Leu Thr Val Asp Ser Gln Met Asp Ala His Met
                405                 410                 415

Ile Pro Tyr Asp Phe Ile Trp Leu Asp Leu Glu Tyr Thr Asn Asp Lys
                420                 425                 430

Lys Tyr Phe Thr Trp Lys Gln His Ser Phe Pro Asn Pro Lys Arg Leu
        435                 440                 445

Leu Ser Lys Leu Lys Lys Leu Gly Arg Asn Leu Val Val Leu Ile Asp
        450                 455                 460

Pro His Leu Lys Lys Asp Tyr Glu Ile Ser Asp Arg Val Ile Asn Glu
465                 470                 475                 480

Asn Val Ala Val Lys Asp His Asn Gly Asn Asp Tyr Val Gly His Cys
                485                 490                 495

Trp Pro Gly Asn Ser Ile Trp Ile Asp Thr Ile Ser Lys Tyr Gly Gln
                500                 505                 510

Lys Ile Trp Lys Ser Phe Phe Glu Arg Phe Met Asp Leu Pro Ala Asp
        515                 520                 525

Leu Thr Asn Leu Phe Ile Trp Asn Asp Met Asn Glu Pro Ser Ile Phe
        530                 535                 540

Asp Gly Pro Glu Thr Thr Ala Pro Lys Asp Leu Ile His Asp Asn Tyr
545                 550                 555                 560

Ile Glu Glu Arg Ser Val His Asn Ile Tyr Gly Leu Ser Val His Glu
                565                 570                 575

Ala Thr Tyr Asp Ala Ile Lys Ser Ile Tyr Ser Pro Ser Asp Lys Arg
                580                 585                 590

Pro Phe Leu Leu Thr Arg Ala Phe Phe Ala Gly Ser Gln Arg Thr Ala
        595                 600                 605

Ala Thr Trp Thr Gly Asp Asn Val Ala Asn Trp Asp Tyr Leu Lys Ile
        610                 615                 620

Ser Ile Pro Met Val Leu Ser Asn Asn Ile Ala Gly Met Pro Phe Ile
625                 630                 635                 640

Gly Ala Asp Ile Ala Gly Phe Ala Glu Asp Pro Thr Pro Glu Leu Ile
                645                 650                 655

Ala Arg Trp Tyr Gln Ala Gly Leu Trp Tyr Pro Phe Phe Arg Ala His
        660                 665                 670

Ala His Ile Asp Thr Lys Arg Arg Glu Pro Tyr Leu Phe Asn Glu Pro
        675                 680                 685

Leu Lys Ser Ile Val Arg Asp Ile Ile Gln Leu Arg Tyr Phe Leu Leu
        690                 695                 700

Pro Thr Leu Tyr Thr Met Phe His Lys Ser Ser Val Thr Gly Phe Pro
705                 710                 715                 720

Ile Met Asn Pro Met Phe Ile Glu His Pro Glu Phe Ala Glu Leu Tyr
                725                 730                 735

His Ile Asp Asn Gln Phe Tyr Trp Ser Asn Ser Gly Leu Leu Val Lys
                740                 745                 750

Pro Val Thr Glu Pro Gly Gln Ser Glu Thr Glu Met Val Phe Pro Pro
        755                 760                 765

Gly Ile Phe Tyr Glu Phe Ala Ser Leu His Ser Phe Ile Asn Asn Gly
```

```
                770                 775                 780
Thr Asp Leu Ile Glu Lys Asn Ile Ser Ala Pro Leu Asp Lys Ile Pro
785                 790                 795                 800

Leu Phe Ile Glu Gly Gly His Ile Ile Thr Met Lys Asp Lys Tyr Arg
                805                 810                 815

Arg Ser Ser Met Leu Met Lys Asn Asp Pro Tyr Val Ile Val Ile Ala
                820                 825                 830

Pro Asp Thr Glu Gly Arg Ala Val Gly Asp Leu Tyr Val Asp Asp Gly
                835                 840                 845

Glu Thr Phe Gly Tyr Gln Arg Gly Glu Tyr Val Glu Thr Gln Phe Ile
                850                 855                 860

Phe Glu Asn Asn Thr Leu Lys Asn Val Arg Ser His Ile Pro Glu Asn
865                 870                 875                 880

Leu Thr Gly Ile His His Asn Thr Leu Arg Asn Thr Asn Ile Glu Lys
                885                 890                 895

Ile Ile Ile Ala Lys Asn Asn Leu Gln His Asn Ile Thr Leu Lys Asp
                900                 905                 910

Ser Ile Lys Val Lys Lys Asn Gly Glu Glu Ser Ser Leu Pro Thr Arg
                915                 920                 925

Ser Ser Tyr Glu Asn Asp Asn Lys Ile Thr Ile Leu Asn Leu Ser Leu
                930                 935                 940

Asp Ile Thr Glu Asp Trp Glu Val Ile Phe
945                 950

<210> SEQ ID NO 6
<211> LENGTH: 992
<212> TYPE: PRT
<213> ORGANISM: Aspergillus nidulans

<400> SEQUENCE: 6

Met Val Arg Phe Leu His Leu Ala Gly Thr Leu Pro Val Leu Ala Ser
1               5                   10                  15

Gly Ala Val Gln Asp Ala Leu Arg Pro Val Ala Glu Ser Ala Ala Thr
                20                  25                  30

Val Thr Ala Thr Ala Thr Val Ala Gly Gln Gln Ala Gln Phe Thr Leu
                35                  40                  45

Ser Asp Tyr Val Asp Val Gly Ala Asp Leu Ile Ala Asn Val Asp Asp
50                  55                  60

Pro Glu Ala Val Asn Ala Gln Ser Val Cys Pro Gly Tyr Lys Ala Ser
65                  70                  75                  80

Asp Ile Gln Gln Thr Asp Leu Gly Phe Thr Ala Ser Leu Arg Leu Ala
                85                  90                  95

Gly Glu Pro Cys Asn Val Tyr Gly Thr Asp Val Glu Ser Leu Thr Leu
                100                 105                 110

Glu Met Gln Tyr Gln Asp Thr Asp Arg Leu Asn Ile Gln Ile Thr Pro
                115                 120                 125

Thr Tyr Val Asp Ala Ser Asn Ala Ser Trp Tyr Ile Leu Pro Glu Glu
                130                 135                 140

Phe Val Pro Arg Pro Lys Pro Ala Ala Gly Ala Ser Glu Ser His Ser
145                 150                 155                 160

Asp Phe Ala Val Thr Trp Ser Asn Glu Pro Thr Phe Asn Phe Gln Val
                165                 170                 175

Thr Arg Lys Ser Thr Gly Glu Val Leu Phe Asp Thr Ala Gly Ser Val
                180                 185                 190
```

```
Leu Val Phe Glu Asn Gln Phe Ile Glu Phe Val Thr Ser Leu Pro Glu
            195                 200                 205

Glu Tyr Asn Leu Tyr Gly Leu Gly Glu Arg Ile Asn Gln Leu Arg Leu
        210                 215                 220

Leu Arg Asn Ala Thr Leu Thr Ser Tyr Ala Ala Asp Ile Gly Asn Pro
225                 230                 235                 240

Ile Asp Ala Asn Ile Tyr Gly Gln His Ala Phe Tyr Val Asp Thr Arg
                245                 250                 255

Tyr Phe Ser Val Asp Glu Ala Gly Lys His Thr Tyr Val Lys Ser Ser
            260                 265                 270

Glu Ala Asp Pro Ser Ala Thr Tyr Thr Ser Tyr Ser His Gly Val Phe
        275                 280                 285

Leu Arg Asn Ser His Gly His Glu Val Val Leu Asn Pro Gln Gly Leu
    290                 295                 300

Thr Trp Arg Thr Ile Gly Gly Ser Ile Asp Leu Thr Leu Tyr Ser Gly
305                 310                 315                 320

Pro Thr Val Ala Glu Val Thr Lys Gln Tyr Gln Arg Ser Thr Val Gly
                325                 330                 335

Leu Pro Ala Met Gln Lys Tyr Asp Thr Leu Gly Phe His Gln Cys Arg
            340                 345                 350

Trp Gly Tyr Asn Asn Trp Ser Val Phe Ala Asp Val Leu Ala Asn Phe
        355                 360                 365

Glu Lys Phe Glu Ile Pro Leu Glu Tyr Leu Trp Ala Asp Ile Asp Tyr
    370                 375                 380

Met His Gly Tyr Arg Asn Phe Glu Asn Asp Glu Tyr Arg Phe Pro Tyr
385                 390                 395                 400

Asn Glu Thr Lys Val Phe Leu Asp Lys Leu His Ala Gly Gly Arg His
                405                 410                 415

Phe Val Pro Ile Val Asp Ala Ala Leu Tyr Ile Pro Asn Pro Gln Asn
            420                 425                 430

Ala Ser Asp Ser Tyr Glu Thr Tyr Thr Arg Gly Ala Ala Arg Asp Val
        435                 440                 445

Phe Leu Lys Asn Pro Asp Gly Ser Leu Tyr Ile Gly Ala Val Trp Pro
450                 455                 460

Gly Tyr Thr Val Phe Pro Asp Trp His His Pro Asp Ala Ala Asp Phe
465                 470                 475                 480

Trp Ala Asn Glu Leu Val Thr Trp Tyr Glu Lys Val Lys Phe Asp Gly
                485                 490                 495

Val Trp Tyr Asp Met Ser Glu Val Ser Ser Phe Cys Val Gly Ser Cys
            500                 505                 510

Gly Ser Arg Asn Arg Thr Leu Asn Pro Val His Pro Pro Phe Arg Leu
        515                 520                 525

Pro Gly Glu Pro Gly Asn Val Asp Tyr Glu Tyr Pro Glu Gly Phe Glu
    530                 535                 540

Leu Ser Asn Ala Thr Glu Ala Ser Ala Ser Ala Ala Ser Ser Ser Ser
545                 550                 555                 560

Gln Ala Ala Thr Thr Ala Thr Glu Thr Thr Ser Thr Ser Ser Tyr
                565                 570                 575

Leu Arg Thr Ser Pro Thr Pro Gly Val Arg Asn Val Asn Tyr Pro Pro
            580                 585                 590

Tyr Val Ile Asn His Val Gln Thr Gly His Asp Leu Ala Val His Ala
        595                 600                 605

Val Ser Pro Asn Ala Thr His Val Asp Gly Tyr His Glu Tyr Asp Val
```

His Ser Leu Tyr Gly His Met Gly Ile Gln Ala Thr Tyr Arg Gly Leu
625                 630                 635                 640

Thr Gln Ile Ala Pro Arg Lys Arg Pro Phe Ile Ile Gly Arg Ser Thr
            645                 650                 655

Phe Ala Gly Ser Gly Lys Trp Ala Gly His Trp Gly Gly Asp Asn Tyr
        660                 665                 670

Ser Arg Trp Ser Ser Met Tyr Phe Ser Ile Ser Gln Ala Leu Gln Phe
            675                 680                 685

Ser Leu Tyr Gly Ile Pro Met Phe Gly Val Asp Thr Cys Gly Phe Ser
690                 695                 700

Gly Asn Thr Ala Glu Glu Leu Cys Asn Arg Trp Met Gln Leu Ser Ala
705                 710                 715                 720

Phe Phe Pro Phe Tyr Arg Asn His Asn Val Leu Gly Thr Ile Pro Gln
                725                 730                 735

Glu Pro Tyr Gln Trp Ala Ser Val Ile Asp Ala Thr Lys Lys Ala Met
            740                 745                 750

Arg Ile Arg Tyr Ala Leu Leu Pro Tyr Phe Tyr Thr Leu Met His Asp
        755                 760                 765

Ala His Thr Thr Gly Ser Thr Val Leu Arg Ala Leu Ala Trp Glu Phe
            770                 775                 780

Pro Asp Asp Pro Ser Leu Ala Ala Ile Asp Asn Gln Phe Leu Val Gly
785                 790                 795                 800

Pro Ser Ile Leu Val Thr Pro Val Leu Glu Pro Gln Val Ser Thr Val
                805                 810                 815

Lys Gly Val Phe Pro Gly Val Gly Gln Gly Glu Val Trp Tyr Asp Trp
            820                 825                 830

Tyr Thr Gln Thr Ala Val Asp Ala Gln Pro Gly Val Asn Thr Thr Ile
        835                 840                 845

Asp Ala Pro Leu Gly His Ile Pro Val Tyr Val Arg Gly Gly Ser Ile
850                 855                 860

Leu Pro Met Gln Glu Pro Ala Leu Thr Thr Arg Asp Ala Arg Lys Thr
865                 870                 875                 880

Pro Trp Ala Leu Leu Val Ala Leu Gly Lys Asp Gly Thr Ala Ser Gly
                885                 890                 895

His Leu Tyr Leu Asp Asp Gly Glu Ser Ile His Pro Lys Val Ser Leu
            900                 905                 910

Asn Val Lys Phe Arg Ala Thr Gln Thr Ala Leu Thr Val Ser Ser Glu
        915                 920                 925

Gly Glu Trp Lys Glu Ala Asn Pro Leu Ala Asn Val Thr Ile Leu Gly
            930                 935                 940

Val Leu Glu Asn Pro Val Ser Val Thr Ser Asn Gly Gln Gln Val Pro
945                 950                 955                 960

Ala Glu Tyr Asp Ala Gln Ser Arg Ile Leu Val Ile Thr Gly Leu Asn
                965                 970                 975

Gln Phe Thr Asn Asn Gly Ala Trp Gly Gln Asp Trp Thr Leu Arg Trp
            980                 985                 990

<210> SEQ ID NO 7
<211> LENGTH: 955
<212> TYPE: PRT
<213> ORGANISM: Aspergillus nidulans

<400> SEQUENCE: 7

```
Met Arg Phe Gln Gln Leu Leu Pro Trp Ala Ala Leu Thr Gly Cys
 1               5                  10                  15

Val Val Ala Gln Ser Gln Ala Gly Val Asp Pro Leu Asp Arg Pro Gly
            20                  25                  30

Asn Asp Leu Tyr Val Lys Asp Leu Ser Asn Cys Thr Gly Tyr Lys Val
            35                  40                  45

Thr Lys His Trp Lys Thr Arg Ser Gly Phe Tyr Ala Asp Leu Ala Leu
 50                  55                  60

Ala Gly Pro Ala Cys Asn Val Tyr Gly Ile Asp Leu Pro Lys Leu Lys
 65                  70                  75                  80

Leu Glu Val Glu Tyr Gln Thr Asp Glu Arg Leu His Val Lys Ile Leu
                85                  90                  95

Asp Thr Asn Asn Thr Val Tyr Gln Val Pro Asp Ser Val Phe Pro Arg
            100                 105                 110

Pro Gly Phe Gly Gln Trp Cys Ser Pro Lys Asn Ser Lys Leu Lys Phe
            115                 120                 125

Asp Phe Lys Pro Asp Pro Phe Ser Phe Thr Val Ser Arg Thr Asp Thr
            130                 135                 140

Gly Glu Val Leu Phe Asp Thr Thr Gly Thr Lys Leu Val Phe Glu Asn
145                 150                 155                 160

Gln Tyr Leu Tyr Leu Lys Thr His Leu Pro Gln Asn Pro His Leu Tyr
                165                 170                 175

Gly Leu Gly Glu His Ser Asp Ser Phe Met Leu Asn Thr Thr Asn Tyr
            180                 185                 190

Thr Arg Thr Ile Tyr Thr Arg Asp Ala Tyr Gly Thr Pro Gln Gly Gln
            195                 200                 205

Asn Leu Tyr Gly Ala His Pro Ile Tyr Phe Asp His Arg Gln Asp Gly
            210                 215                 220

Thr His Gly Val Phe Leu Leu Asn Ser Asn Gly Met Asp Ile Tyr Ile
225                 230                 235                 240

Asp Asn Glu Gly Gly Gln Phe Leu Glu Tyr Asn Ile Ile Gly Gly Val
                245                 250                 255

Phe Asp Phe Tyr Phe Ile Ala Gly Pro Ser Pro Gln Asp Val Ala Arg
            260                 265                 270

Gln Tyr Ala Glu Ile Val Gln Pro Pro Leu Met Val Pro Tyr Trp Gly
            275                 280                 285

Leu Gly Phe His Gln Cys Arg Tyr Gly Tyr Gln Asp Val Tyr Glu Val
            290                 295                 300

Ala Ala Val Thr Ala Asn Tyr Ser Val His Asp Ile Pro Leu Glu Thr
305                 310                 315                 320

Ile Trp Thr Asp Ile Asp Tyr Met Asp Arg Arg Ile Phe Thr Leu
                325                 330                 335

Asp Pro Glu Arg Phe Pro Pro Glu Leu Val Lys Asp Leu Val Asp Thr
            340                 345                 350

Leu His Ala Arg Asp Gln His Tyr Ile Val Met Val Asp Pro Ala Val
            355                 360                 365

Tyr Tyr Ser Glu Pro Asn Pro Ala Leu Asp Ala Gly Leu Lys Tyr Asp
            370                 375                 380

Ala Phe Met Lys Glu Leu Asn Gly Thr His Tyr Gln Gly Val Val Trp
385                 390                 395                 400

Ala Gly Pro Ser Tyr Phe Pro Asp Trp Phe His Pro Asn Ala Gln Glu
            405                 410                 415

Tyr Trp Thr Glu Gln Phe Leu Asn Phe Phe Asp Gly Val Asn Gly Pro
```

-continued

```
                420             425             430
Asp Ile Asp Ala Leu Trp Ile Asp Met Asn Glu Pro Ala Asn Phe Tyr
            435             440             445

Asn Arg Pro Tyr Pro Gly Asn Asn Thr Thr Pro Glu Glu Phe Ala Glu
450             455             460

Ala Asn Asp Asn Pro Glu Pro Pro Ala Val Arg Asp Gly Pro Asp
465             470             475             480

Ala Pro Ile Pro Gly Phe Pro Asp Ser Leu Gln Pro Asn Phe Ala Ser
            485             490             495

Gly Gln Thr Asn Glu Lys Arg Ala Val Val Thr Val Glu Arg Arg Ala
            500             505             510

Arg Ser Gln Ser His Arg Gln Leu Gly Ala Gly Arg Trp Arg Ser Ala
            515             520             525

Val Arg His Trp Pro Arg Asp Pro Lys Ala Gly Trp Gln His Gly Arg
            530             535             540

Lys Ser Gly Ser Gly Cys Gly Pro His Glu Cys Arg Gly Leu Pro Asn
545             550             555             560

Arg Glu Leu Ile Arg Pro Pro Tyr Met Ile Gln Asn Gly Ala Gly Pro
                565             570             575

Thr Leu Ala Asp Asn Thr Ala Asp Thr Asp Ile Val Gln Ser Gly Gly
                580             585             590

Tyr Val Gln Tyr Asp Thr His Ser Leu Tyr Gly Ala Met Met Ser Thr
            595             600             605

His Ser His Asn Ala Met Arg Ala Arg Arg Pro Asp Asp Arg Ala Leu
            610             615             620

Val Ile Thr Arg Ser Thr Phe Ala Gly Ser Gly Lys Asp Val Ser His
625             630             635             640

Trp Leu Gly Asp Asn Ile Ser Asp Trp Leu Ser Tyr Arg Leu Ser Ile
                645             650             655

Ser Gln Ile Leu Gln Phe Ala Ser Leu Tyr Gln Ile Pro Val Val Gly
                660             665             670

Pro Asp Val Cys Gly Phe Gly Gly Asn Val Thr Glu Thr Leu Cys Ala
            675             680             685

Arg Trp Ala Thr Leu Gly Ser Phe Tyr Thr Phe Arg Asn His Ala
            690             695             700

Glu Ile Phe Ala Asn Pro Gln Glu Phe Tyr Arg Trp Pro Ile Val Ala
705             710             715             720

Glu Ala Ala Arg Asn Gly Ile Ala Ile Arg Tyr Gln Leu Leu Asp Tyr
                725             730             735

Ile Tyr Thr Ala Ile Tyr Lys Gln Thr Gln Thr Gly Thr Pro Ser Leu
            740             745             750

Asn Pro Leu Phe Phe Asn Tyr Pro Phe Asp Gln Asn Thr Tyr Gly Ile
            755             760             765

Asp Leu Gln Phe Phe Tyr Gly Pro Gly Ile Leu Val Ser Pro Val Thr
770             775             780

Glu Glu Asn Ser Thr Ser Val Ser Tyr Tyr Leu Pro Asp Asp Ile Phe
785             790             795             800

Tyr Glu Trp Gly Thr Gly Lys Pro Val Arg Gly His Gly Glu Tyr Val
            805             810             815

Ser Ala Glu Val Asp Val Thr His Ile Thr Val His Tyr Lys Gly Gly
            820             825             830

Leu Val Tyr Pro Gln Arg Ile Glu Ser Ala Asn Thr Thr Ala Leu
835             840             845
```

Arg Gln Lys Gly Phe Asn Ile Val Ile Ala Pro Gly Leu Asp Gly Ser
            850                 855                 860

Ala His Gly Glu Leu Tyr Leu Asp Asp Gly Leu Ser Gln Val Gln Asp
865                 870                 875                 880

Lys Val Ser Glu Ile Asp Phe Ser Tyr Val Asp Gly Val Phe Glu Met
                885                 890                 895

Lys Gly Ser Phe Glu Tyr Asp Pro Gly Val Gly Ile Glu Arg Ile Thr
            900                 905                 910

Ile Leu Gly Val Gly Ala Lys Pro Glu Val Ala Ala Glu Asp Ala Glu
                915                 920                 925

Val Glu Tyr Asp Glu Glu Asn Gln Lys Leu Val Leu His Val Asp Val
            930                 935                 940

Pro Leu Thr Arg Lys Ser Ser Ile Lys Ile Ala
945                 950                 955

<210> SEQ ID NO 8
<211> LENGTH: 864
<212> TYPE: PRT
<213> ORGANISM: Mucor javanicus

<400> SEQUENCE: 8

Met Ala Lys Val Ser Phe Ile Phe Val Ala Ile Ala Leu Ile Thr Gly
1               5                   10                  15

Asn Val Leu Cys Gln Thr Asp Ala Thr Tyr Ala Val Ser Ser Ser Ala
                20                  25                  30

Pro Gly Tyr Lys Ile Asp Gly His Val Arg Lys Thr Glu Ala Gly Leu
            35                  40                  45

His Ile Pro Leu Thr Leu Asn Ser Arg Gly Asn Lys Lys Thr Gly Ile
        50                  55                  60

Asp Thr Phe Gly Lys Thr Ile Lys Asp Ile Thr Val Asp Val Glu Tyr
65                  70                  75                  80

Glu Thr Glu Glu Arg Leu His Val Lys Ile Ser Asp Lys Ala Lys Lys
                85                  90                  95

Gln Tyr Leu Val Pro Asp Ser Pro Leu Gly Phe Glu Arg Pro Gln Ile
            100                 105                 110

Lys His Tyr Val Ser Pro Lys His Ser Asn Leu Asp Phe Gln Tyr Thr
        115                 120                 125

Ala Lys Pro Phe Ser Phe Lys Val Val Arg Lys Asp Asp Lys Thr Thr
    130                 135                 140

Ile Phe Asp Thr Thr Asn Met Pro Leu Val Phe Glu Asp Gln Tyr Leu
145                 150                 155                 160

Glu Leu Ser Thr Lys Val Pro Glu Asp Ala Asn Ile Tyr Gly Ile Gly
                165                 170                 175

Glu Val Thr Ala Pro Phe Arg Arg Thr His Asn Val Thr Thr Leu Trp
            180                 185                 190

Ala Arg Asp Asn Pro Asp Asp Phe Tyr Arg Asn Ile Tyr Gly Ala His
        195                 200                 205

Pro Tyr Tyr Gln Glu Val Arg Asp Gly Lys Ala His Gly Ala Leu Leu
    210                 215                 220

Met Asn Ala His Gly Met Asp Val Ile Thr Thr Glu Gly Arg Ile Thr
225                 230                 235                 240

Tyr Lys Val Ile Gly Gly Ile Leu Asp Phe Tyr Phe Phe Ala Pro Lys
                245                 250                 255

Ser Gly Lys Pro Asn Asp Leu Ser Ile Ala Tyr Thr Asp Leu Ile Gly

```
            260                 265                 270
Lys Pro Met Met Pro Ser His Trp Met Leu Gly Trp His His Cys Arg
        275                 280                 285
Tyr Gly Tyr Pro Asn Ile Asp Lys Val Glu Thr Val Lys Arg Lys Tyr
        290                 295                 300
Lys Glu Ala Asn Ile Pro Leu Gln Thr Val Trp Val Asp Ile Asp Tyr
305                 310                 315                 320
Met Glu Glu Thr Lys Asp Phe Thr Phe Asp Lys Val Asn Phe Pro Gln
                325                 330                 335
Asp Arg Met Ile Gly Leu Gly Glu Gln Leu His Lys Asp Gly Gln Asn
                340                 345                 350
Tyr Val Val Met Val Asp Pro Ala Ile Ser Ala Asn Thr Thr Tyr Glu
            355                 360                 365
Pro Tyr Val Arg Gly Thr Glu Met Asp Val Trp Ile Lys Asn Ala Asp
        370                 375                 380
Gly Ser Asp Phe Ile Gly Ser Val Trp Pro Gly Phe Thr Thr Phe Pro
385                 390                 395                 400
Asp Trp Trp His Pro Asn Ala Thr Lys Tyr Trp Asn Lys Glu Ile Ile
                405                 410                 415
Asp Phe Val Asp Met Leu Gly Val Asp Gly Leu Trp Ile Asp Met Asn
                420                 425                 430
Glu Pro Ala Ser Phe Cys Leu Gly Ser Cys Gly Ser Gly Lys Val Asp
                435                 440                 445
Ala Gly Asn Gln Pro Tyr Arg Trp Thr Tyr Thr Glu Glu Gln Ala
        450                 455                 460
Ala Asn His Thr Arg Trp Glu Lys Glu Leu Lys Ala Met Gly Asn Pro
465                 470                 475                 480
Pro Gly Glu Glu Arg Asn Leu Leu Tyr Pro Lys Tyr Ala Ile Asn Asn
                485                 490                 495
Gly Ala Gly Asn Leu Ser Glu Phe Thr Val Ala Thr Thr Ala Leu His
                500                 505                 510
Tyr Gly Asn Ile Pro His Tyr Asp Ile His Asn Leu Tyr Gly His Ala
            515                 520                 525
Glu Ser His Ile Thr Arg Gln Ala Leu Ile Lys His Lys Asn Lys Ile
        530                 535                 540
Arg Pro Phe Val Leu Thr Arg Ser Ser Phe Pro Gly Ser Gly Lys Ser
545                 550                 555                 560
Val Gly His Trp Thr Gly Asp Asn His Ser Phe Trp Pro Tyr Leu Lys
                565                 570                 575
Asn Ser Ile Ala Asn Ile Leu Asn Phe Gln Met Phe Gly Val Ser Tyr
                580                 585                 590
Ser Gly Ala Asp Val Cys Gly Phe Asn Ser Asp Thr Thr Glu Glu Leu
            595                 600                 605
Cys Thr Arg Trp Met Glu Ile Gly Ala Phe Tyr Pro Phe Ala Arg Asn
        610                 615                 620
His Asn Asn Asn Ala Ala Lys Asp Gln Glu Pro Tyr Leu Trp Glu Ser
625                 630                 635                 640
Thr Ala Glu Ala Ser Arg Ile Ala Ile Asn Thr Arg Tyr Glu Met Leu
                645                 650                 655
Pro Tyr Phe Tyr Thr Leu Phe Glu Glu Ser Asn Arg Leu Gly Leu Gly
                660                 665                 670
Val Trp Arg Pro Leu Ile Phe Glu Tyr Pro Ala Tyr Glu Glu Leu Val
            675                 680                 685
```

Ser Asn Asp Val Gln Thr Leu Val Gly Ser Asp Ile Leu Ser Pro
    690                 695                 700

Val Leu Asp Glu Gly Lys Thr Ser Val Lys Ala Gln Phe Pro Gly Gly
705                 710                 715                 720

Gln Trp Tyr Asp Trp Tyr Thr His Glu Leu Thr Val Asp Asn Lys Ser
                725                 730                 735

Asn Lys Lys Val Lys Thr Val Thr Leu Asp Ala Pro Leu Thr His Ile
            740                 745                 750

Pro Ile His Ile Arg Gly Gly Ala Ile Pro Thr Lys Thr Pro Lys
        755                 760                 765

Tyr Thr Val Gly Glu Thr Phe Ala Thr Pro Tyr Asn Leu Val Ile Ala
770                 775                 780

Leu Asp Lys Lys Gly Gln Ala Ser Gly Arg Leu Tyr Ile Asp Asp Gly
785                 790                 795                 800

Glu Ser Leu Glu Val Lys Ser Ser Gly Tyr His Phe His Leu Gln
                805                 810                 815

Glu Trp Ser Pro Gln Gly Phe Trp Gln Val Trp Leu Gln Glu Gly Arg
                820                 825                 830

Lys Asp Trp Leu His His Tyr Trp Gln Ala Arg Gln Gln Val Ala
        835                 840                 845

Lys Gly Ser Arg Trp Gln Glu Asp Tyr Gln Ile Asp Pro Trp Gln Glu
    850                 855                 860

<210> SEQ ID NO 9
<211> LENGTH: 985
<212> TYPE: PRT
<213> ORGANISM: Aspergillus oryzae

<400> SEQUENCE: 9

Met Ala Gly Leu Lys Ser Phe Leu Ala Ser Ser Trp Leu Leu Pro Val
1               5                   10                  15

Ala Cys Gly Ala Ser Gln Ser Ile Val Pro Ser Thr Ser Ala Thr Ala
            20                  25                  30

Ala Tyr Ser Gln Phe Thr Ile Pro Ala Ser Ala Asp Val Gly Ala Asn
        35                  40                  45

Leu Val Ala Asn Ile Asp Asp Pro Gln Ala Val Asn Ala Gln Ser Val
50                  55                  60

Cys Pro Gly Tyr Lys Ala Ser Asp Val Lys His Ser Ser Gln Gly Phe
65                  70                  75                  80

Thr Ala Ser Leu Glu Leu Ala Gly Asp Pro Cys Asn Val Tyr Gly Thr
                85                  90                  95

Asp Val Asp Ser Leu Thr Leu Thr Val Glu Tyr Gln Ala Lys Asp Arg
            100                 105                 110

Leu Asn Ile Gln Ile Val Pro Thr Tyr Phe Asp Ala Ser Asn Ala Ser
        115                 120                 125

Trp Tyr Ile Leu Ser Glu Glu Leu Val Pro Arg Pro Lys Ala Ser Gln
    130                 135                 140

Asn Ala Ser Val Pro Gln Ser Asp Phe Val Val Ser Trp Ser Asn Glu
145                 150                 155                 160

Pro Ser Phe Asn Phe Lys Val Ile Arg Lys Ala Thr Gly Asp Val Leu
                165                 170                 175

Phe Asn Thr Lys Gly Ser Thr Leu Val Tyr Glu Asn Gln Phe Ile Glu
            180                 185                 190

Phe Val Thr Leu Leu Pro Glu Glu Tyr Asn Leu Tyr Gly Leu Gly Glu

-continued

```
            195                 200                 205
Arg Met Asn Gln Leu Arg Leu Leu Glu Asn Ala Asn Leu Thr Leu Tyr
    210                 215                 220

Ala Ala Asp Ile Ala Asp Pro Ile Asp Asp Asn Ile Tyr Gly His His
225                 230                 235                 240

Ala Phe Tyr Leu Asp Thr Arg Tyr Tyr Lys Val Gly Gly Gln Asn Lys
                245                 250                 255

Ser His Thr Ile Val Lys Ser Ser Glu Ala Glu Pro Ser Gln Glu Tyr
                260                 265                 270

Val Ser Tyr Ser His Gly Val Phe Leu Arg Asn Ala His Gly Gln Glu
                275                 280                 285

Ile Leu Leu Arg Asp Gln Lys Leu Ile Trp Arg Thr Leu Gly Gly Ser
    290                 295                 300

Val Asp Leu Thr Phe Tyr Ser Gly Pro Thr Gln Ala Glu Val Thr Lys
305                 310                 315                 320

Gln Tyr Gln Leu Ser Thr Val Gly Leu Pro Ala Met Gln Gln Tyr Asn
                325                 330                 335

Thr Leu Gly Phe His Gln Cys Arg Trp Gly Tyr Asn Asn Trp Ser Glu
                340                 345                 350

Phe Glu Asp Val Leu Ala Asn Phe Glu Arg Phe Glu Ile Pro Leu Glu
                355                 360                 365

Tyr Leu Trp Ala Asp Ile Asp Tyr Met His Gly Tyr Arg Asn Phe Asp
    370                 375                 380

Asn Asp Gln His Arg Phe Ser Tyr Glu Glu Gly Glu Lys Phe Leu Asn
385                 390                 395                 400

Lys Leu His Ala Gly Gly Arg Arg Trp Val Pro Ile Val Asp Gly Ala
                405                 410                 415

Leu Tyr Ile Pro Asn Pro Glu Asn Ala Ser Asp Ala Tyr Glu Thr Tyr
                420                 425                 430

Asp Arg Gly Ala Lys Asp Asp Val Phe Ile Lys Asn Pro Asp Gly Ser
                435                 440                 445

Leu Tyr Ile Gly Ala Val Trp Pro Gly Tyr Thr Val Tyr Pro Asp Trp
    450                 455                 460

His His Pro Lys Ala Ser Asp Phe Trp Ala Asn Glu Leu Val Thr Trp
465                 470                 475                 480

Trp Asn Lys Leu His Tyr Asp Gly Val Trp Tyr Asp Met Ala Glu Val
                485                 490                 495

Ser Ser Phe Cys Val Gly Ser Cys Gly Thr Gly Asn Leu Ser Met Asn
                500                 505                 510

Pro Ala His Pro Pro Phe Ala Leu Pro Gly Glu Pro Gly Asn Val Val
                515                 520                 525

Tyr Asp Tyr Pro Glu Gly Phe Asn Ile Thr Asn Ala Thr Glu Ala Ala
    530                 535                 540

Ser Ala Ser Ala Gly Ala Ala Ser Gln Ser Ala Ala Ala Ser Ser Thr
545                 550                 555                 560

Thr Thr Ser Ala Pro Tyr Leu Arg Thr Thr Pro Thr Pro Gly Val Arg
                565                 570                 575

Asn Val Asp His Pro Pro Tyr Val Ile Asn His Val Gln Pro Gly His
                580                 585                 590

Asp Leu Ser Val His Ala Ile Ser Pro Asn Ser Thr His Ser Asp Gly
    595                 600                 605

Val Gln Glu Tyr Asp Val His Ser Leu Tyr Gly His Gln Gly Ile Asn
    610                 615                 620
```

Ala Thr Tyr His Gly Leu Leu Lys Val Trp Glu Asn Lys Arg Pro Phe
625                 630                 635                 640

Ile Ile Ala Arg Ser Thr Phe Ser Gly Ser Lys Trp Ala Gly His
            645                 650                 655

Trp Gly Gly Asp Asn Phe Ser Lys Trp Gly Ser Met Phe Phe Ser Ile
                660                 665                 670

Ser Gln Ala Leu Gln Phe Ser Leu Phe Gly Ile Pro Met Phe Gly Val
            675                 680                 685

Asp Thr Cys Gly Phe Asn Gly Asn Thr Asp Glu Glu Leu Cys Asn Arg
690                 695                 700

Trp Met Gln Leu Ser Ala Phe Phe Pro Phe Tyr Arg Asn His Asn Val
705                 710                 715                 720

Leu Ser Ala Ile Pro Gln Glu Pro Tyr Arg Trp Ala Ser Val Ile Asp
                725                 730                 735

Ala Thr Lys Ala Ala Met Asn Ile Arg Tyr Ala Ile Leu Pro Tyr Phe
            740                 745                 750

Tyr Thr Leu Phe His Leu Ala His Thr Thr Gly Ser Thr Val Met Arg
            755                 760                 765

Ala Leu Ala Trp Glu Phe Pro Asn Asp Pro Ser Leu Ala Ala Val Gly
770                 775                 780

Thr Gln Phe Leu Val Gly Pro Ser Val Met Val Ile Pro Val Leu Glu
785                 790                 795                 800

Pro Gln Val Asp Thr Val Gln Gly Val Phe Pro Gly Val Gly His Gly
                805                 810                 815

Glu Val Trp Tyr Asp Trp Tyr Ser Gln Thr Ala Val Asp Ala Lys Pro
                820                 825                 830

Gly Val Asn Thr Thr Ile Ser Ala Pro Leu Gly His Ile Pro Val Phe
            835                 840                 845

Val Arg Gly Gly Ser Ile Leu Pro Met Gln Glu Val Ala Leu Thr Thr
850                 855                 860

Arg Asp Ala Arg Lys Thr Pro Trp Ser Leu Leu Ala Ser Leu Ser Ser
865                 870                 875                 880

Asn Gly Thr Ala Ser Gly Gln Leu Tyr Leu Asp Asp Gly Glu Ser Val
            885                 890                 895

Tyr Pro Glu Asp Thr Leu Ser Val Asp Phe Leu Ala Ser Arg Ser Thr
            900                 905                 910

Leu Arg Ala Ser Ala Arg Gly Thr Trp Lys Glu Ala Asn Pro Leu Ala
            915                 920                 925

Asn Val Thr Val Leu Gly Val Thr Glu Lys Pro Ser Ser Val Thr Leu
            930                 935                 940

Asn Gly Glu Thr Leu Ser Ser Asp Ser Val Lys Tyr Asn Ala Thr Ser
945                 950                 955                 960

His Val Leu His Val Gly Gly Leu Gln Lys Thr Ala Asp Gly Ala
            965                 970                 975

Trp Ala Lys Asp Trp Val Leu Lys Trp
            980                 985

<210> SEQ ID NO 10
<211> LENGTH: 1053
<212> TYPE: PRT
<213> ORGANISM: Mortierella alliacea

<400> SEQUENCE: 10

Met Thr Lys Arg Thr Thr Ala Pro Arg Ala Pro Leu Val Leu Leu Ala

-continued

```
1               5                   10                  15
Ala Thr Ala Leu Ala Ile Leu Ala Ala Gly Ala Pro Ser Gly Ile Pro
            20                  25                  30

Ser Asn Ser Ser Gln Ile Ala Pro Leu Ala Val Asp Asp Met Cys Ser
            35                  40                  45

Asn Val Gln Thr Arg Lys Asp Cys Gly Tyr Leu Gly Val Asp Lys Asp
    50                  55                  60

Gly Cys Asp Gln Arg Gln Cys Cys Trp Ala Glu Ser Lys Asp Pro Ile
65                  70                  75                  80

Pro Trp Cys Phe Gln Lys Glu Asn Lys Glu Tyr Ala Cys Ser Thr Asp
                85                  90                  95

Met Ala Ala Arg Arg Asp Arg Gly Phe Leu Gly Ile Thr Asp Gln Gln
            100                 105                 110

Cys Arg Glu Arg Asn Cys Cys Trp Asp Ser Thr Pro Asn Lys Leu Asn
            115                 120                 125

Ala Pro Tyr Cys Phe Ile Gln Gln His Ala Cys Gln Gly Tyr Gln Val
            130                 135                 140

Lys Ala Ala Gln Gly Thr Ala Asn Gly Val Asn Leu Asp Leu Glu Leu
145                 150                 155                 160

Leu Gly Gly Cys Ala Arg Phe Gly Lys Asp Ile Ala Arg Leu Thr Val
                165                 170                 175

Asn Val Asp Phe Glu Thr Glu Ser Arg Ile Arg Val Lys Ile Thr Asp
            180                 185                 190

Lys Asp Lys Gln Arg Tyr Glu Val Pro Lys Glu Ala Leu Pro Ser Thr
            195                 200                 205

Glu Ser Thr Ile Arg Arg Gly Glu Lys Arg Gly Tyr Glu Phe Lys Tyr
210                 215                 220

Ala Lys Asn Pro Phe Thr Phe Ser Ile Lys Arg Ile Ser Asp Gly Glu
225                 230                 235                 240

Val Leu Phe Asp Ser Ala Val Ala Gly Met Asp Ser Leu Val Phe Glu
            245                 250                 255

Asp Glu Tyr Leu Glu Ile Ser Ser Val Val Pro Ala Asp Ala Asn Ile
            260                 265                 270

Tyr Gly Leu Gly Glu Val Val Ser Ser Phe Arg Arg Asp Pro Gly Asn
            275                 280                 285

Thr Arg Arg Thr Met Trp Ala Arg Asp Ala Pro Thr Pro Val Asp Gln
290                 295                 300

Asn Leu Tyr Gly Ser His Pro Phe His Leu Glu Met Arg Lys Gly Ala
305                 310                 315                 320

Ala His Gly Val Phe Leu Arg Asn Ser Asn Gly Met Asp Val Ile Leu
            325                 330                 335

Thr Pro Lys Lys Val Thr Tyr Lys Thr Ile Gly Ile Gly Leu Asp Phe
            340                 345                 350

Thr Val Phe Val Gly Pro Lys Pro Glu Glu Val Ile Asn Gln Tyr Thr
            355                 360                 365

Glu Val Ile Gly Arg Pro His Met Pro Pro Ala Trp Ala Leu Gly Trp
            370                 375                 380

His Gln Ser Arg Tyr Gly Tyr Lys Thr Ile Asp Ala Val Glu Ala Thr
385                 390                 395                 400

Val Gln Arg Tyr Lys Lys Glu Gly Leu Pro Leu Asp Gly Met Trp Ile
            405                 410                 415

Asp Ile Asp Tyr Met Asp Arg Phe Arg Asp Phe Thr Tyr Asp Glu Ala
            420                 425                 430
```

```
Arg Phe Pro Gln Ser Arg Met Lys Ala Leu Ala Ala Asn Leu Ala Ser
            435                 440                 445

Ser Asn Gln Ser Met Val Leu Ile Ile Asp Pro Gly Ile Pro Ile Ala
    450                 455                 460

Pro Gly Tyr Glu Pro Tyr Asp Ser Gly Met Arg Asp Gly Val Phe Ile
465                 470                 475                 480

Lys Thr Leu Gln Gly Gln Pro Ile Glu Gly Arg Val Trp Pro Gly Gln
                485                 490                 495

Thr Tyr Phe Pro Asp Phe Met Asn Thr Lys Glu Thr Trp Ala Tyr Trp
            500                 505                 510

Glu Arg Gln Leu Lys Lys Thr Arg Asp Asp Ile Gly Ala Asn Val Tyr
            515                 520                 525

Pro Trp Ile Asp Met Asn Glu Pro Ser Asn Phe Cys Asn Gly Pro Cys
530                 535                 540

Thr Lys Asp Gly Ala Ser Ala Ser Ala Leu Asp Asp Ala Ser Glu Lys
545                 550                 555                 560

Gln Lys Phe Ala Lys Arg Asp Val Ala Ala Ser Ala Ser Thr Ser Ile
                565                 570                 575

Lys Tyr Ser Ile Asn Asn Ala Gly Arg Gln Ala Pro Leu Asp Glu Lys
            580                 585                 590

Thr Leu Ala Thr Asn Ala Val Ser Lys Asn Gly Met Leu Leu Thr Asp
            595                 600                 605

Thr His Asn Leu Tyr Gly His Met Glu Ser Ala Ala Thr His Asp Ala
    610                 615                 620

Leu Leu Asn Ile Asp Pro Asn Thr Arg Pro Phe Ile Leu Thr Arg Ser
625                 630                 635                 640

Ser Phe Pro Gly Thr Gly Ala Tyr Ala Ala His Trp Thr Gly Asp Asn
                645                 650                 655

Trp Ser Gln Trp Glu His Leu Lys Tyr Ser Ile Ser Gly Val Leu Ser
            660                 665                 670

Phe Gly Leu Phe Gly Met Pro Phe Thr Gly Ser Asp Ile Cys Gly Phe
            675                 680                 685

Asn Gly Asn Ala Gln Glu Glu Leu Cys Leu Arg Trp His Gln Leu Gly
    690                 695                 700

Ala Leu Tyr Pro Phe Ala Arg Asn His Asn Asp Ile Lys Gly Ser Asp
705                 710                 715                 720

Gln Glu Pro Tyr Val Trp Pro Asn Thr Val Leu Pro Ala Ala Lys Lys
                725                 730                 735

Ala Leu Glu Ile Arg Tyr Ser Leu Met Pro Tyr Phe Tyr Ser Leu Phe
            740                 745                 750

Glu Gln Ala His Lys Thr Gly Lys Pro Val Trp Gln Pro Leu Phe Phe
            755                 760                 765

Gln Tyr Pro Gln Asp Ala Gln Ala Leu Lys Ile Asp Ser Gln Phe Leu
    770                 775                 780

Leu Gly Asp Gly Ile Leu Val Ser Pro Ser Leu Thr Ala Gly Glu Val
785                 790                 795                 800

Gln Val Lys Ala Tyr Phe Pro Gly Asn Gly Arg Trp Phe Asp Leu Trp
                805                 810                 815

Thr His Glu Val Val Met Glu Ala Gly Ala Ser Asn Arg Tyr Ala Ser
            820                 825                 830

Leu Lys Ala Asn Ala Gln Ser Asp Ser Ile Pro Met Ser Leu Ala Gly
            835                 840                 845
```

Gly His Met Val Pro Ile Gln Lys Pro Gly Leu Thr Val Ala Glu Thr
850                 855                 860

Arg Ala Asn Pro Val Ser Leu Val Ile Ala Leu Asp Gly Ser Gly Ala
865                 870                 875                 880

Ala Lys Gly Glu Met Phe Val Asp Asp Gly Lys Ser Val Lys Thr Asp
                885                 890                 895

Asn Gln Ala His Ile Thr Phe Ala Met Thr Ala Gly Gln Lys Leu Val
                900                 905                 910

Ser Asn Val Thr Ser Ala Val Gln Ala Gln Gln Leu Lys Ala Gly Leu
            915                 920                 925

Gly Gly Lys His Gly Asp Arg Ile Glu Lys Ile Val Val Met Gly Leu
930                 935                 940

Asn Phe Gly Lys Ala Ala Ser Ala Glu Pro Lys Asn Val Lys Val Ser
945                 950                 955                 960

Lys Arg Gly Asp Lys Val Arg Asp Ile Val His Val Ser Lys Gly His
                965                 970                 975

Val Thr Val Ser Thr Thr Ala Ala Ala Ala Ala Lys Val Ser Lys
                980                 985                 990

Phe Ser Ser Leu Asn Ile Asn Gly Val Glu Met Ala Phe Gly Ala Ser
            995                 1000                1005

Asn Leu Asp Arg Ser Lys Gly Gln Asp Pro Ala Ser Gly Leu Ala
      1010                1015                1020

Trp Glu Val Asn Gln Glu Lys Gly Ser Leu Thr Leu Thr Gly Leu
      1025                1030                1035

Gln Met Asn Leu Phe Glu Ser Trp Phe Ile Asn Trp Lys Met Glu
      1040                1045                1050

<210> SEQ ID NO 11
<211> LENGTH: 969
<212> TYPE: PRT
<213> ORGANISM: Schizosaccharomyces pombe

<400> SEQUENCE: 11

Met Met Ile Ser Thr Ala Tyr Gln Ser Leu Phe Leu Thr Ala Leu Phe
1               5                   10                  15

Ser Ala Ile Ser Ile Ala Val Gly Asn Val Tyr Gln Thr Leu Asn Val
                20                  25                  30

Ile Gly Asp Arg Asn Val Thr Ile Pro Thr Asn Gly Ile Pro Gln Arg
            35                  40                  45

Leu Ser Val Tyr Asp Pro Tyr Arg Gly Val Asn Cys Gln Gly Tyr Gln
50                  55                  60

Ala Val Asn Ile Ser Glu Ser Gln Asn Gly Val Thr Ala Tyr Leu Ala
65                  70                  75                  80

Leu Leu Gly Glu Pro Cys Tyr Ala Tyr Gly Thr Asp Tyr Pro Leu Leu
                85                  90                  95

Phe Leu Asn Val Thr Tyr Glu Glu Ala Asp Arg Val His Ile Ser Ile
                100                 105                 110

Lys Asp Ala Asn Asn Thr Gln Phe Gln Phe Thr Ser Arg Lys Asp Leu
            115                 120                 125

Trp Asp Ala Pro Leu Tyr Ser Pro Ser Tyr Asn Thr Asn Leu Leu
130                 135                 140

Tyr Asn Phe Ser Tyr Asn Ala Asn Pro Phe Glu Phe Trp Val Thr Arg
145                 150                 155                 160

Lys Ser Asp Gly Glu Val Leu Phe Asp Thr Arg Gly Gln Lys Leu Val
                165                 170                 175

```
Phe Glu Asp Gln Tyr Ile Glu Leu Thr Thr Asn Met Val Glu Asn Tyr
                180                 185                 190

Asn Leu Tyr Gly Leu Ala Glu Thr Ile His Gly Leu Arg Leu Gly Asn
            195                 200                 205

Asn Leu Thr Arg Thr Phe Trp Ala Asn Asp Glu Ala Ser Pro Val Asp
210                 215                 220

Gln Asn Met Tyr Gly Ser His Pro Tyr Leu Glu Gln Arg Tyr Lys
225                 230                 235                 240

Ala Asp Gly Ile Asn Ser Thr Leu Asn Glu Thr Thr Tyr Thr Ser Ser
                245                 250                 255

Ser His Gly Val Leu Met Leu Thr Ala Asn Gly Met Asp Val Leu Leu
                260                 265                 270

Arg Gln Asp Tyr Leu Gln Tyr Arg Met Ile Gly Gly Val Ile Asp Leu
            275                 280                 285

Phe Val Tyr Ser Gly Ser Thr Glu Ser Pro Lys Glu Thr Val Lys Gln
            290                 295                 300

Phe Val Gln Ser Ile Gly Lys Pro Ala Met His Gln Tyr Trp Thr Leu
305                 310                 315                 320

Gly Tyr His Ser Cys Arg Trp Gly Tyr Thr Asn Ile Thr Glu Ile Met
                325                 330                 335

Asp Val Arg Gln Asn Tyr Ile Asp Ala Asp Ile Pro Val Glu Thr Phe
            340                 345                 350

Trp Ser Asp Ile Asp Tyr Met Glu Lys Tyr Arg Asp Phe Thr Val Asp
            355                 360                 365

Pro Val Ser Tyr Ser Lys Ser Asp Met Gln Thr Phe Phe Ser Asp Leu
            370                 375                 380

Val Ser Asn His Gln His Tyr Val Pro Ile Ile Asp Ala Ala Ile Tyr
385                 390                 395                 400

Ala Ala Asn Pro Tyr Asn His Thr Asp Asp Ser Tyr Tyr Pro Tyr Tyr
                405                 410                 415

Ala Gly Val Glu Lys Asp Ile Phe Leu Lys Asn Pro Asn Gly Ser Ile
            420                 425                 430

Tyr Ile Gly Ala Val Trp Pro Gly Phe Thr Ala Phe Pro Asp Phe Thr
            435                 440                 445

Asn Pro Asp Val Val Asp Tyr Trp Lys Asp Cys Leu Ile Asn Leu Thr
450                 455                 460

Tyr Ala Phe Gly Ser Asn Gly Thr Val Pro Phe Ser Gly Ile Trp Thr
465                 470                 475                 480

Asp Met Asn Glu Pro Ser Ser Phe Cys Val Gly Ser Cys Gly Ser Ala
                485                 490                 495

Met Ile Asp Leu Asn Pro Ala Glu Pro Leu Val Gly Ile Ser Lys Gln
                500                 505                 510

Tyr Ser Ile Pro Glu Gly Phe Asn Val Ser Asn Val Thr Glu Tyr Ser
            515                 520                 525

Ser Ala Tyr Ser Ala Ser Leu Ser Asn Tyr Tyr Ala Thr Ala Thr Ser
            530                 535                 540

Ser Val Phe Gln Ile Val Ser Pro Thr Ala Thr Pro Leu Gly Leu Lys
545                 550                 555                 560

Pro Asp Tyr Asn Ile Asn Trp Pro Pro Tyr Ala Ile Asn Asn Glu Gln
                565                 570                 575

Gly Asn His Asp Ile Ala Asn His Ile Val Ser Pro Asn Ala Thr Thr
                580                 585                 590
```

His Asp Gly Thr Gln Arg Tyr Asp Ile Phe Asn Met Tyr Gly Tyr Gly
             595                 600                 605

Glu Thr Lys Val Ser Tyr Ala Ala Leu Thr Gln Ile Ser Pro Asn Glu
610                 615                 620

Arg Pro Phe Ile Leu Ser Arg Ser Thr Phe Leu Gly Ser Gly Val Tyr
625                 630                 635                 640

Gly Ala His Trp Leu Gly Asp Asn His Ser Leu Trp Ser Asn Met Phe
                645                 650                 655

Phe Ser Ile Ser Gly Met Ile Val Phe Asn Met Met Gly Ile Pro Met
                660                 665                 670

Val Gly Ala Asp Val Cys Gly Phe Leu Gly Asp Ser Asp Glu Glu Leu
            675                 680                 685

Cys Ser Arg Trp Met Ala Met Gly Ala Phe Ser Pro Phe Tyr Arg Asn
690                 695                 700

His Asn Asn Ile Tyr Gln Ile Ser Gln Glu Pro Tyr Thr Trp Ser Ser
705                 710                 715                 720

Val Ala Glu Ala Ser Arg Arg Ala Met Tyr Ile Arg Tyr Ser Leu Leu
                725                 730                 735

Pro Tyr Trp Tyr Thr Ile Met Ala Lys Ala Ser Gln Asp Gly Thr Pro
                740                 745                 750

Ala Leu Arg Ala Leu Phe Val Glu Phe Pro Asn Asp Pro Thr Leu Ala
            755                 760                 765

Asp Val Asp Arg Gln Phe Met Val Gly Asp Ser Leu Leu Val Thr Pro
            770                 775                 780

Val Leu Glu Pro Asn Val Glu Tyr Val Gln Gly Val Phe Pro Gly Asp
785                 790                 795                 800

Asn Ser Thr Val Trp Tyr Asp Trp Tyr Asn His Thr Glu Ile Val Arg
                805                 810                 815

Gln Tyr Asn Glu Asn Val Thr Leu Tyr Ala Pro Leu Glu His Ile Asn
                820                 825                 830

Val Ala Ile Arg Gly Gly Ser Val Leu Pro Met Gln Gln Pro Ser Leu
            835                 840                 845

Thr Thr Tyr Glu Ser Arg Gln Asn Pro Phe Asn Leu Leu Val Ala Leu
850                 855                 860

Asp Arg Asp Gly Ser Ala Thr Gly Glu Leu Tyr Leu Asp Asp Gly Val
865                 870                 875                 880

Ser Ile Glu Leu Asn Ala Thr Leu Ser Val Ser Phe Thr Phe Ser Asp
                885                 890                 895

Gly Val Leu Ser Ala Val Pro Thr Gly Ser Tyr Glu Val Ser Gln Pro
            900                 905                 910

Leu Ala Asn Val Thr Ile Leu Gly Leu Thr Glu Ser Pro Ser Ser Ile
            915                 920                 925

Thr Leu Asn Gly Gln Asn Val Ser Phe Gln Tyr Ser Asn Asp Thr
930                 935                 940

Glu Glu Leu Leu Ile Thr Gly Leu Gln Asn Ile Thr Ser Ser Gly Ala
945                 950                 955                 960

Phe Ala Asn Ser Trp Asn Leu Thr Leu
                965

<210> SEQ ID NO 12
<211> LENGTH: 960
<212> TYPE: PRT
<213> ORGANISM: Debaryomyces occidentalis

<400> SEQUENCE: 12

-continued

```
Met Ile Phe Leu Lys Leu Ile Lys Ser Ile Val Ile Gly Leu Gly Leu
1               5                   10                  15

Val Ser Ala Ile Gln Ala Ala Pro Ala Ser Ser Ile Gly Ser Ser Ala
            20                  25                  30

Ser Ala Ser Ser Ser Ser Glu Ser Ser Gln Ala Thr Ile Pro Asn Asp
        35                  40                  45

Val Thr Leu Gly Val Lys Gln Ile Pro Asn Ile Phe Asn Asp Ser Ala
50                  55                  60

Val Asp Ala Asn Ala Ala Lys Gly Tyr Asp Leu Val Asn Val Thr
65                  70                  75                  80

Asn Thr Pro Arg Gly Leu Thr Gly Ile Leu Lys Leu Lys Glu Ala Thr
                85                  90                  95

Asn Ile Tyr Gly Tyr Asp Phe Asp Tyr Leu Asn Leu Thr Val Glu Tyr
                100                 105                 110

Gln Ala Asp Thr Arg Leu Asn Val His Ile Glu Pro Thr Asp Leu Ser
            115                 120                 125

Asp Val Phe Val Leu Pro Glu His Leu Val Val Lys Pro Leu Val Glu
130                 135                 140

Gly Asp Ala Gln Ser Tyr Asn Phe Asp Asn Ser Asp Leu Val Phe Glu
145                 150                 155                 160

Tyr Ser Asn Thr Asp Phe Ser Phe Glu Val Ile Arg Ser Ser Thr Lys
                165                 170                 175

Glu Val Leu Phe Ser Thr Lys Gly Asn Pro Leu Val Phe Ser Asn Gln
            180                 185                 190

Phe Ile Gln Phe Asn Ser Ser Leu Pro Lys Asn His Val Ile Thr Gly
        195                 200                 205

Leu Gly Glu Ser Ile His Gly Leu Val Asn Gly Pro Gly Ser Val Lys
210                 215                 220

Thr Leu Phe Ala Asn Asp Val Gly Asp Pro Ile Asp Gly Asn Ile Tyr
225                 230                 235                 240

Gly Val His Pro Val Tyr Leu Asp Gln Arg Tyr Asp Thr Glu Thr Thr
                245                 250                 255

His Ala Val Tyr Trp Arg Thr Ser Ala Ile Gln Glu Val Leu Ile Gly
            260                 265                 270

Glu Glu Ser Ile Thr Trp Arg Ala Leu Ser Gly Val Ile Asp Leu Tyr
        275                 280                 285

Phe Phe Ser Gly Pro Thr Pro Lys Asp Ala Ile Gln Gln Tyr Val Lys
290                 295                 300

Glu Ile Gly Leu Pro Ala Phe Gln Pro Tyr Trp Ser Leu Gly Tyr His
305                 310                 315                 320

Gln Cys Arg Trp Gly Tyr Asp Thr Ile Glu Lys Leu Ser Glu Val Val
                325                 330                 335

Glu Asn Phe Lys Lys Phe Asn Ile Pro Leu Glu Thr Ile Trp Ser Asp
            340                 345                 350

Ile Asp Tyr Met Asp Ser Tyr Lys Asp Phe Thr Tyr Asp Pro His Arg
        355                 360                 365

Phe Pro Leu Asp Glu Tyr Arg Lys Phe Leu Asp Glu Leu His Lys Asn
370                 375                 380

Asn Gln His Tyr Val Pro Ile Leu Asp Ala Ala Ile Tyr Val Pro Asn
385                 390                 395                 400

Pro Asn Asn Ala Thr Asp Asn Glu Tyr Gln Pro Phe His Tyr Gly Asn
                405                 410                 415
```

```
Glu Thr Asp Val Phe Leu Lys Asn Pro Asp Gly Ser Leu Tyr Ile Gly
                420                 425                 430

Ala Val Trp Pro Gly Tyr Thr Val Phe Pro Asp Phe Leu Ala Glu Asn
            435                 440                 445

Ile Gln Glu Tyr Trp Asn Lys Val Ile Lys Asp Trp Tyr Glu Leu Thr
        450                 455                 460

Pro Phe Asp Gly Ile Trp Ala Asp Met Asn Glu Val Ser Ser Phe Cys
465                 470                 475                 480

Val Gly Ser Cys Gly Thr Gly Lys Tyr Phe Glu Asn Pro Ala Tyr Pro
                485                 490                 495

Pro Phe Thr Val Gly Ser Lys Ala Thr Ser Tyr Pro Val Gly Phe Asp
            500                 505                 510

Val Ser Asn Ala Ser Glu Trp Lys Ser Ile Gln Ser Ser Ile Ser Ala
        515                 520                 525

Thr Ala Lys Thr Ser Ser Thr Ser Ser Val Ser Ser Ser Ser Ser Thr
530                 535                 540

Ile Asp Ser Met Asn Thr Leu Ala Pro Gly Lys Gly Asn Ile Asn Tyr
545                 550                 555                 560

Pro Pro Tyr Ala Ile Tyr Asn Met Gln Gly Asp Ser Asp Leu Ala Thr
                565                 570                 575

His Ala Val Ser Pro Asn Ala Thr His Ala Asp Gly Thr Val Glu Tyr
            580                 585                 590

Asp Ile His Asn Leu Tyr Gly Tyr Leu Gln Glu Asn Ala Thr Tyr His
        595                 600                 605

Ala Leu Leu Glu Val Phe Pro Asn Lys Arg Pro Phe Met Ile Ser Arg
610                 615                 620

Ser Thr Phe Pro Gly Ala Gly Lys Trp Thr Gly His Trp Gly Gly Asp
625                 630                 635                 640

Asn Thr Ala Asp Trp Ala Tyr Ala Tyr Phe Ser Ile Pro Gln Ala Phe
                645                 650                 655

Ser Met Gly Ile Ala Gly Leu Pro Phe Phe Gly Ala Asp Val Cys Gly
            660                 665                 670

Phe Asn Gly Asn Ser Asp Ser Glu Leu Cys Ser Arg Trp Met Gln Leu
        675                 680                 685

Gly Ser Phe Phe Pro Phe Tyr Arg Asn His Asn Tyr Leu Gly Ala Ile
690                 695                 700

Asp Gln Glu Pro Tyr Val Trp Glu Ser Val Ala Glu Ala Thr Arg Thr
705                 710                 715                 720

Ser Met Ala Ile Arg Tyr Leu Leu Leu Pro Tyr Tyr Tyr Thr Leu Leu
                725                 730                 735

His Glu Ser His Thr Thr Gly Leu Pro Ile Leu Arg Ala Phe Ser Trp
            740                 745                 750

Gln Phe Pro Asn Asp Arg Ser Leu Ser Gly Val Asp Asn Gln Phe Phe
        755                 760                 765

Val Gly Asp Gly Leu Val Val Thr Pro Val Leu Glu Pro Gly Val Asp
770                 775                 780

Lys Val Lys Gly Val Phe Pro Ala Gly Lys Glu Glu Val Tyr Tyr
785                 790                 795                 800

Asp Trp Tyr Thr Gln Arg Glu Val His Phe Lys Asp Gly Lys Asn Glu
                805                 810                 815

Thr Leu Asp Ala Pro Leu Gly His Ile Pro Leu His Ile Arg Gly Gly
            820                 825                 830

Asn Val Leu Pro Thr Gln Glu Pro Gly Tyr Thr Val Ser Glu Ser Arg
```

```
                    835                 840                 845
Gln Asn Pro Phe Gly Leu Ile Val Ala Leu Asp Asn Asp Gly Lys Ala
    850                 855                 860
Gln Gly Ser Leu Tyr Leu Asp Asp Gly Glu Ser Leu Val Val Asp Ser
865                 870                 875                 880
Ser Leu Leu Val Ser Phe Ser Val Ser Asp Asn Thr Leu Ser Ala Ser
                885                 890                 895
Pro Ser Gly Asp Tyr Lys Ala Asp Gln Pro Leu Ala Asn Val Thr Ile
            900                 905                 910
Leu Gly Val Gly His Lys Pro Lys Ser Val Lys Phe Glu Asn Ala Asn
        915                 920                 925
Val Asp Phe Thr Tyr Lys Lys Ser Thr Val Phe Val Thr Gly Leu Asp
    930                 935                 940
Lys Tyr Thr Lys Asp Gly Ala Phe Ser Lys Asp Phe Thr Ile Thr Trp
945                 950                 955                 960

<210> SEQ ID NO 13
<211> LENGTH: 879
<212> TYPE: PRT
<213> ORGANISM: Hordeum vulgare

<400> SEQUENCE: 13

Met Ala Thr Arg Ser Leu Leu Leu Cys Leu Cys Leu Phe
1               5                   10                  15
Ala Pro Arg Leu Cys Ser Ser Lys Glu Glu Gly Pro Leu Ala Ala Gly
                20                  25                  30
Gly Tyr Arg Val Ser Arg Val Ala Asp Asp Gly Arg Arg Leu
                35                  40                  45
Arg Ala Glu Ala Ala Ala Thr Gly Gly Ala Ser Ser Thr Gly Asp
50                  55                  60
Val Gln Arg Leu Ala Val Tyr Ala Ser Leu Glu Thr Asp Ser Arg Leu
65                  70                  75                  80
Arg Val Arg Ile Thr Asp Ala Asp His Pro Arg Trp Glu Val Pro Gln
                85                  90                  95
Asp Ile Ile Pro Arg Pro Ala Pro Ala Asp Val Leu His Asp Ala Pro
            100                 105                 110
Pro Ala Ser Ser Ala Pro Leu Gln Gly Ser Arg Val Leu Ser Ala Ala
        115                 120                 125
Gly Ser Asp Leu Val Leu Thr Val His Ala Ser Pro Phe Arg Phe Thr
    130                 135                 140
Val Ser Arg Arg Ser Thr Gly Asp Ile Leu Phe Asp Thr Ala Pro Gly
145                 150                 155                 160
Leu Val Phe Arg Asp Lys Tyr Leu Glu Val Thr Ser Ala Leu Pro Ala
                165                 170                 175
Gly Arg Ala Ser Leu Tyr Gly Leu Gly Glu His Thr Lys Ser Ser Phe
            180                 185                 190
Arg Leu Arg His Asn Asp Ser Phe Thr Leu Trp Asn Ala Asp Ile Gly
        195                 200                 205
Ala Ser Tyr Val Asp Val Asn Leu Tyr Gly Ser His Pro Phe Tyr Met
    210                 215                 220
Asp Val Arg Pro Pro Gly Thr Ala His Gly Val Leu Leu Leu Ser Ser
225                 230                 235                 240
Asn Gly Met Asp Val Leu Tyr Gly Gly Ser Tyr Val Thr Tyr Lys Val
                245                 250                 255
```

```
Ile Gly Gly Val Leu Asp Phe Tyr Phe Ala Gly Pro Asn Pro Leu
                260             265                 270

Ala Val Val Asp Gln Tyr Thr Gln Leu Ile Gly Arg Pro Ala Pro Met
            275                 280                 285

Pro Tyr Trp Ser Phe Gly Phe His Gln Cys Arg Tyr Gly Tyr Leu Asn
        290                 295                 300

Val Ser Asp Leu Glu Arg Val Ala Gly Tyr Ala Lys Ala Arg Ile
305                 310                 315                 320

Pro Leu Glu Val Met Trp Thr Asp Ile Asp Tyr Met Asp Gly Phe Lys
                325                 330                 335

Asp Phe Thr Leu Asp Arg Val Asn Phe Thr Ala Ala Glu Leu Arg Pro
                340                 345                 350

Phe Val Asp Arg Leu His Arg Asn Ala Gln Lys Tyr Val Leu Ile Leu
                355                 360                 365

Asp Pro Gly Ile Arg Ile Asp Ala Thr Tyr Gly Thr Phe Val Arg Gly
            370                 375                 380

Met Gln Gln Asp Ile Phe Leu Lys Arg Asn Gly Thr Asn Phe Val Gly
385                 390                 395                 400

Asn Val Trp Pro Gly Asp Val Tyr Phe Pro Asp Phe Met His Pro Arg
                405                 410                 415

Ala Ala Glu Phe Trp Ala Arg Glu Ile Ser Leu Phe Arg Arg Thr Ile
            420                 425                 430

Pro Val Asp Gly Leu Trp Ile Asp Met Asn Glu Ile Ser Asn Phe Tyr
                435                 440                 445

Asn Pro Glu Pro Met Asn Ala Leu Asp Asp Pro Pro Tyr Arg Ile Asn
450                 455                 460

Asn Asp Gly Thr Gly Arg Pro Ile Asn Asn Lys Thr Val Pro Ala Ser
465                 470                 475                 480

Ala Val His Tyr Gly Gly Val Thr Glu Tyr Asp Ala His Asn Leu Phe
            485                 490                 495

Gly Leu Leu Glu Ala Arg Ala Thr His Arg Ala Leu Leu Arg Asp Thr
                500                 505                 510

Gly Arg Arg Pro Phe Val Leu Ser Arg Ser Thr Phe Val Gly Ser Gly
            515                 520                 525

Arg Tyr Thr Ala His Trp Thr Gly Asp Asn Ala Ala Thr Trp Gly Asp
    530                 535                 540

Leu Arg Tyr Ser Ile Asn Thr Met Leu Ser Phe Gly Leu Phe Gly Met
545                 550                 555                 560

Pro Met Ile Gly Ala Asp Ile Cys Gly Phe Asn Gly Asn Thr Thr Glu
                565                 570                 575

Glu Leu Cys Gly Arg Trp Ile Gln Leu Gly Ala Phe Tyr Pro Phe Ser
            580                 585                 590

Arg Asp His Ser Ala Ile Phe Thr Val Arg Arg Glu Leu Tyr Leu Trp
            595                 600                 605

Pro Ser Val Ala Ala Ser Ala Arg Lys Ala Leu Gly Leu Arg Tyr Gln
            610                 615                 620

Leu Leu Pro Tyr Phe Tyr Thr Leu Met Tyr Glu Ala His Met Thr Gly
625                 630                 635                 640

Ala Pro Ile Ala Arg Pro Leu Phe Phe Ser Tyr Pro His Asp Val Ala
                645                 650                 655

Thr Tyr Gly Val Asp Arg Gln Phe Leu Leu Gly Arg Gly Val Leu Val
            660                 665                 670

Ser Pro Val Leu Glu Pro Gly Ala Thr Thr Val Asp Ala Tyr Phe Pro
```

-continued

```
                675                 680                 685
Ala Gly Arg Trp Tyr Ser Leu Tyr Asp Tyr Ser Leu Ala Val Ala Thr
690                 695                 700

Arg Thr Gly Lys His Val Thr Leu Pro Ala Pro Ala Asp Thr Val Asn
705                 710                 715                 720

Val His Val Ala Gly Thr Ile Leu Pro Leu Gln Gln Ser Ala Leu
                725                 730                 735

Thr Thr Ser Arg Ala Arg Arg Thr Ala Phe His Leu Leu Val Ala Leu
                740                 745                 750

Ala Glu Asp Gly Thr Ala Ser Gly Asp Leu Phe Leu Asp Asp Gly Glu
                755                 760                 765

Ser Pro Glu Met Gly Gly Arg Ser Asp Trp Ser Met Val Arg Phe Ser
770                 775                 780

Cys Glu Met Gly Ser Asp Gly Ala Ile Lys Val Lys Ser Glu Val Val
785                 790                 795                 800

His Asn Ser Tyr Ala Gln Ser Arg Thr Leu Val Ile Ser Lys Val Val
                805                 810                 815

Leu Met Gly His Arg Ser Pro Ala Ala Pro Lys Lys Leu Thr Val His
                820                 825                 830

Val Asn Ser Ala Glu Val Glu Ala Ser Ser Ala Gly Thr Arg Tyr
                835                 840                 845

Gln Asn Ala Gly Gly Leu Gly Gly Val Ala His Ile Gly Gly Leu Ser
                850                 855                 860

Leu Val Val Gly Glu Glu Phe Glu Leu Lys Val Ala Met Ser Tyr
865                 870                 875
```

<210> SEQ ID NO 14
<211> LENGTH: 902
<212> TYPE: PRT
<213> ORGANISM: Arabidopsis thaliana

<400> SEQUENCE: 14

```
Met Ser Ser Leu His Trp Phe Pro Asn Ile Phe Ile Val Val Val
1               5                   10                  15

Phe Phe Ser Leu Arg Ser Ser Gln Val Val Leu Glu Glu Glu Ser
                20                  25                  30

Thr Val Val Gly Tyr Gly Tyr Val Val Arg Ser Val Gly Val Asp Ser
                35                  40                  45

Asn Arg Gln Val Leu Thr Ala Lys Leu Asp Leu Ile Lys Pro Ser Ser
50                  55                  60

Val Tyr Ala Pro Asp Ile Lys Ser Leu Asn Leu His Val Ser Leu Glu
65                  70                  75                  80

Thr Ser Glu Arg Leu Arg Ile Arg Ile Thr Asp Ser Ser Gln Gln Arg
                85                  90                  95

Trp Glu Ile Pro Glu Thr Val Ile Pro Arg Ala Gly Asn His Ser Pro
                100                 105                 110

Arg Arg Phe Ser Thr Glu Glu Asp Gly Gly Asn Ser Pro Glu Asn Asn
                115                 120                 125

Phe Leu Ala Asp Pro Ser Ser Asp Leu Val Phe Thr Leu His Asn Thr
130                 135                 140

Thr Pro Phe Gly Phe Ser Val Ser Arg Arg Ser Ser Gly Asp Ile Leu
145                 150                 155                 160

Phe Asp Thr Ser Pro Asp Ser Ser Asp Ser Asn Thr Tyr Phe Ile Phe
                165                 170                 175
```

-continued

```
Lys Asp Gln Phe Leu Gln Leu Ser Ser Ala Leu Pro Glu Asn Arg Ser
                180                 185                 190
Asn Leu Tyr Gly Ile Gly Glu His Thr Lys Arg Ser Phe Arg Leu Ile
            195                 200                 205
Pro Gly Glu Thr Met Thr Leu Trp Asn Ala Asp Ile Gly Ser Glu Asn
210                 215                 220
Pro Asp Val Asn Leu Tyr Gly Ser His Pro Phe Tyr Met Asp Val Arg
225                 230                 235                 240
Gly Ser Lys Gly Asn Glu Glu Ala Gly Thr Thr His Gly Val Leu Leu
                245                 250                 255
Leu Asn Ser Asn Gly Met Asp Val Lys Tyr Glu Gly His Arg Ile Thr
                260                 265                 270
Tyr Asn Val Ile Gly Gly Val Ile Asp Leu Tyr Val Phe Ala Gly Pro
            275                 280                 285
Ser Pro Glu Met Val Met Asn Gln Tyr Thr Glu Leu Ile Gly Arg Pro
            290                 295                 300
Ala Pro Met Pro Tyr Trp Ser Phe Gly Phe His Gln Cys Arg Tyr Gly
305                 310                 315                 320
Tyr Lys Asn Val Ser Asp Leu Glu Tyr Val Val Asp Gly Tyr Ala Lys
                325                 330                 335
Ala Gly Ile Pro Leu Glu Val Met Trp Thr Asp Ile Asp Tyr Met Asp
                340                 345                 350
Gly Tyr Lys Asp Phe Thr Leu Asp Pro Val Asn Phe Pro Glu Asp Lys
            355                 360                 365
Met Gln Ser Phe Val Asp Thr Leu His Lys Asn Gly Gln Lys Tyr Val
370                 375                 380
Leu Ile Leu Asp Pro Gly Ile Gly Val Asp Ser Ser Tyr Gly Thr Tyr
385                 390                 395                 400
Asn Arg Gly Met Glu Ala Asp Val Phe Ile Lys Arg Asn Gly Glu Pro
                405                 410                 415
Tyr Leu Gly Glu Val Trp Pro Gly Lys Val Tyr Phe Pro Asp Phe Leu
            420                 425                 430
Asn Pro Ala Ala Ala Thr Phe Trp Ser Asn Glu Ile Lys Met Phe Gln
            435                 440                 445
Glu Ile Leu Pro Leu Asp Gly Leu Trp Ile Asp Met Asn Glu Leu Ser
450                 455                 460
Asn Phe Ile Thr Ser Pro Leu Ser Ser Gly Ser Ser Leu Asp Asp Pro
465                 470                 475                 480
Pro Tyr Lys Ile Asn Asn Ser Gly Asp Lys Arg Pro Ile Asn Asn Lys
                485                 490                 495
Thr Val Pro Ala Thr Ser Ile His Phe Gly Asn Ile Ser Glu Tyr Asp
            500                 505                 510
Ala His Asn Leu Tyr Gly Leu Leu Glu Ala Lys Ala Thr His Gln Ala
            515                 520                 525
Val Val Asp Ile Thr Gly Lys Arg Pro Phe Ile Leu Ser Arg Ser Thr
530                 535                 540
Phe Val Ser Ser Gly Lys Tyr Thr Ala His Trp Thr Gly Asp Asn Ala
545                 550                 555                 560
Ala Lys Trp Glu Asp Leu Ala Tyr Ser Ile Pro Gly Ile Leu Asn Phe
                565                 570                 575
Gly Leu Phe Gly Ile Pro Met Val Gly Ala Asp Ile Cys Gly Phe Ser
            580                 585                 590
His Asp Thr Thr Glu Glu Leu Cys Arg Arg Trp Ile Gln Leu Gly Ala
```

```
                    595                 600                 605
Phe Tyr Pro Phe Ala Arg Asp His Ser Ser Leu Gly Thr Ala Arg Gln
610                 615                 620

Glu Leu Tyr Leu Trp Asp Ser Val Ala Ser Ser Ala Arg Lys Val Leu
625                 630                 635                 640

Gly Leu Arg Met Arg Leu Leu Pro His Leu Tyr Thr Leu Met Tyr Glu
                    645                 650                 655

Ala His Val Ser Gly Asn Pro Ile Ala Arg Pro Leu Phe Phe Ser Phe
                    660                 665                 670

Pro Gln Asp Thr Lys Thr Tyr Glu Ile Asp Ser Gln Phe Leu Ile Gly
                    675                 680                 685

Lys Ser Ile Met Val Ser Pro Ala Leu Lys Gln Gly Ala Val Ala Val
690                 695                 700

Asp Ala Tyr Phe Pro Ala Gly Asn Trp Phe Asp Leu Phe Asn Tyr Ser
705                 710                 715                 720

Phe Ala Val Gly Gly Asp Ser Gly Lys His Val Arg Leu Asp Thr Pro
                    725                 730                 735

Ala Asp His Val Asn Val His Val Arg Glu Gly Ser Ile Val Ala Met
                    740                 745                 750

Gln Gly Glu Ala Leu Thr Thr Arg Asp Ala Arg Lys Thr Pro Tyr Gln
                    755                 760                 765

Leu Leu Val Val Ala Ser Arg Leu Glu Asn Ile Ser Gly Glu Leu Phe
770                 775                 780

Leu Asp Asp Gly Glu Asn Leu Arg Met Gly Ala Gly Gly Asn Arg
785                 790                 795                 800

Asp Trp Thr Leu Val Lys Phe Arg Cys Tyr Val Thr Gly Lys Ser Val
                    805                 810                 815

Val Leu Arg Ser Glu Val Val Asn Pro Glu Tyr Ala Ser Lys Met Lys
                    820                 825                 830

Trp Ser Ile Gly Lys Val Thr Phe Val Gly Phe Glu Asn Val Glu Asn
                    835                 840                 845

Val Lys Thr Tyr Glu Val Arg Thr Ser Glu Arg Leu Arg Ser Pro Arg
850                 855                 860

Ile Ser Leu Ile Lys Thr Val Ser Asp Asn Asp Pro Arg Phe Leu
865                 870                 875                 880

Ser Val Glu Val Ser Lys Leu Ser Leu Leu Val Gly Lys Lys Phe Glu
                    885                 890                 895

Met Arg Leu Arg Leu Thr
            900

<210> SEQ ID NO 15
<211> LENGTH: 903
<212> TYPE: PRT
<213> ORGANISM: Spinacia oleracea

<400> SEQUENCE: 15

Met Lys Lys Lys Ile Pro Ser Leu Ala Leu Gly Ile Leu Leu Val Phe
1               5                   10                  15

Leu Leu Gln Tyr Leu Val Ala Gly Ile Ser Thr Ser Glu Asn Asp Pro
                20                  25                  30

Glu Gly Val Ile Gly Tyr Gly Tyr Lys Val Lys Ser Val Lys Val Asp
            35                  40                  45

Ser Gly Thr Arg Arg Ser Leu Thr Ala Leu Pro Gln Leu Val Lys Asn
        50                  55                  60
```

```
Ser Ser Val Tyr Gly Pro Asp Ile Gln Leu Leu Ser Ile Thr Ala Ser
 65                  70                  75                  80

Leu Glu Ser Asn Asp Arg Leu Arg Val Arg Ile Thr Asp Ala Lys His
                 85                  90                  95

Arg Arg Trp Glu Ile Pro Asp Asn Ile Leu His Arg His Gln Pro Pro
            100                 105                 110

Pro Pro Pro His Ser Leu Ser Ser Leu Tyr Arg Thr Leu Leu Ser
        115                 120                 125

Ser Pro Thr Thr Asn Arg Arg Lys Ile Leu Leu Ser His Pro Asn Ser
130                 135                 140

Asp Leu Thr Phe Ser Leu Ile Asn Thr Thr Pro Phe Gly Phe Thr Ile
145                 150                 155                 160

Ser Arg Lys Ser Thr His Asp Val Leu Phe Asp Ala Thr Pro Asp Pro
                165                 170                 175

Thr Asn Pro Asn Thr Phe Leu Ile Phe Ile Asp Gln Tyr Leu His Leu
            180                 185                 190

Thr Ser Ser Leu Pro Gly Thr Arg Ala His Ile Tyr Gly Leu Gly Glu
        195                 200                 205

His Ser Lys Pro Thr Phe Gln Leu Ala His Asn Gln Thr Leu Thr Met
210                 215                 220

Arg Ala Ala Asp Ile Pro Ser Ser Asn Pro Asp Val Asn Leu Tyr Gly
225                 230                 235                 240

Ser His Pro Phe Tyr Met Asp Val Arg Ser Pro Val Ala Gly Ser
                245                 250                 255

Thr His Gly Val Leu Leu Leu Asn Ser Asn Gly Met Asp Val Glu Tyr
            260                 265                 270

Thr Gly Asn Arg Ile Thr Tyr Lys Val Ile Gly Gly Ile Ile Asp Leu
        275                 280                 285

Tyr Phe Phe Ala Gly Pro Ser Pro Gly Gln Val Val Glu Gln Phe Thr
290                 295                 300

Arg Val Ile Gly Arg Pro Ala Pro Met Pro Tyr Trp Ala Phe Gly Phe
305                 310                 315                 320

Gln Gln Cys Arg Tyr Gly Tyr His Asp Val Tyr Glu Leu Gln Ser Val
                325                 330                 335

Val Ala Gly Tyr Ala Lys Ala Lys Ile Pro Leu Glu Val Met Trp Thr
            340                 345                 350

Asp Ile Asp Tyr Met Asp Ala Tyr Lys Asp Phe Thr Leu Asp Pro Val
        355                 360                 365

Asn Phe Pro Leu Asp Lys Met Lys Lys Phe Val Asn Asn Leu His Lys
370                 375                 380

Asn Gly Gln Lys Tyr Val Val Ile Leu Asp Pro Gly Ile Ser Thr Asn
385                 390                 395                 400

Lys Thr Tyr Glu Thr Tyr Ile Arg Gly Met Lys His Asp Val Phe Leu
                405                 410                 415

Lys Arg Asn Gly Lys Pro Tyr Leu Gly Ser Val Trp Pro Gly Pro Val
            420                 425                 430

Tyr Phe Pro Asp Phe Leu Lys Pro Ser Ala Leu Thr Phe Trp Thr Asp
        435                 440                 445

Glu Ile Lys Arg Phe Leu Asn Leu Leu Pro Val Asp Gly Leu Trp Ile
450                 455                 460

Asp Met Asn Glu Ile Ser Asn Phe Ile Ser Ser Pro Pro Ile Pro Gly
465                 470                 475                 480

Ser Thr Leu Asp Asn Pro Pro Tyr Lys Ile Asn Asn Ser Gly Val Met
```

```
            485                 490                 495
Leu Pro Ile Ile Asn Lys Thr Ile Pro Pro Thr Ala Met His Tyr Gly
            500                 505                 510

Asp Ile Pro Glu Tyr Asn Val His Asn Leu Phe Gly Tyr Leu Glu Ala
            515                 520                 525

Arg Val Thr Arg Ala Ala Leu Ile Lys Leu Thr Glu Lys Arg Pro Phe
            530                 535                 540

Val Leu Ser Arg Ser Thr Phe Ser Gly Ser Gly Lys Tyr Thr Ala His
545                 550                 555                 560

Trp Thr Gly Asp Asn Ala Ala Thr Trp Asn Asp Leu Val Tyr Ser Ile
                565                 570                 575

Pro Ser Met Leu Asp Phe Gly Leu Phe Gly Ile Pro Met Val Gly Ala
            580                 585                 590

Asp Ile Cys Gly Phe Leu Gly Asn Thr Thr Glu Glu Leu Cys Arg Arg
            595                 600                 605

Trp Ile Gln Leu Gly Ala Phe Tyr Pro Phe Ser Arg Asp His Ser Ser
            610                 615                 620

Leu Gly Thr Thr Tyr Gln Glu Leu Tyr Arg Trp Glu Ser Val Ala Ala
625                 630                 635                 640

Ser Ala Arg Lys Val Leu Gly Leu Arg Tyr Thr Leu Leu Pro Tyr Phe
                645                 650                 655

Tyr Thr Leu Met Tyr Glu Ala Gln Leu Asn Gly Ile Pro Ile Ala Arg
            660                 665                 670

Pro Leu Phe Phe Ser Phe Pro Asp Asp Ile Lys Thr Tyr Gly Ile Ser
            675                 680                 685

Ser Gln Phe Leu Leu Gly Lys Gly Val Met Val Ser Pro Val Leu Lys
            690                 695                 700

Pro Gly Val Val Ser Val Thr Ala Tyr Phe Pro Arg Gly Asn Trp Phe
705                 710                 715                 720

Asp Leu Phe Asp Tyr Thr Arg Ser Val Thr Ala Ser Thr Gly Arg Tyr
                725                 730                 735

Val Thr Leu Ser Ala Pro Pro Asp His Ile Asn Val His Ile Gln Glu
            740                 745                 750

Gly Asn Ile Leu Ala Met Gln Gly Lys Ala Met Thr Thr Gln Ala Ala
            755                 760                 765

Arg Lys Thr Pro Phe His Leu Leu Val Val Met Ser Asp Cys Gly Ala
            770                 775                 780

Ser Phe Gly Glu Leu Phe Leu Asp Asp Gly Val Glu Val Thr Met Gly
785                 790                 795                 800

Val Asn Arg Gly Lys Trp Thr Phe Val Lys Phe Ile Ala Ala Ser Ala
                805                 810                 815

Lys Gln Thr Cys Ile Ile Thr Ser Asp Val Val Ser Gly Glu Phe Ala
            820                 825                 830

Val Ser Gln Lys Trp Val Ile Asp Lys Val Thr Ile Leu Gly Leu Arg
            835                 840                 845

Lys Gly Thr Lys Ile Asn Gly Tyr Thr Val Arg Thr Gly Ala Val Thr
            850                 855                 860

Arg Lys Gly Asp Lys Ser Lys Leu Lys Ser Thr Pro Asp Arg Lys Gly
865                 870                 875                 880

Glu Phe Ile Val Ala Glu Ile Ser Gly Leu Asn Leu Leu Gly Arg
                885                 890                 895

Glu Phe Lys Leu Val Leu His
            900
```

<210> SEQ ID NO 16
<211> LENGTH: 913
<212> TYPE: PRT
<213> ORGANISM: Beta vulgaris

<400> SEQUENCE: 16

```
Met Glu Arg Ser Lys Leu Pro Arg Tyr Ile Cys Pro Thr Leu Ala Val
1               5                   10                  15

Val Leu Pro Leu Val Leu Cys Met Val Val Glu Gly Ala Thr Thr Ser
            20                  25                  30

Lys Asn Asp Asn Gln Gly Glu Ala Ile Gly Tyr Gly Tyr Gln Val Lys
        35                  40                  45

Asn Ala Lys Val Asp Asn Ser Thr Gly Lys Ser Leu Thr Ala Leu Leu
    50                  55                  60

Gln Leu Ile Arg Asn Ser Pro Val Tyr Gly Pro Asp Ile His Phe Leu
65                  70                  75                  80

Ser Phe Thr Ala Ser Phe Glu Glu Asp Asp Thr Leu Arg Ile Arg Phe
                85                  90                  95

Thr Asp Ala Asn Asn Arg Arg Trp Glu Ile Pro Asn Glu Val Leu Pro
            100                 105                 110

Arg Pro Pro Pro Pro Ser Pro Pro Leu Ser Ser Leu Gln His
        115                 120                 125

Leu Pro Lys Pro Ile Pro Gln Asn Gln Pro Thr Thr Thr Val Leu Ser
    130                 135                 140

His Pro His Ser Asp Leu Ala Phe Thr Leu Phe His Thr Thr Pro Phe
145                 150                 155                 160

Gly Phe Thr Ile Tyr Arg Lys Ser Thr His Asp Val Leu Phe Asp Ala
                165                 170                 175

Thr Pro Ile Pro Ser Asn Pro Thr Thr Phe Leu Ile Tyr Lys Asp Gln
            180                 185                 190

Tyr Leu Gln Leu Ser Ser Ser Leu Pro Ala Gln Ala His Leu Tyr
        195                 200                 205

Gly Leu Gly Glu His Thr Lys Pro Thr Phe Gln Leu Ala His Asn Gln
    210                 215                 220

Ile Leu Thr Leu Trp Asn Ala Asp Ile Ala Ser Phe Asn Arg Asp Leu
225                 230                 235                 240

Asn Leu Tyr Gly Ser His Pro Phe Tyr Met Asp Val Arg Ser Ser Pro
                245                 250                 255

Met Val Gly Ser Thr His Gly Val Phe Leu Leu Asn Ser Asn Gly Met
            260                 265                 270

Asp Val Glu Tyr Thr Gly Asp Arg Ile Thr Tyr Lys Val Ile Gly Gly
        275                 280                 285

Ile Ile Asp Leu Tyr Ile Phe Ala Gly Arg Thr Pro Glu Met Val Leu
    290                 295                 300

Asp Gln Tyr Thr Lys Leu Ile Gly Arg Pro Ala Pro Met Pro Tyr Trp
305                 310                 315                 320

Ala Phe Gly Phe His Gln Cys Arg Trp Gly Tyr Arg Asp Val Asn Glu
                325                 330                 335

Ile Glu Thr Val Val Asp Lys Tyr Ala Glu Ala Arg Ile Pro Leu Glu
            340                 345                 350

Val Met Trp Thr Asp Ile Asp Tyr Met Asp Ala Phe Lys Asp Phe Thr
        355                 360                 365

Leu Asp Pro Val His Phe Pro Leu Asp Lys Met Gln Gln Phe Val Thr
```

```
                370                 375                 380
Lys Leu His Arg Asn Gly Gln Arg Tyr Val Pro Ile Leu Asp Pro Gly
385                 390                 395                 400

Ile Asn Thr Asn Lys Ser Tyr Gly Thr Phe Ile Arg Gly Met Gln Ser
                405                 410                 415

Asn Val Phe Ile Lys Arg Asn Gly Asn Pro Tyr Leu Gly Ser Val Trp
                420                 425                 430

Pro Gly Pro Val Tyr Tyr Pro Asp Phe Leu Asp Pro Ala Ala Arg Ser
                435                 440                 445

Phe Trp Val Asp Glu Ile Lys Arg Phe Arg Asp Ile Leu Pro Ile Asp
450                 455                 460

Gly Ile Trp Ile Asp Met Asn Glu Ala Ser Asn Phe Ile Thr Ser Ala
465                 470                 475                 480

Pro Thr Pro Gly Ser Thr Leu Asp Asn Pro Pro Tyr Lys Ile Asn Asn
                485                 490                 495

Ser Gly Gly Arg Val Pro Ile Asn Ser Lys Thr Ile Pro Ala Thr Ala
                500                 505                 510

Met His Tyr Gly Asn Val Thr Glu Tyr Asn Ala His Asn Leu Tyr Gly
                515                 520                 525

Phe Leu Glu Ser Gln Ala Thr Arg Glu Ala Leu Val Arg Pro Ala Thr
                530                 535                 540

Arg Gly Pro Phe Leu Leu Ser Arg Ser Thr Phe Ala Gly Ser Gly Lys
545                 550                 555                 560

Tyr Thr Ala His Trp Thr Gly Asp Asn Ala Ala Arg Trp Asp Asp Leu
                565                 570                 575

Gln Tyr Ser Ile Pro Thr Met Leu Asn Phe Gly Leu Phe Gly Met Pro
                580                 585                 590

Met Ile Gly Ala Asp Ile Cys Gly Phe Ala Glu Ser Thr Thr Glu Glu
                595                 600                 605

Leu Cys Cys Arg Trp Ile Gln Leu Gly Ala Phe Tyr Pro Phe Ser Arg
                610                 615                 620

Asp His Ser Ala Arg Asp Thr Thr His Gln Glu Leu Tyr Leu Trp Glu
625                 630                 635                 640

Ser Val Ala Ala Ser Ala Arg Thr Val Leu Gly Leu Arg Tyr Glu Leu
                645                 650                 655

Leu Pro Tyr Tyr Tyr Thr Leu Met Tyr Asp Ala Asn Leu Arg Gly Ser
                660                 665                 670

Pro Ile Ala Arg Pro Leu Ser Phe Thr Phe Pro Asp Asp Val Ala Thr
                675                 680                 685

Tyr Gly Ile Ser Ser Gln Phe Leu Ile Gly Arg Gly Ile Met Val Ser
                690                 695                 700

Pro Val Leu Gln Pro Gly Ser Ser Ile Val Asn Ala Tyr Ser Pro Arg
705                 710                 715                 720

Gly Asn Trp Val Ser Leu Ser Asn Tyr Thr Ser Ser Val Ser Val Ser
                725                 730                 735

Ala Gly Thr Tyr Val Ser Leu Ser Ala Pro Pro Asp His Ile Asn Val
                740                 745                 750

His Ile His Glu Gly Asn Ile Val Ala Met Gln Gly Glu Ala Met Thr
                755                 760                 765

Thr Gln Ala Ala Arg Ser Thr Pro Phe His Leu Leu Val Val Met Ser
                770                 775                 780

Asp His Val Ala Ser Thr Gly Glu Leu Phe Leu Asp Asn Gly Ile Glu
785                 790                 795                 800
```

```
Met Asp Ile Gly Gly Pro Gly Lys Trp Thr Leu Val Arg Phe Phe
            805                 810                 815

Ala Glu Ser Gly Ile Asn Asn Leu Thr Ile Ser Ser Glu Val Val Asn
        820                 825                 830

Arg Gly Tyr Ala Met Ser Gln Arg Trp Val Met Asp Lys Ile Thr Ile
        835                 840                 845

Leu Gly Leu Lys Arg Arg Val Lys Ile Lys Glu Tyr Thr Val Gln Lys
        850                 855                 860

Asp Ala Gly Ala Ile Lys Val Lys Gly Leu Gly Arg Arg Thr Ser Ser
865                 870                 875                 880

His Asn Gln Gly Gly Phe Phe Val Ser Val Ile Ser Asp Leu Arg Gln
                885                 890                 895

Leu Val Gly Gln Ala Phe Lys Leu Glu Leu Glu Phe Glu Gly Ala Thr
        900                 905                 910

Arg

<210> SEQ ID NO 17
<211> LENGTH: 919
<212> TYPE: PRT
<213> ORGANISM: Solanum tuberosum

<400> SEQUENCE: 17

Met Arg Ala Pro Leu Leu Leu Tyr Pro Leu Leu Leu Leu Leu Leu Phe
1               5                   10                  15

Val Thr Ser Ala Tyr Ser Trp Lys Lys Glu Glu Phe Arg Asn Cys Asp
            20                  25                  30

Gln Thr Pro Phe Cys Lys Arg Ala Arg Ser Arg Lys Pro Gly Ser Cys
        35                  40                  45

Asn Leu Arg Val Ala Asp Val Ser Ile Ser Asp Gly Asp Leu Ile Ala
    50                  55                  60

Lys Leu Val Pro Lys Glu Glu Asn Pro Glu Ser Glu Gln Pro Asn Lys
65                  70                  75                  80

Pro Leu Val Leu Thr Leu Ser Val Tyr Gln Asp Gly Val Met Arg Val
                85                  90                  95

Lys Ile Asp Glu Asp Gln Asn Leu Asn Pro Pro Lys Lys Arg Phe Glu
            100                 105                 110

Val Pro Glu Val Ile Glu Asp Phe Leu Asn Thr Lys Leu Trp Leu
        115                 120                 125

Thr Arg Val Lys Glu Glu Gln Ile Asp Gly Val Ser Ser Phe Ser Ser
    130                 135                 140

Val Phe Tyr Leu Ser Asp Gly Tyr Glu Gly Val Leu Arg His Asp Pro
145                 150                 155                 160

Phe Glu Val Phe Ala Arg Glu Ser Gly Ser Gly Lys Arg Val Leu Ser
                165                 170                 175

Ile Asn Ser Asn Gly Leu Phe Asp Phe Glu Gln Leu Arg Glu Lys Lys
            180                 185                 190

Glu Gly Asp Asp Trp Glu Glu Lys Phe Arg Ser His Thr Asp Thr Arg
        195                 200                 205

Pro Tyr Gly Pro Gln Ser Ile Ser Phe Asp Val Ser Pro Tyr Gly Ala
    210                 215                 220

Asp Phe Val Tyr Gly Ile Pro Glu His Ala Thr Ser Phe Ala Leu Lys
225                 230                 235                 240

Pro Thr Lys Gly Pro Asn Val Glu Glu Tyr Ser Glu Pro Tyr Arg Leu
                245                 250                 255
```

```
Phe Asn Leu Asp Val Phe Glu Tyr Leu His Glu Ser Pro Phe Gly Leu
            260                 265                 270

Tyr Gly Ser Ile Pro Phe Met Ile Ser His Gly Lys Ala Arg Gly Ser
            275                 280                 285

Ser Gly Phe Phe Trp Leu Asn Ala Ala Glu Met Gln Ile Asp Val Leu
290                 295                 300

Gly Ser Gly Trp Asn Ser Asp Glu Ser Ser Lys Ile Met Leu Pro Ser
305                 310                 315                 320

Asp Lys His Arg Ile Asp Thr Leu Trp Met Ser Glu Ser Gly Val Val
                325                 330                 335

Asp Thr Phe Phe Phe Ile Gly Pro Gly Pro Lys Asp Val Val Arg Gln
            340                 345                 350

Tyr Thr Ser Val Thr Gly Arg Pro Ser Met Pro Gln Leu Phe Ala Thr
            355                 360                 365

Ala Tyr His Gln Cys Arg Trp Asn Tyr Arg Asp Glu Glu Asp Val Tyr
            370                 375                 380

Asn Val Asp Ser Lys Phe Asp Glu His Asp Ile Pro Tyr Asp Val Leu
385                 390                 395                 400

Trp Leu Asp Ile Glu His Thr Asp Gly Lys Lys Tyr Phe Thr Trp Asp
                405                 410                 415

Arg Val Leu Phe Pro Asn Pro Glu Glu Met Gln Lys Lys Leu Ala Ala
            420                 425                 430

Lys Gly Arg His Met Val Thr Ile Val Asp Pro His Ile Lys Arg Asp
                435                 440                 445

Glu Ser Tyr His Ile Pro Lys Glu Ala Leu Glu Lys Gly Tyr Tyr Val
            450                 455                 460

Lys Asp Ala Thr Gly Lys Asp Tyr Asp Gly Trp Cys Trp Pro Gly Ser
465                 470                 475                 480

Ser Ser Tyr Thr Asp Leu Leu Asn Pro Glu Ile Lys Ser Trp Trp Ser
                485                 490                 495

Asp Lys Phe Ser Leu Asp Ser Tyr Val Gly Ser Thr Lys Tyr Leu Tyr
            500                 505                 510

Ile Trp Asn Asp Met Asn Glu Pro Ser Val Phe Asn Gly Pro Glu Val
            515                 520                 525

Thr Met Pro Arg Asp Ala Leu His His Gly Val Glu His Arg Glu
            530                 535                 540

Leu His Asn Ser Tyr Gly Tyr Phe His Met Gly Thr Ser Asp Gly
545                 550                 555                 560

Leu Leu Lys Arg Gly Asp Gly Lys Asp Arg Pro Phe Val Leu Ala Arg
                565                 570                 575

Ala Phe Phe Ala Gly Ser Gln Arg Tyr Gly Ala Ile Trp Thr Gly Asp
            580                 585                 590

Asn Thr Ala Glu Trp Glu His Leu Arg Val Ser Val Pro Met Val Leu
            595                 600                 605

Thr Leu Ser Ile Ser Gly Ile Val Phe Ser Gly Ala Asp Val Gly Gly
            610                 615                 620

Phe Phe Gly Asn Pro Asp Thr Glu Leu Leu Val Arg Trp Tyr Gln Val
625                 630                 635                 640

Gly Ala Tyr Tyr Pro Phe Phe Arg Gly His Ala His His Asp Thr Lys
                645                 650                 655

Arg Arg Glu Pro Trp Leu Phe Gly Glu Arg Asn Thr Gln Leu Met Arg
            660                 665                 670
```

-continued

```
Glu Ala Ile His Val Arg Tyr Met Tyr Leu Pro Tyr Phe Tyr Thr Leu
            675                 680                 685

Phe Arg Glu Ala Asn Ser Ser Gly Thr Pro Val Ala Arg Pro Leu Trp
    690                 695                 700

Met Glu Phe Pro Gly Asp Glu Lys Ser Phe Ser Asn Asp Glu Ala Phe
705                 710                 715                 720

Met Val Gly Asn Gly Leu Leu Val Gln Gly Val Tyr Thr Glu Lys Pro
                725                 730                 735

Lys His Val Ser Val Tyr Leu Pro Gly Glu Ser Trp Tyr Asp Leu
            740                 745                 750

Arg Ser Ala Ser Ala Tyr Asn Gly Gly His Thr His Lys Tyr Glu Val
            755                 760                 765

Ser Glu Asp Ser Ile Pro Ser Phe Gln Arg Ala Gly Thr Ile Ile Pro
770                 775                 780

Arg Lys Asp Arg Leu Arg Arg Ser Ser Thr Gln Met Glu Asn Asp Pro
785                 790                 795                 800

Tyr Thr Leu Val Ile Ala Leu Asn Ser Ser Lys Ala Ala Glu Gly Glu
                805                 810                 815

Leu Tyr Ile Asp Asp Gly Lys Ser Tyr Glu Phe Lys Gln Gly Ala Phe
            820                 825                 830

Ile Leu Lys Trp Glu Ala Tyr Ile Phe Gln Met Gln Pro Arg Leu Gln
            835                 840                 845

Leu Ala Val Thr His Phe Pro Ser Glu Cys Thr Val Glu Arg Ile Ile
850                 855                 860

Leu Leu Gly Leu Ser Pro Gly Ala Lys Thr Ala Leu Ile Glu Pro Gly
865                 870                 875                 880

Asn Lys Lys Val Glu Ile Glu Leu Gly Pro Leu Phe Ile Gln Gly Asn
                885                 890                 895

Arg Gly Ser Val Pro Thr Ile Arg Lys Pro Asn Val Arg Ile Thr Asp
            900                 905                 910

Asp Trp Ser Ile Gln Ile Leu
        915

<210> SEQ ID NO 18
<211> LENGTH: 985
<212> TYPE: PRT
<213> ORGANISM: Aspergillus niger

<400> SEQUENCE: 18

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125
```

```
Phe Leu Ser Glu Asn Leu Val Pro Arg Pro Lys Ala Ser Leu Asn Ala
    130                 135                 140
Ser Val Ser Gln Ser Asp Leu Phe Val Ser Trp Ser Asn Glu Pro Ser
145                 150                 155                 160
Phe Asn Phe Lys Val Ile Arg Lys Ala Thr Gly Asp Ala Leu Phe Ser
                165                 170                 175
Thr Glu Gly Thr Val Leu Val Tyr Glu Asn Gln Phe Ile Glu Phe Val
                180                 185                 190
Thr Ala Leu Pro Glu Glu Tyr Asn Leu Tyr Gly Leu Gly Glu His Ile
            195                 200                 205
Thr Gln Phe Arg Leu Gln Arg Asn Ala Asn Leu Thr Ile Tyr Pro Ser
210                 215                 220
Asp Asp Gly Thr Pro Ile Asp Gln Asn Leu Tyr Gly Gln His Pro Phe
225                 230                 235                 240
Tyr Leu Asp Thr Arg Tyr Tyr Lys Gly Asp Arg Gln Asn Gly Ser Tyr
                245                 250                 255
Ile Pro Val Lys Ser Ser Glu Ala Asp Ala Ser Gln Asp Tyr Ile Ser
                260                 265                 270
Leu Ser His Gly Val Phe Leu Arg Asn Ser His Gly Leu Glu Ile Leu
            275                 280                 285
Leu Arg Ser Gln Lys Leu Ile Trp Arg Thr Leu Gly Gly Ile Asp
290                 295                 300
Leu Thr Phe Tyr Ser Gly Pro Ala Pro Ala Asp Val Thr Arg Gln Tyr
305                 310                 315                 320
Leu Thr Ser Thr Val Gly Leu Pro Ala Met Gln Gln Tyr Asn Thr Leu
                325                 330                 335
Gly Phe His Gln Cys Arg Cys Gly Tyr Asn Asn Trp Ser Asp Leu Ala
            340                 345                 350
Asp Val Val Ala Asn Phe Glu Lys Phe Glu Ile Pro Leu Glu Tyr Ile
            355                 360                 365
Trp Thr Asp Ile Asp Tyr Met His Gly Tyr Arg Asn Phe Asp Asn Asp
370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
                420                 425                 430
Gly Ala Ala Asp Asp Val Phe Leu Lys Asn Pro Asp Gly Ser Leu Tyr
            435                 440                 445
Ile Gly Ala Val Trp Pro Gly Tyr Thr Val Phe Pro Asp Trp His His
            450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Ser
                485                 490                 495
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
            515                 520                 525
Tyr Pro Glu Ala Phe Asn Ile Thr Asn Ala Thr Glu Ala Ala Ser Ala
530                 535                 540
```

```
Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
    610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
    690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
            725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
    770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
            805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
    850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
        900                 905                 910

Leu Arg Ser Ser Ala Gln Gly Arg Trp Lys Glu Arg Asn Pro Leu Ala
    915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
```

```
                              965                 970                 975
Trp Ala Glu Asn Trp Val Leu Glu Trp
            980                 985

<210> SEQ ID NO 19
<211> LENGTH: 985
<212> TYPE: PRT
<213> ORGANISM: Aspergillus niger

<400> SEQUENCE: 19

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Asp Gly Tyr Asn Asn Trp Ser Asp Leu Ala
            340                 345                 350
```

-continued

```
Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
        435                 440                 445

Ile Gly Ala Val Trp Pro Gly Tyr Thr Val Phe Pro Asp Trp His His
    450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
    530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
    610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
    690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
```

-continued

```
                770                 775                 780
Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
                915                 920                 925

Asn Val Thr Val Leu Gly Val Asn Lys Glu Pro Ser Ala Val Thr Leu
                930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 20
<211> LENGTH: 985
<212> TYPE: PRT
<213> ORGANISM: Aspergillus niger

<400> SEQUENCE: 20

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
                35                  40                  45

Ala Asn Ile Asp Asp Pro Gln Ala Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
                100                 105                 110

Ile Gln Ile Leu Pro Thr His Val Asp Ser Thr Asn Ala Ser Trp Tyr
                115                 120                 125

Phe Leu Ser Glu Asn Leu Val Pro Arg Pro Lys Ala Ser Leu Asn Ala
                130                 135                 140

Ser Val Ser Gln Ser Asp Leu Phe Val Ser Trp Ser Asn Glu Pro Ser
145                 150                 155                 160
```

```
Phe Asn Phe Lys Val Ile Arg Lys Ala Thr Gly Asp Ala Leu Phe Ser
            165                 170                 175

Thr Glu Gly Thr Val Leu Val Tyr Glu Asn Gln Phe Ile Glu Phe Val
        180                 185                 190

Thr Ala Leu Pro Glu Glu Tyr Asn Leu Tyr Gly Leu Gly Glu His Ile
    195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Met Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn Asp
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
        435                 440                 445

Ile Gly Ala Val Trp Pro Gly Tyr Thr Val Phe Pro Asp Trp His His
    450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
    530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
```

```
            580                 585                 590
Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
        610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
        690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
        850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
        930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 21
```

```
<211> LENGTH: 985
<212> TYPE: PRT
<213> ORGANISM: Aspergillus niger

<400> SEQUENCE: 21

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg His Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn Asp
370                 375                 380

Gln His Arg Phe Ser Tyr Ser Glu Gly Asp Glu Phe Leu Ser Lys Leu
```

-continued

```
            385                 390                 395                 400
        His Glu Ser Gly Arg Tyr Tyr Val Pro Ile Val Asp Ala Ala Leu Tyr
                        405                 410                 415
        Ile Pro Asn Pro Glu Asn Ala Ser Asp Ala Tyr Ala Thr Tyr Asp Arg
                        420                 425                 430
        Gly Ala Ala Asp Asp Val Phe Leu Lys Asn Pro Asp Gly Ser Leu Tyr
                        435                 440                 445
        Ile Gly Ala Val Trp Pro Gly Tyr Thr Val Phe Pro Asp Trp His His
                450                 455                 460
        Pro Lys Ala Val Asp Phe Trp Ala Asn Glu Leu Val Ile Trp Ser Lys
        465                 470                 475                 480
        Lys Val Ala Phe Asp Gly Val Trp Tyr Asp Met Ser Glu Val Ser Ser
                        485                 490                 495
        Phe Cys Val Gly Ser Cys Gly Thr Gly Asn Leu Thr Leu Asn Pro Ala
                        500                 505                 510
        His Pro Ser Phe Leu Leu Pro Gly Glu Pro Gly Asp Ile Ile Tyr Asp
                        515                 520                 525
        Tyr Pro Glu Ala Phe Asn Ile Thr Asn Ala Thr Glu Ala Ala Ser Ala
                530                 535                 540
        Ser Ala Gly Ala Ser Ser Gln Ala Ala Thr Ala Thr Thr Thr Ser
        545                 550                 555                 560
        Thr Ser Val Ser Tyr Leu Arg Thr Thr Pro Thr Pro Gly Val Arg Asn
                        565                 570                 575
        Val Glu His Pro Pro Tyr Val Ile Asn His Asp Gln Glu Gly His Asp
                        580                 585                 590
        Leu Ser Val His Ala Val Ser Pro Asn Ala Thr His Val Asp Gly Val
                        595                 600                 605
        Glu Glu Tyr Asp Val His Gly Leu Tyr Gly His Gln Gly Leu Asn Ala
                        610                 615                 620
        Thr Tyr Gln Gly Leu Leu Glu Val Trp Ser His Lys Arg Arg Pro Phe
        625                 630                 635                 640
        Ile Ile Gly Arg Ser Thr Phe Ala Gly Ser Gly Lys Trp Ala Gly His
                        645                 650                 655
        Trp Gly Gly Asp Asn Tyr Ser Lys Trp Trp Ser Met Tyr Tyr Ser Ile
                        660                 665                 670
        Ser Gln Ala Leu Ser Phe Ser Leu Phe Gly Ile Pro Met Phe Gly Ala
                        675                 680                 685
        Asp Thr Cys Gly Phe Asn Gly Asn Ser Asp Glu Glu Leu Cys Asn Arg
                        690                 695                 700
        Trp Met Gln Leu Ser Ala Phe Phe Pro Phe Tyr Arg Asn His Asn Glu
        705                 710                 715                 720
        Leu Ser Thr Ile Pro Gln Glu Pro Tyr Arg Trp Ala Ser Val Ile Glu
                        725                 730                 735
        Ala Thr Lys Ser Ala Met Arg Ile Arg Tyr Ala Ile Leu Pro Tyr Phe
                        740                 745                 750
        Tyr Thr Leu Phe Asp Leu Ala His Thr Thr Gly Ser Thr Val Met Arg
                        755                 760                 765
        Ala Leu Ser Trp Glu Phe Pro Asn Asp Pro Thr Leu Ala Ala Val Glu
                        770                 775                 780
        Thr Gln Phe Met Val Gly Pro Ala Ile Met Val Pro Val Leu Glu
        785                 790                 795                 800
        Pro Leu Val Asn Thr Val Lys Gly Val Phe Pro Gly Val Gly His Gly
                        805                 810                 815
```

```
Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 22
<211> LENGTH: 985
<212> TYPE: PRT
<213> ORGANISM: Aspergillus niger

<400> SEQUENCE: 22

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Asp Ala Gln Ser Val Cys Pro
 50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
```

-continued

```
              195                 200                 205
Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                    245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Ala Gly Tyr Asn Asn Trp Ser Asp Leu Ala
                340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                    405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
                500                 505                 510

His Pro Ser Phe Leu Leu Pro Gly Glu Pro Gly Asp Ile Ile Tyr Asp
            515                 520                 525

Tyr Pro Glu Ala Phe Asn Ile Thr Asn Ala Thr Glu Ala Ala Ser Ala
            530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
                580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
610                 615                 620
```

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
                660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 23
<211> LENGTH: 985
<212> TYPE: PRT
<213> ORGANISM: Aspergillus niger

<400> SEQUENCE: 23

Met Val Lys Leu Thr His Leu Leu Ala Arg Ala Trp Leu Val Pro Leu

-continued

```
1               5                   10                  15
Ala Tyr Gly Ala Ser Gln Ser Leu Leu Ser Thr Thr Ala Pro Ser Gln
            20                  25                  30
Pro Gln Phe Thr Ile Pro Ala Ser Ala Asp Val Gly Ala Gln Leu Ile
            35                  40                  45
Ala Asn Ile Asp Asp Pro Gln Ala Asp Ala Gln Ser Val Cys Pro
50                  55                  60
Gly Tyr Lys Ala Ser Lys Val Gln His Asn Ser Arg Gly Phe Thr Ala
65                  70                  75                  80
Ser Leu Gln Leu Ala Gly Arg Pro Cys Asn Val Tyr Gly Thr Asp Val
                85                  90                  95
Glu Ser Leu Thr Leu Ser Val Glu Tyr Gln Asp Ser Asp Arg Leu Asn
                100                 105                 110
Ile Gln Ile Leu Pro Thr His Val Asp Ser Thr Asn Ala Ser Trp Tyr
                115                 120                 125
Phe Leu Ser Glu Asn Leu Val Pro Arg Pro Lys Ala Ser Leu Asn Ala
            130                 135                 140
Ser Val Ser Gln Ser Asp Leu Phe Val Ser Trp Ser Asn Glu Pro Ser
145                 150                 155                 160
Phe Asn Phe Lys Val Ile Arg Lys Ala Thr Gly Asp Ala Leu Phe Ser
                165                 170                 175
Thr Glu Gly Thr Val Leu Val Tyr Glu Asn Gln Phe Ile Glu Phe Val
                180                 185                 190
Thr Ala Leu Pro Glu Glu Tyr Asn Leu Tyr Gly Leu Gly Glu His Ile
                195                 200                 205
Thr Gln Phe Arg Leu Gln Arg Asn Ala Asn Leu Thr Ile Tyr Pro Ser
            210                 215                 220
Asp Asp Gly Thr Pro Ile Asp Gln Asn Leu Tyr Gly Gln His Pro Phe
225                 230                 235                 240
Tyr Leu Asp Thr Arg Tyr Tyr Lys Gly Asp Arg Gln Asn Gly Ser Tyr
                245                 250                 255
Ile Pro Val Lys Ser Ser Glu Ala Asp Ala Ser Gln Asp Tyr Ile Ser
                260                 265                 270
Leu Ser His Gly Val Phe Leu Arg Asn Ser His Gly Leu Glu Ile Leu
            275                 280                 285
Leu Arg Ser Gln Lys Leu Ile Trp Arg Thr Leu Gly Gly Gly Ile Asp
            290                 295                 300
Leu Thr Phe Tyr Ser Gly Pro Ala Pro Ala Asp Val Thr Arg Gln Tyr
305                 310                 315                 320
Leu Thr Ser Thr Val Gly Leu Pro Ala Met Gln Gln Tyr Asn Thr Leu
                325                 330                 335
Gly Phe His Gln Cys Arg Phe Gly Tyr Asn Asn Trp Ser Asp Leu Ala
            340                 345                 350
Asp Val Val Ala Asn Phe Glu Lys Phe Glu Ile Pro Leu Glu Tyr Ile
            355                 360                 365
Trp Thr Asp Ile Asp Tyr Met His Gly Tyr Arg Asn Phe Asp Asn Asp
        370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
            420                 425                 430
```

```
Gly Ala Ala Asp Asp Val Phe Leu Lys Asn Pro Asp Gly Ser Leu Tyr
        435                 440                 445

Ile Gly Ala Val Trp Pro Gly Tyr Thr Val Phe Pro Asp Trp His His
    450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
                500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
    530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
        660                 665                 670

Ser Gln Ala Leu Ser Phe Ser Leu Phe Gly Ile Pro Met Phe Gly Ala
    675                 680                 685

Asp Thr Cys Gly Phe Asn Gly Asn Ser Asp Glu Glu Leu Cys Asn Arg
        690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
        740                 745                 750

Tyr Thr Leu Phe Asp Leu Ala His Thr Thr Gly Ser Thr Val Met Arg
    755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
        820                 825                 830

Gly Val Asn Thr Thr Ile Ser Ala Pro Leu Gly His Ile Pro Val Tyr
    835                 840                 845
```

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
                915                 920                 925

Asn Val Thr Val Leu Gly Val Asn Lys Glu Pro Ser Ala Val Thr Leu
                930                 935                 940

Asn Gly Gln Ala Val Phe Pro Gly Ser Val Tyr Asn Ser Thr Ser
945                 950                 955                 960

Gln Val Leu Phe Val Gly Leu Gln Asn Leu Thr Lys Gly Gly Ala
                965                 970                 975

Trp Ala Glu Asn Trp Val Leu Glu Trp
                980                 985

<210> SEQ ID NO 24
<211> LENGTH: 985
<212> TYPE: PRT
<213> ORGANISM: Aspergillus niger

<400> SEQUENCE: 24

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Ala Asp Ala Gln Ser Val Cys Pro
        50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Gly Tyr Gln Asp Ser Asp Arg Leu Asn
                100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
        130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
            195                 200                 205

Thr Gln Phe Arg Leu Gln Arg Asn Ala Asn Leu Thr Ile Tyr Pro Ser
        210                 215                 220

Asp Asp Gly Thr Pro Ile Asp Gln Asn Leu Tyr Gly Gln His Pro Phe
225                 230                 235                 240

-continued

```
Tyr Leu Asp Thr Arg Tyr Tyr Lys Gly Asp Arg Gln Asn Gly Ser Tyr
            245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
            325                 330                 335

Gly Phe His Gln Cys Arg Gly Gly Tyr Asn Asn Trp Ser Asp Leu Ala
            340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
            370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
            405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
            485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
            515                 520                 525

Tyr Pro Glu Ala Phe Asn Ile Thr Asn Ala Thr Glu Ala Ala Ser Ala
            530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655
```

```
Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
        690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 25
<211> LENGTH: 985
<212> TYPE: PRT
<213> ORGANISM: Aspergillus niger

<400> SEQUENCE: 25

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45
```

```
Ala Asn Ile Asp Asp Pro Gln Ala Asp Ala Gln Ser Val Cys Pro
 50                  55                  60

Gly Tyr Lys Ala Ser Lys Val Gln His Asn Ser Arg Gly Phe Thr Ala
 65                  70                  75                  80

Ser Leu Gln Leu Ala Gly Arg Pro Cys Asn Val Tyr Gly Thr Asp Val
                 85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
            130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
            195                 200                 205

Thr Gln Phe Arg Leu Gln Arg Asn Ala Asn Leu Thr Ile Tyr Pro Ser
            210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Gly Ile Asp
            290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Thr Gly Tyr Asn Asn Trp Ser Asp Leu Ala
            340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
            370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460
```

-continued

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
            485                 490                 495

Phe Cys Val Gly Ser Cys Gly Thr Gly Asn Leu Thr Leu Asn Pro Ala
        500                 505                 510

His Pro Ser Phe Leu Leu Pro Gly Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile

```
                885                 890                 895
Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Leu Gln Asn Leu Thr Lys Gly Gly Ala
            965                 970                 975

Trp Ala Glu Asn Trp Val Leu Glu Trp
            980                 985

<210> SEQ ID NO 26
<211> LENGTH: 985
<212> TYPE: PRT
<213> ORGANISM: Aspergillus niger

<400> SEQUENCE: 26

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270
```

-continued

```
Leu Ser His Gly Val Phe Leu Arg Asn Ser His Gly Leu Glu Ile Leu
        275                 280                 285
Leu Arg Ser Gln Lys Leu Ile Trp Arg Thr Leu Gly Gly Ile Asp
290                 295                 300
Leu Thr Phe Tyr Ser Gly Pro Ala Pro Ala Asp Val Thr Arg Gln Tyr
305                 310                 315                 320
Leu Thr Ser Thr Val Gly Leu Pro Ala Met Gln Gln Tyr Asn Thr Leu
                325                 330                 335
Gly Phe His Gln Cys Arg Glu Gly Tyr Asn Asn Trp Ser Asp Leu Ala
            340                 345                 350
Asp Val Val Ala Asn Phe Glu Lys Phe Glu Ile Pro Leu Glu Tyr Ile
        355                 360                 365
Trp Thr Asp Ile Asp Tyr Met His Gly Tyr Arg Asn Phe Asp Asn Asp
370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
            420                 425                 430
Gly Ala Ala Asp Asp Val Phe Leu Lys Asn Pro Asp Gly Ser Leu Tyr
        435                 440                 445
Ile Gly Ala Val Trp Pro Gly Tyr Thr Val Phe Pro Asp Trp His His
        450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Ser
                485                 490                 495
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
        515                 520                 525
Tyr Pro Glu Ala Phe Asn Ile Thr Asn Ala Thr Glu Ala Ala Ser Ala
530                 535                 540
Ser Ala Gly Ala Ser Ser Gln Ala Ala Thr Ala Thr Thr Thr Ser
545                 550                 555                 560
Thr Ser Val Ser Tyr Leu Arg Thr Thr Pro Thr Pro Gly Val Arg Asn
                565                 570                 575
Val Glu His Pro Pro Tyr Val Ile Asn His Asp Gln Glu Gly His Asp
            580                 585                 590
Leu Ser Val His Ala Val Ser Pro Asn Ala Thr His Val Asp Gly Val
        595                 600                 605
Glu Glu Tyr Asp Val His Gly Leu Tyr Gly His Gln Gly Leu Asn Ala
        610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
                645                 650                 655
Trp Gly Gly Asp Asn Tyr Ser Lys Trp Trp Ser Met Tyr Tyr Ser Ile
            660                 665                 670
Ser Gln Ala Leu Ser Phe Ser Leu Phe Gly Ile Pro Met Phe Gly Ala
        675                 680                 685
Asp Thr Cys Gly Phe Asn Gly Asn Ser Asp Glu Glu Leu Cys Asn Arg
```

```
                690                 695                 700
Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 27
<211> LENGTH: 985
<212> TYPE: PRT
<213> ORGANISM: Aspergillus niger

<400> SEQUENCE: 27

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Asp Ala Gln Ser Val Cys Pro
        50                  55                  60

Gly Tyr Lys Ala Ser Lys Val Gln His Asn Ser Arg Gly Phe Thr Ala
65                  70                  75                  80
```

```
Ser Leu Gln Leu Ala Gly Arg Pro Cys Asn Val Tyr Gly Thr Asp Val
             85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
            195                 200                 205

Thr Gln Phe Arg Leu Gln Arg Asn Ala Asn Leu Thr Ile Tyr Pro Ser
            210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Val Gly Tyr Asn Asn Trp Ser Asp Leu Ala
            340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
            370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
```

```
                500               505                  510
    His Pro Ser Phe Leu Leu Pro Gly Glu Pro Gly Asp Ile Ile Tyr Asp
                515                   520                 525
    Tyr Pro Glu Ala Phe Asn Ile Thr Asn Ala Thr Glu Ala Ala Ser Ala
                530                   535                 540
    Ser Ala Gly Ala Ser Ser Gln Ala Ala Thr Ala Thr Thr Thr Ser
    545                   550                 555                 560
    Thr Ser Val Ser Tyr Leu Arg Thr Thr Pro Thr Pro Gly Val Arg Asn
                565                   570                 575
    Val Glu His Pro Pro Tyr Val Ile Asn His Asp Gln Glu Gly His Asp
                580                   585                 590
    Leu Ser Val His Ala Val Ser Pro Asn Ala Thr His Val Asp Gly Val
                595                   600                 605
    Glu Glu Tyr Asp Val His Gly Leu Tyr Gly His Gln Gly Leu Asn Ala
                610                   615                 620
    Thr Tyr Gln Gly Leu Leu Glu Val Trp Ser His Lys Arg Arg Pro Phe
    625                   630                 635                 640
    Ile Ile Gly Arg Ser Thr Phe Ala Gly Ser Gly Lys Trp Ala Gly His
                645                   650                 655
    Trp Gly Gly Asp Asn Tyr Ser Lys Trp Trp Ser Met Tyr Tyr Ser Ile
                660                   665                 670
    Ser Gln Ala Leu Ser Phe Ser Leu Phe Gly Ile Pro Met Phe Gly Ala
                675                   680                 685
    Asp Thr Cys Gly Phe Asn Gly Asn Ser Asp Glu Glu Leu Cys Asn Arg
                690                   695                 700
    Trp Met Gln Leu Ser Ala Phe Phe Pro Phe Tyr Arg Asn His Asn Glu
    705                   710                 715                 720
    Leu Ser Thr Ile Pro Gln Glu Pro Tyr Arg Trp Ala Ser Val Ile Glu
                725                   730                 735
    Ala Thr Lys Ser Ala Met Arg Ile Arg Tyr Ala Ile Leu Pro Tyr Phe
                740                   745                 750
    Tyr Thr Leu Phe Asp Leu Ala His Thr Thr Gly Ser Thr Val Met Arg
                755                   760                 765
    Ala Leu Ser Trp Glu Phe Pro Asn Asp Pro Thr Leu Ala Ala Val Glu
                770                   775                 780
    Thr Gln Phe Met Val Gly Pro Ala Ile Met Val Pro Val Leu Glu
    785                   790                 795                 800
    Pro Leu Val Asn Thr Val Lys Gly Val Phe Pro Gly Val Gly His Gly
                805                   810                 815
    Glu Val Trp Tyr Asp Trp Tyr Thr Gln Ala Ala Val Asp Ala Lys Pro
                820                   825                 830
    Gly Val Asn Thr Thr Ile Ser Ala Pro Leu Gly His Ile Pro Val Tyr
                835                   840                 845
    Val Arg Gly Gly Asn Ile Leu Pro Met Gln Glu Pro Ala Leu Thr Thr
                850                   855                 860
    Arg Glu Ala Arg Gln Thr Pro Trp Ala Leu Leu Ala Ala Leu Gly Ser
    865                   870                 875                 880
    Asn Gly Thr Ala Ser Gly Gln Leu Tyr Leu Asp Asp Gly Glu Ser Ile
                885                   890                 895
    Tyr Pro Asn Ala Thr Leu His Val Asp Phe Thr Ala Ser Arg Ser Ser
                900                   905                 910
    Leu Arg Ser Ser Ala Gln Gly Arg Trp Lys Glu Arg Asn Pro Leu Ala
                915                   920                 925
```

Asn Val Thr Val Leu Gly Val Asn Lys Glu Pro Ser Ala Val Thr Leu
          930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
              965                 970                 975

Trp Ala Glu Asn Trp Val Leu Glu Trp
          980                 985

<210> SEQ ID NO 28
<211> LENGTH: 985
<212> TYPE: PRT
<213> ORGANISM: Aspergillus niger

<400> SEQUENCE: 28

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300

Leu Thr Phe Tyr Ser Gly Pro Ala Pro Ala Asp Val Thr Arg Gln Tyr

```
            305                 310                 315                 320
Leu Thr Ser Thr Val Gly Leu Pro Ala Met Gln Gln Tyr Asn Thr Leu
                325                 330                 335
Gly Phe His Gln Cys Arg Gln Gly Tyr Asn Asn Trp Ser Asp Leu Ala
                340                 345                 350
Asp Val Val Ala Asn Phe Glu Lys Phe Glu Ile Pro Leu Glu Tyr Ile
                355                 360                 365
Trp Thr Asp Ile Asp Tyr Met His Gly Tyr Arg Asn Phe Asp Asn Asp
        370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
                420                 425                 430
Gly Ala Ala Asp Asp Val Phe Leu Lys Asn Pro Asp Gly Ser Leu Tyr
                435                 440                 445
Ile Gly Ala Val Trp Pro Gly Tyr Thr Val Phe Pro Asp Trp His His
        450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Ser
                485                 490                 495
Phe Cys Val Gly Ser Cys Gly Thr Gly Asn Leu Thr Leu Asn Pro Ala
                500                 505                 510
His Pro Ser Phe Leu Leu Pro Gly Glu Pro Gly Asp Ile Ile Tyr Asp
                515                 520                 525
Tyr Pro Glu Ala Phe Asn Ile Thr Asn Ala Thr Glu Ala Ala Ser Ala
                530                 535                 540
Ser Ala Gly Ala Ser Ser Gln Ala Ala Ala Thr Ala Thr Thr Thr Ser
545                 550                 555                 560
Thr Ser Val Ser Tyr Leu Arg Thr Thr Pro Thr Pro Gly Val Arg Asn
                565                 570                 575
Val Glu His Pro Pro Tyr Val Ile Asn His Asp Gln Glu Gly His Asp
                580                 585                 590
Leu Ser Val His Ala Val Ser Pro Asn Ala Thr His Val Asp Gly Val
                595                 600                 605
Glu Glu Tyr Asp Val His Gly Leu Tyr Gly His Gln Gly Leu Asn Ala
                610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
                645                 650                 655
Trp Gly Gly Asp Asn Tyr Ser Lys Trp Trp Ser Met Tyr Tyr Ser Ile
                660                 665                 670
Ser Gln Ala Leu Ser Phe Ser Leu Phe Gly Ile Pro Met Phe Gly Ala
                675                 680                 685
Asp Thr Cys Gly Phe Asn Gly Asn Ser Asp Glu Glu Leu Cys Asn Arg
                690                 695                 700
Trp Met Gln Leu Ser Ala Phe Phe Pro Phe Tyr Arg Asn His Asn Glu
705                 710                 715                 720
Leu Ser Thr Ile Pro Gln Glu Pro Tyr Arg Trp Ala Ser Val Ile Glu
                725                 730                 735
```

```
Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
    770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
    850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 29
<211> LENGTH: 985
<212> TYPE: PRT
<213> ORGANISM: Aspergillus niger

<400> SEQUENCE: 29

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
```

```
            115                 120                 125
Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
                195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
                275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Asn Gly Tyr Asn Asn Trp Ser Asp Leu Ala
                340                 345                 350

Asp Val Val Ala Asn Phe Glu Lys Phe Glu Ile Pro Leu Glu Tyr Ile
                355                 360                 365

Trp Thr Asp Ile Asp Tyr Met His Gly Tyr Arg Asn Phe Asp Asn Asp
                370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
                435                 440                 445

Ile Gly Ala Val Trp Pro Gly Tyr Thr Val Phe Pro Asp Trp His His
                450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
                500                 505                 510

His Pro Ser Phe Leu Leu Pro Gly Glu Pro Gly Asp Ile Ile Tyr Asp
                515                 520                 525

Tyr Pro Glu Ala Phe Asn Ile Thr Asn Ala Thr Glu Ala Ala Ser Ala
530                 535                 540
```

```
Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
                660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
        690                 695                 700

Trp Met Gln Leu Ser Ala Phe Phe Pro Phe Tyr Arg Asn His Asn Glu
705                 710                 715                 720

Leu Ser Thr Ile Pro Gln Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
        850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
        930                 935                 940

Asn Gly Gln Ala Val Phe Pro Gly Ser Val Thr Tyr Asn Ser Thr Ser
945                 950                 955                 960
```

Gln Val Leu Phe Val Gly Gly Leu Gln Asn Leu Thr Lys Gly Gly Ala
            965                 970                 975

Trp Ala Glu Asn Trp Val Leu Glu Trp
        980                 985

<210> SEQ ID NO 30
<211> LENGTH: 985
<212> TYPE: PRT
<213> ORGANISM: Aspergillus niger

<400> SEQUENCE: 30

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
    50                  55                  60

Gly Tyr Lys Ala Ser Lys Val Gln His Asn Ser Arg Gly Phe Thr Ala
65              70                  75                  80

Ser Leu Gln Leu Ala Gly Arg Pro Cys Asn Val Tyr Gly Thr Asp Val
            85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Ile Gly Tyr Asn Asn Trp Ser Asp Leu Ala
            340                 345                 350

-continued

```
Asp Val Val Ala Asn Phe Glu Lys Phe Glu Ile Pro Leu Glu Tyr Ile
            355                 360                 365
Trp Thr Asp Ile Asp Tyr Met His Gly Tyr Arg Asn Phe Asp Asn Asp
    370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
            420                 425                 430
Gly Ala Ala Asp Asp Val Phe Leu Lys Asn Pro Asp Gly Ser Leu Tyr
            435                 440                 445
Ile Gly Ala Val Trp Pro Gly Tyr Thr Val Phe Pro Asp Trp His His
            450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Ser
                485                 490                 495
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
            515                 520                 525
Tyr Pro Glu Ala Phe Asn Ile Thr Asn Ala Thr Glu Ala Ala Ser Ala
            530                 535                 540
Ser Ala Gly Ala Ser Ser Gln Ala Ala Ala Thr Ala Thr Thr Thr Ser
545                 550                 555                 560
Thr Ser Val Ser Tyr Leu Arg Thr Thr Pro Thr Pro Gly Val Arg Asn
                565                 570                 575
Val Glu His Pro Pro Tyr Val Ile Asn His Asp Gln Glu Gly His Asp
            580                 585                 590
Leu Ser Val His Ala Val Ser Pro Asn Ala Thr His Val Asp Gly Val
            595                 600                 605
Glu Glu Tyr Asp Val His Gly Leu Tyr Gly His Gln Gly Leu Asn Ala
    610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
                645                 650                 655
Trp Gly Gly Asp Asn Tyr Ser Lys Trp Trp Ser Met Tyr Tyr Ser Ile
            660                 665                 670
Ser Gln Ala Leu Ser Phe Ser Leu Phe Gly Ile Pro Met Phe Gly Ala
            675                 680                 685
Asp Thr Cys Gly Phe Asn Gly Asn Ser Asp Glu Glu Leu Cys Asn Arg
            690                 695                 700
Trp Met Gln Leu Ser Ala Phe Phe Pro Phe Tyr Arg Asn His Asn Glu
705                 710                 715                 720
Leu Ser Thr Ile Pro Gln Glu Pro Tyr Arg Trp Ala Ser Val Ile Glu
                725                 730                 735
Ala Thr Lys Ser Ala Met Arg Ile Arg Tyr Ala Ile Leu Pro Tyr Phe
            740                 745                 750
Tyr Thr Leu Phe Asp Leu Ala His Thr Thr Gly Ser Thr Val Met Arg
            755                 760                 765
```

```
Ala Leu Ser Trp Glu Phe Pro Asn Asp Pro Thr Leu Ala Ala Val Glu
    770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 31
<211> LENGTH: 985
<212> TYPE: PRT
<213> ORGANISM: Aspergillus niger

<400> SEQUENCE: 31

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160
```

```
Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn Asp
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
        435                 440                 445

Ile Gly Ala Gly Trp Pro Gly Tyr Thr Val Phe Pro Asp Trp His His
    450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
    530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575
```

```
Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
    610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
                660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
    690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
    770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
    850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985
```

```
<210> SEQ ID NO 32
<211> LENGTH: 985
<212> TYPE: PRT
<213> ORGANISM: Aspergillus niger

<400> SEQUENCE: 32

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn Asp
    370                 375                 380
```

-continued

```
Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
            405                 410                 415

Ile Pro Asn Pro Glu Asn Ala Ser Asp Ala Tyr Ala Thr Tyr Asp Arg
        420                 425                 430

Gly Ala Ala Asp Asp Val Phe Leu Lys Asn Pro Asp Gly Ser Leu Tyr
    435                 440                 445

Ile Gly Ala Asp Trp Pro Gly Tyr Thr Val Phe Pro Asp Trp His His
450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
            485                 490                 495

Phe Cys Val Gly Ser Cys Gly Thr Gly Asn Leu Thr Leu Asn Pro Ala
        500                 505                 510

His Pro Ser Phe Leu Leu Pro Gly Glu Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
        660                 665                 670

Ser Gln Ala Leu Ser Phe Ser Leu Phe Gly Ile Pro Met Phe Gly Ala
    675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
            725                 730                 735

Ala Thr Lys Ser Ala Met Arg Ile Arg Tyr Ala Ile Leu Pro Tyr Phe
        740                 745                 750

Tyr Thr Leu Phe Asp Leu Ala His Thr Thr Gly Ser Thr Val Met Arg
    755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
```

-continued

```
                805                 810                 815
Glu Val Trp Tyr Asp Trp Tyr Thr Gln Ala Ala Val Asp Ala Lys Pro
            820                 825                 830
Gly Val Asn Thr Thr Ile Ser Ala Pro Leu Gly His Ile Pro Val Tyr
            835                 840                 845
Val Arg Gly Gly Asn Ile Leu Pro Met Gln Glu Pro Ala Leu Thr Thr
        850                 855                 860
Arg Glu Ala Arg Gln Thr Pro Trp Ala Leu Leu Ala Ala Leu Gly Ser
865                 870                 875                 880
Asn Gly Thr Ala Ser Gly Gln Leu Tyr Leu Asp Asp Gly Glu Ser Ile
                885                 890                 895
Tyr Pro Asn Ala Thr Leu His Val Asp Phe Thr Ala Ser Arg Ser Ser
            900                 905                 910
Leu Arg Ser Ser Ala Gln Gly Arg Trp Lys Glu Arg Asn Pro Leu Ala
            915                 920                 925
Asn Val Thr Val Leu Gly Val Asn Lys Glu Pro Ser Ala Val Thr Leu
        930                 935                 940
Asn Gly Gln Ala Val Phe Pro Gly Ser Val Thr Tyr Asn Ser Thr Ser
945                 950                 955                 960
Gln Val Leu Phe Val Gly Leu Gln Asn Leu Thr Lys Gly Gly Ala
                965                 970                 975
Trp Ala Glu Asn Trp Val Leu Glu Trp
            980                 985
```

<210> SEQ ID NO 33
<211> LENGTH: 985
<212> TYPE: PRT
<213> ORGANISM: Aspergillus niger

<400> SEQUENCE: 33

```
Met Val Lys Leu Thr His Leu Leu Ala Arg Ala Trp Leu Val Pro Leu
1               5                   10                  15
Ala Tyr Gly Ala Ser Gln Ser Leu Leu Ser Thr Thr Ala Pro Ser Gln
            20                  25                  30
Pro Gln Phe Thr Ile Pro Ala Ser Ala Asp Val Gly Ala Gln Leu Ile
        35                  40                  45
Ala Asn Ile Asp Asp Pro Gln Ala Ala Asp Ala Gln Ser Val Cys Pro
    50                  55                  60
Gly Tyr Lys Ala Ser Lys Val Gln His Asn Ser Arg Gly Phe Thr Ala
65                  70                  75                  80
Ser Leu Gln Leu Ala Gly Arg Pro Cys Asn Val Tyr Gly Thr Asp Val
                85                  90                  95
Glu Ser Leu Thr Leu Ser Val Glu Tyr Gln Asp Ser Asp Arg Leu Asn
            100                 105                 110
Ile Gln Ile Leu Pro Thr His Val Asp Ser Thr Asn Ala Ser Trp Tyr
        115                 120                 125
Phe Leu Ser Glu Asn Leu Val Pro Arg Pro Lys Ala Ser Leu Asn Ala
    130                 135                 140
Ser Val Ser Gln Ser Asp Leu Phe Val Ser Trp Ser Asn Glu Pro Ser
145                 150                 155                 160
Phe Asn Phe Lys Val Ile Arg Lys Ala Thr Gly Asp Ala Leu Phe Ser
                165                 170                 175
Thr Glu Gly Thr Val Leu Val Tyr Glu Asn Gln Phe Ile Glu Phe Val
            180                 185                 190
```

```
Thr Ala Leu Pro Glu Glu Tyr Asn Leu Tyr Gly Leu Gly Glu His Ile
            195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
    275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
    355                 360                 365

Trp Thr Asp Ile Asp Tyr Met His Gly Tyr Arg Asn Phe Asp Asn Asp
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
            420                 425                 430

Gly Ala Ala Asp Asp Val Phe Leu Lys Asn Pro Asp Gly Ser Leu Tyr
    435                 440                 445

Ile Gly Ala Glu Trp Pro Gly Tyr Thr Val Phe Pro Asp Trp His His
    450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
```

```
                610              615              620
Thr Tyr Gln Gly Leu Leu Glu Val Trp Ser His Lys Arg Arg Pro Phe
625              630              635              640

Ile Ile Gly Arg Ser Thr Phe Ala Gly Ser Gly Lys Trp Ala Gly His
                645              650              655

Trp Gly Gly Asp Asn Tyr Ser Lys Trp Ser Met Tyr Tyr Ser Ile
            660              665              670

Ser Gln Ala Leu Ser Phe Ser Leu Phe Gly Ile Pro Met Phe Gly Ala
            675              680              685

Asp Thr Cys Gly Phe Asn Gly Asn Ser Asp Glu Glu Leu Cys Asn Arg
            690              695              700

Trp Met Gln Leu Ser Ala Phe Phe Pro Phe Tyr Arg Asn His Asn Glu
705              710              715              720

Leu Ser Thr Ile Pro Gln Glu Pro Tyr Arg Trp Ala Ser Val Ile Glu
                725              730              735

Ala Thr Lys Ser Ala Met Arg Ile Arg Tyr Ala Ile Leu Pro Tyr Phe
                740              745              750

Tyr Thr Leu Phe Asp Leu Ala His Thr Thr Gly Ser Thr Val Met Arg
            755              760              765

Ala Leu Ser Trp Glu Phe Pro Asn Asp Pro Thr Leu Ala Ala Val Glu
            770              775              780

Thr Gln Phe Met Val Gly Pro Ala Ile Met Val Val Pro Val Leu Glu
785              790              795              800

Pro Leu Val Asn Thr Val Lys Gly Val Phe Pro Gly Val Gly His Gly
                805              810              815

Glu Val Trp Tyr Asp Trp Tyr Thr Gln Ala Ala Val Asp Ala Lys Pro
                820              825              830

Gly Val Asn Thr Thr Ile Ser Ala Pro Leu Gly His Ile Pro Val Tyr
            835              840              845

Val Arg Gly Gly Asn Ile Leu Pro Met Gln Glu Pro Ala Leu Thr Thr
            850              855              860

Arg Glu Ala Arg Gln Thr Pro Trp Ala Leu Leu Ala Ala Leu Gly Ser
865              870              875              880

Asn Gly Thr Ala Ser Gly Gln Leu Tyr Leu Asp Asp Gly Glu Ser Ile
                885              890              895

Tyr Pro Asn Ala Thr Leu His Val Asp Phe Thr Ala Ser Arg Ser Ser
                900              905              910

Leu Arg Ser Ser Ala Gln Gly Arg Trp Lys Glu Arg Asn Pro Leu Ala
            915              920              925

Asn Val Thr Val Leu Gly Val Asn Lys Glu Pro Ser Ala Val Thr Leu
            930              935              940

Asn Gly Gln Ala Val Phe Pro Gly Ser Val Thr Tyr Asn Ser Thr Ser
945              950              955              960

Gln Val Leu Phe Val Gly Gly Leu Gln Asn Leu Thr Lys Gly Gly Ala
                965              970              975

Trp Ala Glu Asn Trp Val Leu Glu Trp
            980              985

<210> SEQ ID NO 34
<211> LENGTH: 985
<212> TYPE: PRT
<213> ORGANISM: Aspergillus niger

<400> SEQUENCE: 34
```

```
Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Gly Ile Asp
        290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
```

```
            420                 425                 430
Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Val
            485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
            515                 520                 525

Tyr Pro Glu Ala Phe Asn Ile Thr Asn Ala Thr Glu Ala Ala Ser Ala
            530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
            610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
            690                 695                 700

Trp Met Gln Leu Ser Ala Phe Pro Phe Tyr Arg Asn His Asn Glu
705                 710                 715                 720

Leu Ser Thr Ile Pro Gln Glu Pro Tyr Arg Trp Ala Ser Val Ile Glu
            725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
            770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
            805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
            835                 840                 845
```

```
Val Arg Gly Gly Asn Ile Leu Pro Met Gln Glu Pro Ala Leu Thr Thr
            850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
            965                 970                 975

Trp Ala Glu Asn Trp Val Leu Glu Trp
            980                 985

<210> SEQ ID NO 35
<211> LENGTH: 985
<212> TYPE: PRT
<213> ORGANISM: Aspergillus niger

<400> SEQUENCE: 35

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Ala Asp Ala Gln Ser Val Cys Pro
        50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
            85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
        130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
            165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
            195                 200                 205

Thr Gln Phe Arg Leu Gln Arg Asn Ala Asn Leu Thr Ile Tyr Pro Ser
        210                 215                 220

Asp Asp Gly Thr Pro Ile Asp Gln Asn Leu Tyr Gly Gln His Pro Phe
```

```
                    225                 230                 235                 240
                Tyr Leu Asp Thr Arg Tyr Tyr Lys Gly Asp Arg Gln Asn Gly Ser Tyr
                                    245                 250                 255

Ile Pro Val Lys Ser Ser Glu Ala Asp Ala Ser Gln Asp Tyr Ile Ser
                                    260                 265                 270

Leu Ser His Gly Val Phe Leu Arg Asn Ser His Gly Leu Glu Ile Leu
                                    275                 280                 285

Leu Arg Ser Gln Lys Leu Ile Trp Arg Thr Leu Gly Gly Ile Asp
                                290                 295                 300

Leu Thr Phe Tyr Ser Gly Pro Ala Pro Ala Asp Val Thr Arg Gln Tyr
                305                 310                 315                 320

Leu Thr Ser Thr Val Gly Leu Pro Ala Met Gln Gln Tyr Asn Thr Leu
                                    325                 330                 335

Gly Phe His Gln Cys Arg Trp Gly Tyr Asn Asn Trp Ser Asp Leu Ala
                                    340                 345                 350

Asp Val Val Ala Asn Phe Glu Lys Phe Glu Ile Pro Leu Glu Tyr Ile
                                    355                 360                 365

Trp Thr Asp Ile Asp Tyr Met His Gly Tyr Arg Asn Phe Asp Asn Asp
                                    370                 375                 380

Gln His Arg Phe Ser Tyr Ser Glu Gly Asp Glu Phe Leu Ser Lys Leu
                385                 390                 395                 400

His Glu Ser Gly Arg Tyr Tyr Val Pro Ile Val Asp Ala Ala Leu Tyr
                                    405                 410                 415

Ile Pro Asn Pro Glu Asn Ala Ser Asp Ala Tyr Ala Thr Tyr Asp Arg
                                    420                 425                 430

Gly Ala Ala Asp Asp Val Phe Leu Lys Asn Pro Asp Gly Ser Leu Tyr
                                    435                 440                 445

Ile Gly Ala Val Trp Pro Gly Tyr Thr Val Phe Pro Asp Trp His His
                                    450                 455                 460

Pro Lys Ala Val Asp Phe Trp Ala Asn Glu Leu Val Ile Trp Ser Lys
                465                 470                 475                 480

Lys Val Ala Phe Asp Gly Val Trp Tyr Asp Met Ser Glu Val Ser Asn
                                    485                 490                 495

Phe Cys Val Gly Ser Cys Gly Thr Gly Asn Leu Thr Leu Asn Pro Ala
                                    500                 505                 510

His Pro Ser Phe Leu Leu Pro Gly Glu Pro Gly Asp Ile Ile Tyr Asp
                                    515                 520                 525

Tyr Pro Glu Ala Phe Asn Ile Thr Asn Ala Thr Glu Ala Ala Ser Ala
                                    530                 535                 540

Ser Ala Gly Ala Ser Ser Gln Ala Ala Ala Thr Ala Thr Thr Thr Ser
                545                 550                 555                 560

Thr Ser Val Ser Tyr Leu Arg Thr Thr Pro Thr Pro Gly Val Arg Asn
                                    565                 570                 575

Val Glu His Pro Pro Tyr Val Ile Asn His Asp Gln Glu Gly His Asp
                                    580                 585                 590

Leu Ser Val His Ala Val Ser Pro Asn Ala Thr His Val Asp Gly Val
                                    595                 600                 605

Glu Glu Tyr Asp Val His Gly Leu Tyr Gly His Gln Gly Leu Asn Ala
                                    610                 615                 620

Thr Tyr Gln Gly Leu Leu Glu Val Trp Ser His Lys Arg Arg Pro Phe
                625                 630                 635                 640

Ile Ile Gly Arg Ser Thr Phe Ala Gly Ser Gly Lys Trp Ala Gly His
                                    645                 650                 655
```

```
Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
    690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
            725                 730                 735

Ala Thr Lys Ser Ala Met Arg Ile Arg Tyr Ala Ile Leu Pro Tyr Phe
        740                 745                 750

Tyr Thr Leu Phe Asp Leu Ala His Thr Thr Gly Ser Thr Val Met Arg
    755                 760                 765

Ala Leu Ser Trp Glu Phe Pro Asn Asp Pro Thr Leu Ala Ala Val Glu
    770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
            805                 810                 815

Glu Val Trp Tyr Asp Trp Tyr Thr Gln Ala Ala Val Asp Ala Lys Pro
        820                 825                 830

Gly Val Asn Thr Thr Ile Ser Ala Pro Leu Gly His Ile Pro Val Tyr
    835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
        900                 905                 910

Leu Arg Ser Ser Ala Gln Gly Arg Trp Lys Glu Arg Asn Pro Leu Ala
    915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Leu Gln Asn Leu Thr Lys Gly Gly Ala
            965                 970                 975

Trp Ala Glu Asn Trp Val Leu Glu Trp
            980                 985

<210> SEQ ID NO 36
<211> LENGTH: 985
<212> TYPE: PRT
<213> ORGANISM: Aspergillus niger

<400> SEQUENCE: 36

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
```

```
            35                  40                  45
Ala Asn Ile Asp Asp Pro Gln Ala Asp Ala Gln Ser Val Cys Pro
 50                  55                  60

Gly Tyr Lys Ala Ser Lys Val Gln His Asn Ser Arg Gly Phe Thr Ala
 65                  70                  75                  80

Ser Leu Gln Leu Ala Gly Arg Pro Cys Asn Val Tyr Gly Thr Asp Val
                 85                  90                  95

Glu Ser Leu Thr Leu Ser Val Glu Tyr Gln Asp Ser Asp Arg Leu Asn
                100                 105                 110

Ile Gln Ile Leu Pro Thr His Val Asp Ser Thr Asn Ala Ser Trp Tyr
                115                 120                 125

Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
                195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
                275                 280                 285

Leu Arg Ser Gln Lys Leu Ile Trp Arg Thr Leu Gly Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
                340                 345                 350

Asp Val Val Ala Asn Phe Glu Lys Phe Glu Ile Pro Leu Glu Tyr Ile
                355                 360                 365

Trp Thr Asp Ile Asp Tyr Met His Gly Tyr Arg Asn Phe Asp Asn Asp
                370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
                435                 440                 445

Ile Gly Ala Val Trp Pro Gly Tyr Thr Val Phe Pro Asp Trp His His
                450                 455                 460
```

```
Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Gln
            485                 490                 495

Phe Cys Val Gly Ser Cys Gly Thr Gly Asn Leu Thr Leu Asn Pro Ala
        500                 505                 510

His Pro Ser Phe Leu Leu Pro Gly Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880
```

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
        900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
        930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
            965                 970                 975

Trp Ala Glu Asn Trp Val Leu Glu Trp
            980                 985

<210> SEQ ID NO 37
<211> LENGTH: 985
<212> TYPE: PRT
<213> ORGANISM: Aspergillus niger

<400> SEQUENCE: 37

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
            85                  90                  95

Glu Ser Leu Thr Leu Ser Val Glu Tyr Gln Asp Ser Asp Arg Leu Asn
        100                 105                 110

Ile Gln Ile Leu Pro Thr His Val Asp Ser Thr Asn Ala Ser Trp Tyr
    115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
            165                 170                 175

Thr Glu Gly Thr Val Leu Val Tyr Glu Asn Gln Phe Ile Glu Phe Val
        180                 185                 190

Thr Ala Leu Pro Glu Glu Tyr Asn Leu Tyr Gly Leu Gly Glu His Ile
    195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
            245                 250                 255

Ile Pro Val Lys Ser Ser Glu Ala Asp Ala Ser Gln Asp Tyr Ile Ser
        260                 265                 270

```
Leu Ser His Gly Val Phe Leu Arg Asn Ser His Gly Leu Glu Ile Leu
        275                 280                 285
Leu Arg Ser Gln Lys Leu Ile Trp Arg Thr Leu Gly Gly Ile Asp
290                 295                 300
Leu Thr Phe Tyr Ser Gly Pro Ala Pro Ala Asp Val Thr Arg Gln Tyr
305                 310                 315                 320
Leu Thr Ser Thr Val Gly Leu Pro Ala Met Gln Gln Tyr Asn Thr Leu
                325                 330                 335
Gly Phe His Gln Cys Arg Asp Gly Tyr Asn Asn Trp Ser Asp Leu Ala
                340                 345                 350
Asp Val Val Ala Asn Phe Glu Lys Phe Glu Ile Pro Leu Glu Tyr Ile
                355                 360                 365
Trp Thr Asp Ile Asp Tyr Met His Gly Tyr Arg Asn Phe Asp Asn Asp
        370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
                420                 425                 430
Gly Ala Ala Asp Asp Val Phe Leu Lys Asn Pro Asp Gly Ser Leu Tyr
                435                 440                 445
Ile Gly Ala Ala Trp Pro Gly Tyr Thr Val Phe Pro Asp Trp His His
        450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Ser
                485                 490                 495
Phe Cys Val Gly Ser Cys Gly Thr Gly Asn Leu Thr Leu Asn Pro Ala
                500                 505                 510
His Pro Ser Phe Leu Leu Pro Gly Glu Pro Gly Asp Ile Ile Tyr Asp
                515                 520                 525
Tyr Pro Glu Ala Phe Asn Ile Thr Asn Ala Thr Glu Ala Ala Ser Ala
        530                 535                 540
Ser Ala Gly Ala Ser Ser Gln Ala Ala Ala Thr Ala Thr Thr Thr Ser
545                 550                 555                 560
Thr Ser Val Ser Tyr Leu Arg Thr Thr Pro Thr Pro Gly Val Arg Asn
                565                 570                 575
Val Glu His Pro Pro Tyr Val Ile Asn His Asp Gln Glu Gly His Asp
                580                 585                 590
Leu Ser Val His Ala Val Ser Pro Asn Ala Thr His Val Asp Gly Val
                595                 600                 605
Glu Glu Tyr Asp Val His Gly Leu Tyr Gly His Gln Gly Leu Asn Ala
610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
                645                 650                 655
Trp Gly Gly Asp Asn Tyr Ser Lys Trp Trp Ser Met Tyr Tyr Ser Ile
                660                 665                 670
Ser Gln Ala Leu Ser Phe Ser Leu Phe Gly Ile Pro Met Phe Gly Ala
                675                 680                 685
```

```
Asp Thr Cys Gly Phe Asn Gly Asn Ser Asp Glu Glu Leu Cys Asn Arg
    690             695                 700

Trp Met Gln Leu Ser Ala Phe Pro Phe Tyr Arg Asn His Asn Glu
705             710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
                755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785             790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
    850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 38
<211> LENGTH: 985
<212> TYPE: PRT
<213> ORGANISM: Aspergillus niger

<400> SEQUENCE: 38

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80
```

```
Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
                100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
        130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
                195                 200                 205

Thr Gln Phe Arg Leu Gln Arg Asn Ala Asn Leu Thr Ile Tyr Pro Ser
            210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Gly Ile Asp
        290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Asp Gly Tyr Asn Asn Trp Ser Asp Leu Ala
                340                 345                 350

Asp Val Val Ala Asn Phe Glu Lys Phe Glu Ile Pro Leu Glu Tyr Ile
                355                 360                 365

Trp Thr Asp Ile Asp Tyr Met His Gly Tyr Arg Asn Phe Asp Asn Asp
        370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
            435                 440                 445

Ile Gly Ala Gly Trp Pro Gly Tyr Thr Val Phe Pro Asp Trp His His
        450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495
```

-continued

```
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
        515                 520                 525
Tyr Pro Glu Ala Phe Asn Ile Thr Asn Ala Thr Glu Ala Ala Ser Ala
    530                 535                 540
Ser Ala Gly Ala Ser Ser Gln Ala Ala Thr Ala Thr Thr Thr Thr Ser
545                 550                 555                 560
Thr Ser Val Ser Tyr Leu Arg Thr Thr Pro Thr Gly Val Arg Asn
                565                 570                 575
Val Glu His Pro Pro Tyr Val Ile Asn His Asp Gln Glu Gly His Asp
            580                 585                 590
Leu Ser Val His Ala Val Ser Pro Asn Ala Thr His Val Asp Gly Val
        595                 600                 605
Glu Glu Tyr Asp Val His Gly Leu Tyr Gly His Gln Gly Leu Asn Ala
    610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
                645                 650                 655
Trp Gly Gly Asp Asn Tyr Ser Lys Trp Trp Ser Met Tyr Tyr Ser Ile
            660                 665                 670
Ser Gln Ala Leu Ser Phe Ser Leu Phe Gly Ile Pro Met Phe Gly Ala
        675                 680                 685
Asp Thr Cys Gly Phe Asn Gly Asn Ser Asp Glu Glu Leu Cys Asn Arg
    690                 695                 700
Trp Met Gln Leu Ser Ala Phe Phe Pro Phe Tyr Arg Asn His Asn Glu
705                 710                 715                 720
Leu Ser Thr Ile Pro Gln Glu Pro Tyr Arg Trp Ala Ser Val Ile Glu
                725                 730                 735
Ala Thr Lys Ser Ala Met Arg Ile Arg Tyr Ala Ile Leu Pro Tyr Phe
            740                 745                 750
Tyr Thr Leu Phe Asp Leu Ala His Thr Thr Gly Ser Thr Val Met Arg
        755                 760                 765
Ala Leu Ser Trp Glu Phe Pro Asn Asp Pro Thr Leu Ala Ala Val Glu
    770                 775                 780
Thr Gln Phe Met Val Gly Pro Ala Ile Met Val Pro Val Leu Glu
785                 790                 795                 800
Pro Leu Val Asn Thr Val Lys Gly Val Phe Pro Gly Val Gly His Gly
                805                 810                 815
Glu Val Trp Tyr Asp Trp Tyr Thr Gln Ala Ala Val Asp Ala Lys Pro
            820                 825                 830
Gly Val Asn Thr Thr Ile Ser Ala Pro Leu Gly His Ile Pro Val Tyr
        835                 840                 845
Val Arg Gly Gly Asn Ile Leu Pro Met Gln Pro Ala Leu Thr Thr
    850                 855                 860
Arg Glu Ala Arg Gln Thr Pro Trp Ala Leu Leu Ala Ala Leu Gly Ser
865                 870                 875                 880
Asn Gly Thr Ala Ser Gly Gln Leu Tyr Leu Asp Asp Gly Glu Ser Ile
                885                 890                 895
Tyr Pro Asn Ala Thr Leu His Val Asp Phe Thr Ala Ser Arg Ser Ser
            900                 905                 910
Leu Arg Ser Ser Ala Gln Gly Arg Trp Lys Glu Arg Asn Pro Leu Ala
```

```
                915                 920                 925
Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 39
<211> LENGTH: 985
<212> TYPE: PRT
<213> ORGANISM: Aspergillus niger

<400> SEQUENCE: 39

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300
```

```
Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
            325                 330                 335

Gly Phe His Gln Cys Arg Asp Gly Tyr Asn Asn Trp Ser Asp Leu Ala
        340                 345                 350

Asp Val Val Ala Asn Phe Glu Lys Phe Glu Ile Pro Leu Glu Tyr Ile
    355                 360                 365

Trp Thr Asp Ile Asp Tyr Met His Gly Tyr Arg Asn Phe Asp Asn Asp
370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
            405                 410                 415

Ile Pro Asn Pro Glu Asn Ala Ser Asp Ala Tyr Ala Thr Tyr Asp Arg
        420                 425                 430

Gly Ala Ala Asp Asp Val Phe Leu Lys Asn Pro Asp Gly Ser Leu Tyr
    435                 440                 445

Ile Gly Ala Val Trp Pro Gly Tyr Thr Val Phe Pro Asp Trp His His
450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ile
            485                 490                 495

Phe Cys Val Gly Ser Cys Gly Thr Gly Asn Leu Thr Leu Asn Pro Ala
        500                 505                 510

His Pro Ser Phe Leu Leu Pro Gly Glu Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
        660                 665                 670

Ser Gln Ala Leu Ser Phe Ser Leu Phe Gly Ile Pro Met Phe Gly Ala
    675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
```

```
            725                 730                 735
Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
            850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 40
<211> LENGTH: 985
<212> TYPE: PRT
<213> ORGANISM: Aspergillus niger

<400> SEQUENCE: 40

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110
```

-continued

```
Ile Gln Ile Leu Pro Thr His Val Asp Ser Thr Asn Ala Ser Trp Tyr
        115                 120                 125
Phe Leu Ser Glu Asn Leu Val Pro Arg Pro Lys Ala Ser Leu Asn Ala
    130                 135                 140
Ser Val Ser Gln Ser Asp Leu Phe Val Ser Trp Ser Asn Glu Pro Ser
145                 150                 155                 160
Phe Asn Phe Lys Val Ile Arg Lys Ala Thr Gly Asp Ala Leu Phe Ser
                165                 170                 175
Thr Glu Gly Thr Val Leu Val Tyr Glu Asn Gln Phe Ile Glu Phe Val
            180                 185                 190
Thr Ala Leu Pro Glu Glu Tyr Asn Leu Tyr Gly Leu Gly Glu His Ile
        195                 200                 205
Thr Gln Phe Arg Leu Gln Arg Asn Ala Asn Leu Thr Ile Tyr Pro Ser
    210                 215                 220
Asp Asp Gly Thr Pro Ile Asp Gln Asn Leu Tyr Gly Gln His Pro Phe
225                 230                 235                 240
Tyr Leu Asp Thr Arg Tyr Tyr Lys Gly Asp Arg Gln Asn Gly Ser Tyr
                245                 250                 255
Ile Pro Val Lys Ser Ser Glu Ala Asp Ala Ser Gln Asp Tyr Ile Ser
            260                 265                 270
Leu Ser His Gly Val Phe Leu Arg Asn Ser His Gly Leu Glu Ile Leu
        275                 280                 285
Leu Arg Ser Gln Lys Leu Ile Trp Arg Thr Leu Gly Gly Ile Asp
    290                 295                 300
Leu Thr Phe Tyr Ser Gly Pro Ala Pro Ala Asp Val Thr Arg Gln Tyr
305                 310                 315                 320
Leu Thr Ser Thr Val Gly Leu Pro Ala Met Gln Gln Tyr Asn Thr Leu
                325                 330                 335
Gly Phe His Gln Cys Arg Asp Gly Tyr Asn Asn Trp Ser Asp Leu Ala
            340                 345                 350
Asp Val Val Ala Asn Phe Glu Lys Phe Glu Ile Pro Leu Glu Tyr Ile
        355                 360                 365
Trp Thr Asp Ile Asp Tyr Met His Gly Tyr Arg Asn Phe Asp Asn Asp
    370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
                405                 410                 415
Ile Pro Asn Pro Glu Asn Ala Ser Asp Ala Tyr Ala Thr Tyr Asp Arg
            420                 425                 430
Gly Ala Ala Asp Asp Val Phe Leu Lys Asn Pro Asp Gly Ser Leu Tyr
        435                 440                 445
Ile Gly Ala Val Trp Pro Gly Tyr Thr Val Phe Pro Asp Trp His His
    450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Arg
                485                 490                 495
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
        515                 520                 525
Tyr Pro Glu Ala Phe Asn Ile Thr Asn Ala Thr Glu Ala Ala Ser Ala
```

```
            530                 535                 540
Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
                580                 585                 590

Leu Ser Val His Ala Val Ser Pro Asn Ala Thr His Val Asp Gly Val
                595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
                660                 665                 670

Ser Gln Ala Leu Ser Phe Ser Leu Phe Gly Ile Pro Met Phe Gly Ala
                675                 680                 685

Asp Thr Cys Gly Phe Asn Gly Asn Ser Asp Glu Glu Leu Cys Asn Arg
                690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Gly Ser Thr Val Met Arg
                755                 760                 765

Ala Leu Ser Trp Glu Phe Pro Asn Asp Pro Thr Leu Ala Ala Val Glu
                770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
                915                 920                 925

Asn Val Thr Val Leu Gly Val Asn Lys Glu Pro Ser Ala Val Thr Leu
                930                 935                 940

Asn Gly Gln Ala Val Phe Pro Gly Ser Val Thr Tyr Asn Ser Thr Ser
945                 950                 955                 960
```

```
Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 41
<211> LENGTH: 985
<212> TYPE: PRT
<213> ORGANISM: Aspergillus niger

<400> SEQUENCE: 41

Met Val Lys Leu Thr His Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
                35                  40                  45

Ala Asn Ile Asp Asp Pro Gln Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
                100                 105                 110

Ile Gln Ile Leu Pro Thr His Val Asp Ser Thr Asn Ala Ser Trp Tyr
                115                 120                 125

Phe Leu Ser Glu Asn Leu Val Pro Arg Pro Lys Ala Ser Leu Asn Ala
                130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
                195                 200                 205

Thr Gln Phe Arg Leu Gln Arg Asn Ala Asn Leu Thr Ile Tyr Pro Ser
                210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
                275                 280                 285

Leu Arg Ser Gln Lys Leu Ile Trp Arg Thr Leu Gly Gly Ile Asp
                290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Met Gly Tyr Asn Asn Trp Ser Asp Leu Ala
```

```
            340                 345                 350
Asp Val Val Ala Asn Phe Glu Lys Phe Glu Ile Pro Leu Glu Tyr Ile
            355                 360                 365
Trp Thr Asp Ile Asp Tyr Met His Gly Tyr Arg Asn Phe Asp Asn Asp
            370                 375                 380
Gln His Arg Phe Ser Tyr Ser Glu Gly Asp Glu Phe Leu Ser Lys Leu
385                 390                 395                 400
His Glu Ser Gly Arg Tyr Tyr Val Pro Ile Val Asp Ala Ala Leu Tyr
            405                 410                 415
Ile Pro Asn Pro Glu Asn Ala Ser Asp Ala Tyr Ala Thr Tyr Asp Arg
            420                 425                 430
Gly Ala Ala Asp Asp Val Phe Leu Lys Asn Pro Asp Gly Ser Leu Tyr
            435                 440                 445
Ile Gly Ala Val Trp Pro Gly Tyr Thr Val Phe Pro Asp Trp His His
            450                 455                 460
Pro Lys Ala Val Asp Phe Trp Ala Asn Glu Leu Val Ile Trp Ser Lys
465                 470                 475                 480
Lys Val Ala Phe Asp Gly Val Trp Tyr Asp Met Ser Glu Val Ser Cys
            485                 490                 495
Phe Cys Val Gly Ser Cys Gly Thr Gly Asn Leu Thr Leu Asn Pro Ala
            500                 505                 510
His Pro Ser Phe Leu Leu Pro Gly Glu Pro Gly Asp Ile Ile Tyr Asp
            515                 520                 525
Tyr Pro Glu Ala Phe Asn Ile Thr Asn Ala Thr Glu Ala Ala Ser Ala
            530                 535                 540
Ser Ala Gly Ala Ser Ser Gln Ala Ala Thr Ala Thr Thr Thr Ser
545                 550                 555                 560
Thr Ser Val Ser Tyr Leu Arg Thr Thr Pro Thr Pro Gly Val Arg Asn
            565                 570                 575
Val Glu His Pro Pro Tyr Val Ile Asn His Asp Gln Glu Gly His Asp
            580                 585                 590
Leu Ser Val His Ala Val Ser Pro Asn Ala Thr His Val Asp Gly Val
            595                 600                 605
Glu Glu Tyr Asp Val His Gly Leu Tyr Gly His Gln Gly Leu Asn Ala
            610                 615                 620
Thr Tyr Gln Gly Leu Leu Glu Val Trp Ser His Lys Arg Arg Pro Phe
625                 630                 635                 640
Ile Ile Gly Arg Ser Thr Phe Ala Gly Ser Gly Lys Trp Ala Gly His
            645                 650                 655
Trp Gly Gly Asp Asn Tyr Ser Lys Trp Trp Ser Met Tyr Tyr Ser Ile
            660                 665                 670
Ser Gln Ala Leu Ser Phe Ser Leu Phe Gly Ile Pro Met Phe Gly Ala
            675                 680                 685
Asp Thr Cys Gly Phe Asn Gly Asn Ser Asp Glu Glu Leu Cys Asn Arg
            690                 695                 700
Trp Met Gln Leu Ser Ala Phe Phe Pro Phe Tyr Arg Asn His Asn Glu
705                 710                 715                 720
Leu Ser Thr Ile Pro Gln Glu Pro Tyr Arg Trp Ala Ser Val Ile Glu
            725                 730                 735
Ala Thr Lys Ser Ala Met Arg Ile Arg Tyr Ala Ile Leu Pro Tyr Phe
            740                 745                 750
Tyr Thr Leu Phe Asp Leu Ala His Thr Thr Gly Ser Thr Val Met Arg
            755                 760                 765
```

```
Ala Leu Ser Trp Glu Phe Pro Asn Asp Pro Thr Leu Ala Ala Val Glu
        770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
    850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
    930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 42
<211> LENGTH: 985
<212> TYPE: PRT
<213> ORGANISM: Aspergillus niger

<400> SEQUENCE: 42

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
                20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Ala Asp Ala Gln Ser Val Cys Pro
        50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
```

```
            145                 150                 155                 160
        Phe Asn Phe Lys Val Ile Arg Lys Ala Thr Gly Asp Ala Leu Phe Ser
                        165                 170                 175
        Thr Glu Gly Thr Val Leu Val Tyr Glu Asn Gln Phe Ile Glu Phe Val
                        180                 185                 190
        Thr Ala Leu Pro Glu Glu Tyr Asn Leu Tyr Gly Leu Gly Glu His Ile
                        195                 200                 205
        Thr Gln Phe Arg Leu Gln Arg Asn Ala Asn Leu Thr Ile Tyr Pro Ser
                        210                 215                 220
        Asp Asp Gly Thr Pro Ile Asp Gln Asn Leu Tyr Gly Gln His Pro Phe
        225                 230                 235                 240
        Tyr Leu Asp Thr Arg Tyr Tyr Lys Gly Asp Arg Gln Asn Gly Ser Tyr
                        245                 250                 255
        Ile Pro Val Lys Ser Ser Glu Ala Asp Ala Ser Gln Asp Tyr Ile Ser
                        260                 265                 270
        Leu Ser His Gly Val Phe Leu Arg Asn Ser His Gly Leu Glu Ile Leu
                        275                 280                 285
        Leu Arg Ser Gln Lys Leu Ile Trp Arg Thr Leu Gly Gly Ile Asp
                        290                 295                 300
        Leu Thr Phe Tyr Ser Gly Pro Ala Pro Ala Asp Val Thr Arg Gln Tyr
        305                 310                 315                 320
        Leu Thr Ser Thr Val Gly Leu Pro Ala Met Gln Gln Tyr Asn Thr Leu
                        325                 330                 335
        Gly Phe His Gln Cys Arg Met Gly Tyr Asn Asn Trp Ser Asp Leu Ala
                        340                 345                 350
        Asp Val Val Ala Asn Phe Glu Lys Phe Glu Ile Pro Leu Glu Tyr Ile
                        355                 360                 365
        Trp Thr Asp Ile Asp Tyr Met His Gly Tyr Arg Asn Phe Asp Asn Asp
                        370                 375                 380
        Gln His Arg Phe Ser Tyr Ser Glu Gly Asp Glu Phe Leu Ser Lys Leu
        385                 390                 395                 400
        His Glu Ser Gly Arg Tyr Tyr Val Pro Ile Val Asp Ala Ala Leu Tyr
                        405                 410                 415
        Ile Pro Asn Pro Glu Asn Ala Ser Asp Ala Tyr Ala Thr Tyr Asp Arg
                        420                 425                 430
        Gly Ala Ala Asp Asp Val Phe Leu Lys Asn Pro Asp Gly Ser Leu Tyr
                        435                 440                 445
        Ile Gly Ala Val Trp Pro Gly Tyr Thr Val Phe Pro Asp Trp His His
                        450                 455                 460
        Pro Lys Ala Val Asp Phe Trp Ala Asn Glu Leu Val Ile Trp Ser Lys
        465                 470                 475                 480
        Lys Val Ala Phe Asp Gly Val Trp Tyr Asp Met Ser Glu Val Ser Thr
                        485                 490                 495
        Phe Cys Val Gly Ser Cys Gly Thr Gly Asn Leu Thr Leu Asn Pro Ala
                        500                 505                 510
        His Pro Ser Phe Leu Leu Pro Gly Glu Pro Gly Asp Ile Ile Tyr Asp
                        515                 520                 525
        Tyr Pro Glu Ala Phe Asn Ile Thr Asn Ala Thr Glu Ala Ala Ser Ala
                        530                 535                 540
        Ser Ala Gly Ala Ser Ser Gln Ala Ala Ala Thr Ala Thr Thr Thr Ser
        545                 550                 555                 560
        Thr Ser Val Ser Tyr Leu Arg Thr Thr Pro Thr Pro Gly Val Arg Asn
                        565                 570                 575
```

```
Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
        930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985
```

<210> SEQ ID NO 43
<211> LENGTH: 2958
<212> TYPE: DNA
<213> ORGANISM: Aspergillus niger

<400> SEQUENCE: 43

```
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420
tccctcaatg catctgtatc ccagagcgac cttttttgtgt catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga gaatataac      600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata aagatatta caaggagat aggcagaatg gtcttatat tcccgtcaaa        780
agcagcgagg ctgatgcctc gcaagattat atctccctct ctcatggcgt gtttctgagg     840
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgttgtg gctacaacaa ctggtcggat ctggcggacg ttgttgcgaa cttgagaag    1080
tttgagatcc cgttggaata tatctggacc gatattgact acatgcacgg atatcgcaac     1140
tttgacaacg atcaacatcg cttttcctac agtgagggcg atgaatttct cagcaagcta     1200
catgagagtg gacgctacta tgtacccatt gttgatgcgg cgctctacat tcctaatccc     1260
gaaaatgcct ctgatgcata cgctacgtat gacagaggag ctgcggacga cgtcttcctc     1320
aagaatcccg atggtagcct ctatattgga gccgtttggc caggatatac agtcttcccc     1380
gattggcatc atcccaaggc agttgacttc tgggctaacg agcttgttat ctggtcgaag     1440
aaagtggcgt tcgatggtgt gtggtacgac atgtctgaag tttcatcctt ctgtgtcggg    1500
agctgtggca caggtaacct gactctgaac ccggcacacc catcgtttct tctccccggt     1560
gagcctggtg atatcatata tgattaccca gaggctttca atatcaccaa cgctacagag     1620
gcggcgtcag cttcggcggg agcttccagt caggctgcag caaccgcgac caccacgtcg     1680
acttcggtat catatctgcg gacaacgccc acgcctggtg tccgcaatgt tgagcaccca     1740
ccctatgtga tcaaccatga ccaagaaggc catgatctca gtgtccatgc ggtgtcgccg     1800
aatgcaacgc atgttgatgg tgttgaggag tatgatgtgc acggtctcta cggacatcaa     1860
ggattgaacg ctacctacca aggtctgctt gaggtctggt ctcataagcg gcggccatt     1920
attattggcc gctcaacctt cgctggctct ggcaaatggg caggccactg ggcggcgac    1980
aactattcca aatggtggtc catgtactac tccatctcgc aagccctctc cttctcactt     2040
ttcggcattc cgatgtttgg tgcggacacc tgtgggttta acggaaactc cgatgaggag     2100
ctctgcaacc gatggatgca actgtccgca ttcttcccat tctaccgaaa ccacaatgag     2160
```

```
ctctccacaa tcccacagga gccttatcgg tgggcttctg ttattgaagc aaccaagtcc    2220
gccatgagaa ttcggtacgc catcctacct tacttttata cgttgtttga cctggcccac    2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                 2958

<210> SEQ ID NO 44
<211> LENGTH: 2958
<212> TYPE: DNA
<213> ORGANISM: Aspergillus niger

<400> SEQUENCE: 44
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420 tccctcaatg catctgtatc ccagagcgac ctttttgtgt catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga gaatataac      600 ttgtatggcc ttggggagca tatcacgcaa ttccgcctcc agagaaatgc taatctgacc     660
atatatcctt cggatgatgg aacacctatt gaccaaaacc tctacggcca catcccttc     720 tatctggata acagatatta caaggagat aggcagaatg ggtcttatat tcccgtcaaa     780
agcagcgagg ctgatgcctc gcaagattat atctccctct ctcatggcgt gtttctgagg     840
aactctcatg gacttgagat actcctccgg tctcaaaaat tgatctggcg acccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgtgatg gctacaacaa ctggtcggat ctggcggacg ttgttgcgaa cttgagaag    1080 tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
```

```
gaaaatgcct ctgatgcata cgctacgtat gacagaggag ctgcggacga cgtcttcctc      1320
aagaatcccg atggtagcct ctatattgga gccgtttggc caggatatac agtcttcccc      1380
gattggcatc atcccaaggc agttgacttc tgggctaacg agcttgttat ctggtcgaag      1440
aaagtggcgt tcgatggtgt gtggtacgac atgtctgaag tttcatcctt ctgtgtcggg      1500
agctgtggca caggtaacct gactctgaac ccggcacacc catcgtttct tctccccggt      1560
gagcctggtg atatcatata tgattaccca gaggctttca atatcaccaa cgctacagag      1620
gcggcgtcag cttcggcggg agcttccagt caggctgcag caaccgcgac caccacgtcg      1680
acttcggtat catatctgcg acaacgcccc acgcctggtg tccgcaatgt tgagcaccca      1740
ccctatgtga tcaaccatga ccaagaaggc catgatctca gtgtccatgc ggtgtcgccg      1800
aatgcaacgc atgttgatgg tgttgaggag tatgatgtgc acggtctcta cggacatcaa      1860
ggattgaacg ctacctacca aggtctgctt gaggtctggt ctcataagcg gcggccattt      1920
attattggcc gctcaacctt cgctggctct ggcaaatggg caggccactg gggcggcgac      1980
aactattcca aatggtggtc catgtactac tccatctcgc aagccctctc cttctcactt      2040
ttcggcattc cgatgtttgg tgcggacacc tgtgggttta acggaaactc cgatgaggag      2100
ctctgcaacc gatggatgca actgtccgca ttcttcccat tctaccgaaa ccacaatgag      2160
ctctccacaa tcccacagga gccttatcgg tgggcttctg ttattgaagc aaccaagtcc      2220
gccatgagaa ttcggtacgc catcctacct tacttttata cgttgtttga cctgccccac      2280
accacgggct ccactgtaat gcgcgcactt tcctgggaat tccctaatga cccaacattg      2340
gctgcggttg agactcaatt catggttggg ccggccatca tggtggtccc ggtattggag      2400
cctctggtca atacggtcaa gggcgtattc ccaggagttg acatggcga agtgtggtac       2460 gattggtaca cccaggctgc agttgatgcg aagcccgggg tcaacacgac catttcggca      2520
ccattgggcc acatcccagt ttatgtacga ggtggaaaca tcttgccgat gcaagagccg      2580
gcattgacca ctcgtgaagc ccggcaaacc cgtgggcctt tgctagctgc actaggaagc      2640
aatggaaccg cgtcggggca gctctatctc gatgatggag agagcatcta ccccaatgcc      2700
accctccatg tggacttcac ggcatcgcgc tcaagcctgc gctcgtcggc tcaaggaaga      2760
tggaaagaga ggaacccgct tgctaatgtg acggtgctcg gagtgaacaa ggagccctct      2820
gcggtgaccc tgaatggaca ggccgtattt cccgggtctg tcacgtacaa ttctacgtcc      2880
caggttctct tgttgggggg gctgcaaaac ttgacgaagg gcggcgcatg ggcggaaaac      2940
tgggtattgg aatggtag                                                   2958

<210> SEQ ID NO 45
<211> LENGTH: 2958
<212> TYPE: DNA
<213> ORGANISM: Aspergillus niger

<400> SEQUENCE: 45
atggtgaagt tgacgcatct ccttgccaga gcatggcttg tccctctggc ttatggagcg       60
agccagtcac tcttatccac cactgcccct tcgcagccgc agtttaccat tcctgcttcc      120
gcagatgtcg gtgcgcagct gattgccaac atcgatgatc ctcaggctgc cgacgcgcag      180
tcggtttgtc cgggctacaa ggcttcaaaa gtgcagcaca attcacgtgg attcactgcc      240
agtcttcagc tcgcgggcag gccatgtaac gtatacggca cagatgttga gtccttgaca      300
ctgtctgtga agtaccagga ttcggatcga ctgaatattc agattctccc cactcatgtt      360
gactccacaa acgcttcttg gtactttctt tcggaaaacc tggtccccag acccaaggct      420
```

-continued

```
tccctcaatg catctgtatc ccagagcgac cttttttgtgt catggtcaaa tgagccgtcg      480
ttcaatttca aggtgatccg aaaggctaca ggcgacgcgc ttttcagtac agaaggcact      540
gtgctcgtat atgagaatca gttcatcgaa tttgtgaccg cgctccctga agaatataac      600
ttgtatggcc ttggggagca tatcacgcaa ttccgcctcc agagaaatgc taatctgacc      660
atatatcctt cggatgatgg aacacctatt gaccaaaacc tctacggcca acatcccttc      720
tatctggata caagatatta caaaggagat aggcagaatg gtcttatat tcccgtcaaa      780 agcagcgagg ctgatgcctc gcaagattat atctccctct ctcatggcgt gtttctgagg      840
aactctcatg gacttgagat actcctccgg tctcaaaaat tgatctggcg gaccctaggt      900
ggaggaatcg atctcacctt ctactcaggc cccgccccgg ccgatgttac caggcaatat      960
cttaccagca ctgtgggatt accggccatg cagcaataca acactcttgg attccaccaa      1020
tgtcgtatgg gctacaacaa ctggtcggat ctggcggacg ttgttgcgaa ctttgagaag      1080
tttgagatcc cgttggaata tatctggacc gatattgact acatgcacgg atatcgcaac      1140
tttgacaacg atcaacatcg cttttcctac agtgagggcg atgaatttct cagcaagcta      1200
catgagagtg gacgctacta tgtacccatt gttgatgcgg cgctctacat tcctaatccc      1260
gaaaatgcct ctgatgcata cgctacgtat gacagaggag ctgcggacga cgtcttcctc      1320
aagaatcccg atggtagcct ctatattgga gccgtttggc caggatatac agtcttcccc      1380
gattggcatc atcccaaggc agttgacttc tgggctaacg agcttgttat ctggtcgaag      1440
aaagtggcgt tcgatggtgt gtggtacgac atgtctgaag tttcatcctt ctgtgtcggg      1500
agctgtggca caggtaacct gactctgaac ccggcacacc catcgtttct tctccccggt      1560
gagcctggtg atatcatata tgattaccca gaggctttca atatcaccaa cgctacagag      1620
gcggcgtcag cttcggcggg agcttccagt caggctgcag caaccgcgac caccacgtcg      1680
acttcggtat catatctgcg gacaacgccc acgcctggtg tccgcaatgt tgagcaccca      1740
ccctatgtga tcaaccatga ccaagaaggc catgatctca gtgtccatgc ggtgtcgccg      1800
aatgcaacgc atgttgatgg tgttgaggag tatgatgtgc acggtctcta cggacatcaa      1860
ggattgaacg ctacctacca aggtctgctt gaggtctggt ctcataagcg gcggccattt      1920
attattggcc gctcaacctt cgctggctct ggcaaatggg caggccactg ggcggcgac      1980 aactattcca aatggtggtc catgtactac tccatctcgc aagccctctc cttctcactt      2040
ttcggcattc cgatgtttgg tgcggacacc tgtgggttta acggaaactc cgatgaggag      2100
ctctgcaacc gatggatgca actgtccgca ttcttcccat tctaccgaaa ccacaatgag      2160
ctctccacaa tcccacagga gccttatcgg tgggcttctg ttattgaagc aaccaagtcc      2220
gccatgagaa ttcggtacgc catcctacct tactttttata cgttgtttga cctggcccac      2280
accacgggct ccactgtaat gcgcgcactt tcctgggaat tccctaatga cccaacattg      2340
gctgcggttg agactcaatt catggttggg ccggccatca tggtggtccc ggtattggag      2400
cctctggtca atacggtcaa gggcgtattc ccaggagttg acatggcga agtgtggtac      2460 gattggtaca cccaggctgc agttgatgcg aagcccgggg tcaacacgac catttcggca      2520
ccattgggcc acatcccagt ttatgtacga ggtggaaaca tcttgccgat gcaagagccg      2580
gcattgacca ctcgtgaagc ccggcaaacc ccgtgggctt tgctagctgc actaggaagc      2640
aatggaaccg cgtcggggca gctctatctc gatgatggag agagcatcta ccccaatgcc      2700
accctccatg tggacttcac ggcatcgcgg tcaagcctgc gctcgtcggc tcaaggaaga      2760
```

```
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttgggggg gctgcaaaac ttgacgaagg gcggcgcatg ggcggaaaac    2940
tgggtattgg aatggtag                                                  2958

<210> SEQ ID NO 46
<211> LENGTH: 2958
<212> TYPE: DNA
<213> ORGANISM: Aspergillus niger

<400> SEQUENCE: 46
atggtgaagt tgacgcatct ccttgccaga gcatggcttg ccctctggc ttatggagcg      60 agccagtcac tcttatccac cactgcccct tcgcagccgc agtttaccat tcctgcttcc    120
gcagatgtcg gtgcgcagct gattgccaac atcgatgatc tcaggctgc cgacgcgcag    180 tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct    420 tccctcaatg catctgtatc ccagagcgac cttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatccttc    720 tatctggata caagatatta caaaggagat aggcagaatg ggtcttatat tcccgtcaaa    780
agcagcgagg ctgatgcctc gcaagattat atctccctct tcatggcgt gtttctgagg    840 aactctcatg gacttgagat actcctccgg tctcaaaaat tgatctggcg acccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtcatg gctacaacaa ctggtcggat ctggcggacg ttgttgcgaa cttttgagaag    1080 tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatccctt ctgtgtcggg    1500 agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
```

```
attattggcc gctcaacctt cgctggctct ggcaaatggg caggccactg gggcggcgac    1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttata cgttgtttga cctgccccac     2280
accacgggct ccactgtaat gcgcgcactt tcctgggaat ccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc cgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                  2958

<210> SEQ ID NO 47
<211> LENGTH: 2958
<212> TYPE: DNA
<213> ORGANISM: Aspergillus niger

<400> SEQUENCE: 47
atggtgaagt tgacgcatct ccttgccaga gcatggcttg tccctctggc ttatggagcg     60
agccagtcac tcttatccac cactgcccct tcgcagccgc agtttaccat tcctgcttcc    120
gcagatgtcg gtgcgcagct gattgccaac atcgatgatc tcaggctgc cgacgcgcag    180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag cccaaggct    420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
agcagcgagg ctgatgcctc gcaagattat atctccctct tcatggcgt gtttctgagg    840
aactctcatg gacttgagat actcctccgg tctcaaaaat tgatctggcg accctaggt    900
ggaggaatcg atctcacctt ctactcaggc cccgccccgg ccgatgttac caggcaatat    960
cttaccagca ctgtgggatt accggccatg cagcaataca acactcttgg attccaccaa    1020
```

```
tgtcgtgcgg gctacaacaa ctggtcggat ctggcggacg ttgttgcgaa ctttgagaag     1080
tttgagatcc cgttggaata tatctggacc gatattgact acatgcacgg atatcgcaac     1140
tttgacaacg atcaacatcg cttttcctac agtgagggcg atgaatttct cagcaagcta     1200
catgagagtg gacgctacta tgtacccatt gttgatgcgg cgctctacat tcctaatccc     1260
gaaaatgcct ctgatgcata cgctacgtat gacagaggag ctgcggacga cgtcttcctc     1320
aagaatcccg atggtagcct ctatattgga gccgtttggc caggatatac agtcttcccc     1380
gattggcatc atcccaaggc agttgacttc tgggctaacg agcttgttat ctggtcgaag     1440
aaagtggcgt tcgatggtgt gtggtacgac atgtctgaag tttcatcctt ctgtgtcggg     1500
agctgtggca caggtaacct gactctgaac ccggcacacc catcgtttct tctccccggt     1560
gagcctggtg atatcatata tgattaccca gaggctttca atatcaccaa cgctacagag     1620
gcggcgtcag cttcggcggg agcttccagt caggctgcag caaccgcgac cacccacgtcg    1680 acttcggtat catatctgcg gacaacgccc acgcctggtg tccgcaatgt tgagcaccca     1740 cccctatgtga tcaaccatga ccaagaaggc catgatctca gtgtccatgc ggtgtcgccg     1800
aatgcaacgc atgttgatgg tgttgaggag tatgatgtgc acggtctcta cggacatcaa     1860
ggattgaacg ctacctacca aggtctgctt gaggtctggt ctcataagcg gcggccattt     1920
attattggcc gctcaacctt cgctggctct ggcaaatggg caggccactg gggcggcgac     1980
aactattcca aatggtggtc catgtactac tccatctcgc aagccctctc cttctcactt     2040
ttcggcattc cgatgtttgg tgcggacacc tgtgggttta acggaaactc cgatgaggag     2100
ctctgcaacc gatggatgca actgtccgca ttcttcccat tctaccgaaa ccacaatgag     2160
ctctccacaa tcccacagga gccttatcgg tgggcttctg ttattgaagc aaccaagtcc     2220
gccatgagaa ttcggtacgc catcctacct tacttttata cgttgtttga cctggcccac     2280
accacgggct ccactgtaat gcgcgcactt tcctgggaat tccctaatga cccaacattg     2340
gctgcggttg agactcaatt catggttggg ccggccatca tggtggtccc ggtattggag     2400
cctctggtca atacggtcaa gggcgtattc ccaggagttg gacatggcga agtgtggtac     2460
gattggtaca cccaggctgc agttgatgcg aagcccgggg tcaacacgac catttcggca     2520
ccattgggcc acatcccagt ttatgtacga ggtggaaaca tcttgccgat gcaagagccg     2580
gcattgacca ctcgtgaagc ccggcaaacc ccgtgggctt tgctagctgc actaggaagc     2640
aatggaaccg cgtcggggca gctctatctc gatgatggag agagcatcta ccccaatgcc     2700
accctccatg tggacttcac ggcatcgcgg tcaagcctgc gctcgtcggc tcaaggaaga     2760
tggaaagaga ggaacccgct tgctaatgtg acggtgctcg gagtgaacaa ggagccctct     2820
gcggtgaccc tgaatggaca ggccgtattt cccgggtctg tcacgtacaa ttctacgtcc     2880
caggttctct ttgttggggg gctgcaaaac ttgacgaagg gcggcgcatg ggcggaaaac     2940
tgggtattgg aatggtag                                                   2958

<210> SEQ ID NO 48
<211> LENGTH: 2958
<212> TYPE: DNA
<213> ORGANISM: Aspergillus niger

<400> SEQUENCE: 48
atggtgaagt tgacgcatct ccttgccaga gcatggcttg ccctctggc ttatggagcg       60 agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
```

```
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag  acccaaggct    420 tccctcaatg catctgtatc ccagagcgac cttttgtgt  catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg gtcttatat  tcccgtcaaa    780 agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgttttg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac cacccacgtcg   1680 acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg ggcggcgac    1980 aactattcca aatggtggtc catgtactac tccatctcgc aagccctctc cttctcactt   2040
ttcggcattc cgatgtttgg tgcggacacc tgtgggttta acgaaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct actttttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga  agtgtggtac   2460 gattggtaca cccaggctgc agttgatgcg aagcccgggg tcaacacgac catttcggca   2520
```

```
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                 2958

<210> SEQ ID NO 49
<211> LENGTH: 2958
<212> TYPE: DNA
<213> ORGANISM: Aspergillus niger

<400> SEQUENCE: 49
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc tcaggctgc cgacgcgcag     180 tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtccccag acccaaggct     420
tccctcaatg catctgtatc ccagagcgac cttttgtgt catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaaggagat aggcagaatg gtcttatat tcccgtcaaa     780 agcagcgagg ctgatgcctc gcaagattat atctccctct ctcatggcgt gtttctgagg     840
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgtgggg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg ctttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctcccggt    1560 gagcctggtg atatcatata tgattaccca gaggctttca atatcaccaa cgctacagag    1620
gcggcgtcag cttcggcggg agcttccagt caggctgcag caaccgcgac caccacgtcg    1680
```

```
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg gggcggcgac   1980
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tacttttata cgttgtttga cctgccccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac    2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg gcggcgcatg ggcggaaaac   2940
tgggtattgg aatggtag                                                 2958

<210> SEQ ID NO 50
<211> LENGTH: 2958
<212> TYPE: DNA
<213> ORGANISM: Aspergillus niger

<400> SEQUENCE: 50
atggtgaagt tgacgcatct ccttgccaga gcatggcttg tccctctggc ttatggagcg     60
agccagtcac tcttatccac cactgcccct tcgcagccgc agtttaccat tcctgcttcc    120
gcagatgtcg gtgcgcagct gattgccaac atcgatgatc tcaggctgc cgacgcgcag     180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct     420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
```

| | |
|---|---|
| agcagcgagg ctgatgcctc gcaagattat atctccctct ctcatggcgt gtttctgagg | 840 |
| aactctcatg gacttgagat actcctccgg tctcaaaaat tgatctggcg gaccctaggt | 900 |
| ggaggaatcg atctcacctt ctactcaggc cccgccccgg ccgatgttac caggcaatat | 960 |
| cttaccagca ctgtgggatt accggccatg cagcaataca acactcttgg attccaccaa | 1020 |
| tgtcgtactg gctacaacaa ctggtcggat ctggcggacg ttgttgcgaa ctttgagaag | 1080 |
| tttgagatcc cgttggaata tatctggacc gatattgact acatgcacgg atatcgcaac | 1140 |
| tttgacaacg atcaacatcg cttttcctac agtgagggcg atgaatttct cagcaagcta | 1200 |
| catgagagtg gacgctacta tgtacccatt gttgatgcgg cgctctacat tcctaatccc | 1260 |
| gaaaatgcct ctgatgcata cgctacgtat gacagaggag ctgcggacga cgtcttcctc | 1320 |
| aagaatcccg atggtagcct ctatattgga gccgtttggc caggatatac agtcttcccc | 1380 |
| gattggcatc atcccaaggc agttgacttc tgggctaacg agcttgttat ctggtcgaag | 1440 |
| aaagtggcgt tcgatggtgt gtggtacgac atgtctgaag tttcatcctt ctgtgtcggg | 1500 |
| agctgtggca caggtaacct gactctgaac ccggcacacc catcgtttct tctccccggt | 1560 |
| gagcctggtg atatcatata tgattaccca gaggctttca atatcaccaa cgctacagag | 1620 |
| gcggcgtcag cttcggcggg agcttccagt caggctgcag caaccgcgac caccacgtcg | 1680 |
| acttcggtat catatctgcg gacaacgccc acgcctggtg tccgcaatgt tgagcaccca | 1740 |
| ccctatgtga tcaaccatga ccaagaaggc catgatctca gtgtccatgc ggtgtcgccg | 1800 |
| aatgcaacgc atgttgatgg tgttgaggag tatgatgtgc acggtctcta cggacatcaa | 1860 |
| ggattgaacg ctacctacca aggtctgctt gaggtctggt ctcataagcg gcggccattt | 1920 |
| attattggcc gctcaacctt cgctggctct ggcaaatggg caggccactg gggcggcgac | 1980 |
| aactattcca aatggtggtc catgtactac tccatctcgc aagccctctc cttctcactt | 2040 |
| ttcggcattc cgatgtttgg tgcggacacc tgtgggttta acggaaactc cgatgaggag | 2100 |
| ctctgcaacc gatggatgca actgtccgca ttcttcccat tctaccgaaa ccacaatgag | 2160 |
| ctctccacaa tcccacagga gccttatcgg tgggcttctg ttattgaagc aaccaagtcc | 2220 |
| gccatgagaa ttcggtacgc catcctacct tactttttata cgttgtttga cctggcccac | 2280 |
| accacgggct ccactgtaat gcgcgcactt tcctgggaat tccctaatga cccaacattg | 2340 |
| gctgcggttg agactcaatt catggttggg ccggccatca tggtggtccc ggtattggag | 2400 |
| cctctggtca atacggtcaa gggcgtattc ccaggagttg acatggcga agtgtggtac | 2460 |
| gattggtaca cccaggctgc agttgatgcg aagcccgggg tcaacacgac catttcggca | 2520 |
| ccattgggcc acatcccagt ttatgtacga ggtggaaaca tcttgccgat gcaagagccg | 2580 |
| gcattgacca ctcgtgaagc ccggcaaacc ccgtgggctt tgctagctgc actaggaagc | 2640 |
| aatggaaccg cgtcggggca gctctatctc gatgatggag agagcatcta ccccaatgcc | 2700 |
| accctccatg tggacttcac ggcatcgcgg tcaagcctgc gctcgtcggc tcaaggaaga | 2760 |
| tggaaagaga ggaacccgct tgctaatgtg acggtgctcg gagtgaacaa ggagccctct | 2820 |
| gcggtgaccc tgaatggaca ggccgtattt cccgggtctg tcacgtacaa ttctacgtcc | 2880 |
| caggttctct tgttgggggg gctgcaaaac ttgacgaagg gcggcgcatg ggcggaaaac | 2940 |
| tgggtattgg aatggtag | 2958 |

<210> SEQ ID NO 51
<211> LENGTH: 2958
<212> TYPE: DNA
<213> ORGANISM: Aspergillus niger

<400> SEQUENCE: 51

```
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420
tccctcaatg catctgtatc ccagagcgac ctttttgtgt catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca catcccttc     720
tatctggata caagatatta caaaggagat aggcagaatg gtcttatat tcccgtcaaa      780
agcagcgagg ctgatgcctc gcaagattat atctccctct ctcatggcgt gtttctgagg     840
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgtgagg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac cacccgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg ggcggcgac    1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tccacagga gccttatcgg tgggcttctg ttattgaagc aaccaagtcc    2220
gccatgagaa ttcggtacgc catcctacct tacttttata cgttgtttga cctggcccac    2280
```

```
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac     2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgc tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                 2958

<210> SEQ ID NO 52
<211> LENGTH: 2958
<212> TYPE: DNA
<213> ORGANISM: Aspergillus niger

<400> SEQUENCE: 52
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtccccag acccaaggct     420
tccctcaatg catctgtatc ccagagcgac ctttttgtgt catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaggagat aggcagaatg gtcttatat tcccgtcaaa      780 agcagcgagg ctgatgcctc gcaagattat atctccctct ctcatggcgt gtttctgagg    840
aactctcatg gacttgagat actcctccgg tctcaaaaat tgatctggcg acccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtgtgg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
```

| | | | | |
|---|---|---|---|---|
| aaagtggcgt | tcgatggtgt | gtggtacgac | atgtctgaag tttcatcctt | ctgtgtcggg | 1500 |
| agctgtggca | caggtaacct | gactctgaac | ccggcacacc catcgtttct | tctccccggt | 1560 |
| gagcctggtg | atatcatata | tgattaccca | gaggctttca atatcaccaa | cgctacagag | 1620 |
| gcggcgtcag | cttcggcggg | agcttccagt | caggctgcag caaccgcgac | cacccacgtcg | 1680 |
| acttcggtat | catatctgcg | gacaacgccc | acgcctggtg tccgcaatgt | tgagcaccca | 1740 |
| ccctatgtga | tcaaccatga | ccaagaaggc | catgatctca gtgtccatgc | ggtgtcgccg | 1800 |
| aatgcaacgc | atgttgatgg | tgttgaggag | tatgatgtgc acggtctcta | cggacatcaa | 1860 |
| ggattgaacg | ctacctacca | aggtctgctt | gaggtctggt ctcataagcg | gcggccattt | 1920 |
| attattggcc | gctcaacctt | cgctggctct | ggcaaatggg caggccactg | ggcggcgac | 1980 |
| aactattcca | atggtggtc | catgtactac | tccatctcgc aagccctctc | cttctcactt | 2040 |
| ttcggcattc | cgatgtttgg | tgcggacacc | tgtgggttta acggaaactc | cgatgaggag | 2100 |
| ctctgcaacc | gatggatgca | actgtccgca | ttcttcccat tctaccgaaa | ccacaatgag | 2160 |
| ctctccacaa | tcccacagga | gccttatcgg | tgggcttctg ttattgaagc | aaccaagtcc | 2220 |
| gccatgagaa | ttcggtacgc | catcctacct | tactttttata cgttgtttga | cctggcccac | 2280 |
| accacgggct | ccactgtaat | gcgcgcactt | tcctgggaat tccctaatga | cccaacattg | 2340 |
| gctgcggttg | agactcaatt | catggttggg | ccggccatca tggtggtccc | ggtattggag | 2400 |
| cctctggtca | atacggtcaa | gggcgtattc | caggagttg gacatggcga | agtgtggtac | 2460 |
| gattggtaca | cccaggctgc | agttgatgcg | aagcccgggg tcaacacgac | catttcggca | 2520 |
| ccattgggcc | acatcccagt | ttatgtacga | ggtggaaaca tcttgccgat | gcaagagccg | 2580 |
| gcattgacca | ctcgtgaagc | ccggcaaacc | ccgtgggctt tgctagctgc | actaggaagc | 2640 |
| aatggaaccg | cgtcggggca | gctctatctc | gatgatggag agagcatcta | ccccaatgcc | 2700 |
| accctccatg | tggacttcac | ggcatcgcgg | tcaagcctgc gctcgtcggc | tcaaggaaga | 2760 |
| tggaaagaga | ggaacccgct | tgctaatgtg | acggtgctcg gagtgaacaa | ggagccctct | 2820 |
| gcggtgaccc | tgaatggaca | ggccgtattt | cccgggtctg tcacgtacaa | ttctacgtcc | 2880 |
| caggttctct | tgttgggggg | gctgcaaaac | ttgacgaagg gcggcgcatg | ggcggaaaac | 2940 |
| tgggtattgg | aatggtag | | | 2958 |

<210> SEQ ID NO 53
<211> LENGTH: 2958
<212> TYPE: DNA
<213> ORGANISM: Aspergillus niger

<400> SEQUENCE: 53

| | | | | |
|---|---|---|---|---|
| atggtgaagt | tgacgcatct | ccttgccaga | gcatggcttg tccctctggc | ttatggagcg | 60 |
| agccagtcac | tcttatccac | cactgcccct | tcgcagccgc agtttaccat | tcctgcttcc | 120 |
| gcagatgtcg | gtgcgcagct | gattgccaac | atcgatgatc ctcaggctgc | cgacgcgcag | 180 |
| tcggtttgtc | cgggctacaa | ggcttcaaaa | gtgcagcaca attcacgtgg | attcactgcc | 240 |
| agtcttcagc | tcgcgggcag | gccatgtaac | gtatacggca cagatgttga | gtccttgaca | 300 |
| ctgtctgtgg | agtaccagga | ttcggatcga | ctgaatattc agattctccc | cactcatgtt | 360 |
| gactccacaa | acgcttcttg | gtactttctt | tcggaaaacc tggtccccag | acccaaggct | 420 |
| tccctcaatg | catctgtatc | ccagagcgac | cttttttgtgt catggtcaaa | tgagccgtcg | 480 |
| ttcaatttca | aggtgatccg | aaaggctaca | ggcgacgcgc ttttcagtac | agaaggcact | 540 |

```
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtcagg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccatt    1920 attattggcc gctcaacctt cgctggctct ggcaaatggg caggccactg ggcggcgac    1980 aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac    2460 gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640 aatgaaccg cgtcgggca gctctatctc gatgatggag agagcatcta ccccaatgcc    2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg gcggcgcatg ggcggaaaac   2940
```

```
tgggtattgg aatggtag                                             2958
```

<210> SEQ ID NO 54
<211> LENGTH: 2958
<212> TYPE: DNA
<213> ORGANISM: Aspergillus niger

<400> SEQUENCE: 54

```
atggtgaagt tgacgcatct ccttgccaga gcatggcttg ccctctggc ttatggagcg      60
agccagtcac tcttatccac cactgcccct tcgcagccgc agtttaccat tcctgcttcc    120
gcagatgtcg gtgcgcagct gattgccaac atcgatgatc ctcaggctgc cgacgcgcag    180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag  acccaaggct    420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaaac tctacggcca acatcccttc    720
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtaatg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc aggatatac  agtcttcccc   1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct tctcccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaaccct cgctggctct ggcaaatggg caggccactg gggcggcgac   1980
aactattcca aatggtggtc catgtactac tccatctcgc aagccctctc cttctcactt   2040
```

| | |
|---|---|
| ttcggcattc cgatgtttgg tgcggacacc tgtgggttta acggaaactc cgatgaggag | 2100 |
| ctctgcaacc gatggatgca actgtccgca ttcttcccat tctaccgaaa ccacaatgag | 2160 |
| ctctccacaa tcccacagga gccttatcgg tgggcttctg ttattgaagc aaccaagtcc | 2220 |
| gccatgagaa ttcggtacgc catcctacct tactttata cgttgtttga cctggcccac | 2280 |
| accacgggct ccactgtaat gcgcgcactt tcctgggaat ccctaatga cccaacattg | 2340 |
| gctgcggttg agactcaatt catggttggg ccggccatca tggtggtccc ggtattggag | 2400 |
| cctctggtca atacggtcaa gggcgtattc ccaggagttg acatggcga agtgtggtac | 2460 |
| gattggtaca cccaggctgc agttgatgcg aagcccgggg tcaacacgac catttcggca | 2520 |
| ccattgggcc acatcccagt ttatgtacga ggtggaaaca tcttgccgat gcaagagccg | 2580 |
| gcattgacca ctcgtgaagc ccggcaaacc ccgtgggctt tgctagctgc actaggaagc | 2640 |
| aatggaaccg cgtcggggca gctctatctc gatgatggag agagcatcta ccccaatgcc | 2700 |
| accctccatg tggacttcac ggcatcgcgg tcaagcctgc gctcgtcggc tcaaggaaga | 2760 |
| tggaaagaga ggaacccgct tgctaatgtg acggtgctcg gagtgaacaa ggagccctct | 2820 |
| gcggtgaccc tgaatggaca ggccgtattt cccgggtctg tcacgtacaa ttctacgtcc | 2880 |
| caggttctct tgttgggggg gctgcaaaac ttgacgaagg gcggcgcatg gcggaaaac | 2940 |
| tgggtattgg aatggtag | 2958 |

<210> SEQ ID NO 55
<211> LENGTH: 2958
<212> TYPE: DNA
<213> ORGANISM: Aspergillus niger

<400> SEQUENCE: 55

| | |
|---|---|
| atggtgaagt tgacgcatct ccttgccaga gcatggcttg tccctctggc ttatggagcg | 60 |
| agccagtcac tcttatccac cactgcccct tcgcagccgc agtttaccat tcctgcttcc | 120 |
| gcagatgtcg gtgcgcagct gattgccaac atcgatgatc ctcaggctgc cgacgcgcag | 180 |
| tcggtttgtc cgggctacaa ggcttcaaaa gtgcagcaca attcacgtgg attcactgcc | 240 |
| agtcttcagc tcgcgggcag gccatgtaac gtatacggca cagatgttga gtccttgaca | 300 |
| ctgtctgtgg agtaccagga ttcggatcga ctgaatattc agattctccc cactcatgtt | 360 |
| gactccacaa acgcttcttg gtactttctt tcggaaaacc tggtccccag acccaaggct | 420 |
| tccctcaatg catctgtatc ccagagcgac ctttttgtgt catggtcaaa tgagccgtcg | 480 |
| ttcaatttca aggtgatccg aaaggctaca ggcgacgcgc ttttcagtac agaaggcact | 540 |
| gtgctcgtat atgagaatca gttcatcgaa tttgtgaccg cgctccctga agaatataac | 600 |
| ttgtatggcc ttggggagca tatcacgcaa ttccgcctcc agagaaatgc taatctgacc | 660 |
| atatatcctt cggatgatgg aacacctatt gaccaaaacc tctacggcca acatcccttc | 720 |
| tatctggata caagatatta caaggagat aggcagaatg ggtcttatat tcccgtcaaa | 780 |
| agcagcgagg ctgatgcctc gcaagattat atctccctct ctcatggcgt gtttctgagg | 840 |
| aactctcatg gacttgagat actcctccgg tctcaaaaat tgatctggcg gaccctaggt | 900 |
| ggaggaatcg atctcacctt ctactcaggc ccgccccgg ccgatgttac caggcaatat | 960 |
| cttaccagca ctgtgggatt accggccatg cagcaataca cactcttggg attccaccaa | 1020 |
| tgtcgtattg gctacaacaa ctggtcggat ctggcggacg ttgttgcgaa ctttgagaag | 1080 |
| tttgagatcc cgttggaata tatctggacc gatattgact acatgcacgg atatcgcaac | 1140 |
| tttgacaacg atcaacatcg cttttcctac agtgagggcg atgaatttct cagcaagcta | 1200 |

```
catgagagtg gacgctacta tgtacccatt gttgatgcgg cgctctacat tcctaatccc    1260
gaaaatgcct ctgatgcata cgctacgtat gacagaggac ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg gggcggcgac    1980
aactattcca atggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttttata cgttgtttga cctggcccac    2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttgggggg gctgcaaaac ttgacgaagg gcggcgcatg ggcggaaaac    2940
tgggtattgg aatggtag                                                 2958
```

<210> SEQ ID NO 56
<211> LENGTH: 2958
<212> TYPE: DNA
<213> ORGANISM: Aspergillus niger

<400> SEQUENCE: 56

```
atggtgaagt tgacgcatct ccttgccaga gcatggcttg tccctctggc ttatggagcg      60
agccagtcac tctatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
```

```
ctgtctgtgg agtaccagga ttcggatcga ctgaatattc agattctccc cactcatgtt    360
gactccacaa acgcttcttg gtactttctt tcggaaaacc tggtcccag acccaaggct     420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgttggg gctacaacaa ctggtcgat  ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgggtggc aggatatac agtcttcccc    1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct ctccccggt    1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg ggcggcgac   1980
aactattcca atggtggtc catgtactac tccatctcgc aagccctctc cttctcactt    2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttata cgttgtttga cctgccccac    2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacgtcaa gggcgtattc ccaggagttg acatggcga agtgtggtac     2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
```

```
acctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttgggggg gctgcaaaac ttgacgaagg gcggcgcatg gcggaaaac    2940 tgggtattgg aatggtag                                                  2958
```

<210> SEQ ID NO 57
<211> LENGTH: 2958
<212> TYPE: DNA
<213> ORGANISM: Aspergillus niger

<400> SEQUENCE: 57

```
atggtgaagt tgacgcatct ccttgccaga gcatggcttg tccctctggc ttatggagcg      60
agccagtcac tcttatccac cactgcccct tcgcagccgc agtttaccat tcctgcttcc    120
gcagatgtcg gtgcgcagct gattgccaac atcgatgatc ctcaggctgc cgacgcgcag    180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct    420 tccctcaatg catctgtatc ccagagcgac cttttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga gaatataaac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgttggg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgattggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
```

| aatgcaacgc atgttgatgg tgttgaggag tatgatgtgc acggtctcta cggacatcaa | 1860 |
| ggattgaacg ctacctacca aggtctgctt gaggtctggt ctcataagcg gcggccattt | 1920 |
| attattggcc gctcaacctt cgctggctct ggcaaatggg caggccactg ggcggcgac | 1980 |
| aactattcca aatggtggtc catgtactac tccatctcgc aagccctctc cttctcactt | 2040 |
| ttcggcattc cgatgtttgg tgcggacacc tgtgggttta acggaaactc cgatgaggag | 2100 |
| ctctgcaacc gatggatgca actgtccgca ttcttcccat tctaccgaaa ccacaatgag | 2160 |
| ctctccacaa tcccacagga gccttatcgg tgggcttctg ttattgaagc aaccaagtcc | 2220 |
| gccatgagaa ttcggtacgc catcctacct tactttttata cgttgtttga cctggcccac | 2280 |
| accacgggct ccactgtaat gcgcgcactt tcctgggaat tccctaatga cccaacattg | 2340 |
| gctgcggttg agactcaatt catggttggg ccggccatca tggtggtccc ggtattggag | 2400 |
| cctctggtca atacggtcaa gggcgtattc ccaggagttg acatggcga agtgtggtac | 2460 |
| gattggtaca cccaggctgc agttgatgcg aagcccgggg tcaacacgac catttcggca | 2520 |
| ccattgggcc acatcccagt ttatgtacga ggtggaaaca tcttgccgat gcaagagccg | 2580 |
| gcattgacca ctcgtgaagc ccggcaaacc ccgtgggctt tgctagctgc actaggaagc | 2640 |
| aatggaaccg cgtcggggca gctctatctc gatgatggag agagcatcta ccccaatgcc | 2700 |
| accctccatg tggacttcac ggcatcgcgg tcaagcctgc gctcgtcggc tcaaggaaga | 2760 |
| tggaaagaga ggaacccgct tgctaatgtg acggtgctcg gagtgaacaa ggagccctct | 2820 |
| gcggtgaccc tgaatggaca ggccgtattt cccgggtctg tcacgtacaa ttctacgtcc | 2880 |
| caggttctct tgttgggggg gctgcaaaac ttgacgaagg gcggcgcatg ggcggaaaac | 2940 |
| tgggtattgg aatggtag | 2958 |

<210> SEQ ID NO 58
<211> LENGTH: 2958
<212> TYPE: DNA
<213> ORGANISM: Aspergillus niger

<400> SEQUENCE: 58

| atggtgaagt tgacgcatct ccttgccaga gcatggcttg tccctctggc ttatggagcg | 60 |
| agccagtcac tcttatccac cactgccccct tcgcagccgc agtttaccat tcctgcttcc | 120 |
| gcagatgtcg gtgcgcagct gattgccaac atcgatgatc ctcaggctgc cgacgcgcag | 180 |
| tcggtttgtc cgggctacaa ggcttcaaaa gtgcagcaca attcacgtgg attcactgcc | 240 |
| agtcttcagc tcgcgggcag gccatgtaac gtatacggca cagatgttga gtccttgaca | 300 |
| ctgtctgtgg agtaccagga ttcggatcga ctgaatattc agattctccc cactcatgtt | 360 |
| gactccacaa acgcttcttg gtactttctt tcggaaaacc tggtccccag acccaaggct | 420 |
| tccctcaatg catctgtatc ccagagcgac cttttttgtgt catggtcaaa tgagccgtcg | 480 |
| ttcaatttca aggtgatccg aaaggctaca ggcgacgcgc ttttcagtac agaaggcact | 540 |
| gtgctcgtat atgagaatca gttcatcgaa tttgtgaccg cgctccctga agaatataac | 600 |
| ttgtatggcc ttggggagca tatcacgcaa ttccgcctcc agagaaatgc taatctgacc | 660 |
| atatatcctt cggatgatgg aacacctatt gaccaaaacc tctacggcca acatcccttc | 720 |
| tatctggata caagatatta caaggagat aggcagaatg ggtcttatat tcccgtcaaa | 780 |
| agcagcgagg ctgatgcctc gcaagattat atctccctct ctcatggcgt gtttctgagg | 840 |
| aactctcatg gacttgagat actcctccgg tctcaaaaat tgatctggcg acccctaggt | 900 |
| ggaggaatcg atctcacctt ctactcaggc cccgccccgg ccgatgttac caggcaatat | 960 |

```
cttaccagca ctgtgggatt accggccatg cagcaataca acactcttgg attccaccaa    1020
tgtcgttggg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgagtggc caggatatac agtcttcccc    1380
gattggcatc atcccaaggc agttgacttc tgggctaacg agcttgttat ctggtcgaag    1440
aaagtggcgt cgatggtgt gtggtacgac atgtctgaag tttcatcctt ctgtgtcggg    1500
agctgtggca caggtaacct gactctgaac cggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg ggcggcgac    1980 aactattcca atggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttata cgttgtttga cctggcccac    2280
accacgggct ccactgtaat gcgcgcactt tcctgggaat ccctaatga cccaacattg    2340 gctgcggttg agactcaatt catggttggg ccggccatca tggtggtccc ggtattggag    2400
cctctggtca atacggtcaa gggcgtattc caggagttg gacatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttggggg gctgcaaaac ttgacgaagg gcggcgcatg ggcggaaaac    2940
tgggtattgg aatggtag                                                 2958

<210> SEQ ID NO 59
<211> LENGTH: 2958
<212> TYPE: DNA
<213> ORGANISM: Aspergillus niger

<400> SEQUENCE: 59
atggtgaagt tgacgcatct ccttgccaga gcatggcttg tccctctggc ttatggagcg       60
```

| | |
|---|---|
| agccagtcac tcttatccac cactgcccct tcgcagccgc agtttaccat tcctgcttcc | 120 |
| gcagatgtcg gtgcgcagct gattgccaac atcgatgatc ctcaggctgc cgacgcgcag | 180 |
| tcggtttgtc cgggctacaa ggcttcaaaa gtgcagcaca attcacgtgg attcactgcc | 240 |
| agtcttcagc tcgcgggcag gccatgtaac gtatacggca cagatgttga gtccttgaca | 300 |
| ctgtctgtgg agtaccagga ttcggatcga ctgaatattc agattctccc cactcatgtt | 360 |
| gactccacaa acgcttcttg gtactttctt tcggaaaacc tggtcccag acccaaggct | 420 |
| tccctcaatg catctgtatc ccagagcgac ctttttgtgt catggtcaaa tgagccgtcg | 480 |
| ttcaatttca aggtgatccg aaaggctaca ggcgacgcgc ttttcagtac agaaggcact | 540 |
| gtgctcgtat atgagaatca gttcatcgaa tttgtgaccg cgctccctga agaatataac | 600 |
| ttgtatggcc ttggggagca tatcacgcaa ttccgcctcc agagaaatgc taatctgacc | 660 |
| atatatcctt cggatgatgg aacacctatt gaccaaaacc tctacggcca acatcccttc | 720 |
| tatctggata caagatatta caaaggagat aggcagaatg ggtcttatat tcccgtcaaa | 780 |
| agcagcgagg ctgatgcctc gcaagattat atctccctct ctcatggcgt gtttctgagg | 840 |
| aactctcatg gacttgagat actcctccgg tctcaaaaat tgatctggcg gaccctaggt | 900 |
| ggaggaatcg atctcacctt ctactcaggc cccgccccgg ccgatgttac caggcaatat | 960 |
| cttaccagca ctgtgggatt accggccatg cagcaataca acactcttgg attccaccaa | 1020 |
| tgtcgttggg gctacaacaa ctggtcggat ctggcggacg ttgttgcgaa cttgagaag | 1080 |
| tttgagatcc cgttggaata tatctggacc gatattgact acatgcacgg atatcgcaac | 1140 |
| tttgacaacg atcaacatcg cttttcctac agtgagggcg atgaatttct cagcaagcta | 1200 |
| catgagagtg gacgctacta tgtacccatt gttgatgcgg cgctctacat tcctaatccc | 1260 |
| gaaaatgcct ctgatgcata cgctacgtat gacagaggag ctgcggacga cgtcttcctc | 1320 |
| aagaatcccg atggtagcct ctatattgga gccgtttggc caggatatac agtcttcccc | 1380 |
| gattggcatc atcccaaggc agttgacttc tgggctaacg agcttgttat ctggtcgaag | 1440 |
| aaagtggcgt tcgatggtgt gtggtacgac atgtctgaag tttcagtttt ctgtgtcggg | 1500 |
| agctgtggca caggtaacct gactctgaac ccggcacacc catcgtttct tctcccggt | 1560 |
| gagcctggtg atatcatata tgattaccca gaggctttca atatcaccaa cgctacagag | 1620 |
| gcggcgtcag cttcggcggg agcttccagt caggctgcag caaccgcgac caccacgtcg | 1680 |
| acttcggtat catatctgcg gacaacgccc acgcctggtg tccgcaatgt tgagcaccca | 1740 |
| ccctatgtga tcaaccatga ccaagaaggc catgatctca gtgtccatgc ggtgtcgccg | 1800 |
| aatgcaacgc atgttgatgg tgttgaggag tatgatgtgc acggtctcta cggacatcaa | 1860 |
| ggattgaacg ctacctacca aggtctgctt gaggtctggt ctcataagcg gcggccattt | 1920 |
| attattggcc gctcaacctt cgctggctct ggcaaatggg caggccactg gggcggcgac | 1980 |
| aactattcca atggtggtc catgtactac tccatctcgc aagccctctc cttctcactt | 2040 |
| ttcggcattc cgatgtttgg tgcggacacc tgtgggttta acggaaactc cgatgaggag | 2100 |
| ctctgcaacc gatggatgca actgtccgca ttcttcccat tctaccgaaa ccacaatgag | 2160 |
| ctctccacaa tcccacagga gccttatcgg tgggcttctg ttattgaagc aaccaagtcc | 2220 |
| gccatgagaa ttcggtacgc catcctacct tactttata cgttgtttga cctggcccac | 2280 |
| accacgggct ccactgtaat gcgcgcactt tcctgggaat tcctaatga cccaacattg | 2340 |
| gctgcggttg agactcaatt catggttggg ccggccatca tggtggtccc ggtattggag | 2400 |
| cctctggtca atacggtcaa gggcgtattc ccaggagttg gacatggcga agtgtggtac | 2460 |

```
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttggggg gctgcaaaac ttgacgaagg gcggcgcatg ggcggaaaac    2940
tgggtattgg aatggtag                                                  2958

<210> SEQ ID NO 60
<211> LENGTH: 2958
<212> TYPE: DNA
<213> ORGANISM: Aspergillus niger

<400> SEQUENCE: 60
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420 tccctcaatg catctgtatc ccagagcgac ctttttgtgt catggtcaaa tgagccgtcg     480 ttcaattca aggtgatccg aaaggctaca ggcgacgcgc ttttcagtac agaaggcact     540
gtgctcgtat atgagaatca gttcatcgaa tttgtgaccg cgctccctga agaatataac    600
ttgtatggcc ttggggagca tatcacgcaa ttccgcctcc agagaaatgc taatctgacc     660
atatatcctt cggatgatgg aacacctatt gaccaaaacc tctacggcca catcccttc     720 tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcaccct tctactcaggc cccgccccgg ccgatgttac caggcaatat    960
cttaccagca ctgtgggatt accggccatg cagcaataca acactcttgg attccaccaa   1020
tgtcgttggg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcaaattt ctgtgtcggg   1500
agctgtggca caggtaacct gactctgaac ccggcacacc catcgtttct tctccccggt   1560
```

| | |
|---|---:|
| gagcctggtg atatcatata tgattaccca gaggctttca atatcaccaa cgctacagag | 1620 |
| gcggcgtcag cttcggcggg agcttccagt caggctgcag caaccgcgac caccacgtcg | 1680 |
| acttcggtat catatctgcg gacaacgccc acgcctggtg tccgcaatgt tgagcaccca | 1740 |
| ccctatgtga tcaaccatga ccaagaaggc catgatctca gtgtccatgc ggtgtcgccg | 1800 |
| aatgcaacgc atgttgatgg tgttgaggag tatgatgtgc acggtctcta cggacatcaa | 1860 |
| ggattgaacg ctacctacca aggtctgctt gaggtctggt ctcataagcg gcggccattt | 1920 |
| attattggcc gctcaacctt cgctggctct ggcaaatggg caggccactg ggcggcgac | 1980 |
| aactattcca atggtggtc catgtactac tccatctcgc aagccctctc cttctcactt | 2040 |
| ttcggcattc cgatgtttgg tgcggacacc tgtgggttta acggaaactc cgatgaggag | 2100 |
| ctctgcaacc gatggatgca actgtccgca ttcttcccat tctaccgaaa ccacaatgag | 2160 |
| ctctccacaa tcccacagga gccttatcgg tgggcttctg ttattgaagc aaccaagtcc | 2220 |
| gccatgagaa ttcggtacgc catcctacct tactttttata cgttgtttga cctggcccac | 2280 |
| accacgggct ccactgtaat gcgcgcactt tcctgggaat tccctaatga cccaacattg | 2340 |
| gctgcggttg agactcaatt catggttggg ccggccatca tggtggtccc ggtattggag | 2400 |
| cctctggtca atacggtcaa gggcgtattc ccaggagttg acatggcga agtgtggtac | 2460 |
| gattggtaca cccaggctgc agttgatgcg aagcccgggg tcaacacgac catttcggca | 2520 |
| ccattgggcc acatcccagt ttatgtacga ggtggaaaca tcttgccgat gcaagagccg | 2580 |
| gcattgacca ctcgtgaagc ccggcaaacc ccgtgggctt tgctagctgc actaggaagc | 2640 |
| aatgaaccg cgtcggggca gctctatctc gatgatggag agagcatcta ccccaatgcc | 2700 |
| accctccatg tggacttcac ggcatcgcgg tcaagcctgc gctcgtcggc tcaaggaaga | 2760 |
| tggaaagaga ggaacccgct tgctaatgtg acggtgctcg gagtgaacaa ggagccctct | 2820 |
| gcggtgaccc tgaatggaca ggccgtattt cccgggtctg tcacgtacaa ttctacgtcc | 2880 |
| caggttctct tgttgggggg gctgcaaaac ttgacgaagg gcggcgcatg ggcggaaaac | 2940 |
| tgggtattgg aatggtag | 2958 |

```
<210> SEQ ID NO 61
<211> LENGTH: 2958
<212> TYPE: DNA
<213> ORGANISM: Aspergillus niger

<400> SEQUENCE: 61
```

| | |
|---|---:|
| atggtgaagt tgacgcatct ccttgccaga gcatggcttg tccctctggc ttatggagcg | 60 |
| agccagtcac tcttatccac cactgcccct tcgcagccgc agtttaccat tcctgcttcc | 120 |
| gcagatgtcg gtgcgcagct gattgccaac atcgatgatc ctcaggctgc cgacgcgcag | 180 |
| tcggtttgtc cgggctacaa ggcttcaaaa gtgcagcaca attcacgtgg attcactgcc | 240 |
| agtcttcagc tcgcgggcag gccatgtaac gtatacggca cagatgttga gtccttgaca | 300 |
| ctgtctgtgg agtaccagga ttcggatcga ctgaatattc agattctccc cactcatgtt | 360 |
| gactccacaa acgcttcttg gtactttctt tcggaaaacc tggtccccag acccaaggct | 420 |
| tccctcaatg catctgtatc ccagagcgac cttttttgtgt catggtcaaa tgagccgtcg | 480 |
| ttcaatttca aggtgatccg aaaggctaca ggcgacgcgc ttttcagtac agaaggcact | 540 |
| gtgctcgtat atgagaatca gttcatcgaa tttgtgaccg cgctccctga agaatataac | 600 |
| ttgtatggcc ttggggagca tatcacgcaa ttccgcctcc agagaaatgc taatctgacc | 660 |
| atatatcctt cggatgatgg aacacctatt gaccaaaacc tctacggcca acatcccttc | 720 |

```
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgttggg gctacaacaa ctggtcgtat ctggcggacg ttgttgcgaa ctttgagaag   1080
tttgagatcc cgttggaata tatctggacc gatattgact acatgcacgg atatcgcaac   1140
tttgacaaca atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcacagtt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg gggcggcgac   1980
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac   2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg gcggcgcatg ggcggaaaac   2940
tgggtattgg aatggtag                                                 2958
```

<210> SEQ ID NO 62

<211> LENGTH: 2958
<212> TYPE: DNA
<213> ORGANISM: Aspergillus niger

<400> SEQUENCE: 62

```
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtccccag acccaaggct     420
tccctcaatg catctgtatc ccagagcgac cttttgtgt catggtcaaa tgagccgtcg      480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaaggagat aggcagaatg ggtcttatat tcccgtcaaa     780
agcagcgagg ctgatgcctc gcaagattat atctccctct tcatggcgt gtttctgagg      840
aactctcatg gacttgagat actcctccgg tctcaaaaat tgatctggcg accctaggt      900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgtgatg gctacaacaa ctggtcggat ctggcggacg ttgttgcgaa ctttgagaag    1080
tttgagatcc gttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgcgtggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctcccggt     1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggcactg gggcggcgac      1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
```

```
gccatgagaa ttcggtacgc catcctacct tactttata cgttgtttga cctggcccac    2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc caggagttg  gacatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatgaaccg  cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                  2958

<210> SEQ ID NO 63
<211> LENGTH: 2958
<212> TYPE: DNA
<213> ORGANISM: Aspergillus niger

<400> SEQUENCE: 63
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag  acccaaggct     420
tccctcaatg catctgtatc ccagagcgac cttttgtgt  catggtcaaa tgagccgtcg     480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaaggagat aggcagaatg ggtcttatat tcccgtcaaa     780
agcagcgagg ctgatgcctc gcaagattat atctccctct ctcatggcgt gtttctgagg     840
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca cactcttggg attccaccaa    1020
tgtcgtgatg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
```

```
aagaatcccg atggtagcct ctatattgga gccgggtggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg acaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg gggcggcgac    1980
aactattcca atggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttttata cgttgtttga cctggcccac    2280
accacgggct ccactgtaat gcgcgcactt tcctgggaat ccctaatgaa cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatgaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttgggggg gctgcaaaac ttgacgaagg gcggcgcatg ggcggaaaac    2940
tgggtattgg aatggtag                                                  2958

<210> SEQ ID NO 64
<211> LENGTH: 2958
<212> TYPE: DNA
<213> ORGANISM: Aspergillus niger

<400> SEQUENCE: 64
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct     420
tccctcaatg catctgtatc ccagagcgac cttttttgtgt catggtcaaa tgagccgtcg     480
```

```
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg gtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg accctaggt     900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtgatg ctacaacaa ctggtcggat ctggcggacg ttgttgcgaa ctttgagaag    1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcaatttt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaaacctt cgctggctct ggcaaatggg caggccactg gggcggcgac   1980
aactattcca atggtggtc catgtactac tccatctcgc aagccctctc cttctcactt    2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac    2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
```

| | |
|---|---:|
| gcggtgaccc tgaatggaca ggccgtattt cccgggtctg tcacgtacaa ttctacgtcc | 2880 |
| caggttctct ttgttggggg gctgcaaaac ttgacgaagg gcggcgcatg ggcggaaaac | 2940 |
| tgggtattgg aatggtag | 2958 |

<210> SEQ ID NO 65
<211> LENGTH: 2958
<212> TYPE: DNA
<213> ORGANISM: Aspergillus niger

<400> SEQUENCE: 65

| | |
|---|---:|
| atggtgaagt tgacgcatct ccttgccaga gcatggcttg tccctctggc ttatggagcg | 60 |
| agccagtcac tcttatccac cactgcccct tcgcagccgc agtttaccat tcctgcttcc | 120 |
| gcagatgtcg gtgcgcagct gattgccaac atcgatgatc ctcaggctgc cgacgcgcag | 180 |
| tcggtttgtc cgggctacaa ggcttcaaaa gtgcagcaca attcacgtgg attcactgcc | 240 |
| agtcttcagc tcgcgggcag gccatgtaac gtatacggca cagatgttga gtccttgaca | 300 |
| ctgtctgtgg agtaccagga ttcggatcga ctgaatattc agattctccc cactcatgtt | 360 |
| gactccacaa acgcttcttg gtactttctt tcggaaaacc tggtcccag acccaaggct | 420 |
| tccctcaatg catctgtatc ccagagcgac ctttttgtgt catggtcaaa tgagccgtcg | 480 |
| ttcaatttca aggtgatccg aaaggctaca ggcgacgcgc ttttcagtac agaaggcact | 540 |
| gtgctcgtat atgagaatca gttcatcgaa tttgtgaccg cgctccctga agaatataac | 600 |
| ttgtatggcc ttggggagca tatcacgcaa ttccgcctcc agagaaatgc taatctgacc | 660 |
| atatatcctt cggatgatgg aacacctatt gaccaaaacc tctacggcca acatcccttc | 720 |
| tatctggata caagatatta caaaggagat aggcagaatg ggtcttatat tcccgtcaaa | 780 |
| agcagcgagg ctgatgcctc gcaagattat atctccctct ctcatggcgt gtttctgagg | 840 |
| aactctcatg gacttgagat actcctccgg tctcaaaaat tgatctggcg gaccctaggt | 900 |
| ggaggaatcg atctcacctt ctactcaggc cccgccccgg ccgatgttac caggcaatat | 960 |
| cttaccagca ctgtgggatt accggccatg cagcaataca acactcttgg attccaccaa | 1020 |
| tgtcgtgatg gctacaacaa ctggtcggat ctggcggacg ttgttgcgaa cttttgagaag | 1080 |
| tttgagatcc cgttggaata tatctggacc gatattgact acatgcacgg atatcgcaac | 1140 |
| tttgacaacg atcaacatcg cttttcctac agtgagggcg atgaatttct cagcaagcta | 1200 |
| catgagagtg gacgctacta tgtacccatt gttgatgcgg cgctctacat tcctaatccc | 1260 |
| gaaaatgcct ctgatgcata cgctacgtat gacagaggag ctgcggacga cgtcttcctc | 1320 |
| aagaatcccg atggtagcct ctatattgga gccgtttggc caggatatac agtcttcccc | 1380 |
| gattggcatc atcccaaggc agttgacttc tgggctaacg agcttgttat ctggtcgaag | 1440 |
| aaagtggcgt tcgatggtgt gtggtacgac atgtctgaag tttcacgttt ctgtgtcggg | 1500 |
| agctgtggca caggtaacct gactctgaac ccggcacacc catcgtttct tctccccggt | 1560 |
| gagcctggtg atatcatata tgattaccca gaggctttca atatcaccaa cgctacagag | 1620 |
| gcggcgtcag cttcggcggg agcttccagt caggctgcag caaccgcgac caccacgtcg | 1680 |
| acttcggtat catatctgcg gacaacgccc acgcctggtg tccgcaatgt tgagcaccca | 1740 |
| ccctatgtga tcaaccatga ccaagaaggc catgatctca gtgtccatgc ggtgtcgccg | 1800 |
| aatgcaacgc atgttgatgg tgttgaggag tatgatgtgc acggtctcta cggacatcaa | 1860 |
| ggattgaacg ctacctacca aggtctgctt gaggtctggt ctcataagcg gcggccattt | 1920 |
| attattggcc gctcaaccct cgctggctct ggcaaatggg caggccactg ggcggcgac | 1980 |

```
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac   2460 gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640 aatgaaccg cgtcgggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg gcggcgcatg ggcggaaaac   2940
tgggtattgg aatggtag                                                 2958

<210> SEQ ID NO 66
<211> LENGTH: 2958
<212> TYPE: DNA
<213> ORGANISM: Aspergillus niger

<400> SEQUENCE: 66
atggtgaagt tgacgcatct ccttgccaga gcatggcttg tccctctggc ttatggagcg     60
agccagtcac tcttatccac cactgcccct tcgcagccgc agtttaccat tcctgcttcc    120
gcagatgtcg gtgcgcagct gattgccaac atcgatgatc ctcaggctgc cgacgcgcag    180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct     420 tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca catcccttc     720 tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcaccct ctactcaggc cccgccccgg ccgatgttac caggcaatat    960
cttaccagca ctgtgggatt accggccatg cagcaataca acactcttgg attccaccaa   1020
tgtcgtatgg gctacaacaa ctggtcggat ctggcggacg ttgttgcgaa ctttgagaag   1080
```

```
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatgttt ctgtgtcggg    1500
agctgtggca caggtaacct gactctgaac ccggcacacc catcgtttct tctcccggt     1560 gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg gggcggcgac    1980
aactattcca aatggtggtc catgtactac tccatctcgc aagccctctc cttctcactt    2040
ttcggcattc cgatgtttgg tgcggacacc tgtgggttta acgaaactc cgatgaggag     2100 ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttata cgttgtttga cctggcccac     2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg gacatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtatt cccgggtctg tcacgtacaa ttctacgtcc      2880
caggttctct ttgttggggg gctgcaaaac ttgacgaagg gcggcgcatg ggcggaaaac    2940
tgggtattgg aatggtag                                                  2958
```

<210> SEQ ID NO 67
<211> LENGTH: 2958
<212> TYPE: DNA
<213> ORGANISM: Aspergillus niger

<400> SEQUENCE: 67

```
atggtgaagt tgacgcatct ccttgccaga gcatggcttg tccctctggc ttatggagcg     60
agccagtcac tcttatccac cactgcccct tcgcagccgc agtttaccat tcctgcttcc    120
gcagatgtcg gtgcgcagct gattgccaac atcgatgatc tcaggctgc cgacgcgcag     180 tcggttttgtc cgggctacaa ggcttcaaaa gtgcagcaca attcacgtgg attcactgcc    240
```

```
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct    420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga agaatataac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caaaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgtatgg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcaacgtt ctgtgtcggg   1500
agctgtggca caggtaacct gactctgaac ccggcacacc catcgtttct tctcccggt    1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcg gctcaacctt cgctggctct ggcaaatggg caggccactg gggcggcgac   1980
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttatat cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac   2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
```

-continued

```
gcattgacca ctcgtgaagc ccggcaaacc ccgtgggctt tgctagctgc actaggaagc    2640
aatggaaccg cgtcgggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg cggcgcatg ggcggaaaac    2940 tgggtattgg aatggtag                                                  2958
```

<210> SEQ ID NO 68
<211> LENGTH: 45
<212> TYPE: PRT
<213> ORGANISM: Homo sapiens

<400> SEQUENCE: 68

Gly Phe Leu His Ser Arg Tyr Glu Tyr Gly Thr Leu Asp Thr Pro Leu
1               5                   10                  15

Ile Gly Glu Val Trp Pro Gly Gln Thr Val Phe Pro Asp Ile Trp Ile
            20                  25                  30

Asp Met Asn Glu Val Ser Asn Phe Val Asp Gly Ser Val
        35                  40                  45

<210> SEQ ID NO 69
<211> LENGTH: 45
<212> TYPE: PRT
<213> ORGANISM: Aspergillus niger

<400> SEQUENCE: 69

Gly Phe His Gln Cys Arg Trp Gly Tyr Asn Asn Trp Ser Ser Leu Tyr
1               5                   10                  15

Ile Gly Ala Val Trp Pro Gly Tyr Thr Val Phe Pro Asp Val Trp Tyr
            20                  25                  30

Asp Met Ser Glu Val Ser Ser Phe Cys Val Gly Ser Cys
        35                  40                  45

<210> SEQ ID NO 70
<211> LENGTH: 45
<212> TYPE: PRT
<213> ORGANISM: Homo sapiens

<400> SEQUENCE: 70

Gly Tyr His Gln Cys Arg Trp Asn Tyr Glu Asp Glu Gln Gln Asp Phe
1               5                   10                  15

Glu Gly Val Cys Trp Pro Gly Leu Ser Ser Tyr Leu Asp Leu Trp Asn
            20                  25                  30

Asp Met Asn Glu Pro Ser Val Phe Arg Gly Pro Glu Asp
        35                  40                  45

<210> SEQ ID NO 71
<211> LENGTH: 45
<212> TYPE: PRT
<213> ORGANISM: Mus musculus

<400> SEQUENCE: 71

Gly Phe His Leu Cys Arg Trp Gly Tyr Ser Ser Thr Ala Gln Pro Leu
1               5                   10                  15

Ile Gly Lys Val Trp Pro Gly Thr Thr Ala Phe Pro Asp Met Trp Leu
            20                  25                  30

Asp Met Asn Glu Pro Ser Asn Phe Val Arg Gly Ser Gln
                35                  40                  45

<210> SEQ ID NO 72
<211> LENGTH: 45
<212> TYPE: PRT
<213> ORGANISM: Saccharomyces cerevisiae

<400> SEQUENCE: 72

Gly Tyr His Gln Cys Arg Trp Asn Tyr Asn Asp Glu Met Asn Asp Tyr
1               5                   10                  15

Val Gly His Cys Trp Pro Gly Asn Ser Ile Trp Ile Asp Ile Trp Asn
                20                  25                  30

Asp Met Asn Glu Pro Ser Ile Phe Asp Gly Pro Glu Thr
                35                  40                  45

<210> SEQ ID NO 73
<211> LENGTH: 2958
<212> TYPE: DNA
<213> ORGANISM: Aspergillus niger

<400> SEQUENCE: 73
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc tcaggctgc cgacgcgcag      180 tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420 tccctcaatg catctgtatc ccagagcgac cttttgtgt catggtcaaa tgagccgtcg      480
ttcaatttca aggtgatccg aaaggctaca ggcgacgcgc ttttcagtac agaaggcact     540
gtgctcgtat atgagaatca gttcatcgaa tttgtgaccg cgctccctga gaatataac     600 ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaaggagat aggcagaatg gtcttatat ccccgtcaaa      780 agcagcgagg ctgatgcctc gcaagattat atctccctct ctcatggcgt gtttctgagg     840
aactctcatg gacttgagat actcctccgg tctcaaaaat tgatctggcg accctaggt      900 ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgttggg gctacaacaa ctggtcggat ctggcggacg ttgttgcgaa ctttgagaag    1080
tttgagatcc cgttggaata tctggacc gatattgact acatgcacgg atatcgcaac     1140
tttgacaacg atcaacatcg ctttttccta cagtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctgtgtcggg    1500
agctgtggca caggtaacct gactctgaac ccggcacacc catcgtttct tctccccggt    1560

```
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg acaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg ggcggcgac    1980
aactattcca atggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttata cgttgtttga cctggcccac    2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                  2958
```

<210> SEQ ID NO 74
<211> LENGTH: 985
<212> TYPE: PRT
<213> ORGANISM: Aspergillus niger

<400> SEQUENCE: 74

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr

-continued

```
            115                 120                 125
Phe Leu Ser Glu Asn Leu Val Pro Arg Pro Lys Ala Ser Leu Asn Ala
        130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
                180                 185                 190

Thr Ala Leu Pro Glu Glu Tyr Asn Leu Tyr Gly Leu Gly Glu His Ile
                195                 200                 205

Thr Gln Phe Arg Leu Gln Arg Asn Ala Asn Leu Thr Ile Tyr Pro Ser
        210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
        290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
                340                 345                 350

Asp Val Val Ala Asn Phe Glu Lys Phe Glu Ile Pro Leu Glu Tyr Ile
                355                 360                 365

Trp Thr Asp Ile Asp Tyr Met His Gly Tyr Arg Asn Phe Asp Asn Asp
        370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
        435                 440                 445

Ile Gly Ala Val Trp Pro Gly Tyr Thr Val Phe Pro Asp Trp His His
        450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Gly Ser
                485                 490                 495

Phe Cys Val Gly Ser Cys Gly Thr Gly Asn Leu Thr Leu Asn Pro Ala
                500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
530                 535                 540
```

```
Ser Ala Gly Ala Ser Ser Gln Ala Ala Thr Ala Thr Thr Thr Ser
545                 550                 555                 560

Thr Ser Val Ser Tyr Leu Arg Thr Thr Pro Thr Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
        675                 680                 685

Asp Thr Cys Gly Phe Asn Gly Asn Ser Asp Glu Glu Leu Cys Asn Arg
        690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
            740                 745                 750

Tyr Thr Leu Phe Asp Leu Ala His Thr Thr Gly Ser Thr Val Met Arg
        755                 760                 765

Ala Leu Ser Trp Glu Phe Pro Asn Asp Pro Thr Leu Ala Ala Val Glu
        770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
        835                 840                 845

Val Arg Gly Gly Asn Ile Leu Pro Met Gln Glu Pro Ala Leu Thr Thr
        850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
        930                 935                 940

Asn Gly Gln Ala Val Phe Pro Gly Ser Val Thr Tyr Asn Ser Thr Ser
945                 950                 955                 960
```

```
Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 75
<211> LENGTH: 985
<212> TYPE: PRT
<213> ORGANISM: Aspergillus niger

<400> SEQUENCE: 75

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Gly Ile Asp
    290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350
```

```
Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
    370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
            450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Pro Ser
                485                 490                 495

Phe Cys Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
            515                 520                 525

Tyr Pro Glu Ala Phe Asn Ile Thr Asn Ala Thr Glu Ala Ala Ser Ala
            530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
            610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
            660                 665                 670

Ser Gln Ala Leu Ser Phe Ser Leu Phe Gly Ile Pro Met Phe Gly Ala
            675                 680                 685

Asp Thr Cys Gly Phe Asn Gly Asn Ser Asp Glu Glu Leu Cys Asn Arg
            690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
            755                 760                 765
```

```
Ala Leu Ser Trp Glu Phe Pro Asn Asp Pro Thr Leu Ala Ala Val Glu
770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
            805                 810                 815

Glu Val Trp Tyr Asp Trp Tyr Thr Gln Ala Ala Val Asp Ala Lys Pro
            820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
            885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
            915                 920                 925

Asn Val Thr Val Leu Gly Val Asn Lys Glu Pro Ser Ala Val Thr Leu
930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
            965                 970                 975

Trp Ala Glu Asn Trp Val Leu Glu Trp
            980                 985

<210> SEQ ID NO 76
<211> LENGTH: 985
<212> TYPE: PRT
<213> ORGANISM: Aspergillus niger

<400> SEQUENCE: 76

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
            35                  40                  45

Ala Asn Ile Asp Asp Pro Gln Ala Ala Asp Ala Gln Ser Val Cys Pro
50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
            85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
            115                 120                 125

Phe Leu Ser Glu Asn Leu Val Pro Arg Pro Lys Ala Ser Leu Asn Ala
            130                 135                 140

Ser Val Ser Gln Ser Asp Leu Phe Val Ser Trp Ser Asn Glu Pro Ser
145                 150                 155                 160
```

```
Phe Asn Phe Lys Val Ile Arg Lys Ala Thr Gly Asp Ala Leu Phe Ser
            165                 170                 175

Thr Glu Gly Thr Val Leu Val Tyr Glu Asn Gln Phe Ile Glu Phe Val
        180                 185                 190

Thr Ala Leu Pro Glu Glu Tyr Asn Leu Tyr Gly Leu Gly Glu His Ile
    195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
            245                 250                 255

Ile Pro Val Lys Ser Ser Glu Ala Asp Ala Ser Gln Asp Tyr Ile Ser
        260                 265                 270

Leu Ser His Gly Val Phe Leu Arg Asn Ser His Gly Leu Glu Ile Leu
    275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
            325                 330                 335

Gly Phe His Gln Cys Arg Trp Gly Tyr Asn Asn Trp Ser Asp Leu Ala
        340                 345                 350

Asp Val Val Ala Asn Phe Glu Lys Phe Glu Ile Pro Leu Glu Tyr Ile
    355                 360                 365

Trp Thr Asp Ile Asp Tyr Met His Gly Tyr Arg Asn Phe Asp Asn Asp
370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
            405                 410                 415

Ile Pro Asn Pro Glu Asn Ala Ser Asp Ala Tyr Ala Thr Tyr Asp Arg
        420                 425                 430

Gly Ala Ala Asp Asp Val Phe Leu Lys Asn Pro Asp Gly Ser Leu Tyr
    435                 440                 445

Ile Gly Ala Val Trp Pro Gly Tyr Thr Val Phe Pro Asp Trp His His
450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Val Ser
            485                 490                 495

Phe Cys Val Gly Ser Cys Gly Thr Gly Asn Leu Thr Leu Asn Pro Ala
        500                 505                 510

His Pro Ser Phe Leu Leu Pro Gly Glu Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575
```

```
Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
        595                 600                 605

Glu Glu Tyr Asp Val His Gly Leu Tyr Gly His Gln Gly Leu Asn Ala
    610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Trp Ser Met Tyr Tyr Ser Ile
                660                 665                 670

Ser Gln Ala Leu Ser Phe Ser Leu Phe Gly Ile Pro Met Phe Gly Ala
                675                 680                 685

Asp Thr Cys Gly Phe Asn Gly Asn Ser Asp Glu Glu Leu Cys Asn Arg
            690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
            755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
            930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985
```

<210> SEQ ID NO 77
<211> LENGTH: 985
<212> TYPE: PRT
<213> ORGANISM: Aspergillus niger

<400> SEQUENCE: 77

```
Met Val Lys Leu Thr His Leu Leu Ala Arg Ala Trp Leu Val Pro Leu
 1               5                   10                  15

Ala Tyr Gly Ala Ser Gln Ser Leu Leu Ser Thr Thr Ala Pro Ser Gln
             20                  25                  30

Pro Gln Phe Thr Ile Pro Ala Ser Ala Asp Val Gly Ala Gln Leu Ile
         35                  40                  45

Ala Asn Ile Asp Asp Pro Gln Ala Ala Asp Ala Gln Ser Val Cys Pro
 50                  55                  60

Gly Tyr Lys Ala Ser Lys Val Gln His Asn Ser Arg Gly Phe Thr Ala
 65                  70                  75                  80

Ser Leu Gln Leu Ala Gly Arg Pro Cys Asn Val Tyr Gly Thr Asp Val
                 85                  90                  95

Glu Ser Leu Thr Leu Ser Val Glu Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190

Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
            260                 265                 270

Leu Ser His Gly Val Phe Leu Arg Asn Ser His Gly Leu Glu Ile Leu
        275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
            340                 345                 350

Asp Val Val Ala Asn Phe Glu Lys Phe Glu Ile Pro Leu Glu Tyr Ile
        355                 360                 365

Trp Thr Asp Ile Asp Tyr Met His Gly Tyr Arg Asn Phe Asp Asn Asp
370                 375                 380
```

-continued

```
Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
            405                 410                 415

Ile Pro Asn Pro Glu Asn Ala Ser Asp Ala Tyr Ala Thr Tyr Asp Arg
        420                 425                 430

Gly Ala Ala Asp Asp Val Phe Leu Lys Asn Pro Asp Gly Ser Leu Tyr
    435                 440                 445

Ile Gly Ala Val Trp Pro Gly Tyr Thr Val Phe Pro Asp Trp His His
450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
            485                 490                 495

Phe Leu Val Gly Ser Cys Gly Thr Gly Asn Leu Thr Leu Asn Pro Ala
        500                 505                 510

His Pro Ser Phe Leu Leu Pro Gly Glu Pro Gly Asp Ile Ile Tyr Asp
    515                 520                 525

Tyr Pro Glu Ala Phe Asn Ile Thr Asn Ala Thr Glu Ala Ala Ser Ala
530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
            565                 570                 575

Val Glu His Pro Pro Tyr Val Ile Asn His Asp Gln Glu Gly His Asp
        580                 585                 590

Leu Ser Val His Ala Val Ser Pro Asn Ala Thr His Val Asp Gly Val
    595                 600                 605

Glu Glu Tyr Asp Val His Gly Leu Tyr Gly His Gln Gly Leu Asn Ala
610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
            645                 650                 655

Trp Gly Gly Asp Asn Tyr Ser Lys Trp Trp Ser Met Tyr Tyr Ser Ile
        660                 665                 670

Ser Gln Ala Leu Ser Phe Ser Leu Phe Gly Ile Pro Met Phe Gly Ala
    675                 680                 685

Asp Thr Cys Gly Phe Asn Gly Asn Ser Asp Glu Glu Leu Cys Asn Arg
690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
            725                 730                 735

Ala Thr Lys Ser Ala Met Arg Ile Arg Tyr Ala Ile Leu Pro Tyr Phe
        740                 745                 750

Tyr Thr Leu Phe Asp Leu Ala His Thr Thr Gly Ser Thr Val Met Arg
    755                 760                 765

Ala Leu Ser Trp Glu Phe Pro Asn Asp Pro Thr Leu Ala Ala Val Glu
770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
```

```
                    805                 810                 815
Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
            835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
            900                 905                 910

Leu Arg Ser Ser Ala Gln Gly Arg Trp Lys Glu Arg Asn Pro Leu Ala
        915                 920                 925

Asn Val Thr Val Leu Gly Val Asn Lys Glu Pro Ser Ala Val Thr Leu
930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
            980                 985

<210> SEQ ID NO 78
<211> LENGTH: 985
<212> TYPE: PRT
<213> ORGANISM: Aspergillus niger

<400> SEQUENCE: 78

Met Val Lys Leu Thr His Leu Leu Ala Arg Ala Trp Leu Val Pro Leu
1               5                   10                  15

Ala Tyr Gly Ala Ser Gln Ser Leu Leu Ser Thr Thr Ala Pro Ser Gln
            20                  25                  30

Pro Gln Phe Thr Ile Pro Ala Ser Ala Asp Val Gly Ala Gln Leu Ile
        35                  40                  45

Ala Asn Ile Asp Asp Pro Gln Ala Ala Asp Ala Gln Ser Val Cys Pro
    50                  55                  60

Gly Tyr Lys Ala Ser Lys Val Gln His Asn Ser Arg Gly Phe Thr Ala
65                  70                  75                  80

Ser Leu Gln Leu Ala Gly Arg Pro Cys Asn Val Tyr Gly Thr Asp Val
                85                  90                  95

Glu Ser Leu Thr Leu Ser Val Gly Tyr Gln Asp Ser Asp Arg Leu Asn
            100                 105                 110

Ile Gln Ile Leu Pro Thr His Val Asp Ser Thr Asn Ala Ser Trp Tyr
        115                 120                 125

Phe Leu Ser Glu Asn Leu Val Pro Arg Pro Lys Ala Ser Leu Asn Ala
    130                 135                 140

Ser Val Ser Gln Ser Asp Leu Phe Val Ser Trp Ser Asn Glu Pro Ser
145                 150                 155                 160

Phe Asn Phe Lys Val Ile Arg Lys Ala Thr Gly Asp Ala Leu Phe Ser
                165                 170                 175

Thr Glu Gly Thr Val Leu Val Tyr Glu Asn Gln Phe Ile Glu Phe Val
            180                 185                 190
```

```
Thr Ala Leu Pro Glu Glu Tyr Asn Leu Tyr Gly Leu Gly Glu His Ile
        195                 200                 205

Thr Gln Phe Arg Leu Gln Arg Asn Ala Asn Leu Thr Ile Tyr Pro Ser
    210                 215                 220

Asp Asp Gly Thr Pro Ile Asp Gln Asn Leu Tyr Gly Gln His Pro Phe
225                 230                 235                 240

Tyr Leu Asp Thr Arg Tyr Tyr Lys Gly Asp Arg Gln Asn Gly Ser Tyr
                245                 250                 255

Ile Pro Val Lys Ser Ser Glu Ala Asp Ala Ser Gln Asp Tyr Ile Ser
                260                 265                 270

Leu Ser His Gly Val Phe Leu Arg Asn Ser His Gly Leu Glu Ile Leu
            275                 280                 285

Leu Arg Ser Gln Lys Leu Ile Trp Arg Thr Leu Gly Gly Ile Asp
290                 295                 300

Leu Thr Phe Tyr Ser Gly Pro Ala Pro Ala Asp Val Thr Arg Gln Tyr
305                 310                 315                 320

Leu Thr Ser Thr Val Gly Leu Pro Ala Met Gln Gln Tyr Asn Thr Leu
                325                 330                 335

Gly Phe His Gln Cys Arg Trp Gly Tyr Asn Asn Trp Ser Asp Leu Ala
                340                 345                 350

Asp Val Val Ala Asn Phe Glu Lys Phe Glu Ile Pro Leu Glu Tyr Ile
            355                 360                 365

Trp Thr Asp Ile Asp Tyr Met His Gly Tyr Arg Asn Phe Asp Asn Asp
        370                 375                 380

Gln His Arg Phe Ser Tyr Ser Glu Gly Asp Glu Phe Leu Ser Lys Leu
385                 390                 395                 400

His Glu Ser Gly Arg Tyr Tyr Val Pro Ile Val Asp Ala Ala Leu Tyr
                405                 410                 415

Ile Pro Asn Pro Glu Asn Ala Ser Asp Ala Tyr Ala Thr Tyr Asp Arg
                420                 425                 430

Gly Ala Ala Asp Asp Val Phe Leu Lys Asn Pro Asp Gly Ser Leu Tyr
            435                 440                 445

Ile Gly Ala Val Trp Pro Gly Tyr Thr Val Phe Pro Asp Trp His His
450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
                485                 490                 495

Phe Ser Val Gly Ser Cys Gly Thr Gly Asn Leu Thr Leu Asn Pro Ala
            500                 505                 510

His Pro Ser Phe Leu Leu Pro Gly Glu Pro Gly Asp Ile Ile Tyr Asp
        515                 520                 525

Tyr Pro Glu Ala Phe Asn Ile Thr Asn Ala Thr Glu Ala Ala Ser Ala
        530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
                565                 570                 575

Val Glu His Pro Pro Tyr Val Ile Asn His Asp Gln Glu Gly His Asp
            580                 585                 590

Leu Ser Val His Ala Val Ser Pro Asn Ala Thr His Val Asp Gly Val
            595                 600                 605

Glu Glu Tyr Asp Val His Gly Leu Tyr Gly His Gln Gly Leu Asn Ala
```

```
                610             615             620
Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
                645                 650                 655

Trp Gly Gly Asp Asn Tyr Ser Lys Trp Ser Met Tyr Tyr Ser Ile
                660                 665                 670

Ser Gln Ala Leu Ser Phe Ser Leu Phe Gly Ile Pro Met Phe Gly Ala
                675                 680                 685

Asp Thr Cys Gly Phe Asn Gly Asn Ser Asp Glu Glu Leu Cys Asn Arg
                690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
                725                 730                 735

Ala Thr Lys Ser Ala Met Arg Ile Arg Tyr Ala Ile Leu Pro Tyr Phe
                740                 745                 750

Tyr Thr Leu Phe Asp Leu Ala His Thr Thr Gly Ser Thr Val Met Arg
                755                 760                 765

Ala Leu Ser Trp Glu Phe Pro Asn Asp Pro Thr Leu Ala Ala Val Glu
                770                 775                 780

Thr Gln Phe Met Val Gly Pro Ala Ile Met Val Val Pro Val Leu Glu
785                 790                 795                 800

Pro Leu Val Asn Thr Val Lys Gly Val Phe Pro Gly Val Gly His Gly
                805                 810                 815

Glu Val Trp Tyr Asp Trp Tyr Thr Gln Ala Ala Val Asp Ala Lys Pro
                820                 825                 830

Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
                915                 920                 925

Asn Val Thr Val Leu Gly Val Asn Lys Glu Pro Ser Ala Val Thr Leu
                930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 79
<211> LENGTH: 2958
<212> TYPE: DNA
<213> ORGANISM: Aspergillus niger

<400> SEQUENCE: 79
```

-continued

```
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420
tccctcaatg catctgtatc ccagagcgac cttttgtgt catggtcaaa tgagccgtcg      480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttgggagca tatcacgcaa ttccgcctcc agagaaatgc taatctgacc      660
atatatcctt cggatgatgg aacacctatt gaccaaaacc tctacggcca acatcccttc     720
tatctggata caagatatta caaggagat aggcagaatg gtcttatat tcccgtcaaa       780
agcagcgagg ctgatgcctc gcaagattat atctccctct tcatggcgt gtttctgagg      840
aactctcatg gacttgagat actcctccgg tctcaaaaat tgatctggcg acccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgttggg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaaagtggcgt tcgatggtgt gtggtacgac atgtctgaag ttgggtcctt ctgtgtcggg    1500
agctgtggca caggtaacct gactctgaac ccggcacacc catcgtttct tctccccggt    1560
gagcctggtg atatcatata tgattaccca gaggcttca atatcaccaa cgctacagag     1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccatt     1920
attattggcc gctcaacctt cgctggctct ggcaaatggg caggccactg ggcggcgac     1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tactttata cgttgtttga cctggcccac    2280
accacgggct ccactgtaat gcgcgcactt tcctgggaat tccctaatga cccaacattg    2340
gctgcggttg agactcaatt catggttggg ccggccatca tggtggtccc ggtattggag    2400
```

```
cctctggtca atacggtcaa gggcgtattc ccaggagttg acatggcga agtgtggtac    2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct tgttgggggg gctgcaaaac ttgacgaagg gcggcgcatg ggcggaaaac    2940
tgggtattgg aatggtag                                                 2958

<210> SEQ ID NO 80
<211> LENGTH: 2958
<212> TYPE: DNA
<213> ORGANISM: Aspergillus niger

<400> SEQUENCE: 80
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420 tccctcaatg catctgtatc ccagagcgac cttttttgtgt catggtcaaa tgagccgtcg    480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaggagat aggcagaatg gtcttatat tcccgtcaaa      780 agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa    1020
tgtcgttggg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag ttccctcctt ctgtgtcggg    1500
```

```
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg gggcggcgac    1980
aactattcca atggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tacttttata cgttgtttga cctggcccac    2280
accacgggct ccactgtaat gcgcgcactt tcctgggaat ccctaatga cccaacattg    2340 gctgcggttg agactcaatt catggttggg ccggccatca tggtggtccc ggtattggag    2400
cctctggtca atacggtcaa gggcgtattc ccaggagttg acatggcga agtgtggtac    2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtatt cccgggtctg tcacgtacaa ttctacgtcc    2880
caggttctct tgttggggg gctgcaaaac ttgacgaagg gcggcgcatg ggcggaaaac    2940
tgggtattgg aatggtag                                                 2958

<210> SEQ ID NO 81
<211> LENGTH: 2958
<212> TYPE: DNA
<213> ORGANISM: Aspergillus niger

<400> SEQUENCE: 81
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420 tccctcaatg catctgtatc ccagagcgac cttttgtgt catggtcaaa tgagccgtcg      480
ttcaatttca aggtgatccg aaaggctaca ggcgacgcgc ttttcagtac agaaggcact     540
gtgctcgtat atgagaatca gttcatcgaa tttgtgaccg cgctccctga agaatataac     600
ttgtatggcc ttggggagca tatcacgcaa ttccgcctcc agagaaatgc taatctgacc     660
```

```
atatatcctt cggatgatgg aacacctatt gaccaaaacc tctacggcca acatcccttc    720
tatctggata caagatatta caaggagat aggcagaatg ggtcttatat tcccgtcaaa    780
agcagcgagg ctgatgcctc gcaagattat atctccctct ctcatggcgt gtttctgagg    840
aactctcatg gacttgagat actcctccgg tctcaaaaat tgatctggcg gaccctaggt    900
ggaggaatcg atctcacctt ctactcaggc cccgccccgg ccgatgttac caggcaatat    960
cttaccagca ctgtgggatt accggccatg cagcaataca acactcttgg attccaccaa   1020
tgtcgttggg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag ttgtgtcctt ctgtgtcggg   1500
agctgtggca caggtaacct gactctgaac ccggcacacc catcgtttct tctccccggt   1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg gggcggcgac   1980
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttttata cgttgtttga cctgccccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac   2460 gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg gcggcgcatg ggcggaaaac   2940
tgggtattgg aatggtag                                                 2958
```

<210> SEQ ID NO 82
<211> LENGTH: 2958
<212> TYPE: DNA
<213> ORGANISM: Aspergillus niger

<400> SEQUENCE: 82

```
atggtgaagt tgacgcatct ccttgccaga gcatggcttg tccctctggc ttatggagcg      60
agccagtcac tcttatccac cactgcccct tcgcagccgc agtttaccat tcctgcttcc     120
gcagatgtcg gtgcgcagct gattgccaac atcgatgatc ctcaggctgc cgacgcgcag     180
tcggtttgtc cgggctacaa ggcttcaaaa gtgcagcaca attcacgtgg attcactgcc     240
agtcttcagc tcgcgggcag gccatgtaac gtatacggca cagatgttga gtccttgaca     300
ctgtctgtgg agtaccagga ttcggatcga ctgaatattc agattctccc cactcatgtt     360
gactccacaa acgcttcttg gtactttctt tcggaaaacc tggtcccag acccaaggct      420
tccctcaatg catctgtatc ccagagcgac cttttgtgt catggtcaaa tgagccgtcg      480
ttcaatttca aggtgatccg aaaggctaca ggcgacgcg ttttcagtac agaaggcact      540
gtgctcgtat atgagaatca gttcatcgaa tttgtgaccg cgctccctga gaatataac      600
ttgtatggcc ttggggagca tatcacgcaa ttccgcctcc agagaaatgc taatctgacc     660
atatatcctt cggatgatgg aacacctatt gaccaaaacc tctacggcca acatcccttc     720
tatctggata caagatatta caaggagat aggcagaatg gtcttatat tcccgtcaaa       780
agcagcgagg ctgatgcctc gcaagattat atctccctct tcatggcgt gtttctgagg      840
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca acactcttgg attccaccaa    1020
tgtcgttggg gctacaacaa ctggtcggat ctggcggacg ttgttgcgaa ctttgagaag    1080
tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt cttggtcggg    1500
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg ggcggcgac     1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
```

```
ctctccacaa tcccacagga gccttatcgg tgggcttctg ttattgaagc aaccaagtcc    2220
gccatgagaa ttcggtacgc catcctacct tactttttata cgttgtttga cctggcccac   2280
accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg acatggcga agtgtggtac    2460 gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta ccccaatgcc    2700
accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                  2958

<210> SEQ ID NO 83
<211> LENGTH: 2958
<212> TYPE: DNA
<213> ORGANISM: Aspergillus niger

<400> SEQUENCE: 83
atggtgaagt tgacgcatct ccttgccaga gcatggcttg tccctctggc ttatggagcg    60
agccagtcac tcttatccac cactgcccct tcgcagccgc agtttaccat tcctgcttcc    120
gcagatgtcg gtgcgcagct gattgccaac atcgatgatc tcaggctgc cgacgcgcag    180 tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtcccag acccaaggct    420 tccctcaatg catctgtatc ccagagcgac cttttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga gaatataac    600 ttgtatggcc ttggggagca tatcacgcaa ttccgcctcc agagaaatgc taatctgacc    660
atatatcctt cggatgatgg aacacctatt gaccaaaaacc tctacggcca acatcccttc    720
tatctggata aagatatta caaaggagat aggcagaatg gtcttatat tcccgtcaaa    780 agcagcgagg ctgatgcctc gcaagattat atctccctct ctcatggcgt gtttctgagg    840
aactctcatg gacttgagat actcctccgg tctcaaaaat tgatctggcg acccctaggt    900
ggaggaatcg atctcacctt ctactcaggc cccgccccgg ccgatgttac caggcaatat    960
cttaccagca ctgtgggatt accggccatg cagcaataca acactcttgg attccaccaa    1020
tgtcgttggg gctacaacaa ctggtcggat ctggcggacg ttgttgcgaa cttttgagaag   1080 tttgagatcc cgttggaata tatctggacc gatattgact acatgcacgg atatcgcaac    1140
tttgacaacg atcaacatcg cttttcctac agtgagggcg atgaatttct cagcaagcta    1200
catgagagtg gacgctacta tgtacccatt gttgatgcgg cgctctacat tcctaatccc    1260
```

-continued

```
gaaaatgcct ctgatgcata cgctacgtat gacagaggag ctgcggacga cgtcttcctc    1320
aagaatcccg atggtagcct ctatattgga gccgtttggc caggatatac agtcttcccc    1380
gattggcatc atcccaaggc agttgacttc tgggctaacg agcttgttat ctggtcgaag    1440
aaagtggcgt tcgatggtgt gtggtacgac atgtctgaag tttcatcctt ctctgtcggg    1500
agctgtggca caggtaacct gactctgaac ccggcacacc catcgtttct tctccccggt    1560
gagcctggtg atatcatata tgattaccca gaggctttca atatcaccaa cgctacagag    1620
gcggcgtcag cttcggcggg agcttccagt caggctgcag caaccgcgac caccacgtcg    1680
acttcggtat catatctgcg gacaacgccc acgcctggtg tccgcaatgt tgagcaccca    1740
ccctatgtga tcaaccatga ccaagaaggc catgatctca gtgtccatgc ggtgtcgccg    1800
aatgcaacgc atgttgatgg tgttgaggag tatgatgtgc acggtctcta cggacatcaa    1860
ggattgaacg ctacctacca aggtctgctt gaggtctggt ctcataagcg gcggccattt    1920
attattggcc gctcaacctt cgctggctct ggcaaatggg caggccactg gggcggcgac    1980
aactattcca aatggtggtc catgtactac tccatctcgc aagccctctc cttctcactt    2040
ttcggcattc cgatgtttgg tgcggacacc tgtgggttta acggaaactc cgatgaggag    2100
ctctgcaacc gatggatgca actgtccgca ttcttcccat tctaccgaaa ccacaatgag    2160
ctctccacaa tcccacagga gccttatcgg tgggcttctg ttattgaagc aaccaagtcc    2220
gccatgagaa ttcggtacgc catcctacct tacttttata cgttgtttga cctgcccac    2280 accacgggct ccactgtaat gcgcgcactt tcctgggaat tccctaatga cccaacattg    2340
gctgcggttg agactcaatt catggttggg ccggccatca tggtggtccc ggtattggag    2400
cctctggtca atacggtcaa gggcgtattc ccaggagttg gacatggcga agtgtggtac    2460
gattggtaca cccaggctgc agttgatgcg aagcccgggg tcaacacgac catttcggca    2520
ccattgggcc acatcccagt ttatgtacga ggtggaaaca tcttgccgat gcaagagccg    2580
gcattgacca ctcgtgaagc ccggcaaacc ccgtgggctt tgctagctgc actaggaagc    2640
aatggaaccg cgtcggggca gctctatctc gatgatggag agagcatcta cccccaatgcc    2700 accctccatg tggacttcac ggcatcgcgg tcaagcctgc gctcgtcggc tcaaggaaga    2760
tggaaagaga ggaacccgct tgctaatgtg acggtgctcg gagtgaacaa ggagccctct    2820
gcggtgaccc tgaatggaca ggccgtattt cccgggtctg tcacgtacaa ttctacgtcc    2880
caggttctct ttgttggggg gctgcaaaac ttgacgaagg gcggcgcatg ggcggaaaac    2940
tgggtattgg aatggtag                                                 2958
```